US008207177B2

(12) United States Patent
Langston et al.

(10) Patent No.: US 8,207,177 B2
(45) Date of Patent: Jun. 26, 2012

(54) INHIBITORS OF E1 ACTIVATING ENZYMES

(75) Inventors: Steven P. Langston, North Andover, MA (US); Edward J. Olhava, Cambridge, MA (US); Stepan Vyskocil, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 807 days.

(21) Appl. No.: 11/700,614

(22) Filed: Jan. 31, 2007

(65) Prior Publication Data
US 2007/0191293 A1   Aug. 16, 2007

Related U.S. Application Data

(60) Provisional application No. 60/764,487, filed on Feb. 2, 2006.

(51) Int. Cl.
C07D 487/04   (2006.01)
A61K 31/519   (2006.01)
A61P 35/00    (2006.01)
A61P 25/28    (2006.01)
A61P 29/00    (2006.01)

(52) U.S. Cl. ..................................... 514/265.1; 544/280
(58) Field of Classification Search .................. 544/280; 514/265.1
See application file for complete search history.

(56) References Cited

U.S. PATENT DOCUMENTS

| 3,622,561 | A | 11/1971 | Robins et al. |
| 5,039,689 | A | 8/1991 | Daluge |
| 5,726,302 | A | 3/1998 | Ugarkar et al. |
| 5,763,596 | A | 6/1998 | Boyer et al. |
| 5,767,097 | A | 6/1998 | Tam |
| 5,824,657 | A | 10/1998 | Hill et al. |
| 5,864,033 | A | 1/1999 | Browne et al. |
| 5,973,161 | A | 10/1999 | Crimmins |
| 6,210,917 | B1 | 4/2001 | Carson et al. |
| 6,734,283 | B1 | 5/2004 | Chau |
| 2006/0189636 | A1 | 8/2006 | Critchley et al. |
| 2011/0136834 | A1* | 6/2011 | Critchley et al. .......... 514/260.1 |

FOREIGN PATENT DOCUMENTS

| EP | 0345076 A1 | 12/1989 |
| EP | 0832091 B1 | 1/2004 |
| EP | 0832092 B1 | 11/2004 |
| GB | 2284811 A | 6/1995 |
| GB | 2287464 A | 9/1995 |
| JP | 62-108897 | 7/1987 |
| JP | 11-228422 | 8/1999 |
| JP | 11-228446 | 8/1999 |
| WO | WO 02/32920 A2 | 4/2002 |
| WO | WO 03/049739 A1 | 6/2003 |
| WO | WO 03/106477 A1 | 12/2003 |
| WO | WO 2005/007621 A2 | 1/2005 |
| WO | WO 2005/037845 A1 | 4/2005 |
| WO | WO 2006/002284 A1 | 1/2006 |
| WO | WO 2006/084281 A1 | 8/2006 |

OTHER PUBLICATIONS

Baker, David C., et al., "An evaluation of certain chain-extended analogues of 9-β-D-arabinofuranosyladenine for antiviral and cardiovascular activity," Journal of Medicinal Chemistry, vol. 26, No. 10 (1983) pp. 1530-1534.

Bernier, Stephane, et al., "Glutamylsulfamoyladenosine and pyroglutamylsulfamoyladenosine are competitive inhibitors of E. coli glutamyl-tRNA synthetase," Journal of Enzyme Inhibition and Medicinal Chemistry, vol. 20, No. 1 (Feb. 2005) pp. 61-67.

Bloch, A., et al., "Inhibition of protein synthesis by 5'-sulfamoyladenosine," Biochemistry, vol. 10, No. 24 (1971) pp. 4394-4398.

Bookser, Brett C., et al., "Adenosine kinase inhibitors. 4. 6,8-disubstituted purine nucleoside derivatives. Synthesis, conformation, and enzyme inhibition," Journal of Medicinal Chemistry, vol. 48, No. 9 (2005) pp. 3389-3399.

Boyer, Serge H., et al., "Adenosine kinase inhibitors. 5. Synthesis, enzyme inhibition, and analgesic activity of diaryl-*erythro*-furanosyltubercidin analogues," Journal of Medicinal Chemistry, vol. 48, No. 20 (2005) pp. 6430-6441.

Brown, Pamela, et al., "Molecular recognition of tyrosinyl adenylate analogues by prokaryotic tyrosyl tRNA synthetases," Bioorganic & Medicinal Chemistry, vol. 7 (1999) pp. 2473-2485.

Crimmins, Michael T., et al., "An efficient, general asymmetric synthesis of carbocyclic nucleosides: application of an asymmetric aldol/ring-closing metathesis strategy," Journal of Organic Chemistry, vol. 65, No. 25 (2000) pp. 8499-8509.

Gough, Geoffrey R., "New inhibitors of platelet aggregation. 5'-phosphate, 5'-phosphorothioate, and 5'-O-sulfamoyl derivatives of 2-substituted adenosine analogues," Journal of Medicinal Chemistry, vol. 21, No. 6 (1978) pp. 520-525.

Huang, Danny T., et al., "Structural basis for recruitment of Ubc12 by an E2 binding domain in NEDD8's E1," Molecular Cell, vol. 17 (Feb. 4, 2005) pp. 341-350.

Kristinsson, Haukur, et al., "A novel synthesis of sulfamoyl nucleosides," Tetrahedron, vol. 50, No. 23 (1994) pp. 6825-6838.

Kristinsson, Haukur, et al., "Herbicidally active sulfamoyl nucleosides," ACS Symposium Series 584, Synthesis and Chemistry of Agrochemicals IV, Chapter 19, Baker, Don R., et al., editors (1995) pp. 206-219.

Kuang, Rongze, et al., Enantioselective syntheses of carbocyclic ribavirin and its analogs: linear versus convergent approaches, Tetrahedron Letters, vol. 41 (2000) pp. 9575-9579.

(Continued)

Primary Examiner — Scarlett Goon
(74) Attorney, Agent, or Firm — Millennium Pharmaceuticals, Inc.

(57) ABSTRACT

This invention relates to compounds that inhibit E1 activating enzymes, pharmaceutical compositions comprising the compounds, and methods of using the compounds. The compounds are useful for treating disorders, particularly cell proliferation disorders, including cancers, inflammatory and neurodegenerative disorders; and inflammation associated with infection and cachexia.

9 Claims, No Drawings

OTHER PUBLICATIONS

Lee, Jeewoo, et al., "N-alkoxysulfamide, N-hydroxysulfamide, and sulfamate analogues of methionyl and isoleucyl adenylates as inhibitors of methionyl-tRNA and isoleucyl-tRNA synthetases," *Bioorganic & Medicinal Chemistry Letters*, vol. 13 (2003) pp. 1087-1092.

Pan, Zhen-Qiang, et al., "Nedd8 on cullin: building an expressway to protein destruction," *Oncogene*, vol. 23 (2004) pp. 1985-1997.

Peterson, Eileen M., et al., "Synthesis and biological evaluation of 5'-sulfamoylated purinyl carbocyclic nucleosides," *Journal of Medicinal Chemistry*, vol. 35, No. 22 (1992) pp. 3991-4000.

Shuman, Dennis A., et al., "The synthesis of nucleoside sulfamates related to nucleocidin," *Journal of the American Chemical Society*, vol. 92, No. 11 (Jun. 3, 1970) pp. 3434-3440.

Somu, Ravindranadh V., et al., "Rationally designed nucleoside antibiotics that inhibit siderophore biosynthesis of *Mycobacterium tuberculosis*," *Journal of Medicinal Chemistry*, vol. 49, No. 1 (2006) pp. 31-34.

Ubukata, Makoto, et al., "Total synthesis of nucleoside antibiotic, ascamycin," *Tetrahedron Letters*, vol. 27, No. 33 (1986) pp. 3907-3908.

Ubukata, Makoto, et al., "Synthesis and biological activity of aminoacyl analogs of ascamycin," *Agricultural and Biological Chemistry*, vol. 52, No. 5 (1988) pp. 1117-1122.

Ugarkar, Bheemarao G., et al., "Adenosine kinase inhibitors. 3. Synthesis, SAR, and anti-inflammatory activity of a series of L-lyxofuranosyl nucleosides," *Journal of Medicinal Chemistry*, vol. 46, No. 22 (2003) pp. 4750-4760.

Winum, Jean-Yves, et al., "Sulfamates and their therapeutic potential," *Medicinal Research Reviews*, vol. 25, No. 2 (2005) pp. 186-228.

Abouabdellah, Ahmed, et al., "Lewis acid-induced ene-cyclization of ω-olefinic trifluoromethyl ketones: access to alicyclic compounds bearing a $CF_3$ group," *Journal of the Chemical Society, Perkin Transactions 1: Organic and Bio-Oganic Chemistry* (1972-1999), vol. 6 (1991) pp. 1397-1403.

Berranger, Thierry, et al., "[2+3]-cycloadditions of enantiomerically pure oxazoline-N-oxides[1:] a short stereoselective synthesis of (+)-carbovir," *Tetrahedron Letters*, vol. 36, No. 31 (1995) pp. 5523-5526.

Biggadike, Keith, et al., "4'-modification of carbocyclic nucleosides: synthesis of 4'-α-fluoro, 4'α-hydroxy and 4',6'-unsaturated derivatives of the antiviral agent 2'-*ara*-fluoro carbocyclic guanosine," *Journal of the Chemical Society, Chemical Communications*, vol. 19 (1990) pp. 1380-1382.

Borthwick, Alan, et al., "Chiral carbocyclic nucleosides: the synthesis and antiviral activity of 4'-hydroxy and 4'-fluorocarbocyclic-2'-deoxyguanosines," *Bioorganic & Medicinal Chemistry Letters*, vol. 3, No. 12 (1993) 2577-2580.

Gosselin, Gilles, et al., "A short and novel synthesis of carbocyclic nucleosides and 4'-*epi*-carbocyclic nucleosides from 2-cyclopenten-1-ones," *Tetrahedron*, vol. 62 (2006) pp. 906-914.

Madhavan, G.V. Bindu, et al., "Synthesis and antiviral evaluation of 6'-substituted aristeromycins: potential mechanism-based inhibitors of S-adenosylhomocysteine hydrolase," *Journal of Medicinal Chemistry*, vol. 31 (1988) pp. 1798-1804.

Meillon, J.-C., et al., "Rapid access to 2'-branched-carbocyclic nucleosides and their 4'-epimers from 2-alkyl-cyclopentene-1-ones," *Nucleosides, Nucleotides, and Nucleic Acids*, vol. 24, No. 5-7 (2005) pp. 695-699.

Morizawa, Yoshitomi, et al., "Stereoselective introduction of fluorine atom: synthesis of racemic carbocyclic analogues of 3'-deoxy-3'-fluororibofuranosides and 3'-deoxy-3'-fluoroarabinofuranosides," *Bulletin of the Chemical Society of Japan*, vol. 66, No. 9 (1993) pp. 2714-2719.

Sugiyama, Hiroshi, et al., "Bleomycin-mediated degradation of aristeromycin-containing DNA. Novel dehydrogenation activity of iron[II]-bleomycin," *Journal of the American Chemical Society*, vol. 113 (1991) pp. 2290-2295.

Toyota, Akemi, et al., "Synthesis of 9-(C-5-hydroxy-C-4-hydroxymethylcyclopent-2-EN-R-1-YL)-9H-adenine [(+)-epinor-BCA]," *Heterocycles*, vol. 38, No. 1 (1994) pp. 27-30.

Trost, Barry M., et al., "A novel Pd-catalyzed cycloalkylation to isoxazoline 2-oxides. Application for the asymmetric synthesis of carbanucleosides," *Journal of the American Chemical Society*, vol. 114 (1992) pp. 8745-8747.

Vanhessche, K., et al., "Total synthesis of (−)-neplanocin A from L-ribulose," *Synlett*, vol. 12 (Dec. 1991) pp. 921-922.

Vince, Robert, et al., "The synthesis and biological evaluation of sulfamoyl nucleosides related to carbovir and AZT," *Nucleosides & Nucleotides*, vol. 14, Nos. 9 & 10 (1995) pp. 2051-2060.

Wachtmeister, Johanna, et al., "Synthesis of 4-substituted carbocyclic 2,3-dideoxy-3-C-hydroxymethyl nucleoside analogues as potential anti-viral agents," *Tetrahedron*, vol. 55 (1999) pp. 10761-10770.

International Search Report with Written Opinion dated Aug. 16, 2007 from PCT/US07/002560 corresponding to U.S. Appl. No. 11/700,614.

International Search Report with Written Opinion dated Jul. 17, 2006 from PCT/US06/004637 corresponding to U.S. Appl. No. 11/346,649.

Amendment and Response filed on Oct. 9, 2009 in pending U.S. Appl. No. 11/346,469.

Office Action dated Jul. 9, 2009 in pending U.S. Appl. No. 11/346,469.

Supplemental Amendment and Response filed on Nov. 6, 2009 in pending U.S. Appl. No. 11/346,469.

\* cited by examiner

INHIBITORS OF E1 ACTIVATING ENZYMES

FIELD OF THE INVENTION

This invention relates to compounds, compositions and methods for the treatment of various disorders, particularly disorders of cell proliferation, including cancers, and inflammatory disorders. In particular, the invention provides compounds which inhibit the activity of E1 type activating enzymes.

BACKGROUND OF THE INVENTION

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

The biological consequence of ubl modification depends on the target in question. Ubiquitin is the best characterized of the ubls and a consequence of modification by ubiquitination is the degradation of poly-ubiquitinated proteins by the 26S proteasome. Ubiquitin is conjugated to its target proteins through an enzymatic cascade involving its specific E1 activating enzyme, Uba1 (ubiquitin activating enzyme, UAE), a conjugating enzyme from the family of E2s, and a ubiquitin ligase from either the RING or HECT classes of E3s. See, Huang et al., *Oncogene*. 23:1958-71 (2004). Target specificity is controlled by the particular combination of E2 and E3 protein, with >40 E2s and >100 E3s being known at present. In addition to ubiquitin, there are at least 10 ubiquitin-like proteins, each believed to be activated by a specific E1 activating enzyme and processed through similar but distinct downstream conjugation pathways. Other ubls for which E1 activating enzymes have been identified include Nedd8 (APPBP1-Uba3), ISG15 (UBE1L) and the SUMO family (Aos1-Uba2).

The ubl Nedd8 is activated by the heterodimer Nedd8-activating enzyme (APPBP1-Uba3) (NAE) and is transferred to a single E2 (Ubc12), ultimately resulting in ligation to cullin proteins. The function of neddylation is the activation of cullin-based ubiquitin ligases involved in the ubiquitination and hence turnover of many cell cycle and cell signaling proteins, including p27 and I-κB. See Pan et al., *Oncogene*. 23:1985-97, (2004). The ubl SUMO is activated by the heterodimer sumo activating enzyme (Aos1-Uba2) (SAE) and is transferred to a single E2 (Ubc9), followed by coordination with multiple E3 ligases, ultimately resulting in sumoylation of target proteins. Sumo modification can affect the cellular localization of target proteins and proteins modified by SUMO family members are involved in nuclear transport, signal transduction and the stress response. See Seeler and Dejean, *Nat Rev Mol Cell Biol*. 4:690-9, (2003). The function of sumoylation includes activation of cell signaling pathways (e.g., cytokine, WNT, growth factor, and steroid hormone signaling) involved in transcription regulation; as well as pathways involved in control of genomic integrity (e.g., DNA replication, response to DNA damage, recombination and repair). See Muller et al, *Oncogene*. 23:1998-2006, (2004). There are other ubls (e.g., ISG15, FAT10, Apg12p) for which the biological functions are still under investigation.

A particular pathway of importance which is regulated via E1 activating enzyme activities is the ubiquitin-proteasome pathway (UPP). As discussed above, the enzymes UAE and NAE regulate the UPP at two different steps in the ubiquitination cascade. UAE activates ubiquitin in the first step of the cascade, while NAE, via activation of Nedd8, is responsible for the activation of the cullin based ligases, which in turn are required for the final transfer of ubiquitin to certain target proteins. A functional UPP pathway is required for normal cell maintenance. The UPP plays a central role in the turnover of many key regulatory proteins involved in transcription, cell cycle progression and apoptosis, all of which are important in disease states, including tumor cells. See, e.g., King et al., *Science* 274: 1652-1659 (1996); Vorhees et al., *Clin. Cancer Res.*, 9: 6316-6325 (2003); and Adams et al., *Nat. Rev. Cancer*, 4: 349-360 (2004). Proliferating cells are particularly sensitive to inhibition of the UPP. See, Drexler, *Proc. Natl. Acad. Sci., USA* 94: 855-860 (1977). The role of the UPP pathway in oncogenesis has led to the investigation of proteasome inhibition as a potential anticancer therapy. For example, modulation of the UPP pathway by inhibition of the 26S proteasome by VELCADE® (bortezomib) has proven to be an effective treatment in certain cancers and is approved for the treatment of relapsed and refractory multiple myeloma. Examples of proteins whose levels are controlled by cullin-based ubiquitin ligases which are downstream of NAE and UAE activity include the CDK inhibitor $p27^{Kip1}$ and the inhibitor of NFκB, IκB. See, Podust et al., *Proc. Natl. Acad. Sci.*, 97: 4579-4584, (2000), and Read et al., *Mol. Cell Biol.*, 20: 2326-2333, (2000). Inhibition of the degradation of p27 is expected to block the progression of cells through the G1 and S phases of the cell cycle. Interfering with the degradation of IκB should prevent the nuclear localization of NF-κB, transcription of various NF-κB-dependent genes associated with the malignant phenotype, and resistance to standard cytotoxic therapies. Additionally, NF-κB plays a key role in the expression of a number of pro-inflammatory mediators, implicating a role for such inhibitors in inflammatory diseases. Furthermore, inhibition of UPP has been implicated as a useful target for additional therapeutics, such as inflammatory disorders, including, e.g., rheumatoid arthritis, asthma, multiple sclerosis, psoriasis and reperfusion injury; neurodegenerative disorders, including, e.g., Parkinson's disease, Alzheimer's disease, triplet repeat disorders; neuropathic pain; ischemic disorders, e.g., stroke, infarction, kidney disorders; and cachexia. See, e.g., Elliott and Ross, *Am J Clin Pathol*. 116:637-46 (2001); Elliott et al., *J Mol Med*. 81:235-45 (2003); Tarlac and Storey, *J. Neurosci. Res*. 74: 406-416 (2003) Mori et al., *Neuropath. Appl. Neurobiol.*, 31: 53-61 (2005); Manning, *Curr Pain Headache Rep*. 8: 192-8 (2004); Dawson and Dawson, *Science* 302: 819-822 (2003); Kukan, *J Physiol Pharmacol*. 55: 3-15 (2004); Wojcik and DiNapoli, *Stroke*. 35:1506-18 (2004); Lazarus et al., *Am J Physiol*. 27:E332-41 (1999).

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

DESCRIPTION OF THE INVENTION

This invention provides compounds that are effective inhibitors of E1 activating enzymes, particularly NAE. The compounds are useful for inhibiting E1 activity in vitro and in vivo, and are useful for the treatment of disorders of cell proliferation, particularly cancers, and other disorders associated with E1 activity. Compounds of the invention are of the general formula (I):

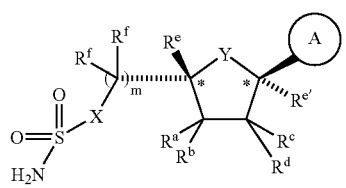

(I)

or a pharmaceutically acceptable salt thereof, wherein:

stereochemical configurations depicted at asterisked positions indicate relative stereochemistry;

Ring A is selected from the group consisting of:

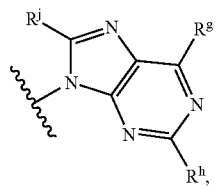

A-i

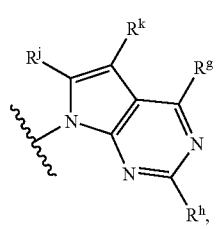

A-ii

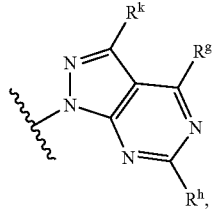

A-iii

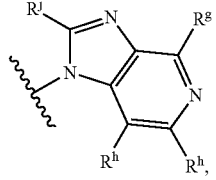

A-iv

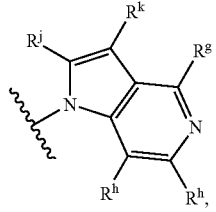

A-v

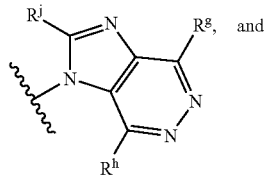

A-vi, and

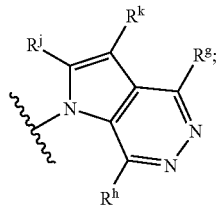

A-vii wherein one ring nitrogen atom in Ring A optionally is oxidized;

X is —C($R^{f1}$)$_2$—, —N($R^{f2}$)—, or —O—;

Y is —O—, —S—, or —C($R^m$)($R^n$)—;

$R^a$ is selected from the group consisting of hydrogen, fluoro, —CN, —N$_3$, —OR$^5$, —N(R$^4$)$_2$, —NR$^4$CO$_2$R$^6$, —NR$^4$C(O)R$^5$, —C(O)N(R)$_2$, —C(O)R$^5$, —OC(O)N(R$^4$)$_2$, —OC(O)R$^5$, —OCO$_2$R$^6$, or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^a$ and R$^b$ together form =O; or R$^a$ and R$^c$ together form a bond;

$R^b$ is selected from the group consisting of hydrogen, fluoro, C$_{1-4}$ aliphatic, and C$_{1-4}$ fluoroaliphatic; or R$^b$ and R$^a$ together form =O; or R$^b$, taken together with R$^d$ and the intervening carbon atoms, forms a fused cyclopropane ring, which is optionally substituted with one or two substituents independently selected from fluoro or C$_{1-4}$ aliphatic; or R$^b$, taken together with R$^e$ and the intervening carbon atoms, forms a fused cyclopropane ring, which is optionally substituted with one or two substituents independently selected from fluoro or C$_{1-4}$ aliphatic;

$R^c$ is selected from the group consisting of hydrogen, fluoro, —CN, —N$_3$, —OR$^5$, —N(R$^4$)$_2$, —NR$^4$CO$_2$R$^6$, —NR$^4$C(O)R, —C(O)N(R)$_2$, —C(O)R, —OC(O)N(R$^4$)$_2$, —OC(O)R$^5$, —OCO$_2$R$^6$, or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^c$ and R$^a$ together form a bond; or R$^c$ and R$^d$ together form =O;

$R^d$ is selected from the group consisting of hydrogen, fluoro, C$_{1-4}$ aliphatic, and C$_{1-4}$ fluoroaliphatic; or R$^d$ and R$^c$ together form =O; or R$^d$, taken together with R$^b$ and the intervening carbon atoms, forms a fused cyclopropane ring, which is optionally substituted with one or two substituents independently selected from fluoro or C$_{1-4}$ aliphatic; or R$^d$, taken together with R$^{e'}$ and the intervening carbon atoms, forms a fused cyclopropane ring, which is optionally substituted with one or two substituents independently selected from fluoro or C$_{1-4}$ aliphatic;

$R^e$ is hydrogen, or C$_{1-4}$ aliphatic; or R$^e$, taken together with one R$^f$ and the intervening carbon atoms, forms a 3- to 6-membered spirocyclic ring, which is optionally substituted with one or two substituents independently selected from fluoro or C$_{1-4}$ aliphatic; or R$^e$, taken together with R$^m$ and the intervening carbon atoms, forms a fused cyclopropane ring, which is optionally substituted with one or two substituents independently selected from fluoro or C$_{1-4}$ aliphatic; or R$^e$, taken together with R$^b$ and the intervening carbon atoms, forms a fused cyclopropane ring, which is optionally substituted with one or two substituents independently selected from fluoro or C$_{1-4}$ aliphatic;

$R^{e'}$ is hydrogen or C$_{1-4}$ aliphatic; or R$^{e'}$, taken together with R$^m$ and the intervening carbon atoms, forms a fused cyclopropane ring, which is optionally substituted with one or two substituents independently selected from fluoro or C$_{1-4}$ aliphatic; or R$^e$, taken together with R$^d$ and the intervening carbon atoms, forms a fused cyclopropane ring, which is optionally substituted with one or two substituents independently selected from fluoro or C$_{1-4}$ aliphatic;

each $R^f$ is independently hydrogen, fluoro, C$_{1-4}$ aliphatic, or C$_{1-4}$ fluoroaliphatic, provided that if X is —O— or —NH—, then R$^f$ is not fluoro; or two R$^f$ taken together form =O; or two R$^f$, taken together with the carbon atom to which they are attached, form a 3- to 6-membered carbocyclic ring; or one R$^f$, taken together with R$^e$ and the intervening carbon atoms, forms a 3- to 6-membered spirocyclic ring, which is optionally substituted with one or two substituents independently selected from fluoro or C$_{1-4}$ aliphatic; or one R$^f$, taken together with an adjacent R$^{f1}$ and the intervening carbon atoms, forms a cyclopropyl ring, which is optionally substituted with one or two substituents independently selected from fluoro or C$_{1-4}$ aliphatic; or one R$^f$ and one R$^{f1}$ together form a double bond;

each $R^{f1}$ is independently hydrogen or fluoro; or one R$^{f1}$, taken together with an adjacent R$^f$ and the intervening carbon atoms forms a cyclopropyl ring, which is optionally substituted with one or two substituents independently selected from fluoro or C$_{1-4}$ aliphatic; or one R$^{f1}$ and one R$^f$ together form a double bond;

$R^{f2}$ is hydrogen, C$_{1-4}$ aliphatic, and C$_{1-4}$ fluoroaliphatic;

$R^g$ is hydrogen, halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OCO$_2$R$^6$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —N(R$^4$)—N(R$^4$)$_2$, —N(R$^4$)—OR$^5$, —C(=NR$^4$)—N(R$^4$)—OR$^5$, —C(R$^6$)=N—OR$^5$, or an optionally substituted aliphatic, aryl, heteroaryl, or heterocyclyl;

each $R^h$ independently is hydrogen, halo, —CN—, —OR$^5$, —N(R$^4$)$_2$, —SR$^6$, or an optionally substituted C$_{1-4}$ aliphatic group;

$R^j$ is hydrogen, —OR$^5$, —SR$^6$, —N(R$^4$)$_2$, or an optionally substituted aliphatic, aryl, or heteroaryl group;

$R^k$ is hydrogen, halo, —OR$^5$, —SR$^6$, —N(R$^4$)$_2$, or an optionally substituted C$_{1-4}$ aliphatic group;

$R^m$ is hydrogen, fluoro, —N(R$^4$)$_2$, or an optionally substituted C$_{1-4}$ aliphatic group; or R$^m$ and R$^n$ together form =O or =C(R$^5$)$_2$; or R$^m$ and R$^e$, taken together with the intervening carbon atoms, form a fused cyclopropane ring, which is optionally substituted with one or two substituents independently selected from fluoro or C$_{1-4}$ aliphatic; or R$^m$ and R$^{e'}$, taken together with the intervening carbon atoms, form a fused cyclopropane ring, which is optionally substituted with one or two substituents independently selected from fluoro or C$_{1-4}$ aliphatic;

$R^n$ is hydrogen, fluoro, or an optionally substituted C$_{1-4}$ aliphatic group; or R$^m$ and R$^n$ together form =O or =C(R$^5$)$_2$;

each $R^4$ independently is hydrogen or an optionally substituted aliphatic, aryl, heteroaryl, or heterocyclyl group; or two R$^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

$R^{4x}$ is hydrogen, C$_{1-4}$ alkyl, C$_{1-4}$ fluoroalkyl, or C$_{6-10}$ ar(C$_{1-4}$)alkyl, the aryl portion of which may be optionally substituted;

$R^{4y}$ is hydrogen, C$_{1-4}$ alkyl, C$_{1-4}$ fluoroalkyl, C$_{6-10}$ ar(C$_{1-4}$)alkyl, the aryl portion of which may be optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S; and each $R^5$ independently is hydrogen or an optionally substituted aliphatic, aryl, heteroaryl, or heterocyclyl group;

each $R^{5x}$ independently is hydrogen, C$_{1-4}$ alkyl, C$_{1-4}$ fluoroalkyl, or an optionally substituted C$_{6-10}$ aryl or C$_{6-10}$ ar(C$_{1-4}$)alkyl;

each $R^6$ independently is an optionally substituted aliphatic, aryl, or heteroaryl group; and m is 0, 1, 2, or 3, provided that Y is —C(R$^m$)(R$^n$)— when m is 0.

In some embodiments, the invention relates to a compound of formula (I), characterized by formula (I-A):

(I-A)

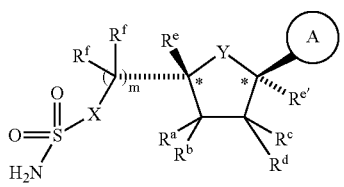

or a pharmaceutically acceptable salt thereof, wherein:
stereochemical configurations depicted at asterisked positions indicate relative stereochemistry;
Ring A is selected from the group consisting of:

A-i

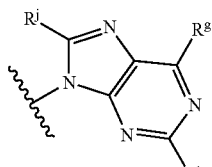

A-ii

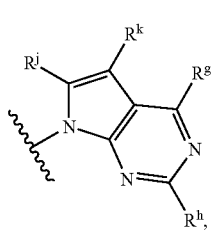

A-iii

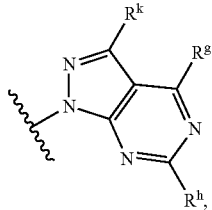

A-iv

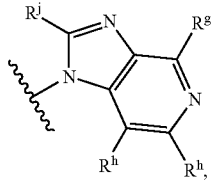

A-v

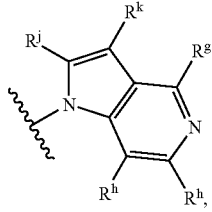

A-vi

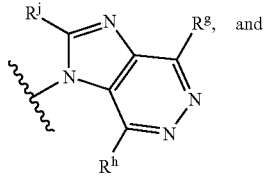
and

A-vii

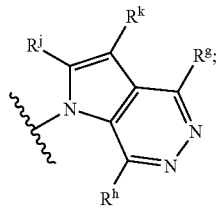

wherein one ring nitrogen atom in Ring A optionally is oxidized;
X is —$CH_2$—, —CHF—, —$CF_2$—, —NH—, or —O—;
Y is —O—, —S—, or —C($R^m$)($R^n$)—;
$R^a$ is selected from the group consisting of hydrogen, fluoro, —CN, —$N_3$, —$OR^5$, —N($R^4$)$_2$, —$NR^4CO_2R^6$, —$NR^4C(O)R^5$, —C(O)N($R^4$)$_2$, —C(O)$R^5$, —OC(O)N($R^4$)$_2$, —OC(O)$R^5$, —OCO$_2R^6$, $C_{1-4}$ fluoroaliphatic, or a $C_{1-4}$ aliphatic optionally substituted with one or two substituents independently selected from the group consisting of —$OR^{5x}$, —N($R^{4x}$)($R^{4y}$), —CO$_2R^{5x}$, or —C(O)N($R^{4x}$)($R^{4y}$);
$R^b$ is selected from the group consisting of hydrogen, fluoro, $C_{1-4}$ aliphatic, and $C_{1-4}$ fluoroaliphatic;
$R^c$ is selected from the group consisting of hydrogen, fluoro, —CN, —$N_3$, —$OR^5$, —N($R^4$)$_2$, —$NR^4CO_2R^6$, —$NR^4C(O)R^5$, —C(O)N($R^4$)$_2$, —C(O)$R^5$, —OC(O)N($R^4$)$_2$, —OC(O)$R^5$, —OCO$_2R^6$, $C_{1-4}$ fluoroaliphatic, or a $C_{1-4}$ aliphatic optionally substituted with one or two substituents independently selected from the group consisting of —$OR^{5x}$, —N($R^{4x}$)($R^{4y}$), —CO$_2R^{5x}$, or —C(O)N($R^{4x}$)($R^{4y}$);
$R^d$ is selected from the group consisting of hydrogen, fluoro, $C_{1-4}$ aliphatic, and $C_{1-4}$ fluoroaliphatic;
$R^e$ is hydrogen, or $C_{1-4}$ aliphatic; or $R^e$, taken together with one $R^f$ and the intervening carbon atoms, forms a 3- to 6-membered spirocyclic ring;
$R^{e'}$ is hydrogen or $C_{1-4}$ aliphatic;
each $R^f$ is independently hydrogen, fluoro, $C_{1-4}$ aliphatic, or $C_{1-4}$ fluoroaliphatic, provided that if X is —O— or —NH—, then $R^f$ is not fluoro; or two $R^f$ taken together form =O; or two $R^f$, taken together with the carbon atom to which they are attached, form a 3- to 6-membered carbocyclic ring; or one $R^f$, taken together with $R^e$ and the intervening carbon atoms, forms a 3- to 6-membered spirocyclic ring;
$R^g$ is hydrogen, halo, —NO$_2$, —CN, —C($R^5$)=C($R^5$)$_2$, —C≡C—R, —$OR^5$, —$SR^6$, —S(O)$R^6$, —SO$_2R^6$, —SO$_2$N($R^4$)$_2$, —N($R^4$)$_2$, —$NR^4C(O)R^5$, —$NR^4C(O)$N($R^4$)$_2$, —N($R^4$)C(=NR)—N($R^4$)$_2$, —N($R^4$)C(=NR$^4$)—$R^6$, —$NR^4CO_2R^6$, —N($R^4$)SO$_2R^6$, —N($R^4$)SO$_2$N($R^4$)$_2$, —O—C(O)$R^5$, —OCO$_2R^6$, —OC(O)N($R^4$)$_2$, —C(O)$R^5$, —CO$_2R^5$, —C(O)N($R^4$)$_2$, —C(O)N($R^4$)—$OR^5$, —C(O)N($R^4$)C(=NR$^4$)—N(R)$_2$, —N($R^4$)C(=NR$^4$)—N($R^4$)—C(O)$R^5$, —C(=NR$^4$)—N($R^4$)$_2$, —C(=NR$^4$)—$OR^5$, —N($R^4$)—N($R^4$)$_2$, —N($R^4$)—$OR^5$, —C(=NR$^4$)—N($R^4$)—$OR^5$, —C($R^6$)=N—$OR^5$, or an optionally substituted aliphatic, aryl, heteroaryl, or heterocyclyl;
each $R^h$ independently is hydrogen, halo, —CN—, —$OR^5$, —N($R^4$)$_2$, —$SR^6$, or an optionally substituted $C_{1-4}$ aliphatic group;
$R^j$ is hydrogen, —$OR^5$, —$SR^6$, —N($R^4$)$_2$, or an optionally substituted aliphatic, aryl, or heteroaryl group;
$R^k$ is hydrogen, halo, —$OR^5$, —$SR^6$, —N($R^4$)$_2$, or an optionally substituted $C_{1-4}$ aliphatic group;

R'" is hydrogen, fluoro, —N(R$^4$)$_2$, or an optionally substituted C$_{1-4}$ aliphatic group; and R" is hydrogen, fluoro, or an optionally substituted C$_{1-4}$ aliphatic group; or R'" and R" together form =O or =C(R$^5$)$_2$;

each R$^4$ independently is hydrogen or an optionally substituted aliphatic, aryl, heteroaryl, or heterocyclyl group; or two R$^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

R$^{4x}$ is hydrogen, C$_{1-4}$ alkyl, C$_{1-4}$ fluoroalkyl, or C$_{6-10}$ ar(C$_{1-4}$)alkyl, the aryl portion of which may be optionally substituted;

R$^{4y}$ is hydrogen, C$_{1-4}$ alkyl, C$_{1-4}$ fluoroalkyl, C$_{6-10}$ ar(C$_{1-4}$)alkyl, the aryl portion of which may be optionally substituted, or an optionally substituted 5- or 6-membered aryl, heteroaryl, or heterocyclyl ring; or R$^{4x}$ and R$^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S; and each R$^5$ independently is hydrogen or an optionally substituted aliphatic, aryl, heteroaryl, or heterocyclyl group;

each R$^{5x}$ independently is hydrogen, C$_{1-4}$ alkyl, C$_{1-4}$ fluoroalkyl, or an optionally substituted C$_{6-10}$ aryl or C$_{6-10}$ ar(C$_{1-4}$)alkyl;

each R$^6$ independently is an optionally substituted aliphatic, aryl, or heteroaryl group; and m is 1, 2, or 3.

Compounds of the invention include those described generally above, and are further defined and illustrated by the detailed description and examples herein.

As used herein, the term "E1," "E1 enzyme," or "E1 activating enzyme" refers to any one of a family of related ATP-dependent activating enzymes involved in activating or promoting ubiquitin or ubiquitin-like (collectively "ubl") conjugation to target molecules. E1 activating enzymes function through an adenylation/thioester intermediate formation to transfer the appropriate ubl to the respective E2 conjugating enzyme through a transthiolation reaction. The resulting activated ubl-E2 promotes ultimate conjugation of the ubl to a target protein. A variety of cellular proteins that play a role in cell signaling, cell cycle, and protein turnover are substrates for ubl conjugation which is regulated through E1 activating enzymes (e.g., NAE, UAE, SAE). Unless otherwise indicated by context, the term "E1 enzyme" is meant to refer to any E1 activating enzyme protein, including, without limitation, nedd8 activating enzyme (NAE (APPBP1/Uba3)), ubiquitin activating enzyme (UAE (Uba1)), sumo activating enzyme (SAE (Aos1/Uba2)), or ISG15 activating enzyme (Ube1L), preferably human NAE, SAE or UAE, and more preferably NAE.

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., ubiquitination, neddylation, sumoylation). In various embodiments, such reduction of E1 enzyme activity is at least about 50%, at least about 75%, at least about 90%, at least about 95%, or at least about 99%. In various embodiments, the concentration of E1 enzyme inhibitor required to reduce an E1 enzymatic activity is less than about 1 µM, less than about 500 nM, less than about 100 nM, less than about 50 nM, or less than about 10 nM.

In some embodiments, such inhibition is selective, i.e., the E1 enzyme inhibitor reduces the ability of one or more E1 enzymes (e.g., NAE, UAE, or SAE) to promote ubl conjugation to substrate peptide or protein at a concentration that is lower than the concentration of the inhibitor that is required to produce another, unrelated biological effect. In some such embodiments, the E1 enzyme inhibitor reduces the activity of one E1 enzyme at a concentration that is lower than the concentration of the inhibitor that is required to reduce enzymatic activity of a different E1 enzyme. In other embodiments, the E1 enzyme inhibitor also reduces the enzymatic activity of another E1 enzyme, preferably one that is implicated in regulation of pathways involved in cancer (e.g., NAE and UAE).

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "aliphatic", as used herein, means straight-chain, branched or cyclic C$_1$-C$_{12}$ hydrocarbons which are completely saturated or which contain one or more units of unsaturation, but which are not aromatic. For example, suitable aliphatic groups include substituted or unsubstituted linear, branched or cyclic alkyl, alkenyl, alkynyl groups and hybrids thereof, such as cycloalkyl, (cycloalkyl)alkyl, (cycloalkenyl)alkyl or (cycloalkyl)alkenyl. In various embodiments, the aliphatic group has one to ten, one to eight, one to six, one to four, or one, two, or three carbons.

The terms "alkyl", "alkenyl", and "alkynyl", used alone or as part of a larger moiety, refer to a straight and branched chain aliphatic group having from one to twelve carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl. The term "alkoxy" refers to an —O-alkyl radical.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on a cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, two adjacent substituents on a heteroaryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as —NH—, —$CH_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain which is optionally substituted.

The term "alkylene" refers to a bivalent alkyl group. An "alkylene chain" is a polymethylene group, i.e., —$(CF_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—, —S(O)—, —$S(O)_2$—, —$S(O)_2N(R^+)$—, —N(R*)—, —$N(R^+)CO$—, —$N(R^+)C(O)N(R^+)$—, —$N(R^+)CO_2$—, —$C(O)N(R^+)$—, —C(O)—, —C(O)—C(O)—, —$CO_2$—, —OC(O)—, —OC(O)O—, —$OC(O)N(R^+)$—, —$C(NR^+)$=N—, —C(OR*)=N—, —$N(R^+)$—N($R^+$)—, or —$N(R^+)S(O)_2$—. Each $R^+$, independently, is hydrogen or an optionally substituted aliphatic, aryl, heteroaryl, or heterocyclyl group, or two $R^+$ on the same nitrogen atom, taken together with the nitrogen atom, form a five to eight membered aromatic or non-aromatic ring having, in addition to the nitrogen atom, zero to two ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —$CH_2OCH_2$—, —$CH_2O(CH_2)_2$—, —$CH_2O(CH_2)_3$—, —$CH_2O(CH_2)_4$—, —$(CH_2)_2OCH$—, —$(CH_2)_2O(CH_2)_2$—, —$(CH_2)_2O(CH_2)_3$—, —$(CH_2)_3O(CH_2)$—, —$(CH_2)_3O(CH_2)_2$—, and —$(CH_2)_4O(CH_2)$—. Other examples of alkylene chains that are "interrupted" with functional groups include —$CH_2GCH_2$—, —$CH_2G(CH_2)_2$—, —$CH_2G(CH_2)_3$—, —$CH_2G(CH_2)_4$—, —$(CH_2)_2GCH_2$—, —$(CH_2)_2G(CH_2)_2$—, —$(CH_2)_2G(CH_2)_3$—, —$(CH_2)_3G(CH_2)$—, —$(CH_2)_3G(CH_2)_2$—, and —$(CH_2)_4G(CH_2)$—, wherein G is one of the "interrupting" functional groups listed above.

For purposes of clarity, all bivalent groups described herein, including, e.g., the alkylene chain linkers described above and the variables $V^1$, $V^2$, $T^1$, $T^2$, $T^3$, and $T^4$, are intended to be read from left to right, with a corresponding left-to-right reading of the formula or structure in which the variable appears.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=$C(R*)_2$, —C≡C—R*, —OR*, —$SR^o$, —S(O)$R^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^o$, —OC(O)$N(R^+)_2$, —O—C(O)R*, —$CO_2R^*$, —C(O)—C(O)R*, —C(O)R*, —C(O)$N(R^+)_2$, —C(=$NR^+$)—$N(R^+)_2$, —C(=$NR^+$)—OR*, —$N(R^+)$—$N(R^+)_2$, —$N(R^+)C$(=$NR^+$)—$N(R^+)_2$, —$NR^+SO_2R^o$, —$NR^+SO_2N(R^+)_2$, —P(O)$(R^*)_2$, —P(O)$(OR^*)_2$, —O—P(O)—OR*, and —P(O)($NR^+$)—$N(R^+)_2$, wherein $R^o$ is an optionally substituted aliphatic or aryl group, and $R^+$ and R* are as defined above, or two adjacent substituents, taken together with their intervening atoms, form a 5- to 6-membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C$(R^*)_2$, =N—$N(R^+)_2$, =N—OR*, =N—NHC(O)R*, =N—$NHCO_2R^o$, =N—$NHSO_2R^o$, or =N—R*, where each R* and $R^o$ is as defined above. For the purposes of clarity, the term "substituted aliphatic" refers to an aliphatic group having at least one non-aliphatic substituent.

Suitable substituents on a substitutable nitrogen atom of a heteroaryl or heterocyclic ring include —R*, —$N(R^*)_2$, —C(O)R*, —$CO_2R^o$, —C(O)—C(O)R*, —C(O)$CH_2C$(O)

R*, —SO$_2$R$^o$, —SO$_2$N(R*)$_2$, —C(=S)N(R*)$_2$, —C(=NH)—N(R*)$_2$, and —NR*SO$_2$R$^o$; wherein each R* and R$^o$ is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It also will be apparent to one skilled in the art that certain compounds of this invention may exist in tautomeric forms, all such tautomeric forms of the compounds being within the scope of the invention. Unless stereochemical configuration is expressly defined, structures depicted herein are meant to include all stereochemical forms of the structure; i.e., the R and S configurations for each asymmetric center. Therefore, unless otherwise indicated, single stereochemical isomers as well as enantiomeric and diastereomeric mixtures of the present compounds are within the scope of the invention. By way of example, the compounds of formula (I) wherein R$^a$ is hydroxy can have R or S configuration at the carbon atom bearing R$^a$. Both the R and the S stereochemical isomers, as well as all mixtures thereof, are included within the scope of the invention.

Where stereochemical configuration at a given asymmetric center is defined by structure, unless stated otherwise, the depicted configuration indicates stereochemistry relative to other asymmetric centers in the molecule. Where stereochemical configuration is defined by chemical name, the designations (rel), (R*), and (S*) indicate relative stereochemistry, while the designations (R), (S), (+), (−), and (abs) indicate absolute stereochemistry.

In the compounds of formula (I), stereochemical configurations depicted at asterisked positions indicate relative stereochemistry, unless expressly stated to indicate absolute stereochemistry. Preferably, the diastereomeric purity of the compound is at least 80%, more preferably at least 90%, still more preferably at least 95%, and most preferably at least 99%. As used herein, the term "diastereomeric purity" refers to the amount of a compound having the depicted relative stereochemistry, expressed as a percentage of the total amount of all diastereomers present.

In some embodiments, stereochemical configurations depicted at asterisked positions indicate absolute as well as relative stereochemistry. Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC, using a chiral column packing material. Enantiomers may also be distinguishable by NMR if first derivatized with an optically enriched derivatizing agent, e.g., Mosher's acid.

In the compounds of formula (I), X is —C(R$^{f1}$)$_2$, —N(R$^{f2}$)—, or —O—. Each R$^{f1}$ is independently hydrogen or fluoro; or one R$^{f1}$, taken together with an adjacent R$^f$ and the intervening carbon atoms forms a cyclopropyl ring; or one R$^{f1}$ and one R$^f$ together form a double bond. R$^{f2}$ is hydrogen, C$_{1-4}$ aliphatic, or C$_{1-4}$ fluoroaliphatic. In some embodiments, X is —CH$_2$—, —CHF—, —CF$_2$—, —NH—, or —O—. In certain embodiments, X is —CH$_2$—, —NH—, or —O—. In certain particular embodiments, X is —O—.

In the compounds of formula (I), Y is —O—, —S—, or —C(R$^m$)(R$^n$)—, where R$^m$ and R$^n$ are as described above. In some embodiments, R$^m$ is hydrogen, fluoro, —NH$_2$, —NH(C$_{1-4}$ aliphatic), —N(C$_{1-4}$ aliphatic)$_2$, or C$_{1-4}$ aliphatic, or R$^m$ and R$^n$ together form =O. In some embodiments, Y is —O— or —CH$_2$.

In the compounds of formula (I), m is 0, 1, 2, or 3, provided that Y is —C(R$^m$)(R$^n$)— when m is 0. In some embodiments, m is 1, 2, or 3. In certain particular embodiments, m is 1.

In the compounds of formula (I), R$^a$ is selected from the group consisting of hydrogen, fluoro, —CN, —N$_3$, —OR$^5$, —N(R$^4$)$_2$, —NR$^4$CO$_2$R$^6$, —NR$^4$C(O)R$^5$, —C(O)N(R$^4$)$_2$, —C(O)R$^5$, —OC(O)N(R$^4$)$_2$, —OC(O)R$^5$, —OCO$_2$R$^6$, or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^a$ and R$^b$ together form =O; or R$^a$ and R$^c$ together form a bond. In some embodiments R$^a$ is selected from the group consisting of hydrogen, fluoro, —CN, N$_3$, C$_{1-4}$ aliphatic, C$_{1-4}$ fluoroaliphatic, —OR$^{5x}$, —NH(R$^4$), —N(H)CO$_2$R$^5$, —N(H)C(O)R$^5$, —C(O)NHR$^4$, —C(O)R$^5$, —OC(O)NHR$^4$, —OC(O)R$^5$, and —OC(O)OR$^5$. In some embodiments, R$^a$ is selected from the group consisting of hydrogen, —OH, —OCH$_3$, C$_{1-4}$ aliphatic, C$_{1-4}$ fluoroaliphatic, and fluoro. In certain embodiments, R$^a$ is selected from the group consisting of hydrogen, —OH, —OCH$_3$, —CH$_3$, and fluoro. In certain particular embodiments, R$^a$ is —OH.

In the compounds of formula (I), R$^c$ is selected from the group consisting of hydrogen, fluoro, —CN, —N$_3$, —OR$^5$, —N(R$^4$)$_2$, —NR$^4$CO$_2$R$^6$, —NR$^4$C(O)R$^5$, —C(O)N(R$^4$)$_2$, —C(O)R$^5$, —OC(O)N(R$^4$)$_2$, —OC(O)R$^5$, —OCO$_2$R$^6$, or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, or —C(O)N(R$^{4x}$)(R$^{4y}$); or R$^c$ and R$^a$ together form a bond; or R$^c$ and R$^d$ together from =O. In some embodiments, R$^c$ is hydrogen, fluoro, —CN, N$_3$, C$_{1-4}$ aliphatic, C$_{1-4}$ fluoroaliphatic, —OR$^{5x}$, —NH(R$^4$), —N(H)CO$_2$R$^5$, —N(H)C(O)R$^5$, —C(O)NHR$^4$, —C(O)R$^5$, —OC(O)NHR$^4$, —OC(O)R$^5$, and —OC(O)OR$^5$. In certain embodiments, R$^c$ is hydrogen, —OH, —OCH$_3$, or fluoro. In certain particular embodiments, R$^c$ is hydrogen or —OH.

In the compounds of formula (I), R$^b$ is selected from the group consisting of hydrogen, fluoro, C$_{1-4}$ aliphatic, and C$_{1-4}$ fluoroaliphatic; or R$^b$ and R$^a$ together form =O; or R$^b$, taken together with R$^d$ and the intervening carbon atoms, forms a fused cyclopropane ring, which is optionally substituted with one or two substituents independently selected from fluoro or C$_{1-4}$ aliphatic; or R$^b$, taken together with R$^e$ and the intervening carbon atoms, forms a fused cyclopropane ring, which is optionally substituted with one or two substituents independently selected from fluoro or C$_{1-4}$ aliphatic.

In the compounds of formula (I), R$^d$ is selected from the group consisting of hydrogen, fluoro, C$_{1-4}$ aliphatic, and C$_{1-4}$ fluoroaliphatic; or R$^d$ and R$^e$ together form =O; or R$^d$, taken together with R$^b$ and the intervening carbon atoms, forms a fused cyclopropane ring, which is optionally substituted with one or two substituents independently selected from fluoro or C₁₋₄ aliphatic; or R$^d$, taken together with R$^{e'}$ and the intervening carbon atoms, forms a fused cyclopropane ring, which is optionally substituted with one or two substituents independently selected from fluoro or C₁₋₄ aliphatic.

In some embodiments, each of R$^b$ and R$^d$ independently is selected from the group consisting of hydrogen, fluoro, C₁₋₄ aliphatic, and C₁₋₄ fluoroaliphatic. In some embodiments, one of R$^b$ and R$^d$ is C₁₋₄ aliphatic and the other is hydrogen. In some embodiments, R$^b$ and R$^d$ are each hydrogen.

In one embodiment, R$^a$ and R$^c$ are each —OH, and R$^b$ and R$^d$ are each hydrogen. In another embodiment, R$^a$ is —OH, and each of R$^b$, R$^c$, and R$^d$ is hydrogen. In another embodiment, R$^a$ is —OH, R$^c$ is fluoro or —OCH₃, and R$^b$ and R$^d$ are each hydrogen. In another embodiment, R$^a$ is —OH, R$^b$ is —CH₃, R$^c$ is hydrogen or —OH, and R$^d$ is hydrogen. In another embodiment, R$^a$ and R$^c$ together form a bond, and R$^b$ and R$^d$ are each hydrogen.

In the compounds of formula (I), each R$^f$ independently is independently hydrogen, fluoro, C₁₋₄ aliphatic, or C₁₋₄ fluoroaliphatic, provided that if X is —O— or —NH—, then R$^f$ is not fluoro; or two R$^f$ taken together form =O; or two R$^f$, taken together with the carbon atom to which they are attached, form a 3- to 6-membered carbocyclic ring; or one R$^f$, taken together with R$^e$ and the intervening carbon atoms, forms a 3- to 6-membered spirocyclic ring, which is optionally substituted with one or two substituents independently selected from fluoro or C₁₋₄ aliphatic; or one R$^f$, taken together with an adjacent R$^{f1}$ and the intervening carbon atoms forms a cyclopropyl ring, which is optionally substituted with one or two substituents independently selected from fluoro or C₁₋₄ aliphatic; or one R$^f$ and one R$^{f1}$ together form a double bond. In some embodiments, each R$^f$ independently is hydrogen or C₁₋₄ aliphatic. In some such embodiments, each R$^f$ independently is hydrogen or —CH₃. In certain embodiments, one R$^f$ is hydrogen or —CH₃, and the other R$^f$ is hydrogen. In certain particular embodiments, each R$^f$ is hydrogen.

In the compounds of formula (I), R$^e$ is hydrogen, or C₁₋₄ aliphatic; or R$^e$, taken together with one R$^f$ and the intervening carbon atoms, forms a 3- to 6-membered spirocyclic ring, which is optionally substituted with one or two substituents independently selected from fluoro or C₁₋₄ aliphatic; or R$^e$, taken together with R$^m$ and the intervening carbon atoms, forms a fused cyclopropane ring, which is optionally substituted with one or two substituents independently selected from fluoro or C₁₋₄ aliphatic; or R$^e$, taken together with R$^b$ and the intervening carbon atoms, forms a fused cyclopropane ring, which is optionally substituted with one or two substituents independently selected from fluoro or C₁₋₄ aliphatic. In some embodiments, R$^e$ is hydrogen or C₁₋₄ aliphatic. In some such embodiments, R$^e$ is hydrogen or —CH₃. In certain embodiments, R$^e$ is hydrogen.

In the compounds of formula (I), R$^{e'}$ is hydrogen or C₁₋₄ aliphatic; or R$^{e'}$, taken together with R$^m$ and the intervening carbon atoms, forms a fused cyclopropane ring, which is optionally substituted with one or two substituents independently selected from fluoro or C₁₋₄ aliphatic; or R$^{e'}$, taken together with R$^d$ and the intervening carbon atoms, forms a fused cyclopropane ring, which is optionally substituted with one or two substituents independently selected from fluoro or C₁₋₄ aliphatic. In some embodiments, R$^{e'}$ is hydrogen or C₁₋₄ aliphatic. In certain particular embodiments, R$^{e'}$ is hydrogen.

In the compounds of formula (I), Ring A is selected from the group consisting of:

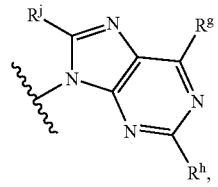
A-i

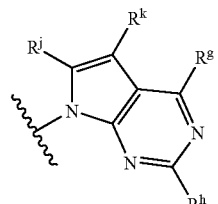
A-ii

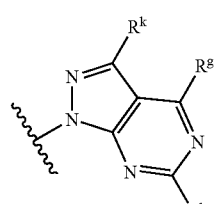
A-iii

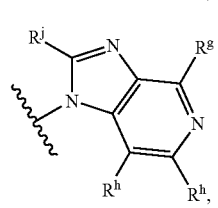
A-iv

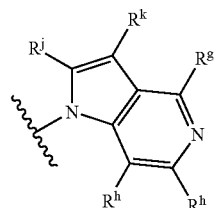
A-v

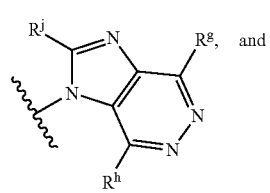
A-vi, and

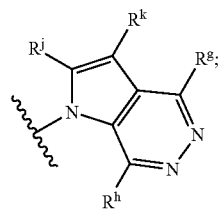
A-vii where R$^g$, R$^h$, R$^j$ and R$^k$ are as defined above and as further defined below.

In the compounds of formula (I), each R$^h$ independently is hydrogen, halo, —CN—, —OR⁵, —N(R⁴)₂, —SR⁶, or an optionally substituted C₁₋₄ aliphatic group. In some embodiments, each R$^h$ independently is hydrogen, halo, —CN, —OH, —O—(C₁₋₄ aliphatic), —NH₂, —NH—(C₄ aliphatic), —N($C_{1-4}$ aliphatic)$_2$, —SH, —S—($C_{1-4}$ aliphatic), or an optionally substituted $C_{1-4}$ aliphatic group. In certain embodiments, $R^h$ is hydrogen or chloro. In certain particular embodiments, $R^h$ is hydrogen.

In the compounds of formula (I), each $R^j$ independently is hydrogen, —OR$^5$, —N(R$^4$)$_2$, —SR, or an optionally substituted aliphatic, aryl, or heteroaryl group. In some embodiments, each $R^j$ independently is hydrogen, —OH, —O—($C_{1-4}$ aliphatic), —NH$_2$, —NH—($C_{1-4}$ aliphatic), —N($C_{1-4}$ aliphatic)$_2$, —SH, —S—($C_{1-4}$ aliphatic), or an optionally substituted $C_{1-4}$ aliphatic group. In certain embodiments, $R^j$ is hydrogen or $C_{1-4}$ aliphatic. In certain particular embodiments, $R^h$ is hydrogen.

In the compounds of formula (I), $R^k$ is hydrogen, halo, —OR$^5$, —N(R$^4$)$_2$, —SR$^6$, or an optionally substituted $C_{1-4}$ aliphatic group. In some embodiments, each $R^k$ independently is hydrogen, halo, —OH, —O—($C_{1-4}$ aliphatic), —NH$_2$, —NH—($C_{1-4}$ aliphatic), —N($C_{1-4}$ aliphatic)$_2$, —SH, —S—($C_{1-4}$ aliphatic), or an optionally substituted $C_{1-4}$ aliphatic group. In certain embodiments, $R^k$ is hydrogen, halo, or $C_{1-4}$ aliphatic. In certain particular embodiments, $R^k$ is hydrogen.

In some embodiments, the compound of formula (I) is characterized by at least one of the following features:
(a) X is —O—;
(b) Y is —O— or —CH$_2$—;
(c) $R^a$ is —OH;
(d) $R^b$ and $R^d$ are each independently hydrogen or $C_{1-4}$ aliphatic;
(e) $R^c$ is hydrogen, fluoro, or —OR$^5$;
(f) $R^e$ and $R^{e'}$ are each hydrogen;
(g) each $R^f$ is hydrogen;
(h) each $R^h$ is hydrogen;
(i) $R^j$ is hydrogen or $C_{1-4}$ aliphatic;
(j) $R^k$ is hydrogen, halo, or $C_{1-4}$ aliphatic;
(k) m is 1; and
(l) stereochemical configurations depicted at asterisked positions indicate absolute stereochemistry.

In the compounds of formula (I), $R^g$ is hydrogen, halo, —NO$_2$, —CN, —C(R$^5$)=C(R$^5$)$_2$, —C≡C—R$^5$, —OR$^5$, —SR$^6$, —S(O)R, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OCO$_2$R$^6$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —N(R$^4$)—N(R$^4$)$_2$, —N(R$^4$)—OR$^5$, —C(=NR$^4$)—N(R$^4$)—OR$^5$, —C(R$^6$)=N—OR$^5$, or an optionally substituted aliphatic, aryl, heteroaryl, or heterocyclyl.

In some embodiments, $R^g$ is hydrogen, $C_{1-6}$ aliphatic, $C_{1-6}$ fluoroaliphatic, halo, —R$^{1g}$, —R$^{2g}$, -T$^1$-R$^{1g}$, -T$^1$-R$^{2g}$, —V$^1$-T$^1$-R$^{2g}$, and —V$^1$-T$^1$-R$^{2g}$, where the variables $R^{1g}$, $R^{2g}$, $V^1$, and $T^1$ have the values described below.

$T^1$ is a $C_{1-6}$ alkylene chain substituted with 0-2 independently selected $R^{3a}$ or $R^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)C(=NR$^4$)—N(R$^4$)—, —N(R$^4$)—C(=NR$^4$)—, —N(R$^4$)CO$_2$—, —N(R$^4$)SO$_2$—, —N(R$^4$)SO$_2$N(R$^4$)—, —OC(O)—, —OC(O)N(R$^4$)—, —C(O)—, —CO$_2$—, —C(O)N(R$^4$)—, —C(=NR$^4$)—N(R$^4$)—, —C(NR$^4$)=N(R$^4$)—, —C(=NR$^4$)—O—, or —C(R$^6$)=N—O—, and wherein $T^1$ or a portion thereof optionally forms part of a 3-7 membered ring.

In some embodiments, $T^1$ is a $C_{1-4}$ alkylene chain optionally substituted with one or two groups independently selected from fluoro or a $C_{1-4}$ aliphatic or $C_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$).

In certain embodiments, $T^1$ is a $C_{1-4}$ alkylene chain optionally substituted with one or two groups independently selected from fluoro, $C_{1-4}$ aliphatic, and $C_{1-4}$ fluoroaliphatic.

Each $R^{3a}$ independently is selected from the group consisting of —F, —OH, —O($C_{1-4}$ alkyl), —CN, —N(R)$_2$, —C(O)($C_{1-4}$ alkyl), —CO$_2$H, —CO$_2$($C_{1-4}$ alkyl), —C(O)NH$_2$, and —C(O)NH($C_{1-4}$ alkyl).

Each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring.

Each $R^7$ independently is an optionally substituted aryl or heteroaryl ring.

$V^1$ is —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)C(=NR$^4$)—N(R$^4$)—, —N(R$^4$)C(=NR$^4$)—, —N(R$^4$)CO$_2$—, —N(R$^4$)SO$_2$—, —N(R$^4$)SO$_2$N(R$^4$)—, —OC(O)—, —OC(O)N(R$^4$)—, —C(O)—, —CO$_2$—, —C(O)N(R$^4$)—, —C(O)N(R$^4$)—O—, —C(O)N(R$^4$)C(=NR$^4$)—N(R$^4$)—, —N(R$^4$)C(=NR$^4$)—N(R$^4$)—C(O)—, —C(=NR$^4$)—N(R$^4$)—, —C(NR$^4$)=N(R$^4$)—, —C(=NR$^4$)—O—, or —C(R$^6$)=N—O—. In some embodiments, $V^1$ is —N(R$^4$)C(O)—, —N(R$^4$)C(O)N(R$^4$)—, —N(R$^4$)SO$_2$—, —N(R$^4$)SO$_2$N(R$^4$)—, or —N(R$^4$)CO$_2$—. In certain such embodiments, $V^1$ is —N(R$^4$)C(O)— or —N(R$^4$)C(O)N(R$^4$)—. In other embodiments, $V^1$ is —C(R$^5$)=C(R$^5$), —C≡C—, —O—, —S—, or —N(R$^4$)—.

Each $R^{1g}$ independently is an optionally substituted aryl, heteroaryl, heterocyclyl, or cycloaliphatic ring.

Each $R^{2g}$ independently is —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OCO$_2$R$^6$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)$^5$, —C(=NR$^4$)—N(R$^4$)$_2$, —C(=NR$^4$)—OR$^5$, —N(R$^4$)—N(R$^4$)$_2$, —N(R$^4$)—OR$^5$, —C(=NR$^4$)—N(R$^4$)—OR$^5$, or —C(R$^6$)=N—OR$^5$.

The invention also relates to a subgenus of the compounds of formula (I), characterized by formula (II):

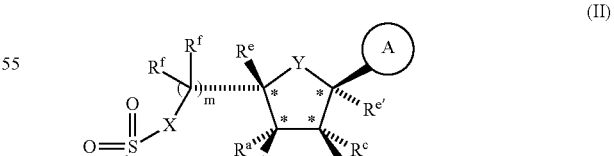

(II)

or a pharmaceutically acceptable salt thereof, wherein Ring A and the variables X, Y, $R^a$, $R^b$, $R^c$, $R^d$, $R^e$, $R^{e'}$, $R^f$, and m have the values and preferred values described above for formula (I).

The invention also relates to a subgenus of the compounds of formula (I), characterized by formula (III):

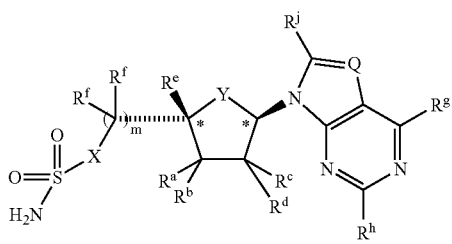

(III)

or a pharmaceutically acceptable salt thereof, wherein Q is =N— or =C(R$^k$)—, and the variables X, Y, R$^a$, R$^b$, R$^c$, R$^d$, R$^e$, R$^f$, R$^g$, R$^h$, R$^j$, R$^k$, and m have the values and preferred values described above for formula (I).

Various particular embodiments of the invention relate to subgenera of the compounds of formula (III), represented by formulae (III-A), (III-B), (III-C), (III-D), (III-E), and (III-F):

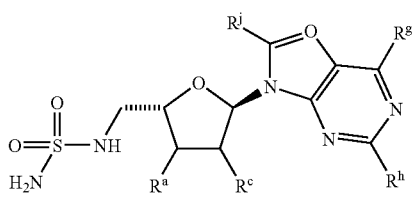

(III-A)

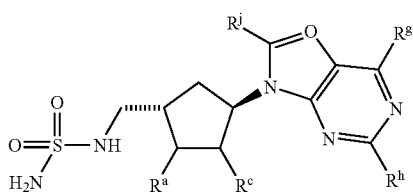

(III-B)

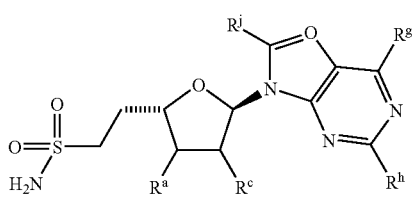

(III-C)

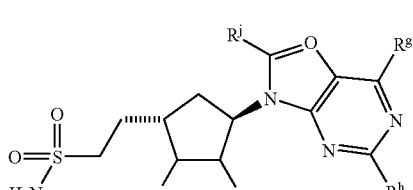

(III-D)

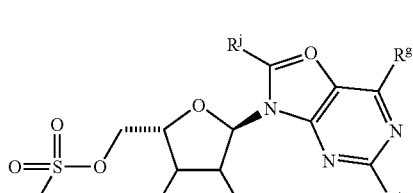

(III-E)

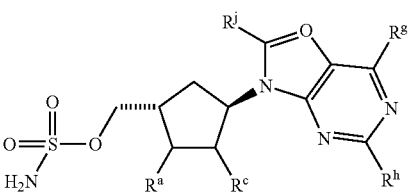

(III-F)

or a pharmaceutically acceptable salt thereof, wherein the variables Q, R$^a$, R$^c$, R$^g$, R$^h$ and R$^j$ have the values and preferred values described herein for formula (I).

One embodiment of the invention relates to a compound of formula (I), wherein R$^g$ is an optionally substituted aryl, heteroaryl, or heterocyclyl group. In some such embodiments, the invention relates to a subgenus of the compounds of formula (I), characterized by formula (IV):

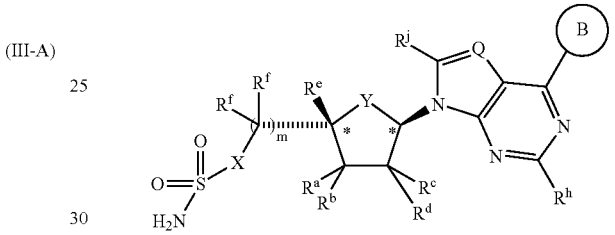

(IV)

or a pharmaceutically acceptable salt thereof, wherein:

Ring B is an optionally substituted 5- or 6-membered aryl or heteroaryl ring having zero to three ring nitrogen atoms and optionally one additional ring heteroatom selected from oxygen and sulfur; and the variables Q X, Y, R$^a$, R$^b$, R$^c$, R$^d$, R$^e$, R$^f$, R$^h$, R$^j$, and m have the values and preferred values described above for formula (I).

In some embodiments, R$^g$ is an optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, or triazinyl, wherein one ring nitrogen atom in R$^g$ optionally is oxidized. In certain particular embodiments, R$^g$ is an optionally substituted phenyl, imidazolyl, or triazolyl.

Substitutable ring carbon atoms in Ring B preferably are substituted with 0-3 substituents independently selected from the group consisting of halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OCO$_2$R$^6$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, —C(R$^6$)=N—OR$^5$, or an optionally substituted aliphatic, or an optionally substituted aryl, heterocyclyl, or heteroaryl group; or two adjacent substituents, taken together with the intervening ring atoms, form an optionally substituted fused 4- to 8-membered aromatic or non-aromatic ring having 0-3 ring heteroatoms selected from the group consisting of O, N, and S.

In some embodiments, Ring B is substituted with 0-2 substituents independently selected from the group consisting of halo, —CN, —N(R$^4$)$_2$, —NR$^4$C(O)R$^5$, —NR$^4$—C(O)N(R$^4$)$_2$, —NR$^4$CO$_2$R$^6$, —C(O)N(R$^4$)$_2$, —CO$_2$R$^5$, —OR$^5$, or a C$_{1-4}$ aliphatic or C$_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$). The variables R$^4$, R$^5$, R$^6$, R$^{4x}$, R$^{4y}$, and R$^{5x}$ have the values described above for formula (I).

Another embodiment of the invention relates to a compound of formula (I), wherein R$^g$ is —V$^1$-T$^1$-R$^{1g}$, —V$^1$—R$^{1g}$, -T$^1$-R$^{1g}$, or -T$^1$-V$^1$—R$^{1g}$. R$^{1g}$ is an optionally substituted mono- or bicyclic aryl, heteroaryl, heterocyclyl, or cycloaliphatic group. In some embodiments, C$_{1-4}$ alkylene chain optionally substituted with one or two groups independently selected from fluoro or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$). In certain embodiments, T$^1$ is a C$_{1-4}$ alkylene chain optionally substituted with one or two groups independently selected from fluoro, C$_{1-4}$ aliphatic, and C$_{1-4}$ fluoroaliphatic. In some embodiments, V$^1$ is —N(R$^4$)C(O)—, —N(R$^4$)C(O)N(R$^4$)—, —N(R$^4$) SO$_2$—, —N(R$^4$)SO$_2$N(R$^4$)—, or —N(R$^4$)CO$_2$—. In certain such embodiments, V$^1$ is —N(R$^4$) C(O)— or —N(R$^4$)C(O)N(R$^4$)—. In other embodiments, V$^1$ is —C(R$^5$)=C(R$^5$), —C≡C—, —O—, —S—, or —N(R$^4$)—. In certain such embodiments, V$^1$ is —N(R$^4$)—.

In some embodiments, the invention relates to a subgenus of the compounds of formula (I), characterized by formula (V):

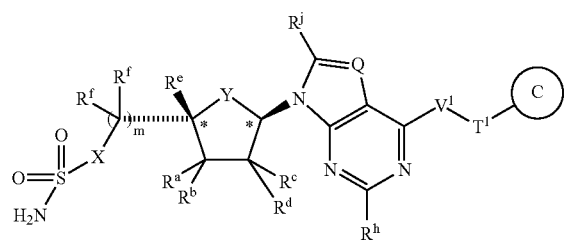

(V)

or a pharmaceutically acceptable salt thereof, wherein:
V$^1$ is —N(R$^8$)—, —O—, or —S—;
R$^8$ is hydrogen or C$_{1-4}$ aliphatic;
T$^1$ is a C$_{1-4}$ alkylene chain optionally substituted with one or two groups independently selected from fluoro or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$);
Ring C is an optionally substituted 3- to 8-membered heterocyclyl or cycloaliphatic ring, or an optionally substituted 5- or 6-membered aryl or heteroaryl ring; and
the variables Q, X, Y, R$^a$, R$^b$, R$^c$, R$^d$, R$^e$, R$^f$, R$^h$, R$^j$, and m have the values and preferred values described above for formula (I).

In some such embodiments, T$^1$ is a C$_{1-4}$ alkylene chain optionally substituted with one or two groups independently selected from fluoro, C$_{1-4}$ aliphatic, and C$_{1-4}$ fluoroaliphatic.

In some embodiments, Ring C is substituted with 0-2 R$^o$ and 0-2 R$^{8o}$, where:
each R$^o$ independently is halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(=NR$^4$)—N(R$^4$)$_2$, —N(R$^4$)C(=NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OCO$_2$R$^6$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, —C(R$^6$)=N—OR$^5$, or an optionally substituted aliphatic, or an optionally substituted aryl, heterocyclyl, or heteroaryl group; or two R$^o$ on the same saturated ring carbon atom, taken together with the carbon atom, form an optionally substituted 3- to 8-membered spirocyclic cycloaliphatic or heterocyclyl ring; or two adjacent R$^o$, taken together with the intervening ring atoms, form an optionally substituted fused 4- to 8-membered aromatic or non-aromatic ring having 0-3 ring heteroatoms selected from the group consisting of O, N, and S;
each R$^{8o}$ independently is selected from the group consisting of C$_{1-4}$ aliphatic, C$_{1-4}$ fluoroaliphatic, halo, —OR$^{5x}$, —N(R$^{4x}$)(R$^{4y}$), or a C$_{1-4}$ aliphatic or C$_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$); and
the variables R$^{4x}$, R$^{4y}$, and R$^{5x}$ have the values described above for formula (I).

In some such embodiments, Ring C is a C$_{3-6}$ cycloaliphatic, phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring, any of which is substituted with 0-2 R$^o$ and 0-2 R$^{8o}$.

In certain embodiments, T$^1$ is a C$_{1-2}$ alkylene chain optionally substituted with one or two groups independently selected from fluoro or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$), and Ring C is a C$_{3-6}$ cycloaliphatic, phenyl, oxazolyl, or isoxazolyl ring, any of which is substituted with 0-2 R$^{8o}$ and optionally is fused to an optionally substituted benzene, dioxolane, or dioxane ring.

Another embodiment of the invention relates to a subgenus of the compounds of formula (I), characterized by formula (VI):

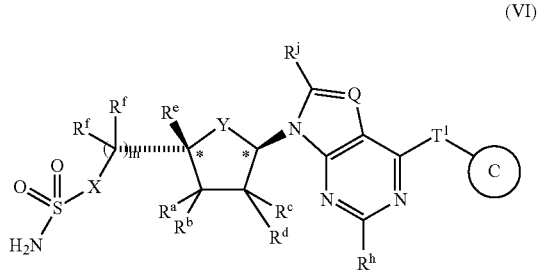

(VI)

or a pharmaceutically acceptable salt thereof, wherein:
T$^1$ is a C$_{1-4}$ alkylene chain optionally substituted with one or two groups independently selected from fluoro or a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —CO$_2$R$^{5x}$, and —C(O)N(R$^{4x}$)(R$^{4y}$);

Ring C is a 3- to 8-membered heterocyclyl or cycloaliphatic ring, or a 5- or 6-membered aryl or heteroaryl ring, any of which rings is substituted with 0-2 $R^o$ and 0-2 $R^{8o}$; and the variable Q, X, Y, $R^a$, $R^b$, $R^c$, $R^d$, $R^e$, $R^f$, $R^h$, $R^j$, $R^o$, $R^{8o}$, $R^{4x}$, $R^{4y}$, $R^{5x}$, and m have the values and preferred values described above for formulae (I)-(V).

In a particular embodiment, the invention relates to a compound of formula (VI) or a pharmaceutically acceptable salt thereof, wherein:

$T^1$ is a $C_{1-2}$ alkylene chain optionally substituted with one or two groups independently selected from fluoro or a $C_{1-4}$ aliphatic or $C_{1-4}$ fluoroaliphatic optionally substituted with one or two substituents independently selected from the group consisting of —$OR^{5x}$, —$N(R^{4x})(R^{4y})$, —$CO_2R^{5x}$, and —$C(O)N(R^{4x})(R^{4y})$; and Ring C is phenyl, which is substituted with 0-2 $R^{8o}$ and optionally is fused to an optionally substituted benzene, dioxolane, or dioxane ring.

Another embodiment of the invention relates to a subgenus of the compounds of formula (I), characterized by formula (VII):

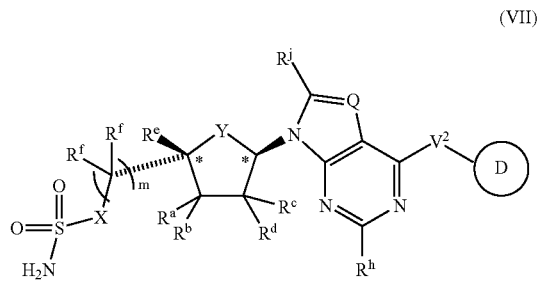

(VII)

or a pharmaceutically acceptable salt thereof, wherein:
$V^2$ is —$N(R^8)$—, —O—, or —S—;
$R^8$ is hydrogen or $C_{1-4}$ aliphatic;
Ring D is an optionally substituted aryl, heteroaryl, heterocyclyl, or cycloaliphatic ring; and
the variables Q, X, Y, $R^a$, $R^b$, $R^c$, $R^d$, $R^e$, $R^f$, $R^h$, $R^j$, and m have the values and preferred values described above for formula (I).

In some embodiments, $V^2$ is —$N(R^8)$—. In certain embodiments, $V^2$ is —NH—.

In some embodiments, Ring D is a mono-, bi-, or ticyclic ring system. In some embodiments, Ring D is a mono- or bicyclic ring system. In some such embodiments, Ring D selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, purinyl, quinolyl, isoquinolyl, cinnolinyl, phthalazinyl, quinazolinyl, quinoxalinyl, naphthyridinyl, pteridinyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, tetrahydroquinolinyl, tetrahydroisoquinolinyl, indanyl, phenanthridinyl, tetrahydronaphthyl, indolinyl, benzodioxanyl, benzodioxolyl, chromanyl, cyclopropyl, cyclobutyl, cyclopentyl, cyclopentenyl, cyclohexyl, cyclohexenyl, cycloheptyl, cycloheptenyl, cyclooctyl, cyclooctenyl, cyclooctadienyl, bicycloheptanyl and bicyclooctanyl. In certain embodiments, Ring D is an optionally substituted indanyl, tetrahydronaphthyl, or chromanyl.

Ring D may be unsubstituted or may be substituted on either or both of its component rings, and the substituents may be the same or different. In particular, each substitutable saturated ring carbon atom in Ring D is unsubstituted or substituted with =O, =S, =$C(R^5)_2$, =N—$N(R^4)_2$, =N—$OR^5$, =N—$NHC(O)R^5$, =N—$NHCO_2R^6$, =N—$NHSO_2R^6$, =N—$R^5$ or —$R^p$. Each substitutable unsaturated ring carbon atom in Ring D is unsubstituted or substituted with —$R^p$. Each substitutable ring nitrogen atom in Ring D is unsubstituted or substituted with —$R^{9p}$. The variables $R^p$ and $R^{9p}$ have the values described below.

Each $R^p$ independently is halo, —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—$C(O)R^5$, —$OCO_2R^6$, —$OC(O)N(R^4)_2$, —$C(O)R^5$, —$CO_2R^5$, —$C(O)N(R^4)_2$, —$C(O)N(R^4)$—$OR^5$, —$C(O)N(R^4)C(=NR^4)$—$N(R^4)_2$, —$N(R^4)C(=NR^4)$—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, —$C(R^6)$=N—$OR^5$, or an optionally substituted aliphatic, or an optionally substituted aryl, heterocyclyl, or heteroaryl group; or two $R^p$ on the same saturated carbon atom, taken together with the carbon atom to which they are attached, form an optionally substituted 3- to 6-membered spirocyclic cycloaliphatic ring.

Each $R^{9p}$ independently is —$C(O)R^5$, —$C(O)N(R^4)_2$, —$C_2R^6$, —$SO_2R^6$, —$SO_2N(R^4)_2$, or a $C_{1-4}$ aliphatic optionally substituted with $R^3$ or $R^7$.

In some embodiments, each $R^p$ independently is selected from the group consisting of halo, $C_{1-6}$ aliphatic, $C_{1-6}$ fluoroaliphatic, —$R^{1p}$, —$R^{2p}$, -$T^2$-$R^{1p}$, and -$T^2$-$R^{2p}$; or two $R^p$ on the same saturated carbon atom, taken together with the carbon atom to which they are attached, form an optionally substituted 3- to 6-membered spirocyclic cycloaliphatic ring. The variables $R^{1p}$, $R^{2p}$, and $T^2$ have the values described below.

$T^2$ is a $C_{1-6}$ alkylene chain optionally substituted with $R^{3a}$ or $R^{3b}$.

Each $R^{1p}$ independently is an optionally substituted aryl, heteroaryl, or heterocyclyl group.

Each $R^{2p}$ independently is —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—$C(O)R^5$, —$OCO_2R^6$, —$OC(O)N(R^4)_2$, —$C(O)R^5$, —$CO_2R^5$, —$C(O)N(R^4)_2$, —$C(O)N(R^4)$—$OR^5$, —$C(O)N(R^4)C(=NR^4)$—$N(R^4)_2$, —$N(R^4)C(=NR^4)$—$N(R^4)$—$C(O)R^5$, —$C(=NR^4)$—$N(R^4)_2$, —$C(=NR^4)$—$OR^5$, —$C(=NR^4)$—$N(R^4)$—$OR^5$, or —$C(R^6)$=N—$OR^5$.

In some embodiments, Ring D is selected from the group consisting of:

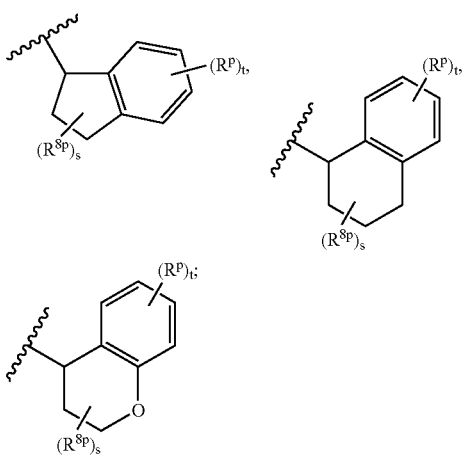

each $R^p$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$;

each $R^{8p}$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$, provided that $R^{8p}$ is other than —$OR^{5x}$ or —$N(R^{4x})(R^{4y})$ when located at a position adjacent to a ring oxygen atom, and further provided that when two $R^{8p}$ are attached to the same carbon atom, one must be selected from the group consisting of fluoro, —$CO_2R^{5x}$, —$C(O)N(R^{4x})(R^{4y})$, and $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^{8p}$ on the same carbon atom together form =O or =$C(R^{5x})_2$; or two $R^{8p}$ on the same carbon atom are taken together with the carbon atom to which they are attached to form a 3- to 6-membered spirocyclic ring;

s is 0, 1, 2, 3, or 4;

t is 0, 1, or 2; and the variables $R^{4x}$, $R^{4y}$, $R^{5x}$ have the values described above for formula (I).

In some embodiments, each $R^{8p}$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^{8p}$ on the same carbon atom are taken together with the carbon atom to which they are attached to form a 3- to 6-membered spirocyclic ring; provided that $R^{8p}$ is other than —$OR^{5x}$ or —$N(R^{4x})(R^{4y})$ when located at a position adjacent to a ring oxygen atom; and s is 0, 1, or 2.

Another embodiment of the invention relates to a compound of formula (I), wherein:

$R^g$ is —$N(R^8)(R^9)$;

$R^8$ is hydrogen or $C_{1-4}$ aliphatic;

$R^9$ is hydrogen, $C_{1-4}$ aliphatic, -$T^3$-$R^{9a}$ or -$T^4$-$R^{9b}$;

$T^3$ is a $C_{1-6}$ alkylene chain substituted with 0-2 independently selected $R^{3a}$ or $R^{3b}$;

$T^4$ is a $C_{2-6}$ alkylene chain substituted with 0-2 independently selected $R^{3a}$ or $R^{3b}$;

$R^{9a}$ is —$C(R^5)$=$C(R^5)_2$, —C≡C—$R^5$, —$S(O)R^6$, —$SO_2R^6$, —$SO_2$—$N(R^4)_2$, —$C(R^5)$=N—$OR^5$, —$CO_2R^5$, —C(O)—$C(O)R^5$, —$C(O)R^5$, —C(O)N($R^4$)$_2$, —C(=$NR^4$)—N($R^4$)$_2$, or —C(=$NR^4$)—$OR^5$; and $R^{9b}$ is halo, —$NO_2$, —CN, —$OR^5$, —$SR^6$, —$N(R^4)_2$, —$N(R^4)C(O)R^5$, —$N(R^4)C(O)N(R^4)_2$, —$N(R^4)CO_2R^5$, —O—$CO_2$—$R^5$, —$OC(O)N(R^4)_2$, —$OC(O)R^5$, —$N(R^4)$—$N(R^4)_2$, —$N(R^4)S(O)_2R^6$, or —$N(R^4)SO_2$—$N(R^4)_2$.

In some such embodiments, $R^9$ is hydrogen or a $C_{1-6}$ aliphatic or $C_{1-6}$ fluoroaliphatic optionally substituted with one or two substituents independently selected from the group consisting of —$OR^{5x}$, —$N(R^{4x})(R^{4y})$, —$CO_2R^{5x}$, —$C(O)N(R^{4x})(R^{4y})$.

In a particular embodiment, the invention relates to a subgenus of the compounds of formula (I), characterized by formula (VIII):

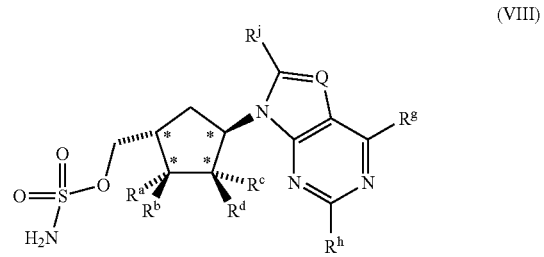

(VIII)

or a pharmaceutically acceptable salt thereof, wherein:

stereochemical configurations depicted at asterisked positions indicate absolute stereochemistry; and the variables Q, $R^a$, $R^b$, $R^c$, $R^d$, $R^g$, $R^h$, and $R^k$ have the values and preferred values described above for formulae (I)-(VII).

In some embodiments, the invention relates to a subgenus of the compounds of formula (VIII), characterized by formula (VIIIa):

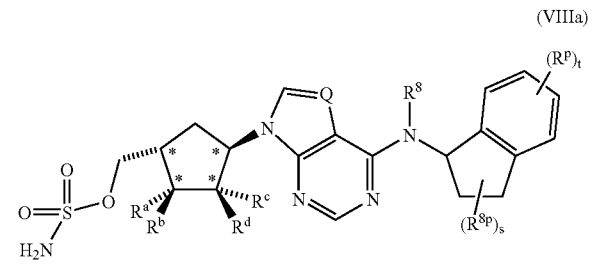

(VIIIa)

or a pharmaceutically acceptable salt thereof, wherein:

$R^a$ is —OH;

$R^b$ and $R^d$ are each independently hydrogen, fluoro, or $C_{1-4}$ aliphatic;

$R^c$ is hydrogen, fluoro, or —$OR^{5x}$;

$R^8$ is hydrogen or $C_{1-4}$ aliphatic;

each $R^p$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$;

each $R^{8p}$ independently is selected from the group consisting of fluoro, —$OR^{5x}$, —$N(R^{4x})(R^{4y})$, —$CO_2R^{5x}$, or —$C(O)N(R^{4x})(R^{4y})$, or a $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$, provided that $R^{8p}$ is other than —$OR^{5x}$ or —$N(R^{4x})(R^{4y})$ when located at a position adjacent to a ring oxygen atom, and further provided that when two $R^{8p}$ are attached to the same carbon atom, one must be selected from the group consisting of fluoro, —$CO_2R^{5x}$, —$C(O)N(R^{4x})(R^{4y})$, and $C_{1-4}$ aliphatic or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^{8p}$ on the same carbon atom together form =O or =$C(R^{5x})_2$;

$R^{4x}$ is hydrogen, $C_{1-4}$ alkyl, $C_{1-4}$ fluoroalkyl, or $C_{6-10}$ ar($C_{1-4}$)alkyl, the aryl portion of which may be optionally substituted;

$R^{4y}$ is hydrogen, $C_{1-4}$ alkyl, $C_{1-4}$ fluoroalkyl, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from N, O, and S;

each $R^{5x}$ independently is hydrogen, $C_{1-4}$ alkyl, $C_{1-4}$ fluoroalkyl, or an optionally substituted $C_{6-10}$ aryl or $C_{6-10}$ ar($C_{1-4}$)alkyl;

s is 0, 1, 2, 3, or 4; and t is 0, 1, or 2.

Subgenus definitions for Ring A and variables X, Y, $R^a$, $R^b$, $R^c$, $R^d$, $R^e$, and $R^f$ described for formula (I) also apply to formulae (II)-(VIII). Compounds embodying any combination of the preferred values for the variables described herein are within the scope of the present invention.

Representative examples of compounds of formula (I) are shown in Table 1.

TABLE 1

E1 Activating Enzyme Inhibitors

I-1

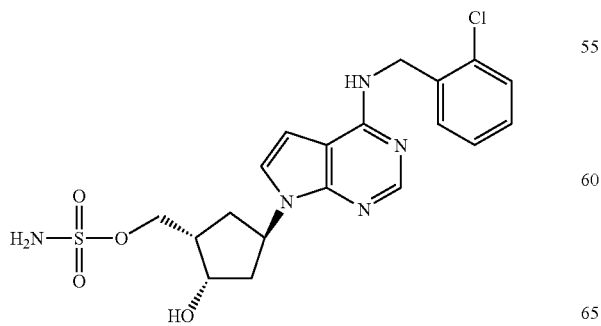

TABLE 1-continued

E1 Activating Enzyme Inhibitors

I-2

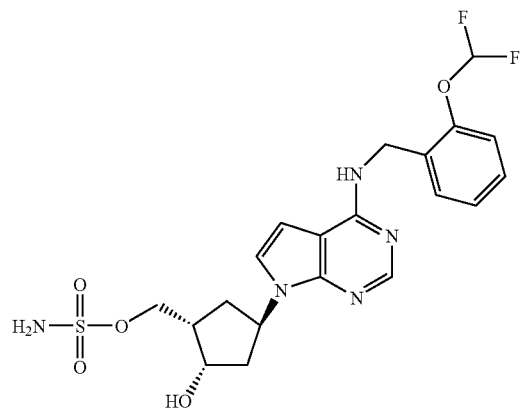

I-3

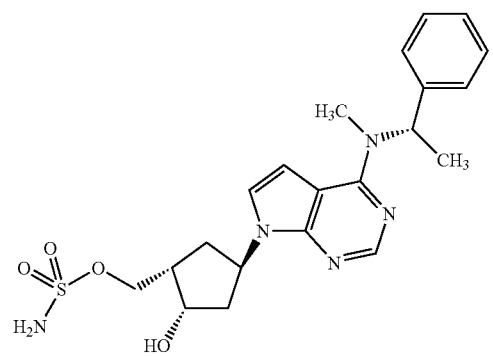

I-4

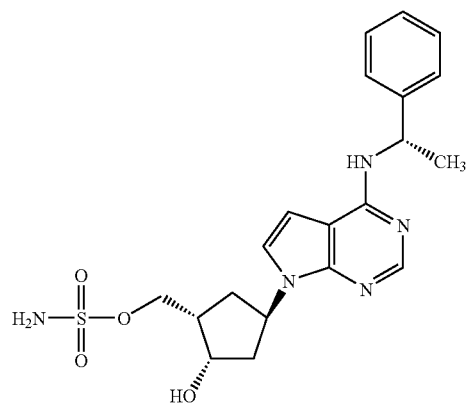

TABLE 1-continued
E1 Activating Enzyme Inhibitors
I-5
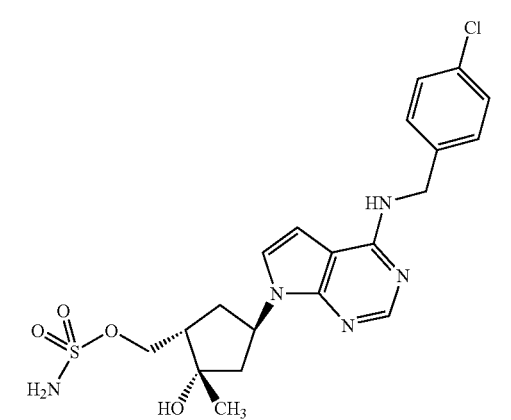
I-6
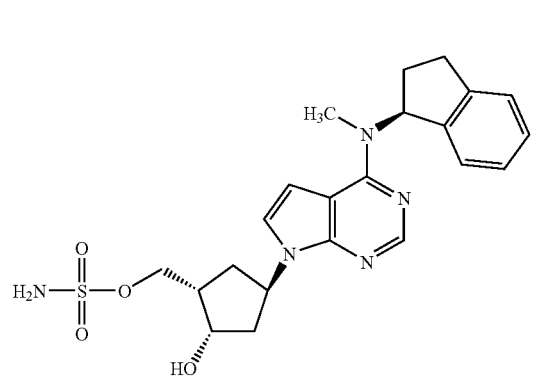
I-7
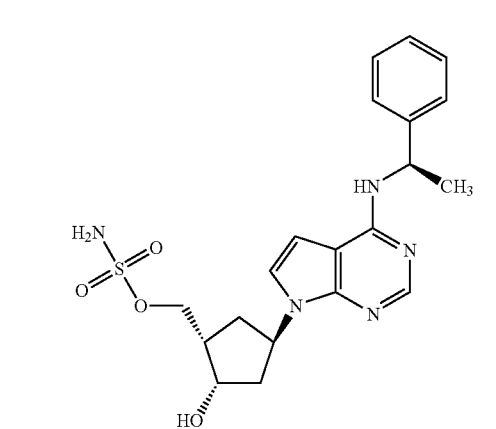
I-8
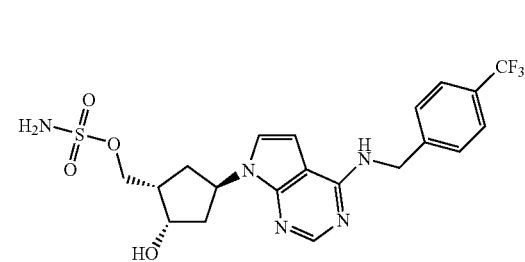
TABLE 1-continued
E1 Activating Enzyme Inhibitors
I-9
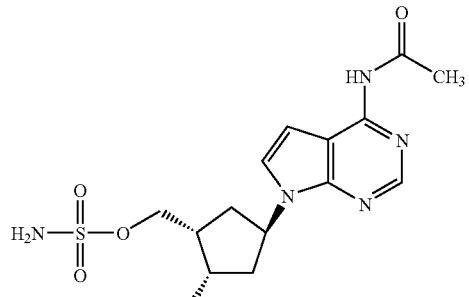
I-10
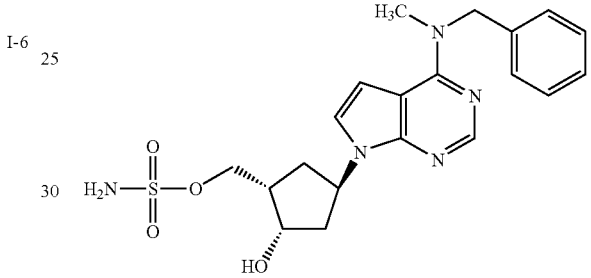
I-11
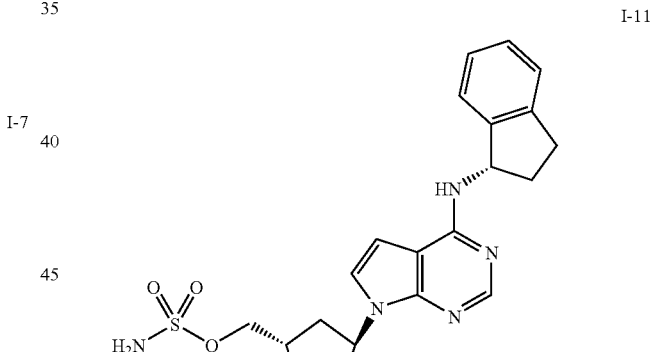
I-12
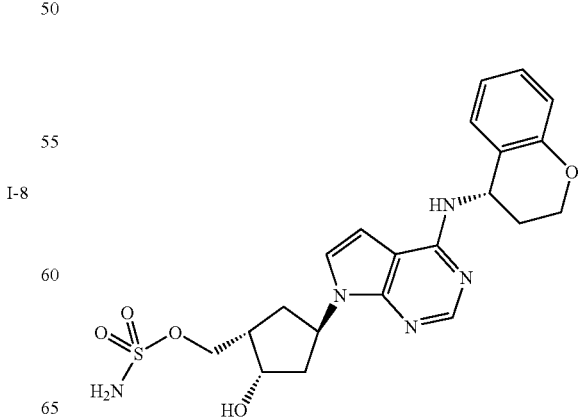

TABLE 1-continued
E1 Activating Enzyme Inhibitors
I-13
I-14
I-15
I-16
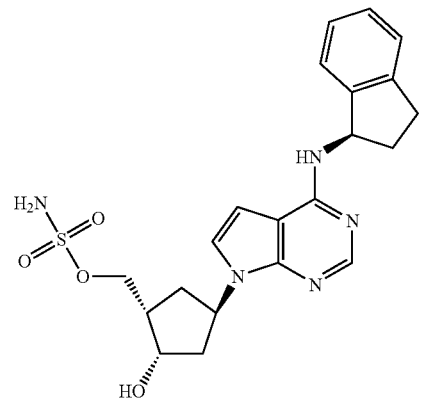
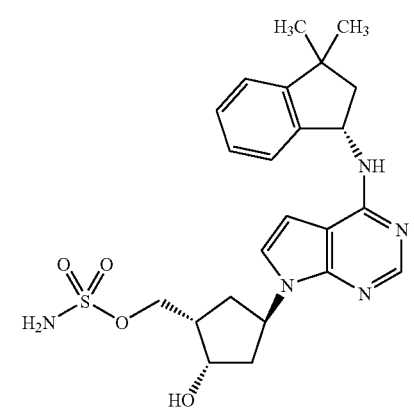
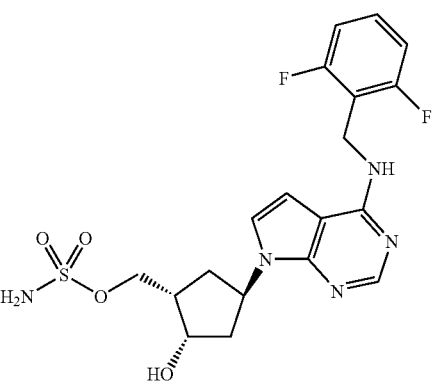
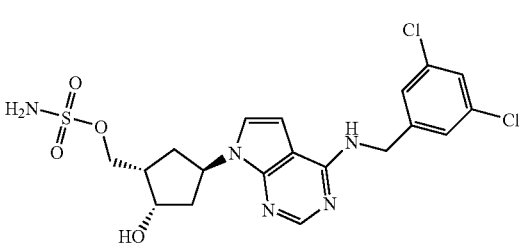
TABLE 1-continued
E1 Activating Enzyme Inhibitors
I-17
I-18
I-19
I-20

TABLE 1-continued
E1 Activating Enzyme Inhibitors
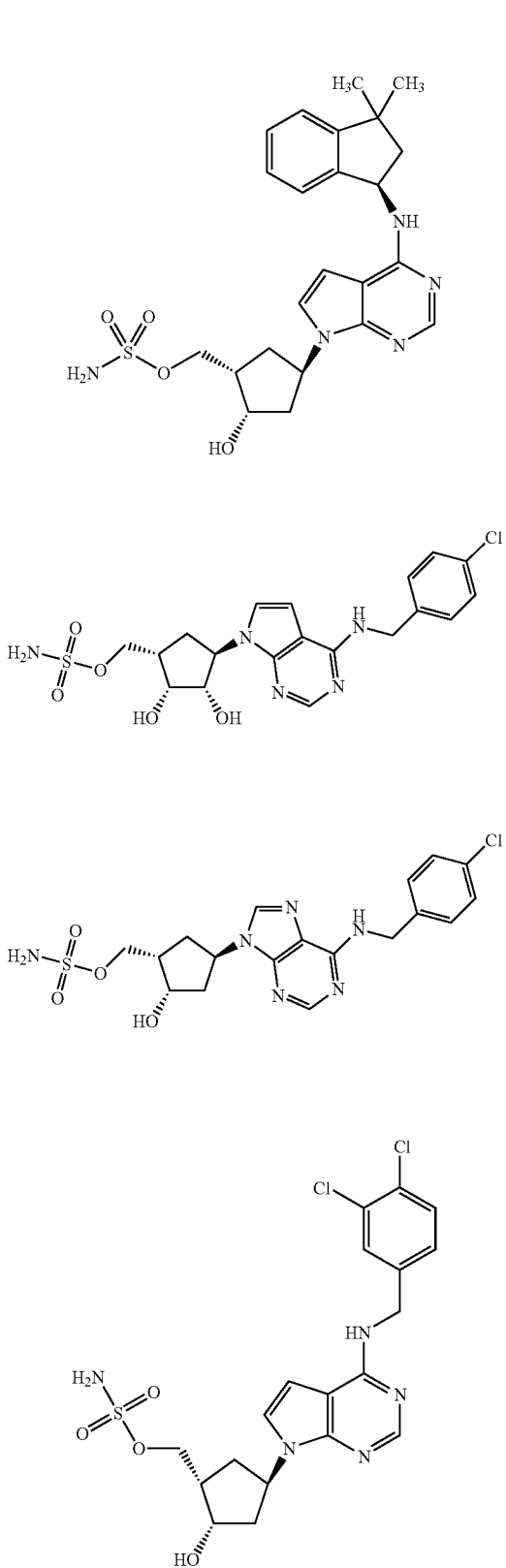
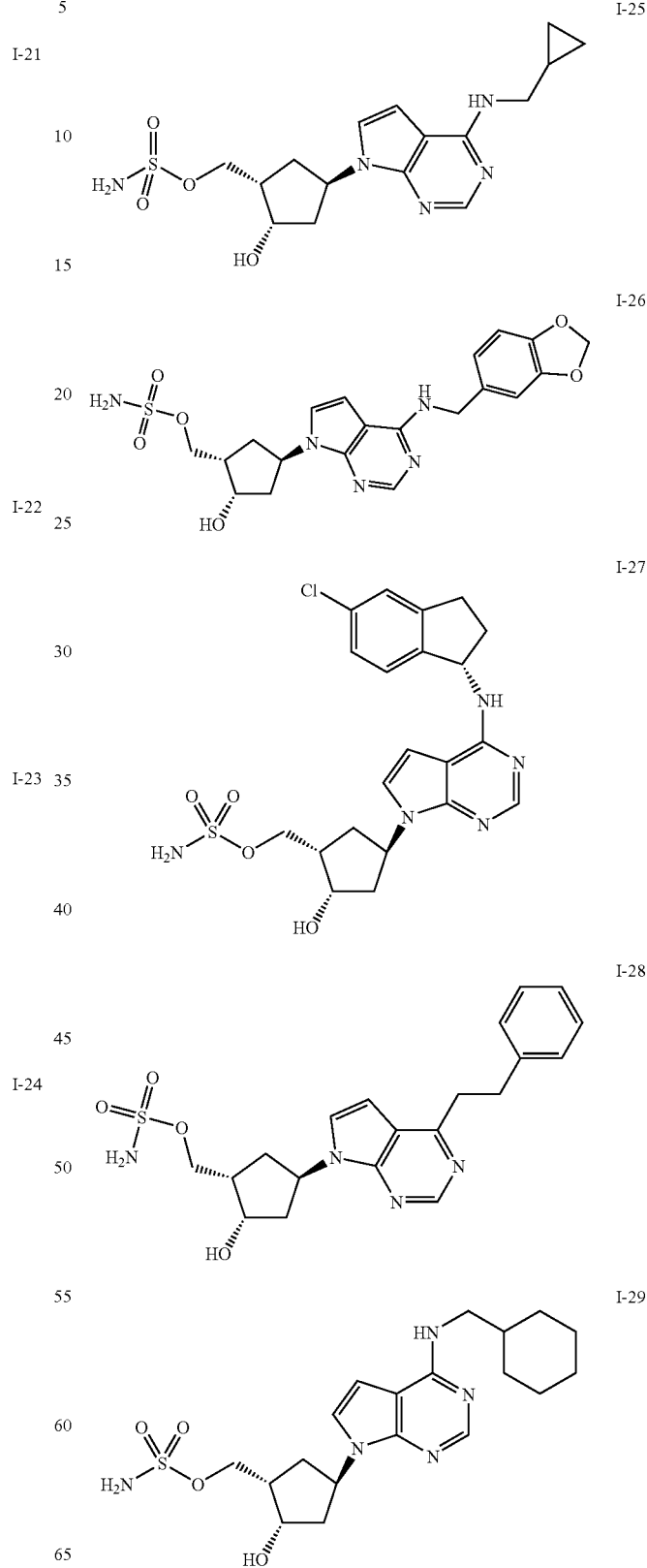

TABLE 1-continued
E1 Activating Enzyme Inhibitors
I-30
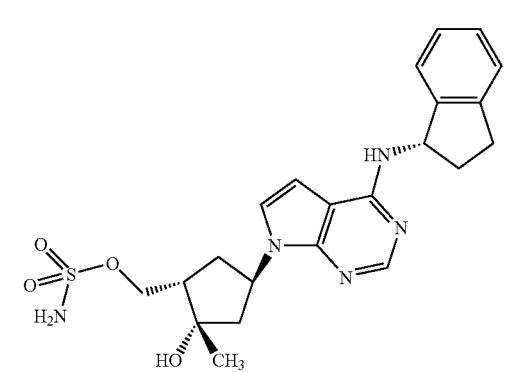
I-31
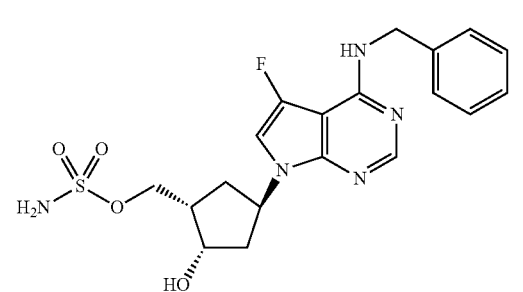
I-32
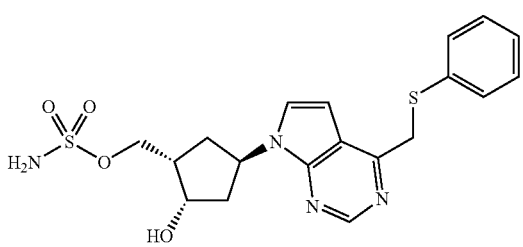
I-33
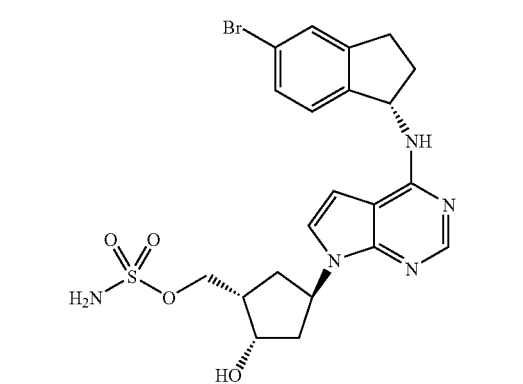
I-34
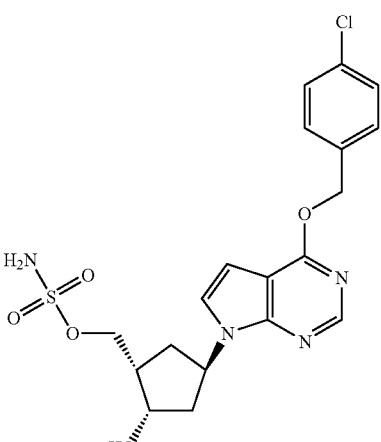
I-35
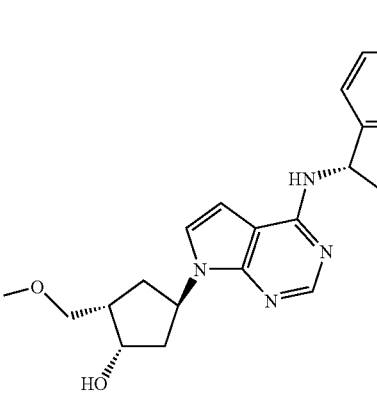
I-36
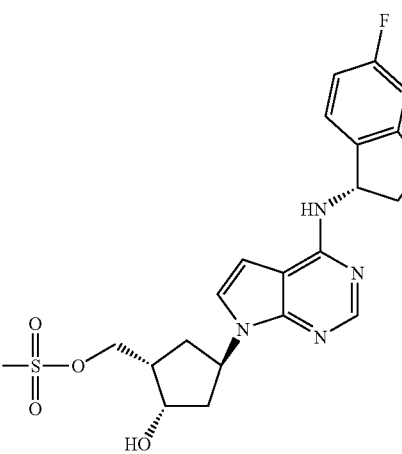

TABLE 1-continued
E1 Activating Enzyme Inhibitors
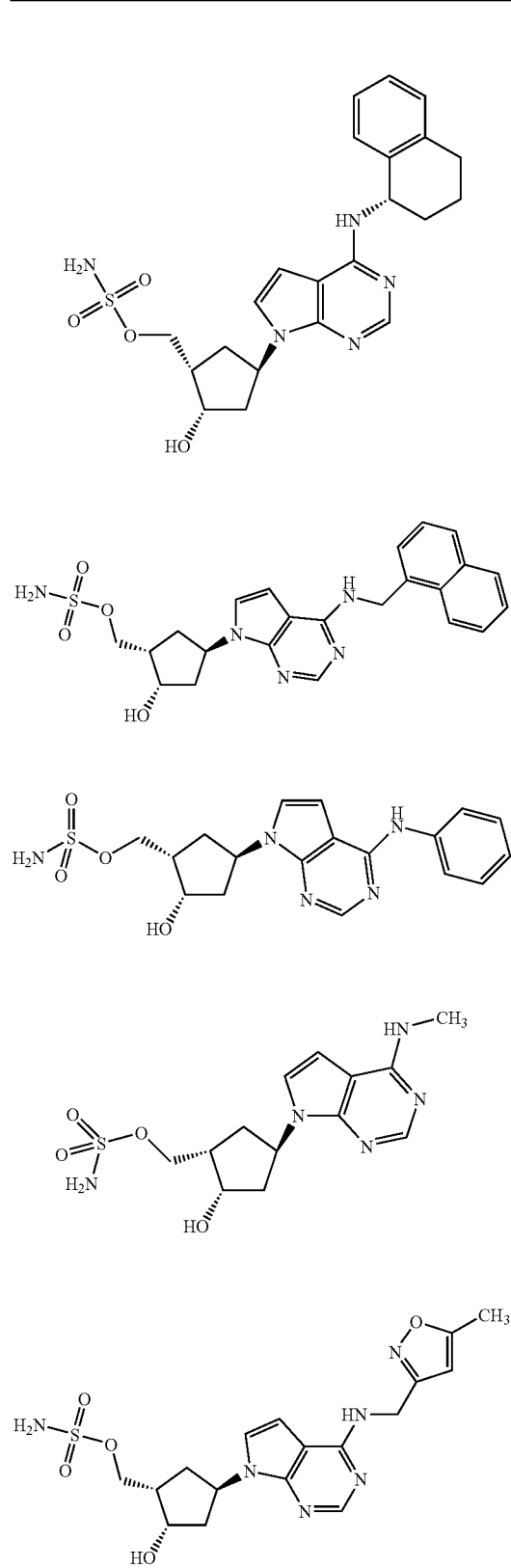
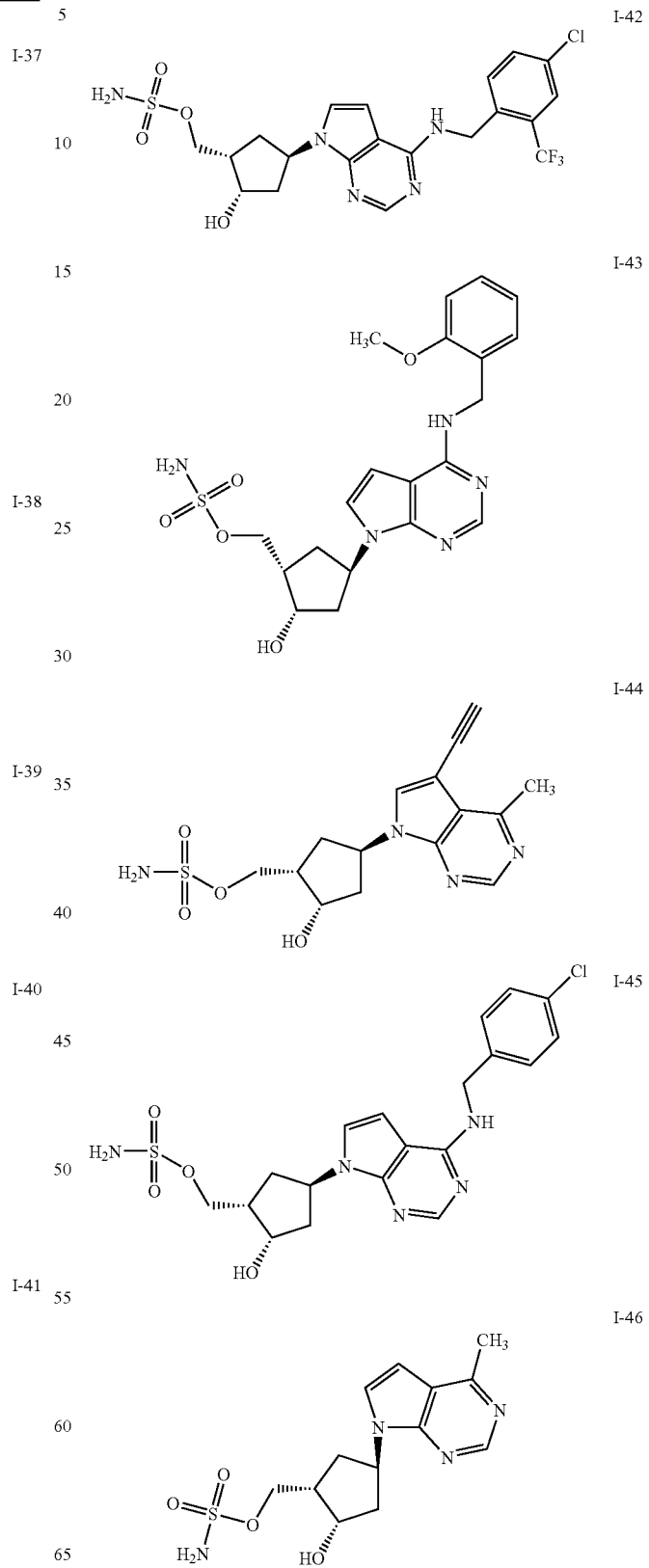

TABLE 1-continued
E1 Activating Enzyme Inhibitors
I-47
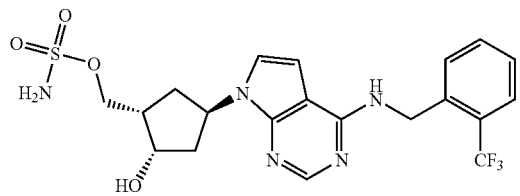
I-48
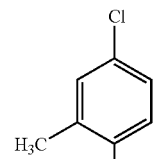
I-49
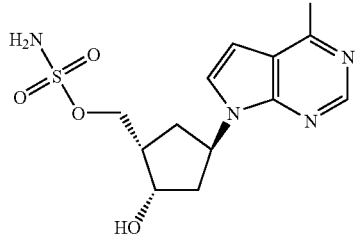
I-50
I-51
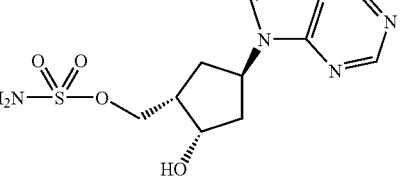
TABLE 1-continued
E1 Activating Enzyme Inhibitors
I-52
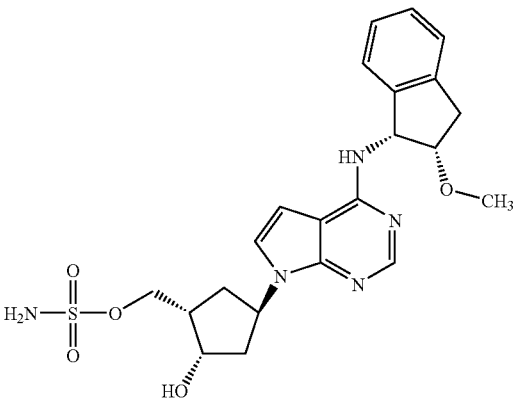
I-53
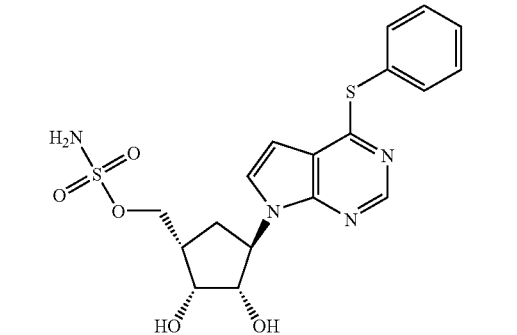
I-54
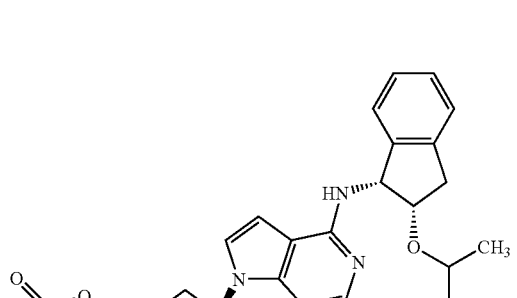
I-55
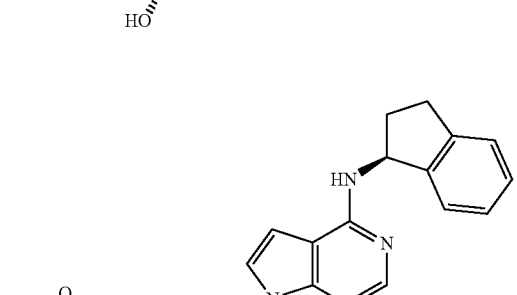

TABLE 1-continued
E1 Activating Enzyme Inhibitors
I-56
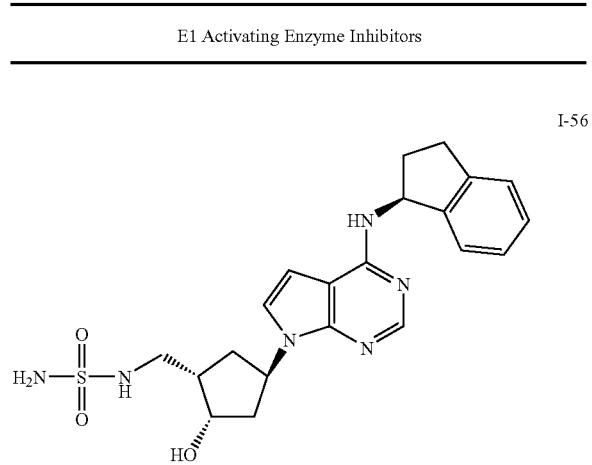
I-57
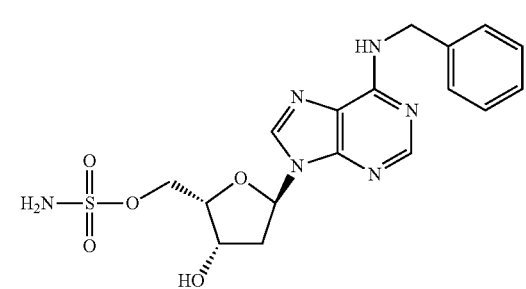
I-58
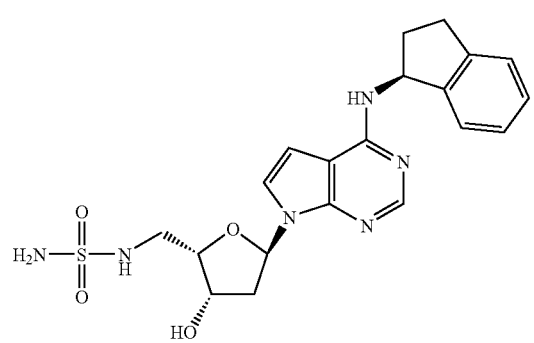
I-59
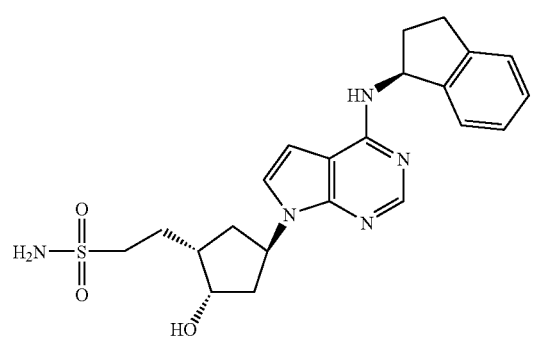
TABLE 1-continued
E1 Activating Enzyme Inhibitors
I-60
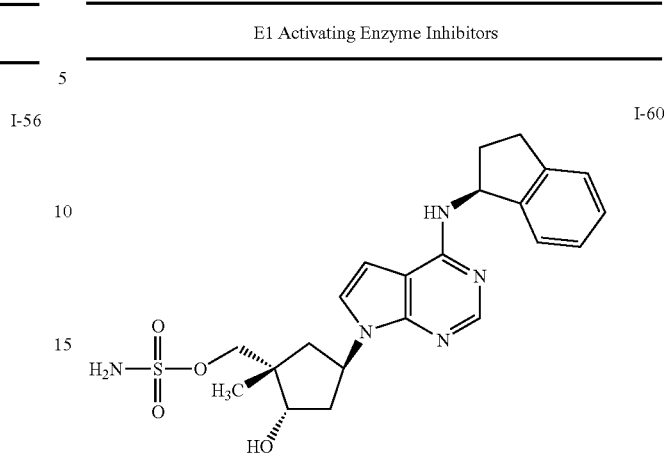
I-61
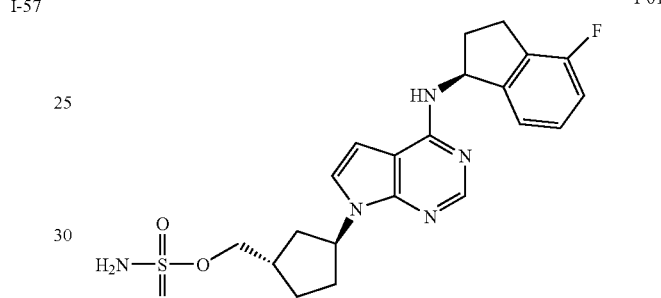
I-62
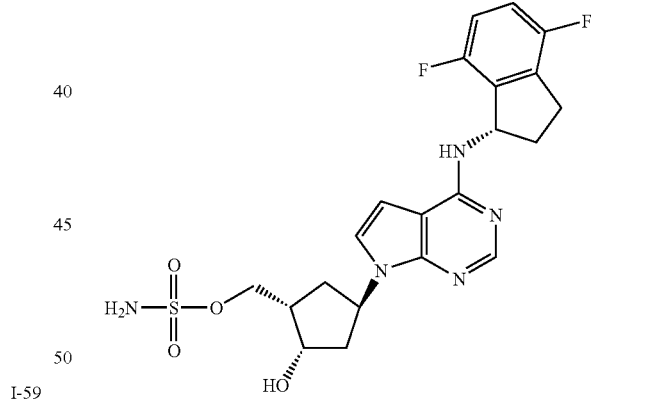
I-63
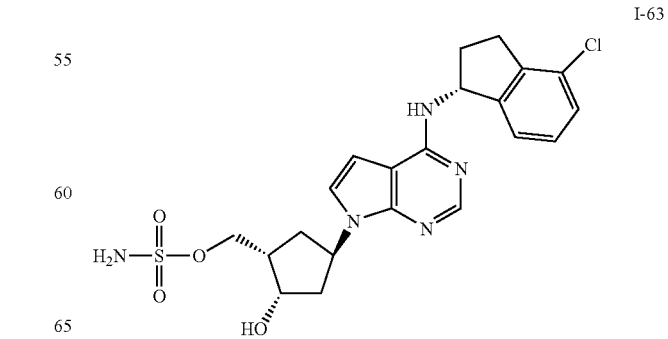

TABLE 1-continued
E1 Activating Enzyme Inhibitors
I-64
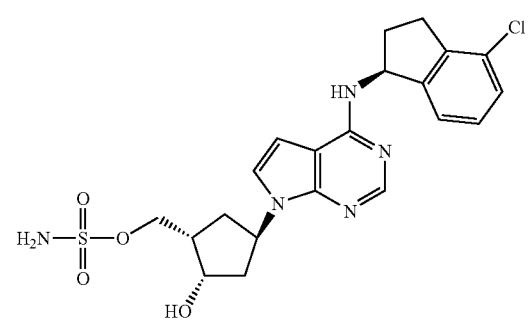
I-65
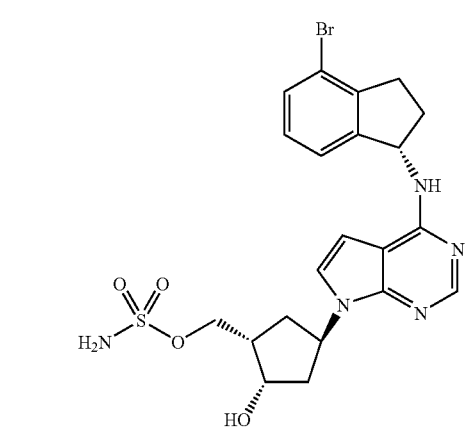
I-66
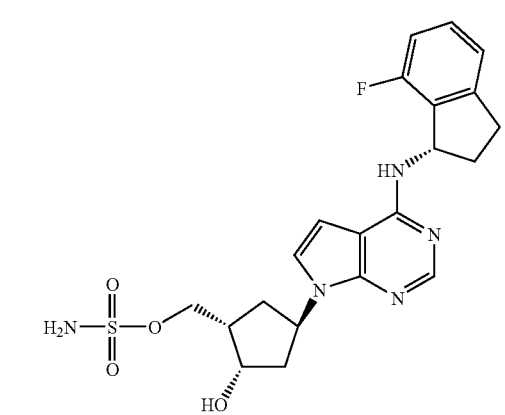
I-67
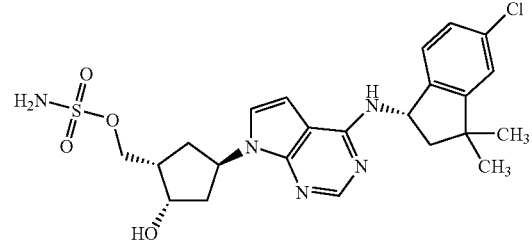
TABLE 1-continued
E1 Activating Enzyme Inhibitors
I-68
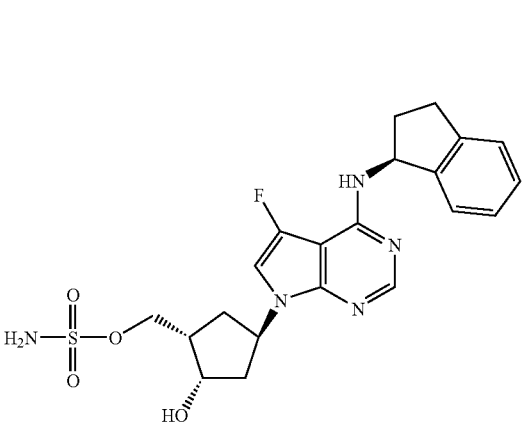
I-69
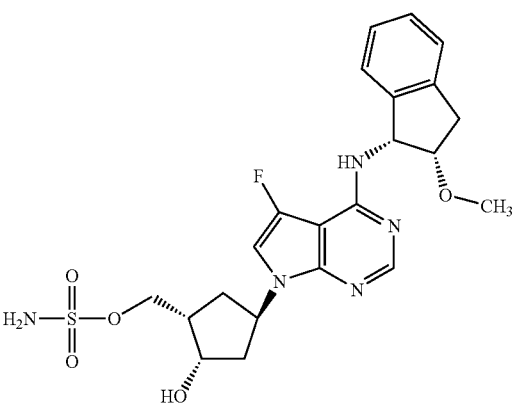
I-70
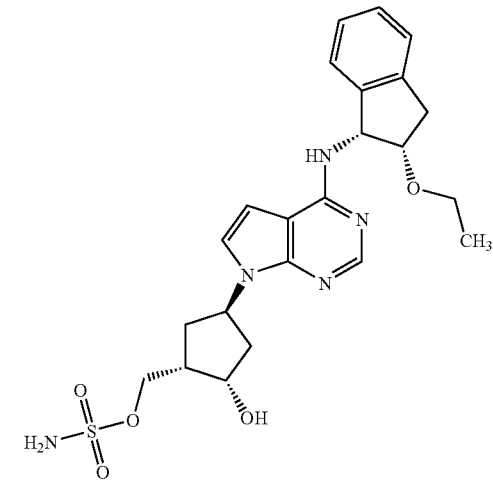

TABLE 1-continued
E1 Activating Enzyme Inhibitors
I-71
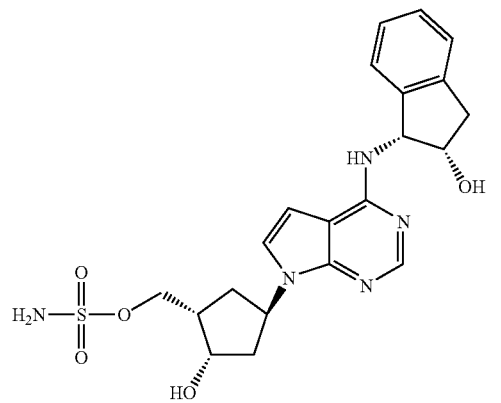
I-72
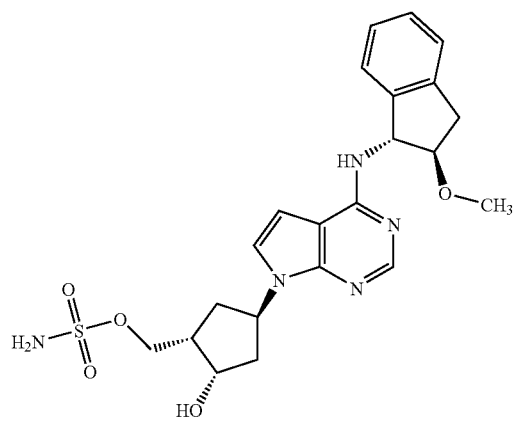
I-73
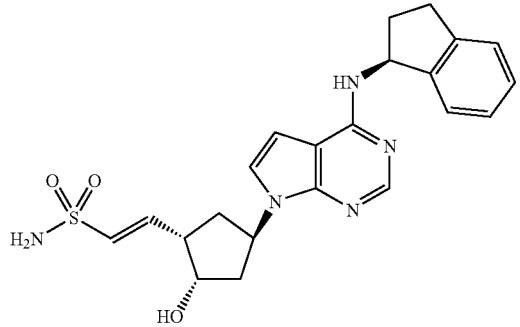
I-74
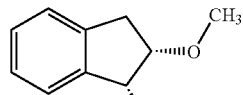
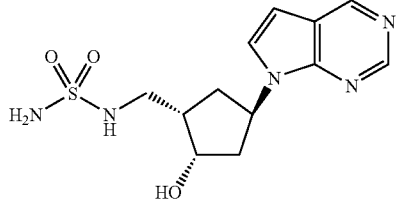
I-75
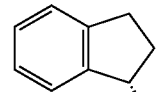
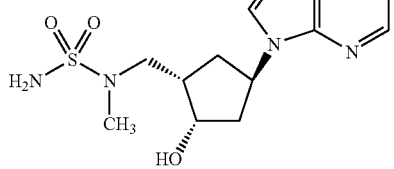
I-76
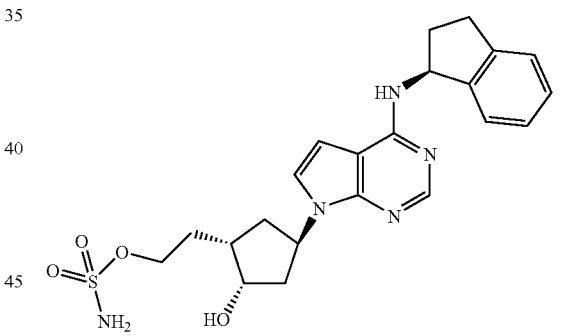
I-77
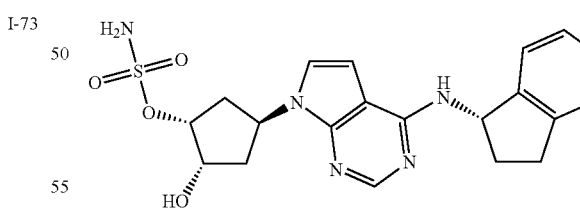
I-78
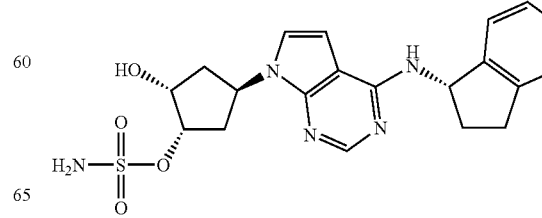

TABLE 1-continued
E1 Activating Enzyme Inhibitors
I-79
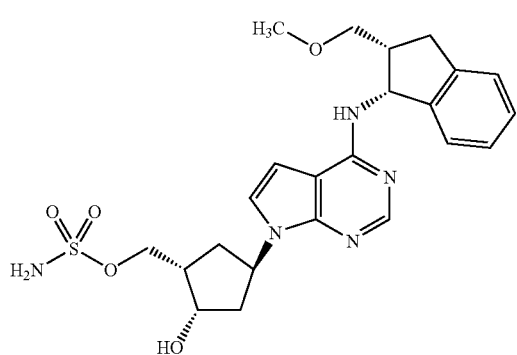
I-80
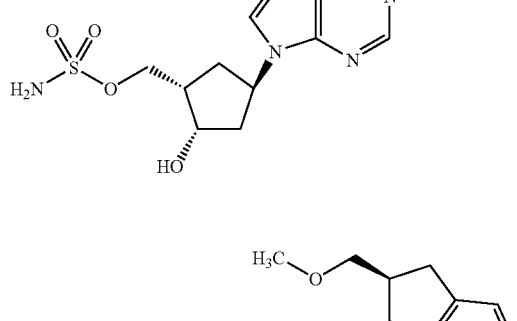
I-81
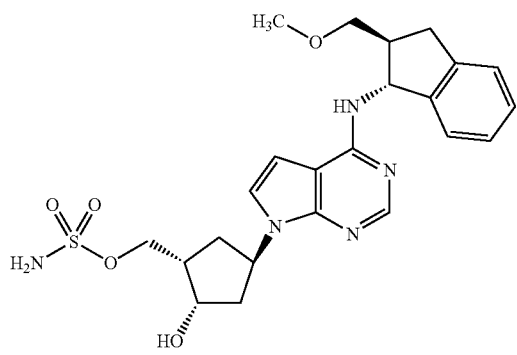
I-82
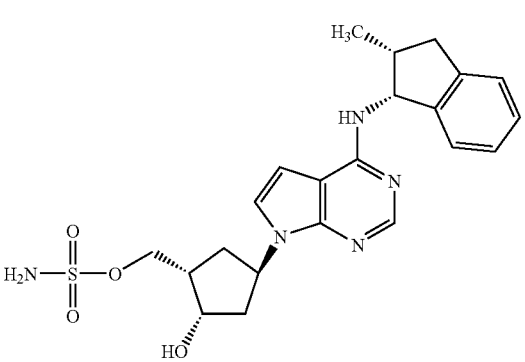
TABLE 1-continued
E1 Activating Enzyme Inhibitors
I-83
I-84
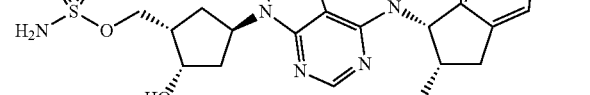
I-85
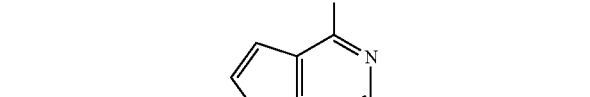
I-86

The compounds in Table 1 above may also be identified by the following chemical names:

| | Chemical Name |
|---|---|
| I-1 | ((1S,2S,4R)-4-{4-[(2-chlorobenzyl)amino]-7H-pyrrolo[2,3-d]pyrimidin-7-yl}-2-hydroxycyclopentyl)methyl sulfamate |
| I-2 | [(1S,2S,4R)-4-(4-{[2-(difluoromethoxy)benzyl]amino}-7H-pyrrolo[2,3-d]-pyrimidin-7-yl)-2-hydroxycyclopentyl]methyl sulfamate |
| I-3 | [(1S,2S,4R)-2-hydroxy-4-(4-{methyl[(1S)-1-phenylethyl]amino}-7H-pyrrolo-[2,3-d]pyrimidin-7-yl)cyclopentyl]methyl sulfamate |
| I-4 | [(1S,2S,4R)-2-hydroxy-4-(4-{[(1S)-1-phenylethyl]amino}-7H-pyrrolo[2,3-d]-pyrimidin-7-yl)cyclopentyl]methyl sulfamate |
| I-5 | ((1S,2S,4R)-4-{4-[(4-chlorobenzyl)amino]-7H-pyrrolo[2,3-d]pyrimidin-7-yl}-2-hydroxy-2-methylcyclopentyl)methyl sulfamate |
| I-6 | ((1S,2S,4R)-4-{4-[(1S)-2,3-dihydro-1H-inden-1-yl(methyl)amino]-7H-pyrrolo-[2,3-d]pyrimidin-7-yl}-2-hydroxycyclopentyl)methyl sulfamate |
| I-7 | [(1S,2S,4R)-2-hydroxy-4-(4-{[(1R)-1-phenylethyl]amino}-7H-pyrrolo[2,3-d]-pyrimidin-7-yl)cyclopentyl]methyl sulfamate |
| I-8 | [(1S,2S,4R)-2-hydroxy-4-(4-{[4-(trifluoromethyl)benzyl]amino}-7H-pyrrolo-[2,3-d]pyrimidin-7-yl)cyclopentyl]methyl sulfamate |
| I-9 | {(1S,2S,4R)-4-[4-(acetylamino)-7H-pyrrolo[2,3-d]pyrimidin-7-yl]-2-hydroxycyclopentyl}methyl sulfamate |
| I-10 | ((1S,2S,4R)-4-}4-[benzyl(methyl)amino]-7H-pyrrolo[2,3-d]pyrimidin-7-yl}-2-hydroxycyclopentyl)methyl sulfamate |
| I-11 | ((1S,3S)-3-{4-[(1S)-2,3-dihydro-1H-inden-1-ylamino]-7H-pyrrolo[2,3-d]-pyrimidin-7-yl}cyclopentyl)methyl sulfamate |
| I-12 | ((1S,2S,4R)-4-{4-[(4S)-3,4-dihydro-2H-chromen-4-ylamino]-7H-pyrrolo[2,3-d]-pyrimidin-7-yl}-2-hydroxycyclopentyl)methyl sulfamate |
| I-13 | ((1S,2S,4R)-4-{4-[(1R)-2,3-dihydro-1H-inden-1-ylamino]-7H-pyrrolo[2,3-d]-pyrimidin-7-yl}-2-hydroxycyclopentyl)methyl sulfamate |
| I-14 | [(1S,2S,4R)-4-(4-{[(1S)-3,3-dimethyl-2,3-dihydro-1H-inden-1-yl]amino}-7H-pyrrolo[2,3-d]pyrimidin-7-yl)-2-hydroxycyclopentyl]methyl sulfamate |
| I-15 | ((1S,2S,4R)-4-{4-[(2,6-difluorobenzyl)amino]-7H-pyrrolo[2,3-d]pyrimidin-7-yl}-2-hydroxycyclopentyl)methyl sulfamate |
| I-16 | ((1S,2S,4R)-4-{4-[(3,5-dichlorobenzyl)amino]-7H-pyrrolo[2,3-d]pyrimidin-7-yl}-2-hydroxycyclopentyl)methyl sulfamate |
| I-17 | ((1S,2R,3S,4R)-4-{4-[(1S)-2,3-dihydro-1H-inden-1-ylamino]-7H-pyrrolo[2,3-d]-pyrimidin-7-yl}-2,3-dihydroxycyclopentyl)methyl sulfamate |
| I-18 | [(1S,2S,4R)-4-(4-amino-7H-pyrrolo[2,3-d]pyrimidin-7-yl)-2-hydroxycyclopentyl]methyl sulfamate |
| I-19 | ((1S,2S,4R)-4-{4-[(2,4-dichlorobenzyl)amino]-7H-pyrrolo[2,3-d]pyrimidin-7-yl}-2-hydroxycyclopentyl)methyl sulfamate |
| I-20 | ((1R,4R)-4-{4-[(1S)-2,3-dihydro-1H-inden-1-ylamino]-7H-pyrrolo[2,3-d]-pyrimidin-7-yl}cyclopent-2-en-1-yl)methyl sulfamate |
| I-21 | [(1S,2S,4R)-4-(4-{[(1R)-3,3-dimethyl-2,3-dihydro-1H-inden-1-yl]amino}-7H-pyrrolo[2,3-d]pyrimidin-7-yl)-2-hydroxycyclopentyl]methyl sulfamate |
| I-22 | ((1S,2R,3S,4R)-4-{4-[(4-chlorobenzyl)amino]-7H-pyrrolo[2,3-d]pyrimidin-7-yl)-2,3-dihydroxycyclopentyl)methyl sulfamate |
| I-23 | ((1S,2S,4R)-4-{6-[(4-chlorobenzyl)amino]-9H-purin-9-yl}-2-hydroxycyclopentyl)methyl sulfamate |
| I-24 | ((1S,2S,4R)-4-{4-[(3,4-dichlorobenzyl)amino]-7H-pyrrolo[2,3-d]pyrimidin-7-yl}-2-hydroxycyclopentyl)methyl sulfamate |
| I-25 | ((1S,2S,4R)-4-{4-[(cyclopropylmethyl)amino]-7H-pyrrolo[2,3-d]pyrimidin-7-yl}-2-hydroxycyclopentyl)methyl sulfamate |
| I-26 | ((1S,2S,4R)-4-{4-[(1,3-benzodioxol-5-ylmethyl)amino]-7H-pyrrolo[2,3-d]-pyrimidin-7-yl}-2-hydroxycyclopentyl)methyl sulfamate |
| I-27 | [(1S,2S,4R)-4-(4-}[(1S)-5-chloro-2,3-dihydro-1H-inden-1-yl]amino}-7H-pyrrolo-[2,3-d]pyrimidin-7-yl)-2-hydroxycyclopentyl]methyl sulfamate |
| I-28 | {(1S,2S,4R)-2-hydroxy-4-[4-(2-phenylethyl)-7H-pyrrolo[2,3-d]pyrimidin-7-yl]-cyclopentyl}methyl sulfamate |
| I-29 | ((1S,2S,4R)-4-{4-[(cyclohexylmethyl)amino]-7H-pyrrolo[2,3-d]pyrimidin-7-yl)-2-hydroxycyclopentyl)methyl sulfamate |
| I-30 | ((1S,2S,4R)-4-{4-[(1S)-2,3-dihydro-1H-inden-1-ylamino]-7H-pyrrolo[2,3-d]-pyrimidin-7-yl}-2-hydroxy-2-methylcyclopentyl)methyl sulfamate |
| I-31 | {(1S,2S,4R)-4-[4-(benzylamino)-5-fluoro-7H-pyrrolo[2,3-d]pyrimidin-7-yl]-2-hydroxycyclopentyl}methyl sulfamate |
| I-32 | {(1S,2S,4R)-4-[4-(benzylsulfanyl)-7H-pyrrolo[2,3-d]pyrimidin-7-yl]-2-hydroxycyclopentyl}methyl sulfamate |
| I-33 | [(1S,2S,4R)-4-(4-{[(1S)-5-bromo-2,3-dihydro-1H-inden-1-yl]amino}-7H-pyrrolo-[2,3-d]pyrimidin-7-yl)-2-hydroxycyclopentyl]methyl sulfamate |
| I-34 | ((1S,2S,4R)-4-{4-[(4-chlorobenzyl)oxy]-7H-pyrrolo[2,3-d]pyrimidin-7-yl}-2-hydroxycyclopentyl)methyl sulfamate |
| I-35 | ((1S,2S,4R)-4-{4-[(1S)-2,3-dihydro-1H-inden-1-ylamino]-7H-pyrrolo[2,3-d]-pyrimidin-7-yl}-2-hydroxycyclopentyl)methyl sulfamate |
| I-36 | [(1S,2S,4R)-4-(4-{[(1S)-5-fluoro-2,3-dihydro-1H-inden-1-yl]amino}-7H-pyrrolo-[2,3-d]pyrimidin-7-yl)-2-hydroxycyclopentyl]methyl sulfamate |
| I-37 | ((1S,2S,4R)-2-hydroxy-4-{4-[(1S)-1,2,3,4-tetrahydronaphthalen-1-ylamino]-7H-pyrrolo[2,3-d]pyrimidin-7-yl}cyclopentyl)methyl sulfamate |

| | Chemical Name |
|---|---|
| I-38 | ((1S,2S,4R)-2-hydroxy-4-{4-[(1-naphthylmethyl)amino]-7H-pyrrolo[2,3-d]-pyrimidin-7-yl}cyclopentyl)methyl sulfamate |
| I-39 | [(1S,2S,4R)-4-(4-anilino-7H-pyrrolo[2,3-d]pyrimidin-7-yl)-2-hydroxycyclopentyl]methyl sulfamate |
| I-40 | {(1S,2S,4R)-2-hydroxy-4-[4-(methylamino)-7H-pyrrolo[2,3-d]pyrimidin-7-yl]-cyclopentyl}methyl sulfamate |
| I-41 | [(1S,2S,4R)-2-hydroxy-4-(4-{[(5-methylisoxazol-3-yl)methyl]amino}-7H-pyrrolo-[2,3-d]pyrimidin-7-yl)cyclopentyl]methyl sulfamate |
| I-42 | [(1S,2S,4R)-4-(4-{[4-chloro-2-(trifluoromethyl)benzyl]amino}-7H-pyrrolo[2,3-d]-pyrimidin-7-yl)-2-hydroxycyclopentyl]methyl sulfamate |
| I-43 | ((1S,2S,4R)-2-hydroxy-4-{4-[(2-methoxybenzyl)amino]-7H-pyrrolo[2,3-d]-pyrimidin-7-yl}cyclopentyl)methyl sulfamate |
| I-44 | [(1S,2S,4R)-4-(5-ethynyl-4-methyl-7H-pyrrolo[2,3-d]pyrimidin-7-yl)-2-hydroxycyclopentyl]methyl sulfamate |
| I-45 | ((1S,2S,4R)-4-{4-[(4-chlorobenzyl)amino]-7H-pyrrolo[2,3-d]pyrimidin-7-yl}-2-hydroxycyclopentyl)methyl sulfamate |
| I-46 | [(1S,2S,4R)-2-hydroxy-4-(4-methyl-7H-pyrrolo[2,3-d]pyrimidin-7-yl)cyclopentyl]methyl sulfamate |
| I-47 | [(1S,2S,4R)-2-hydroxy-4-(4-{[2-(trifluoromethyl)benzyl]amino}-7H-pyrrolo-[2,3-d]pyrimidin-7-yl)cyclopentyl]methyl sulfamate |
| I-48 | ((1S,2S,4R)-4-{4-[(4-chloro-2-methylbenzyl)amino]-7H-pyrrolo[2,3-d]pyrimidin-7-yl}-2-hydroxycyclopentyl)methyl sulfamate |
| I-49 | {(1S,2S,4R)-4-[4-(benzylamino)-7H-pyrrolo[2,3-d]pyrimidin-7-yl]-2-hydroxycyclopentyl}methyl sulfamate |
| I-50 | {(1S,2S,4R)-2-hydroxy-4-[4-(2-methyl-2-phenylpropyl)-7H-pyrrolo[2,3-d]-pyrimidin-7-yl]cyclopentyl}methyl sulfamate |
| I-51 | ((1S,2S,4R)-4-{4-[(3-chlorobenzyl)amino]-7H-pyrrolo[2,3-d]pyrimidin-7-yl}-2-hydroxycyclopentyl)methyl sulfamate |
| I-52 | [(1S,2S,4R)-2-hydroxy-4-(4-{[(1R,2S)-2-methoxy-2,3-dihydro-1H-inden-1-yl]-amino}-7H-pyrrolo[2,3-d]pyrimidin-7-yl)cyclopentyl]methyl sulfamate |
| I-53 | {(1S,2R,3S,4R)-2,3-dihydroxy-4-[4-(phenylsulfanyl)-7H-pyrrolo[2,3-d]-pyrimidin-7-yl]cyclopentyl}methyl sulfamate |
| I-54 | [(1S,2S,4R)-2-hydroxy-4-(4-{[(1R,2S)-2-isopropoxy-2,3-dihydro-1H-inden-1-yl]-amino}-7H-pyrrolo[2,3-d]pyrimidin-7-yl)cyclopentyl]methyl sulfamate |
| I-55 | ((2S,3S,5R)-5-{4-[(1S)-2,3-dihydro-1H-inden-1-ylamino]-7H-pyrrolo[2,3-d]-pyrimidin-7-yl}-3-hydroxytetrahydrofuran-2-yl)methyl sulfamate |
| I-56 | N-[((1S,2S,4R)-4-{4-[(1S)-2,3-dihydro-1H-inden-1-ylamino]-7H-pyrrolo[2,3-d]-pyrimidin-7-yl}-2-hydroxycyclopentyl)methyl]sulfamide |
| I-57 | {(2S,3S,5R)-5-[6-(benzylamino)-9H-purin-9-yl]-3-hydroxytetrahydrofuran-2-yl}-methyl sulfamate |
| I-58 | N-[((2S,3S,5R)-5-{4-[(1S)-2,3-dihydro-1H-inden-1-ylamino]-7H-pyrrolo[2,3-d]-pyrimidin-7-yl}-3-hydroxytetrahydrofuran-2-yl)methyl]sulfamide |
| I-59 | 2-((1S,2S,4R)-4-{4-[(1S)-2,3-dihydro-1H-inden-1-ylamino]-7H-pyrrolo[2,3-d]-pyrimidin-7-yl}-2-hydroxycyclopentyl)ethanesulfonamide |
| I-60 | ((1S,2S,4R)-4-{4-[(1S)-2,3-dihydro-1H-inden-1-ylamino]-7H-pyrrolo[2,3-d]-pyrimidin-7-yl}-2-hydroxy-1-methylcyclopentyl)methyl sulfamate |
| I-61 | [(1S,2S,4R)-4-(4-{[(1S)-4-fluoro-2,3-dihydro-1H-inden-1-yl]amino}-7H-pyrrolo[2,3-d]pyrimidin-7-yl)-2-hydroxycyclopentyl]methyl sulfamate |
| I-62 | [(1S,2S,4R)-4-(4-{[(1S)-4,7-difluoro-2,3-dihydro-1H-inden-1-yl]amino}-7H-pyrrolo[2,3-d]pyrimidin-7-yl)-2-hydroxycyclopentyl]methyl sulfamate |
| I-63 | [(1S,2S,4R)-4-(4-{[(1R)-4-chloro-2,3-dihydro-1H-inden-1-yl]amino}-7H-pyrrolo[2,3-d]pyrimidin-7-yl)-2-hydroxycyclopentyl]methyl sulfamate |
| I-64 | [(1S,2S,4R)-4-(4-{[(1S)-4-chloro-2,3-dihydro-1H-inden-1-yl]amino}-7H-pyrrolo[2,3-d]pyrimidin-7-yl)-2-hydroxycyclopentyl]methyl sulfamate |
| I-65 | [(1S,2S,4R)-4-(4-{[(1S)-4-bromo-2,3-dihydro-1H-inden-1-yl]amino}-7H-pyrrolo[2,3-d]pyrimidin-7-yl)-2-hydroxycyclopentyl]methyl sulfamate |
| I-66 | [(1S,2S,4R)-4-(4-{[(1S)-7-fluoro-2,3-dihydro-1H-inden-1-yl]amino}-7H-pyrrolo[2,3-d]pyrimidin-7-yl)-2-hydroxycyclopentyl]methyl sulfamate |
| I-67 | [(1S,2S,4R)-4-(4-{[(1S)-5-chloro-3,3-dimethyl-2,3-dihydro-1H-inden-1-yl]amino)-7H-pyrrolo[2,3-d]pyrimidin-7-yl)-2-hydroxycyclopentyl]methyl sulfamate |
| I-68 | ((1S,2S,4R)-4-{4-[(1S)-2,3-dihydro-1H-inden-1-ylamino]-5-fluoro-7H-pyrrolo[2,3-d]pyrimidin-7-yl}-2-hydroxycyclopentyl)methyl sulfamate |
| I-69 | [(1S,2S,4R)-4-(5-fluoro-4-{[(1R,2S)-2-methoxy-2,3-dihydro-1H-inden-1-yl]amino}-7H-pyrrolo[2,3-d]pyrimidin-7-yl)-2-hydroxycyclopentyl]methyl sulfamate |
| I-70 | [(1S,2S,4R)-4-(4-{[(1R,2S)-2-ethoxy-2,3-dihydro-1H-inden-1-yl]amino}-7H-pyrrolo[2,3-d]pyrimidin-7-yl)-2-hydroxycyclopentyl]methyl sulfamate |
| I-71 | [(1S,2S,4R)-2-hydroxy-4-(4-{[(1R,2S)-2-hydroxy-2,3-dihydro-1H-inden-1-yl]amino}-7H-pyrrolo[2,3-d]pyrimidin-7-yl)cyclopentyl]methyl sulfamate |
| I-72 | [(1S,2S,4R)-2-hydroxy-4-(4-{[(1R,2R)-2-methoxy-2,3-dihydro-1H-inden-1-yl]amino}-7H-pyrrolo[2,3-d]pyrimidin-7-yl)cyclopentyl]methyl sulfamate |
| I-73 | (E)-2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethylenesulfonamide |
| I-74 | N-{[(1S,2S,4R)-2-hydroxy-4-(4-{[(1R,2S)-2-methoxy-2,3-dihydro-1H-inden-1-yl]amino}-7H-pyrrolo[2,3-d]pyrimidin-7-yl)cyclopentyl]methyl}sulfamide |
| I-75 | N-[((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl]-N-methylsulfamide |

|  | Chemical Name |
|---|---|
| I-76 | 2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethyl sulfamate |
| I-77 | (1S,2R,4R)-4-{4-[(1S)-2,3-dihydro-1H-inden-1-ylamino]-7H-pyrrolo[2,3-d]pyrimidin-7-yl}-2-hydroxycyclopentyl sulfamate |
| I-78 | (1R,2S,4S)-4-{4-[(1S)-2,3-dihydro-1H-inden-1-ylamino]-7H-pyrrolo[2,3-d]pyrimidin-7-yl}-2-hydroxycyclopentyl sulfamate |
| I-79 | [(1S,2S,4R)-2-hydroxy-4-(4-{[(1R,2R)-2-(methoxymethyl)-2,3-dihydro-1H-inden-1-yl]amino}-7H-pyrrolo[2,3-d]pyrimidin-7-yl)cyclopentyl]methyl sulfamate |
| I-80 | [(1S,2S,4R)-2-hydroxy-4-(4-{[(1S,2S)-2-(methoxymethyl)-2,3-dihydro-1H-inden-1-yl]amino}-7H-pyrrolo[2,3-d]pyrimidin-7-yl)cyclopentyl]methyl sulfamate |
| I-81 | [(1S,2S,4R)-2-hydroxy-4-(4-{[(1R,2R)-2-methyl-2,3-dihydro-1H-inden-1-yl]amino)-7H-pyrrolo[2,3-d]pyrimidin-7-yl)cyclopentyl]methyl sulfamate |
| I-82 | [(1S,2S,4R)-2-hydroxy-4-(4-{[(1S,2S)-2-methyl-2,3-dihydro-1H-inden-1-yl]amino}-7H-pyrrolo[2,3-d]pyrimidin-7-yl)cyclopentyl]methyl sulfamate |
| I-83 | [(1S,2S,4R)-4-(4-{[(1R,2R)-2-ethyl-2,3-dihydro-1H-inden-1-yl]amino}-7H-pyrrolo[2,3-d]pyrimidin-7-yl)-2-hydroxycyclopentyl]methyl sulfamate |
| I-84 | [(1S,2S,4R)-4-(4-{[(1S,2S)-2-ethyl-2,3-dihydro-1H-inden-1-yl]amino}-7H-pyrrolo[2,3-d]pyrimidin-7-yl)-2-hydroxycyclopentyl]methyl sulfamate |
| I-85 | [(1S,2S,4R)-2-hydroxy-4-(4-{[(1R,2S)-2-methoxy-1,2,3,4-tetrahydronaphthalen-1-yl]amino}-7H-pyrrolo[2,3-d]pyrimidin-7-yl)cyclopentyl]methyl sulfamate |
| I-86 | ((1S,2S,4R)-4-{4-[(1S)-2,3-dihydro-1H-inden-1-ylamino]-7H-pyrrolo[2,3-d]pyrimidin-7-yl}-2-methoxycyclopentyl)methyl sulfamate |

General Synthetic Methodology

The compounds of the present invention can be prepared by methods known to one of ordinary skill in the art and/or by reference to the schemes shown below and the synthetic examples that follow. Exemplary synthetic routes are set forth in Schemes 1-10 below, and in the Examples.

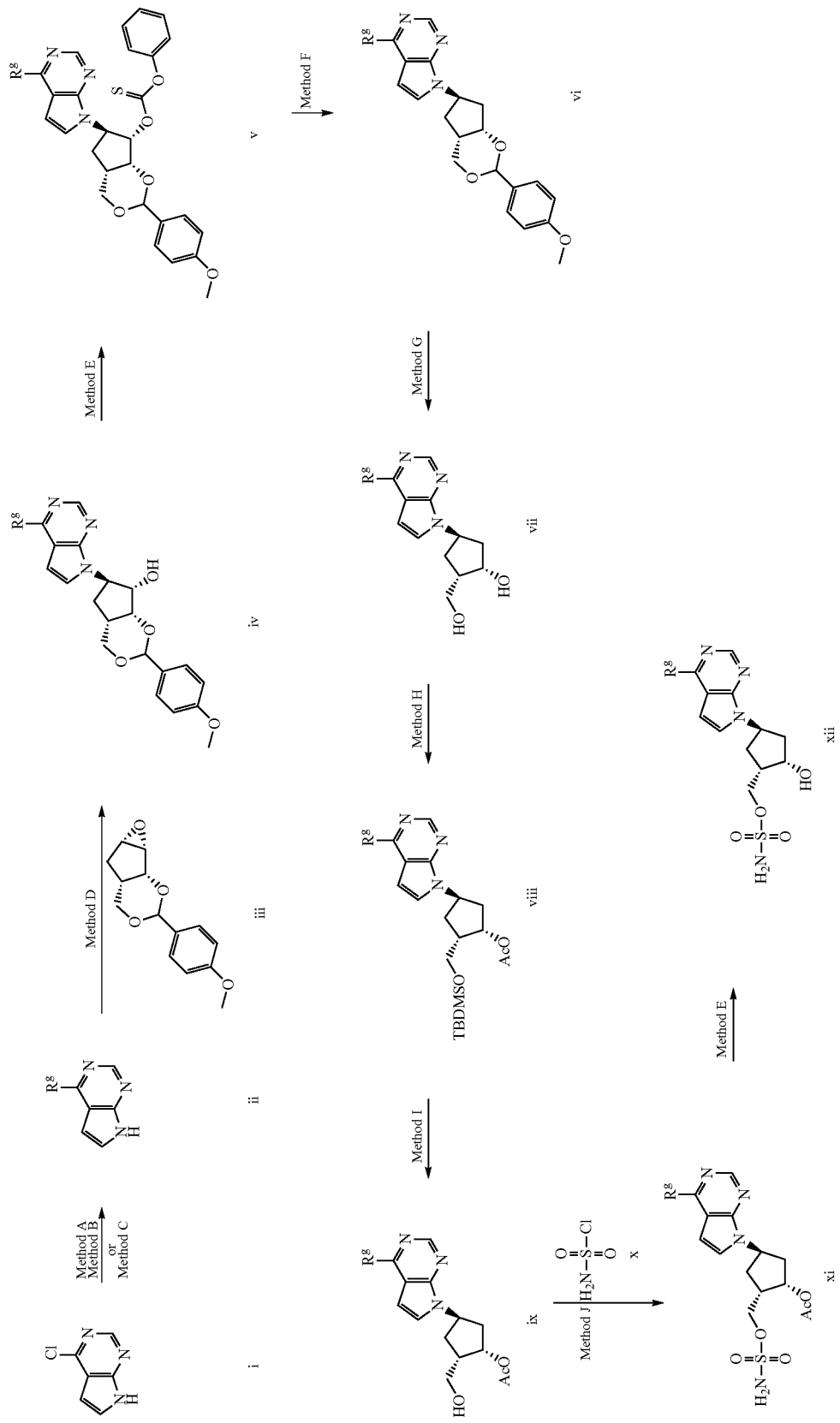

Scheme 1 above shows a general route for preparing compounds of formula (I), wherein Ring A has formula A-ii. Those of ordinary skill in the art will recognize that compounds of formula (I) wherein Ring A is other than A-ii can be prepared by the same general route, beginning with appropriate starting materials analogous to i.

Methods for the synthesis of chloro-substituted pyrrolopyrimidines such as formula i are known (P. Reigan et al., *Bioorg. Med. Chem. Lett.,* 2004, 14, 5247-5250; *J. Heterocyclic Chem.,* 1988, 25, 1633-1639). As shown in Scheme 1, conversion of compounds of formula i to substituted pyrrolopyrimidines is accomplished by coupling with the appropriately substituted amines or mercaptans (see Pathak, A. K.; Pathak, V.; Seitz, L. E.; Suling, W. J.; Reynolds, R. C., *J. Med. Chem.* 2004, 47, 273-276) at elevated temperature in protic solvents, such as butanol or isopropanol, using an appropriate base, such as DIPEA or $Et_3N$ (Method A). Alternatively, pyrrolopyrimidines i can be coupled with an appropriately substituted alcohol in $H_2O$ in the presence of a base, such as KOH, at reflowing temperatures (Method B). Compounds of formula i can also be treated with Grignard reagents in the presence of ferric acetylacetonate in THF (Method C) to provide carbon-substituted pyrrolopyrimidines. Compounds iv are prepared from ii by the opening of epoxide iii with a suitable base, such as NaH, LiHMDS, or cesium carbonate, at elevated temperatures in DMF (Method D).

For preparation of compounds of formula (I), wherein $R^c$ and $R^d$ are each hydrogen, deoxygenation can be effected at this stage. Thus, alkylation of compounds of formula iv to provide xanthates v is effected by treatment with chlorophenylthionocarbonate and a suitable base, such as DMAP, in DCM (Method E). Deoxygenation of compounds of formula v is achieved by treatment with a radical source, such as $Bu_3SnH$, and a radical initiator, such as AIBN, in refluxing toluene (Method F). Subsequent deprotection with an aqueous acid, such as AcOH (Method G), provides compounds of formula vii.

The primary alcohol of the diols of formula vii is selectively protected, e.g., with a bulky silyl protecting group such as TBDMS. Subsequent treatment with acetic anhydride affords the protected alcohols of formula viii (Method H). Selective deprotection of the primary alcohol using a fluoride reagent, such as pyridine hydrofluoride, in a basic solvent, such as pyridine, provides compounds of formula ix (Method I). Further treatment with freshly prepared chlorosulfonamide x affords the penultimate sulfamates xi (Method J). Acetate removal by treatment with a base, such as ammonia, in MeOH according to Method K yields compounds of formula xii.

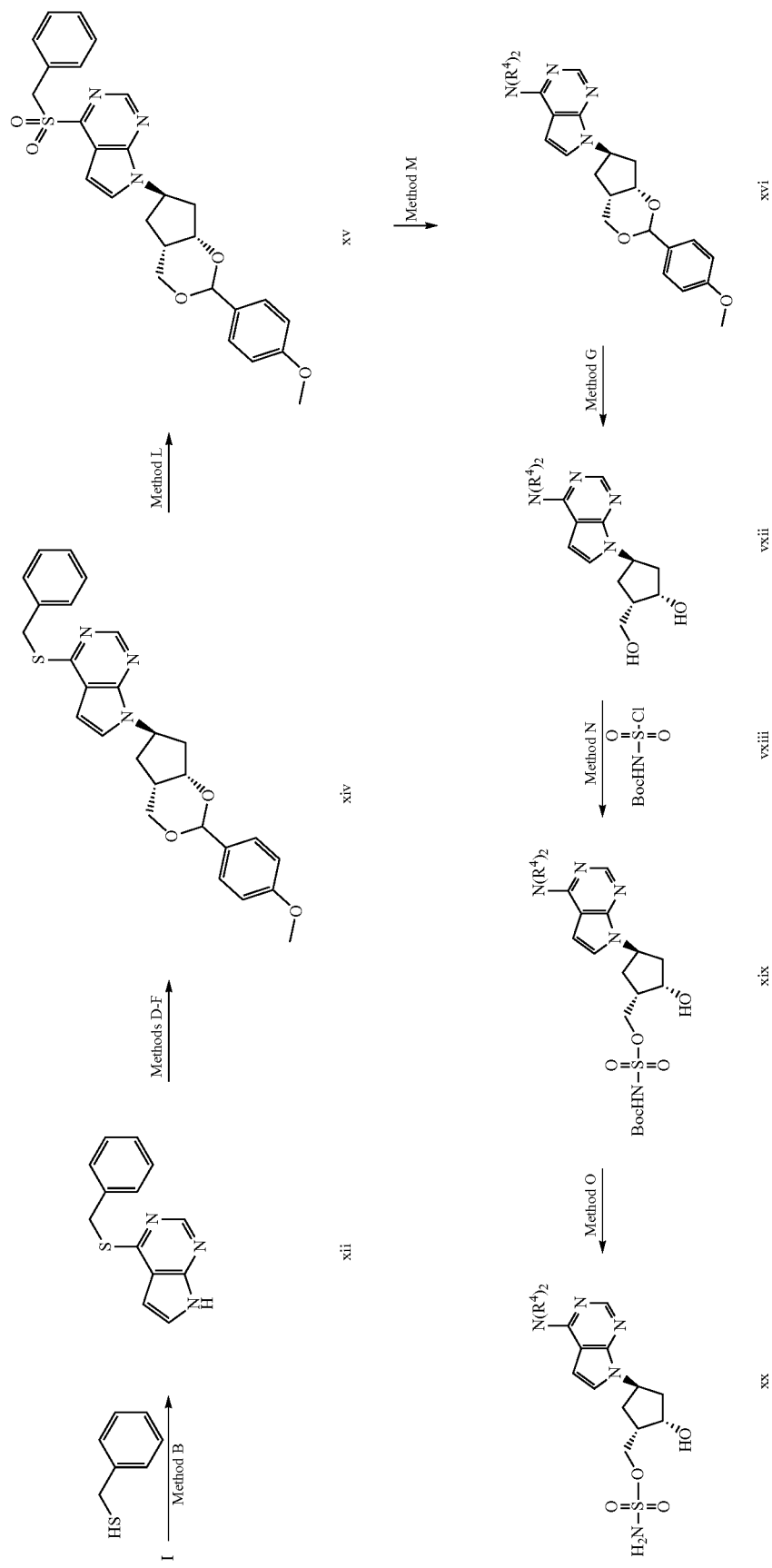

Compounds of formula (I), wherein $R^g$ is —$N(R^4)_2$ may be prepared by an alternative procedure in which a later stage intermediate incorporating a leaving group such as a sulfone is directly displaced by a substituted amine. As shown in Scheme 2, treatment of compounds of formula i with benzylmercaptan under conditions described in Method B provides benzylsulfanyl pyrrolopyrimidines of formula xiii. Subsequent treatment with the conditions outlined in Methods D-F affords compounds of formula xiv. Compounds xiv are reacted with an oxidizing agent, such as m-CPBA, in DCM in the presence of a base, such as sodium bicarbonate, to provide sulfones of formula xv (Method L).

Compounds of formula xvi are then synthesized by treatment of xv with an appropriately substituted amine using a base, such as DIPEA, in a high-boiling protic solvent, such as EtOH, at elevated temperatures (Method M) similar to literature procedures (Lin, X.; Robins, M. J., *Organic Lett.* 2000, 2, 3497-3499). Removal of the protecting group is accomplished in a manner analogous to that depicted in Scheme 1, using the procedure described in Method G, to give diols of formula xvii. Methods for the synthesis of tert-butyl chlorosulfonylcarbamate xviii are known (Hirayama et al., *Biorg. Med. Chem.*, 2002, 10, 1509-1523), and this reagent is reacted selectively with the primary alcohol using a hindered base, such as 2,6-di-tert-butyl-4-methylpyridine, in a solvent, such as AcCN, to afford Boc sulfamates of formula xix (Method N). TFA-deprotection according to Method O yields the compounds of formula xx. The conversion of compounds xv to xvi has the potential advantage of being amenable to solution phase library synthesis.

Scheme 4: General route for the synthesis of substituted aminoindans

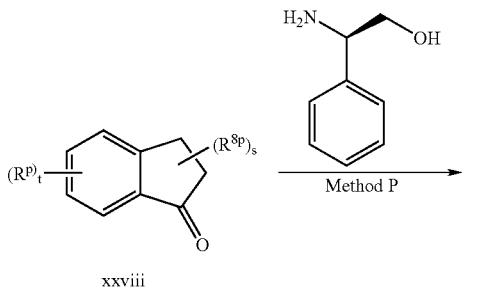

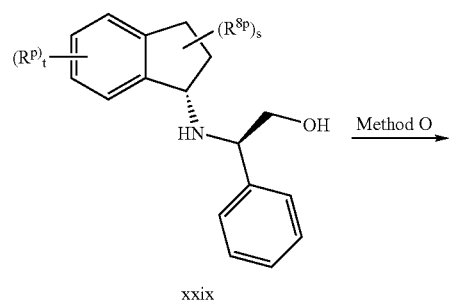

Scheme 3: Synthesis of substituted epoxides

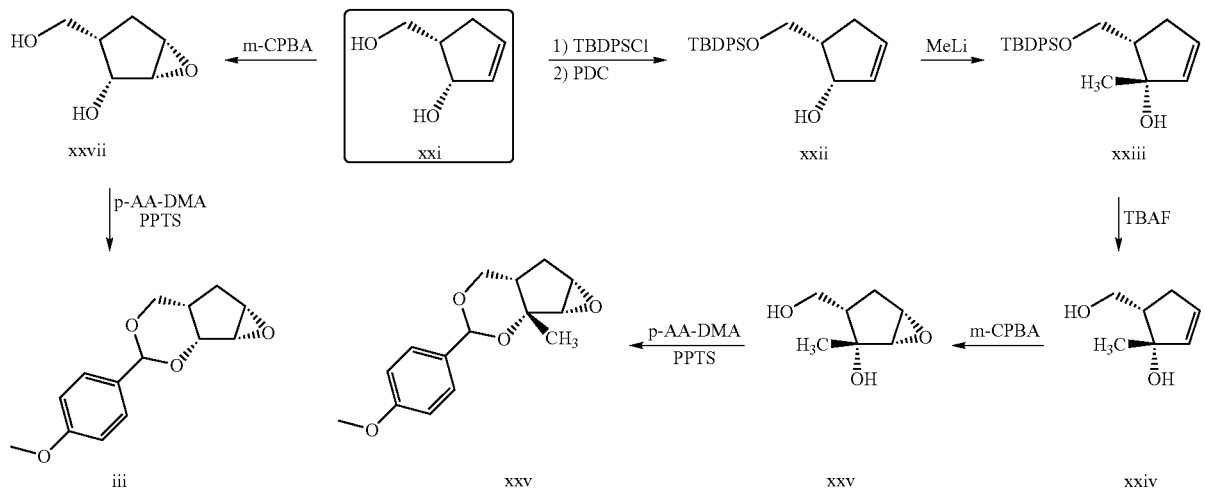

Methods for the synthesis of the intermediate alkene diol xxi are known (*Nucleosides, Nucleotides & Nucleic Acids*, 2002, 21, 65-72). Upon treatment with m-CPBA, diol xxi is converted to epoxy diol xxvii. Subsequent protection of the diol using p-anisaldehyde dimethyl acetal provides epoxide iii. Alternatively, TBDPS-protection of the primary alcohol of xxi followed by PDC oxidation gives the α,β-unsaturated ketone xxii. Addition of MeLi to the ketone in Et$_2$O gives tertiary alcohol xxiii, and treatment with TBAF in THF provides diol xxiv. Epoxidation and diol protection affords the protected substituted epoxide xxvi.

-continued

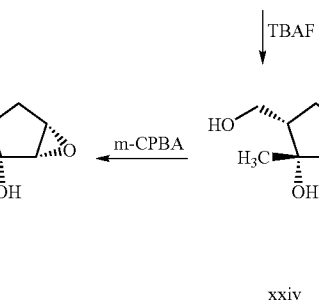

The aminoindans used for the preparation of 4-aminoindanyl compounds of formula xxx are either commercially available, or they are prepared through the literature methods highlighted in Scheme 4. Appropriately substituted indanones of formula xxviii are treated with (R)-2-amino-2-phenylethanol to provide the desired intermediate imine. Subsequent reaction with an appropriate reducing agent, such as sodium borohydride in the presence of AcOH, gives amino alcohols of formula xxix (Method P). Treatment with lead tetraacetate, followed by refluxing in HCl, gives aminoindans of formula xxx (Method Q). One skilled in the art will recognize that the use of (S)-2-amino-2-phenylethanol in Method P can be used to afford the opposite enantiomer of indan xxx.

Compounds of formula (I), wherein $R^c$ is —$OR^5$ can be prepared as outlined in Scheme 5. Thus, compounds of formula iv, as prepared in Scheme 1, are directly converted to triols of formula xxxi (Method G). Protection of the two secondary alcohols with 2,2-dimethoxypropane and an acid catalyst, such as p-TSA monohydrate, in acetone affords isopropylidenes xxxii (Method R). Further reaction with chlorosulfonamide x by Method J, as described in Scheme 1, affords sulfamates of formula xxxiii. Removal of the isopropylidene using an acid, such as TFA, in the presence of water yields compounds of formula xxxiv (II-C), according to Method S. Alternatively, triol xxxi can be selectively sulfamoylated at the primary hydroxyl and deprotected as described in Scheme 2, Methods N-O to give compounds of formula xxxiv.

Scheme 5: General route for the synthesis of 4-substituted ((1S,2S,4R)-2,3-dihydroxy-4-{7H-pyrrolo[2,3-d]pyrimidin-7-yl}cyclopentyl)methyl sulfamates

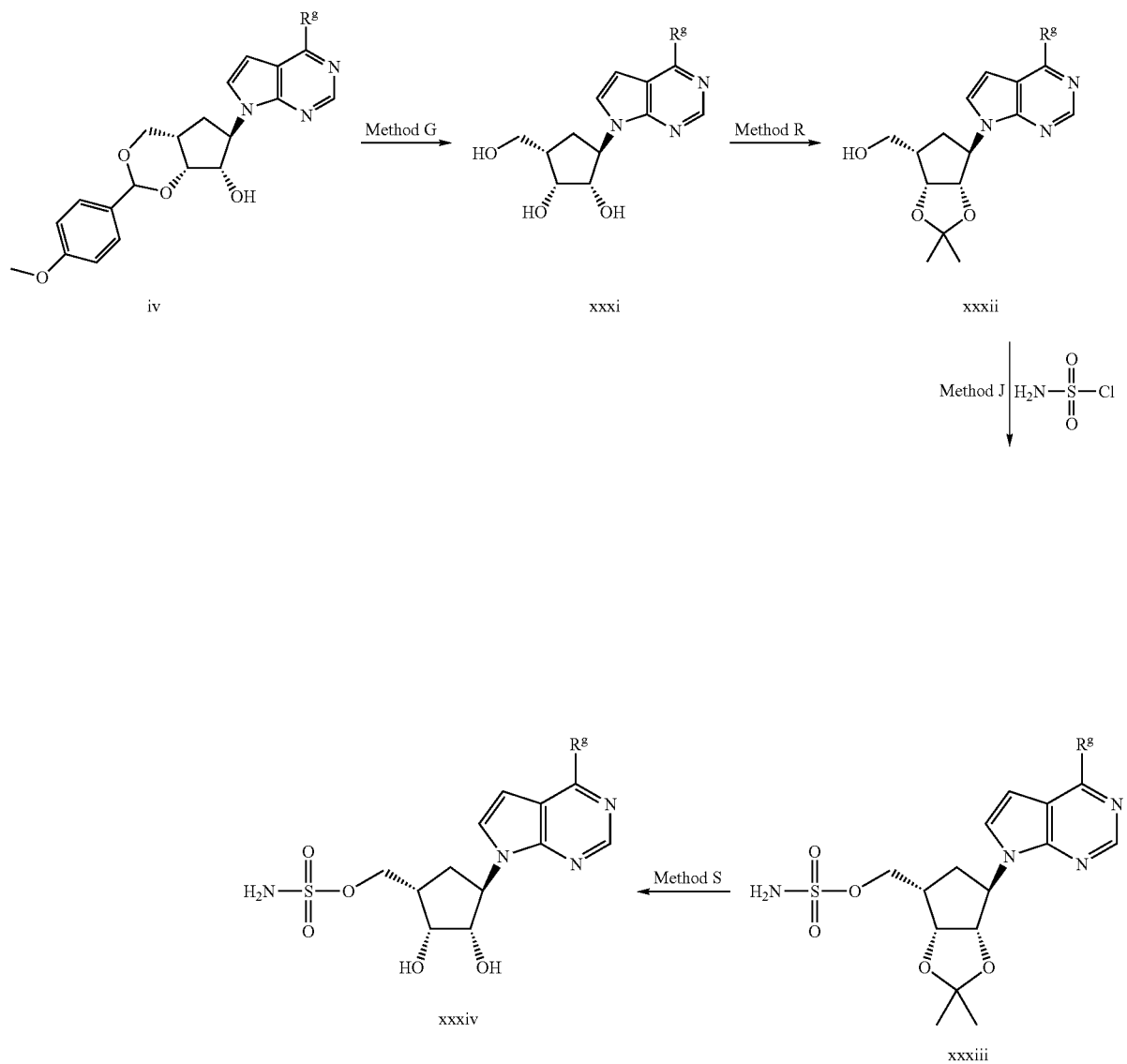

Scheme 6: General route for the synthesis of 4-amino and 4-acylamino substituted ((1S,2S,4R)-2-hydroxy-4-{7H-pyrrolo[2,3-d]pyrimidin-7-yl}-cyclopentyl)methyl sulfamates

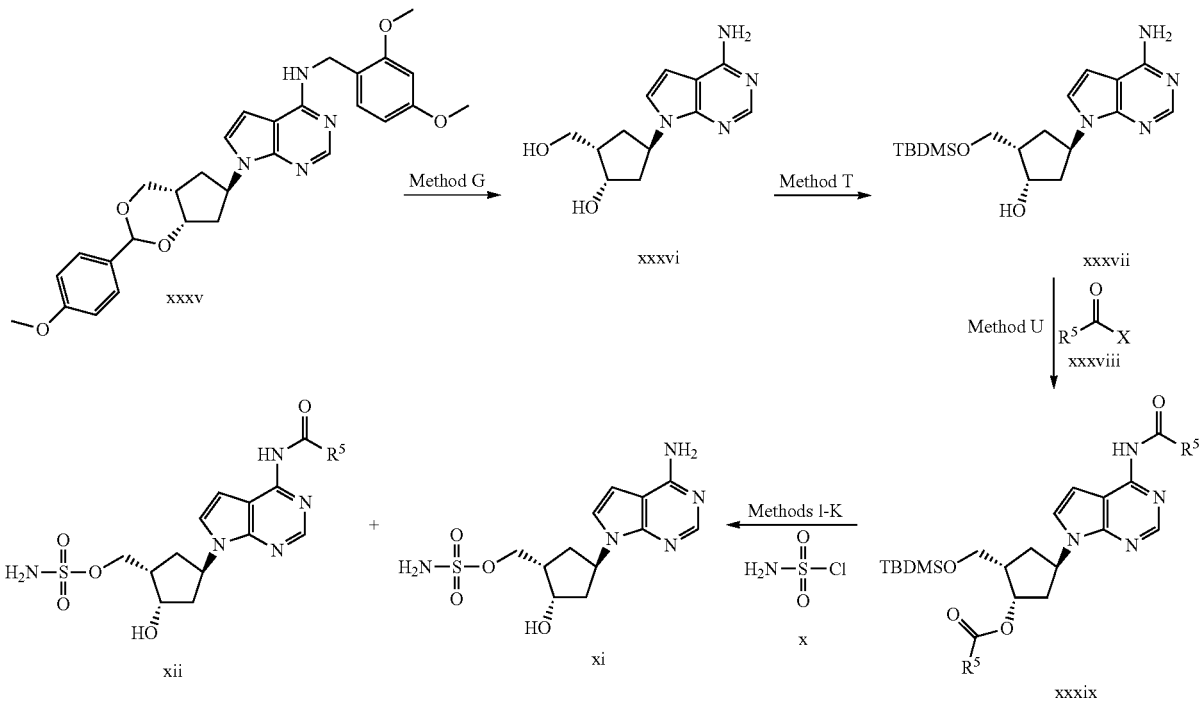

Compounds of formula xxxv are prepared by the methods described in Scheme 1. Treatment of benzylamines xxxv with an aqueous acid, such as AcOH, affords amines xxxvi (Method G). Selective protection of the primary alcohol using TBDMSCl and an appropriate base, such as imidazole, in DMF gives compounds of formula xxxvii (Method T). Bis-acylation is effected by treatment with appropriately substituted acylating reagent of formula xxxviii (X=Cl, OH, —OC(O)R$^5$) and an appropriate base, such as pyridine, to afford compounds of formula xxxix (Method U). Subjecting compounds xxxix to the conditions described in Methods I-K affords both the fully deprotected analogs xl as well as amides xli.

Scheme 7: General route for the synthesis of 4-substituted ((1S,2S,4R)-4-{7H-pyrrolo[2,3-d]pyrimidin-7-yl}-cyclopentyl)methyl sulfamates

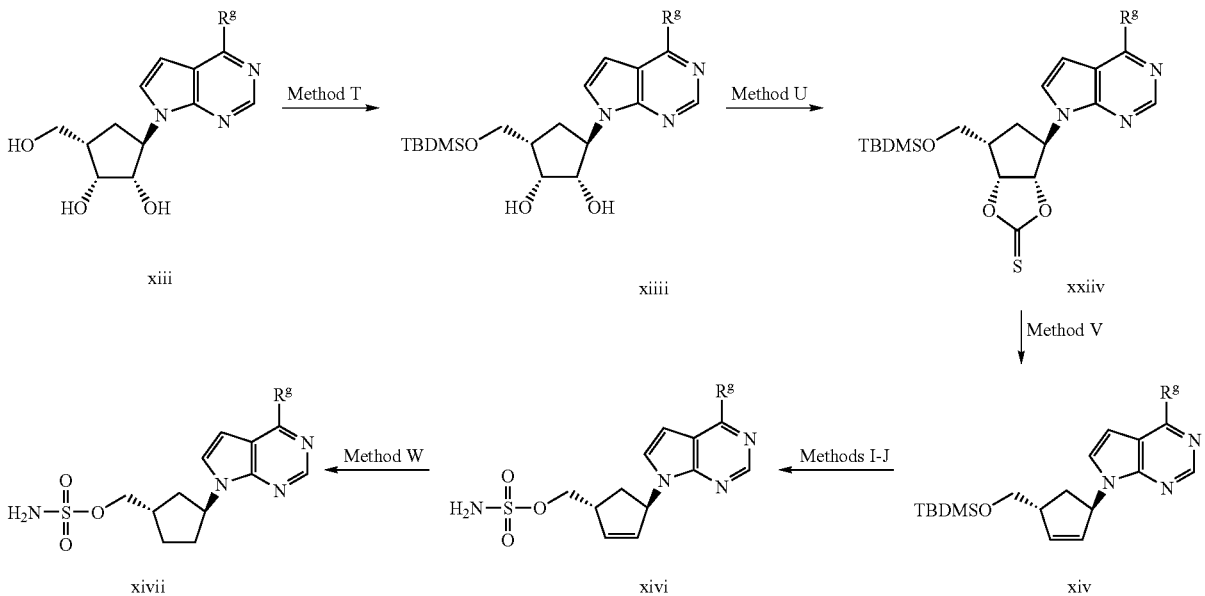

Compounds of formula (I) wherein $R^a$ and $R^c$ together form a bond, and compounds of formula (I) wherein each of $R^a$-$R^d$ is hydrogen, can be prepared as outlined in Scheme 7. Triols of formula xlii are prepared following the procedure in Scheme 5. The primary alcohol is selectively protected to give the diols of formula xliii (Method T), which are then alkylated by 1,1'-thiocarbonyldiimidazole in a suitable solvent, such as DMF, to yield dioxole-thiones xliv (Method U). Treatment with 1,3-dimethyl-2-phenyl-1,3,2-diazaphospholidine in an appropriate solvent, such as THF, affords alkenes of formula xlv (Method V), which are exposed to the conditions outlined in Methods I-J to afford sulfamates xlvi. Hydrogenation under an atmosphere of hydrogen in the presence of a catalyst, such as palladium on carbon, in EtOAc gives saturated sulfamates of formula xlvii (Method W).

Scheme 8: Synthesis of 5-fluoro pyrrolo[2,3-d]pyrimidines

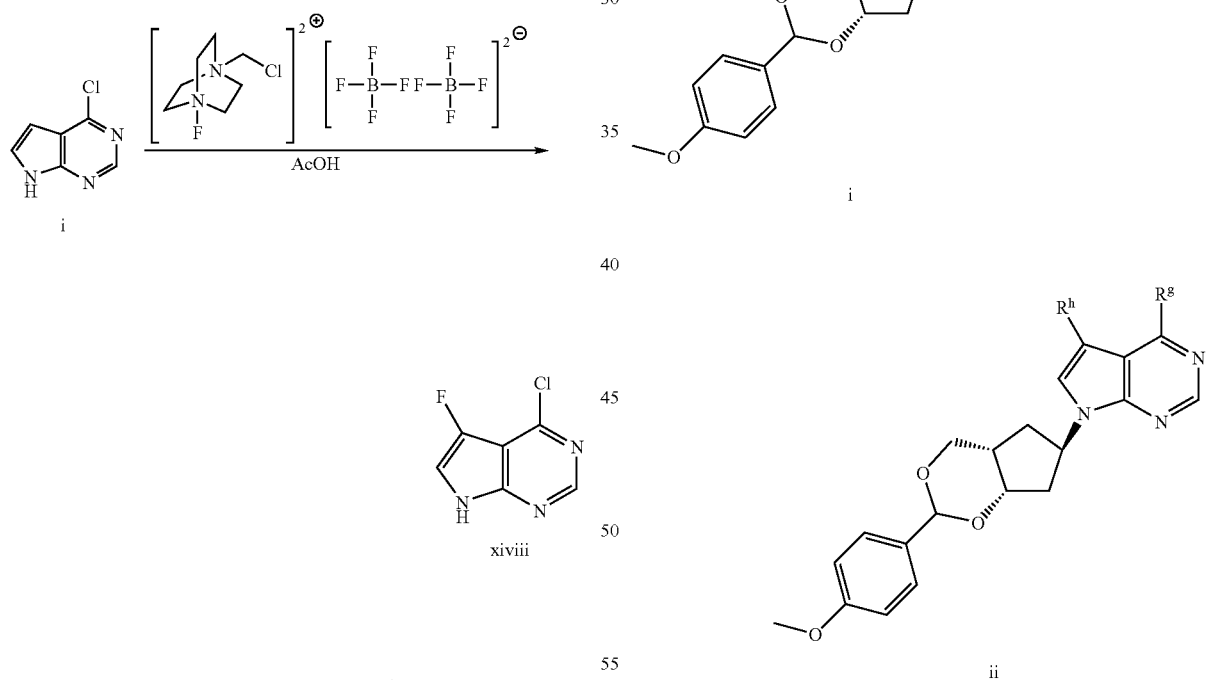

Compounds of formula (I) wherein $R^k$ is other than hydrogen are prepared as outlined in Schemes 8-9. Conversion of i to fluoro chloro pyrrolopyrimidine xlvii is effected by treatment with Selectfluor™ (1-chloromethyl-4-fluoro-1,4-diazoniabicyclo[2.2.2]octane bis(tetrafluoroborate)) and AcOH in AcCN. Compound xlviii is then substituted with the appropriate substituents according to Methods A-C and carried on to compounds of formula (I) according to Scheme 1.

Scheme 9: Alternate route to of 4,5-disubstituted ((1S,2S,4R)-2-hydroxy-4-{7H-pyrrolo-[2,3-d]pyrimidin-7-yl}cyclopentyl)methyl sulfamates

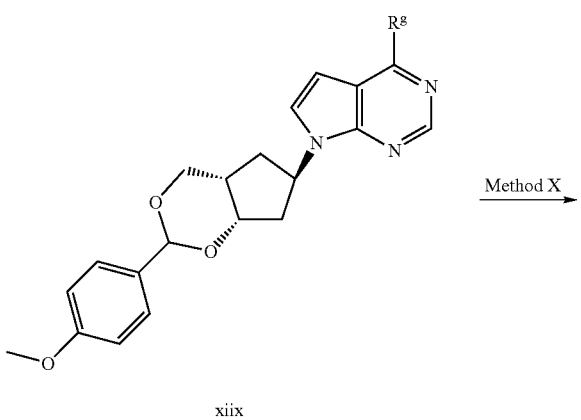

Compounds of formula xlix are prepared as shown in Scheme 1, and are converted to iodide 1 by treatment with NIS (Method X). Iodide 1 can be converted to compounds of formula li using a variety of palladium-catalyzed coupling conditions, such as Sonagashira coupling (CuI, PdCl$_2$(PPh$_3$)$_2$, DIPEA, $R^i$C≡CH, Method Y). Following the methods shown in Scheme 1, compounds of formula li are converted to final compounds of formula (I).

Scheme 10: Synthesis of ((2S,3S,4R,5R)-5-(4-(alkylamino)-7H-pyrrolo[2,3]pyrimidin-7-yl)-3,4-dihydroxy-tetrahydrofuran-2-yl)methyl sulfamates

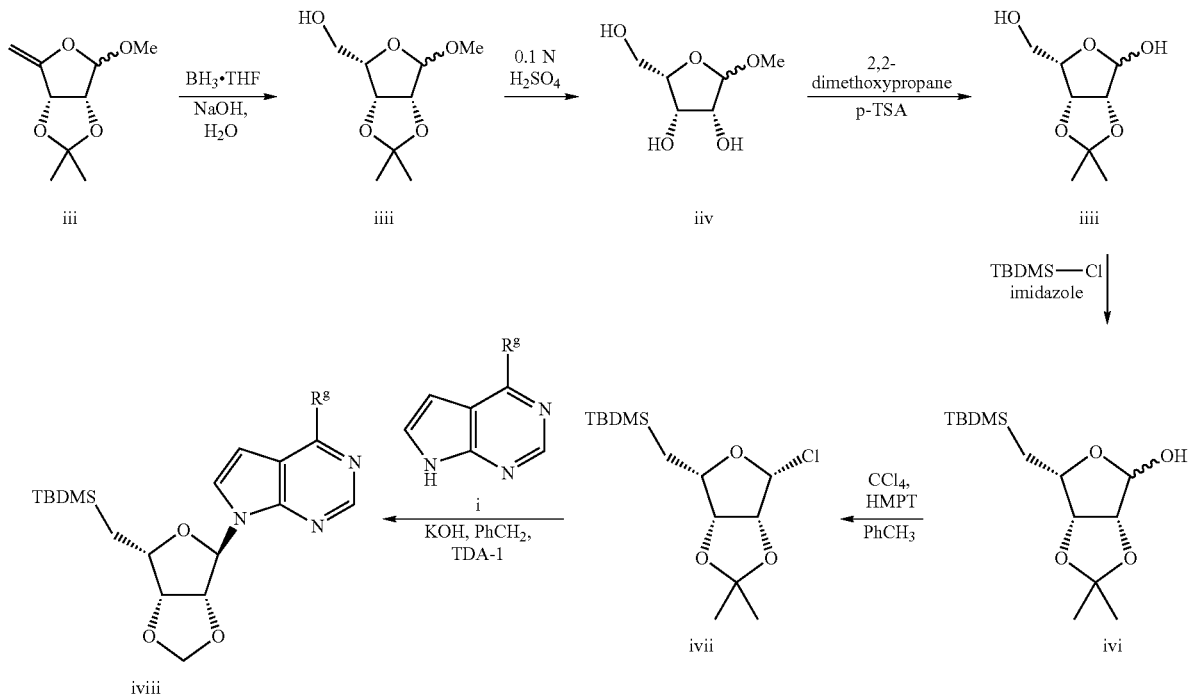

Compounds of formula (I) wherein Y is —O— can be prepared from compounds lviii. The synthesis of compounds of formula lviii is reported in the literature (Ugarkar, B. G.; Castellino, A. J.; DaRe, J. S.; Ramirez-Weinhouse, M.; Kopcho, J. J.; Rosengren, S.; Erion, M. D., *J. Med. Chem.*, 2003, 46, 4750-4760), and is outlined in Scheme 10. Methods for the conversion of D-ribose to lii are known (Inokawa, S.; Kitagawa, H.; Seo, K.; Yoshida, H.; Ogata, T., *Carbohydr. Hydr. Res.*, 1973, 30, 127-132). Hydroboration-oxidation using borane-THF complex affords liii, which is globally deprotected using sulfuric acid. Tetraol liv is protected using 2,2-dimethoxypropane and subsequent protection of the primary alcohol using TBDMS-Cl gives alcohol lvi. Selective chlorination using CCl₄ and HMPT in toluene affords the single enantiomer lvii. Glycosylation using compounds of formula i gives intermediates of formula lviii, which can be further elaborated as described in Schemes 1, 2, and 6 above.

Scheme 11: Synthesis of 2-(((1S,2S,4R)-4-4-[(1S)-2,3-dihydro-1H-inden-1-ylamino]-7H-pyrrolo[2,3-d]pyrimidin-7-yl-2-hydroxycyclopentyl)ethanesulfonamide

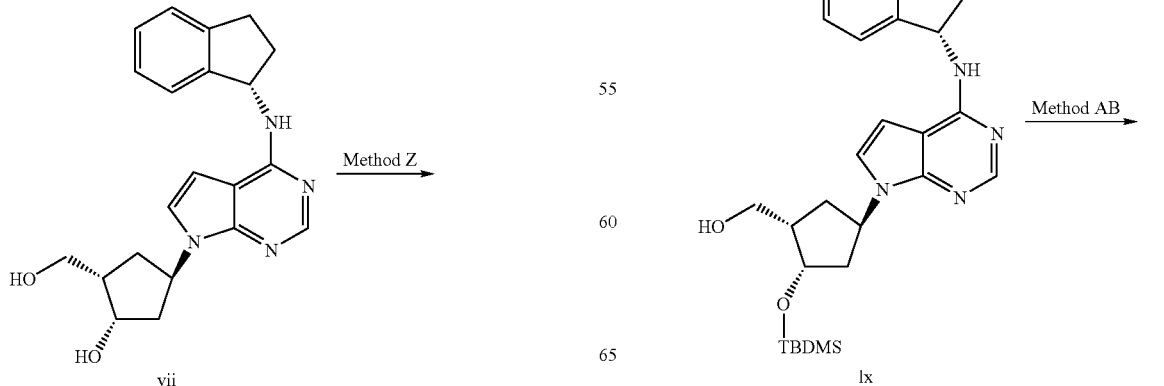

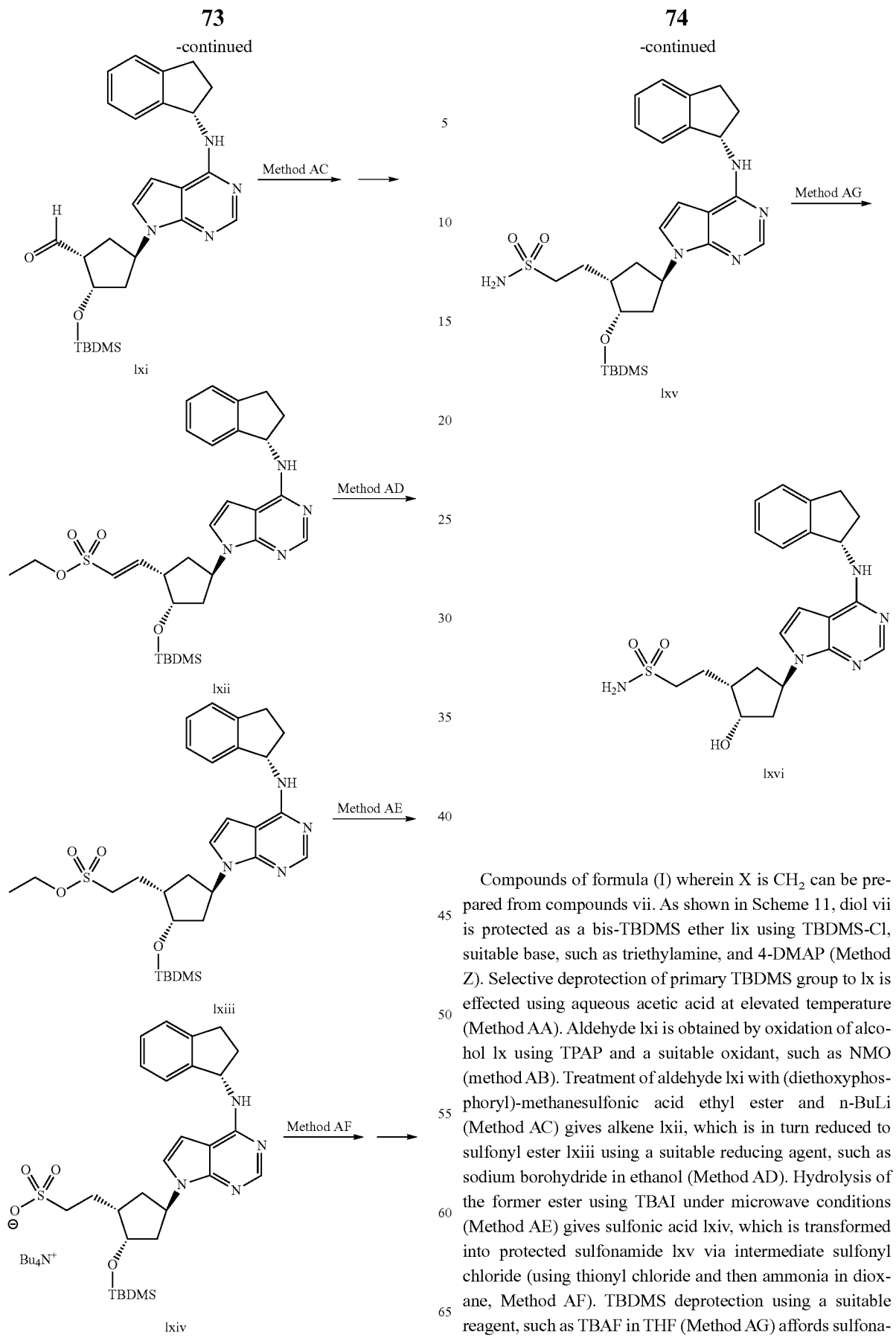

Compounds of formula (I) wherein X is CH$_2$ can be prepared from compounds vii. As shown in Scheme 11, diol vii is protected as a bis-TBDMS ether lix using TBDMS-Cl, suitable base, such as triethylamine, and 4-DMAP (Method Z). Selective deprotection of primary TBDMS group to lx is effected using aqueous acetic acid at elevated temperature (Method AA). Aldehyde lxi is obtained by oxidation of alcohol lx using TPAP and a suitable oxidant, such as NMO (method AB). Treatment of aldehyde lxi with (diethoxyphosphoryl)-methanesulfonic acid ethyl ester and n-BuLi (Method AC) gives alkene lxii, which is in turn reduced to sulfonyl ester lxiii using a suitable reducing agent, such as sodium borohydride in ethanol (Method AD). Hydrolysis of the former ester using TBAI under microwave conditions (Method AE) gives sulfonic acid lxiv, which is transformed into protected sulfonamide lxv via intermediate sulfonyl chloride (using thionyl chloride and then ammonia in dioxane, Method AF). TBDMS deprotection using a suitable reagent, such as TBAF in THF (Method AG) affords sulfonamide lxvi.

Scheme 12: Synthesis of (E)-2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethylenesulfonamide

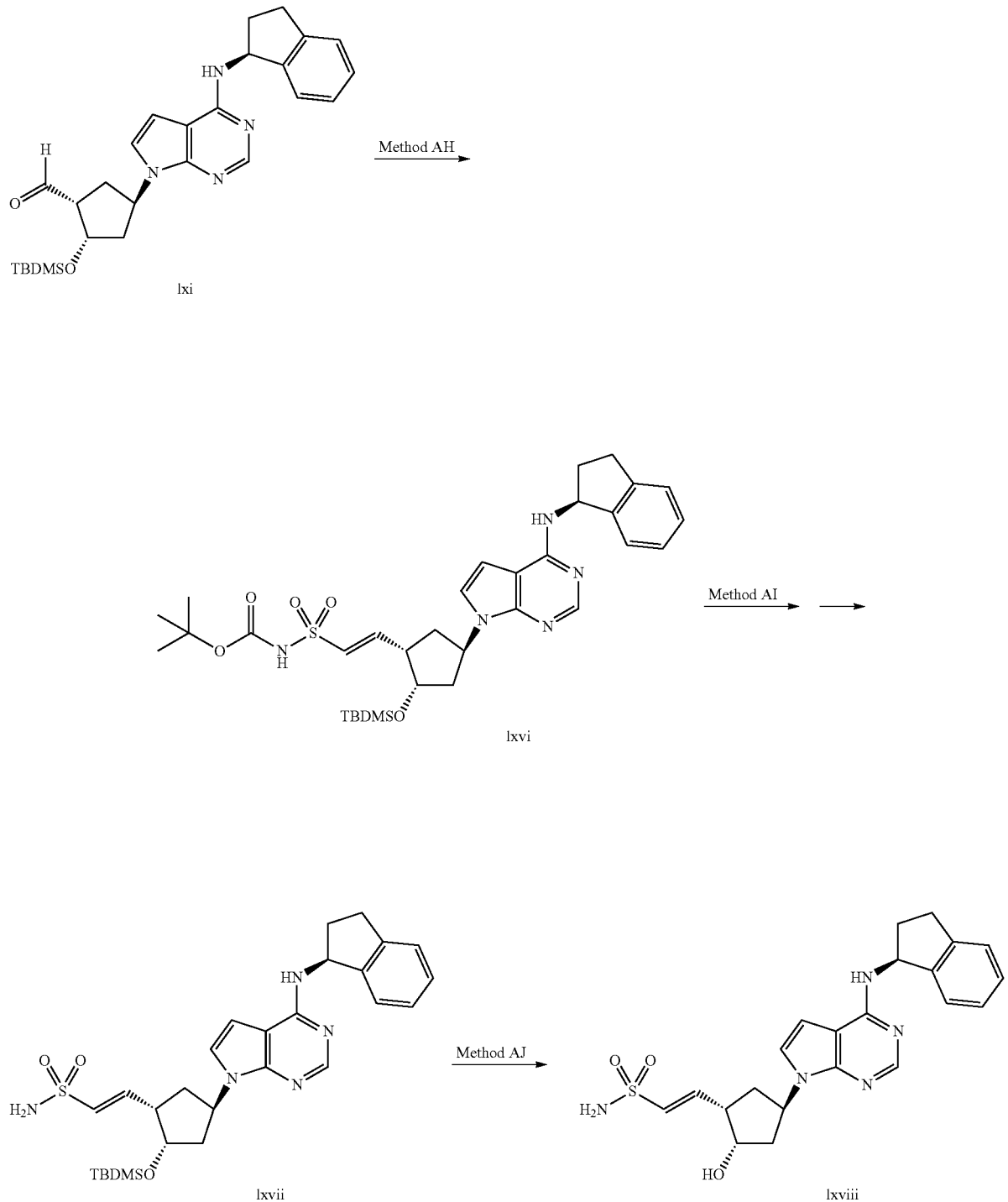

Compounds of formula (I) wherein X is —CH= can be prepared from compounds lxi. As shown in Scheme 12, tert-butyl{[(diphenylphosphoryl)methyl]sulfonyl}carbamate is treated with n-BuLi and the formed reagent is mixed with aldehyde lxi (Method AH) to give protected vinyl sulfonamide lxvi. The Boc group is deprotected using a suitable Lewis acid, such as ZnBr$_2$ (Method AI) to afford lxvii. The final deprotection of a TBDMS group is carried out using a suitable reagent, such as TBAF in THF (Method AJ) to give lxviii.

Scheme 13: General route to 4-substituted((1S,2S,4R)-2-hydroxy-4-{7H-pyrrolo[2,3-d]pyrimidin-7-yl}cyclopentyl)methyl sulfonamide

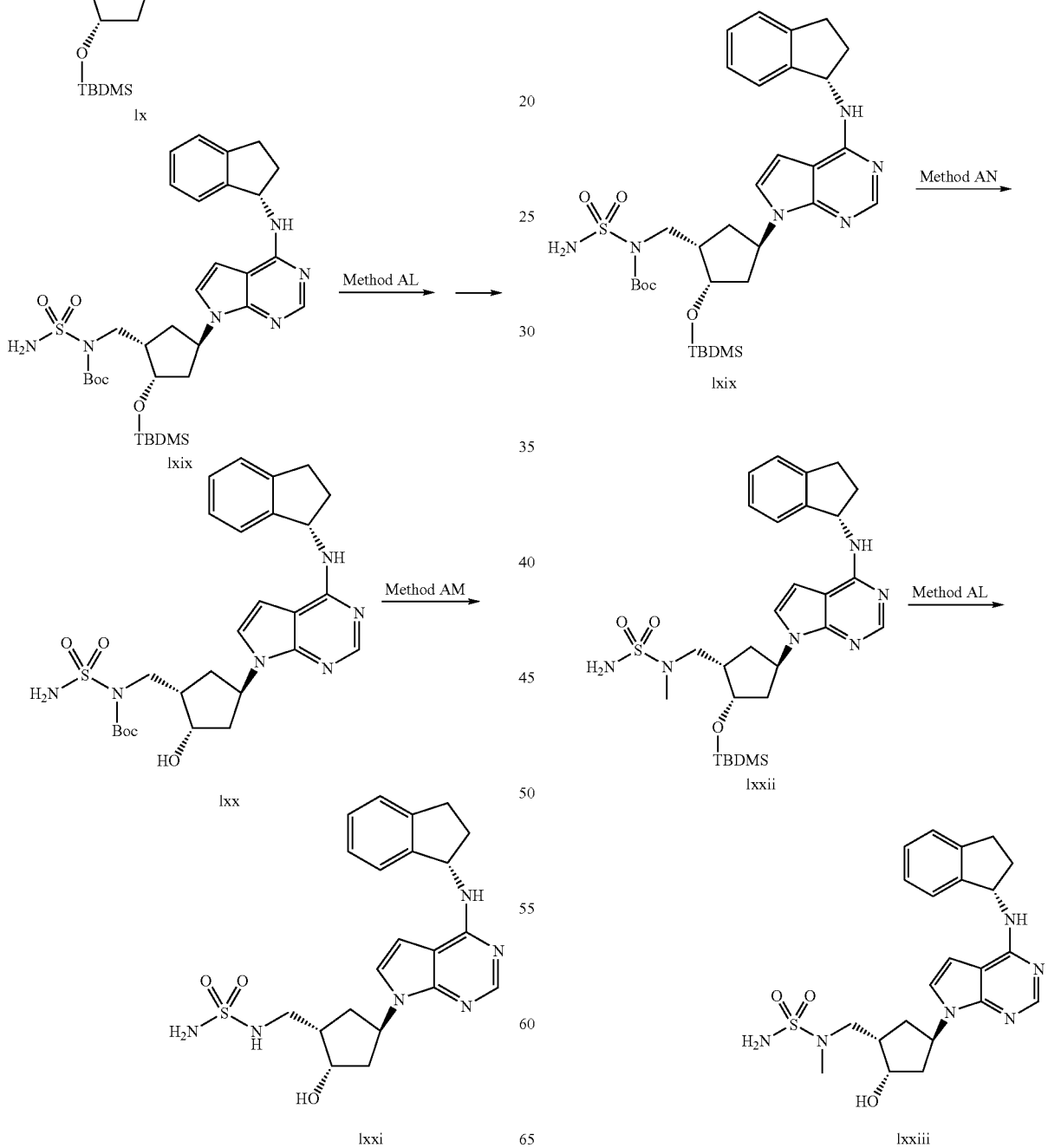

Compounds of formula (I) wherein X is NH can be prepared from compounds lx. As shown in Scheme 13, alcohol lx is treated with N-Boc-sulfonamide under Mitsunobu conditions, such as triphenylphosphine and DEAD in ethyl acetate under elevated temperature to afford protected sulfamide lxix (Method AK). The TBDMS group is deprotected using a suitable acid, such as aqueous HCl (Method AL) to afford lxx. The final deprotection of a Boc group is carried out using a suitable reagent, such as TFA in methylene chloride (Method AM) to give lxxi.

Scheme 14: General route to 4-substituted ((1S,2S,4R)-2-hydroxy-4-{7H-pyrrolo[2,3-d]-pyrimidin-7-yl}cyclopentyl)methylsulfamides Compounds of formula (I) wherein X is —N(CH₃)— can be prepared from compounds lxix. As shown in Scheme 14, sulfamide lxix is reduced with a suitable agent, such as LiAlH₄ in THF under elevated temperature to afford protected N-methyl sulfamide lxxii (Method AN). The TBDMS group is deprotected using a suitable acid, such as aqueous HCl (Method AL) to afford lxxiii.

Scheme 15: Synthesis of ((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)methyl methanesulonate

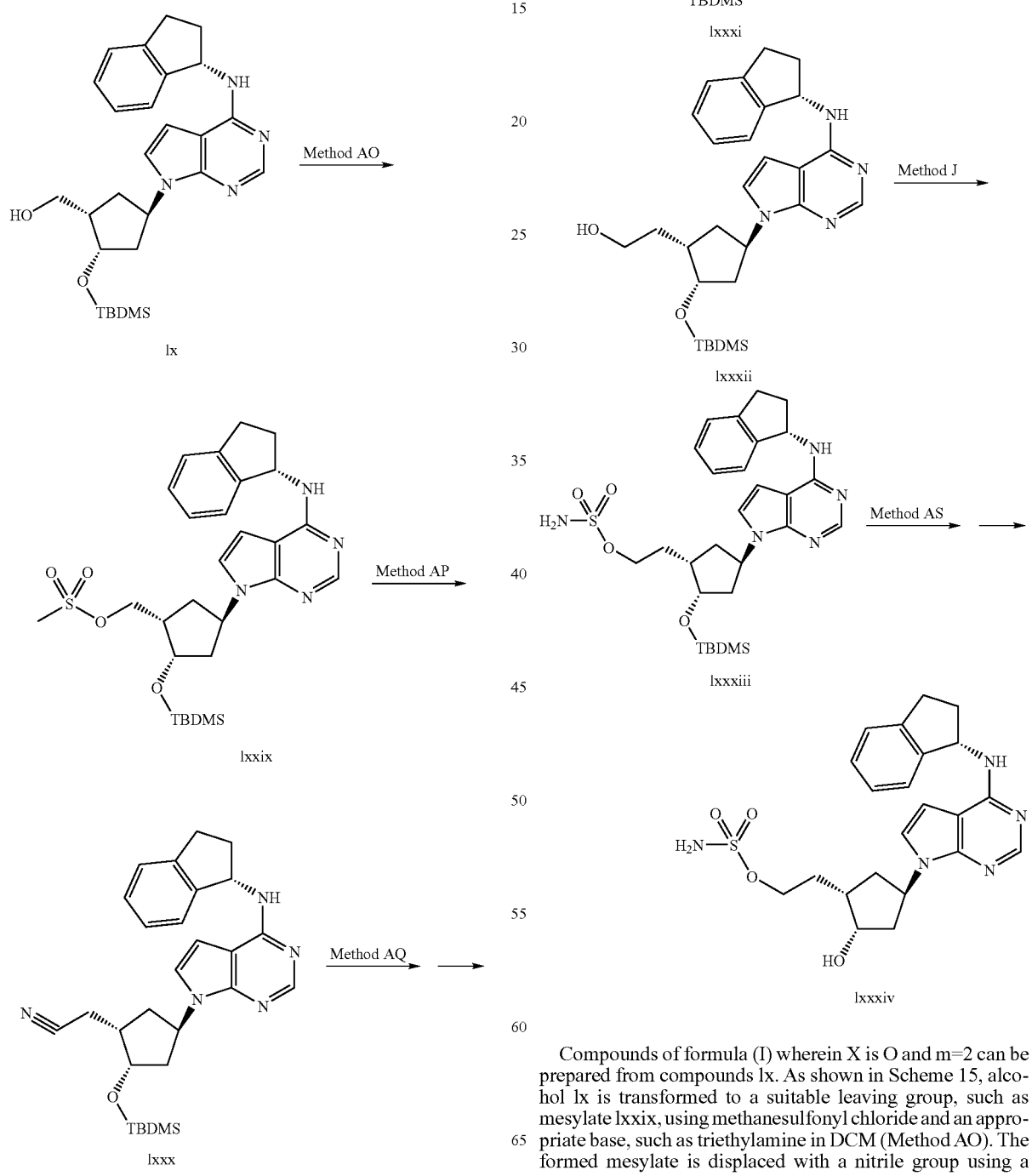

Compounds of formula (I) wherein X is O and m=2 can be prepared from compounds lx. As shown in Scheme 15, alcohol lx is transformed to a suitable leaving group, such as mesylate lxxix, using methanesulfonyl chloride and an appropriate base, such as triethylamine in DCM (Method AO). The formed mesylate is displaced with a nitrile group using a suitable nucleophile, such as sodium cyanide in DMSO under elevated temperature (Method AP) to afford nitrile lxxx, which is reduced to aldehyde lxxxi using a suitable reducing agent, such as DIBAL in DCM (Method AQ). Further reduction of lxxxi using a suitable reagent, such as sodium tetrahydroborate in methanol affords alcohol lxxxii (Method AR). Treatment of lxxxii with a sulfamating reagent, such as chlorosulfonamide in acetonitrile in a presence of an appropriate base, such as triethylamine affords protected sulfamate lxxxiii (Method J). TBDMS removal by treatment with an acid, such as HF.pyridine, in pyridine/THF according to Method AS yields compounds of formula lxxxiv.

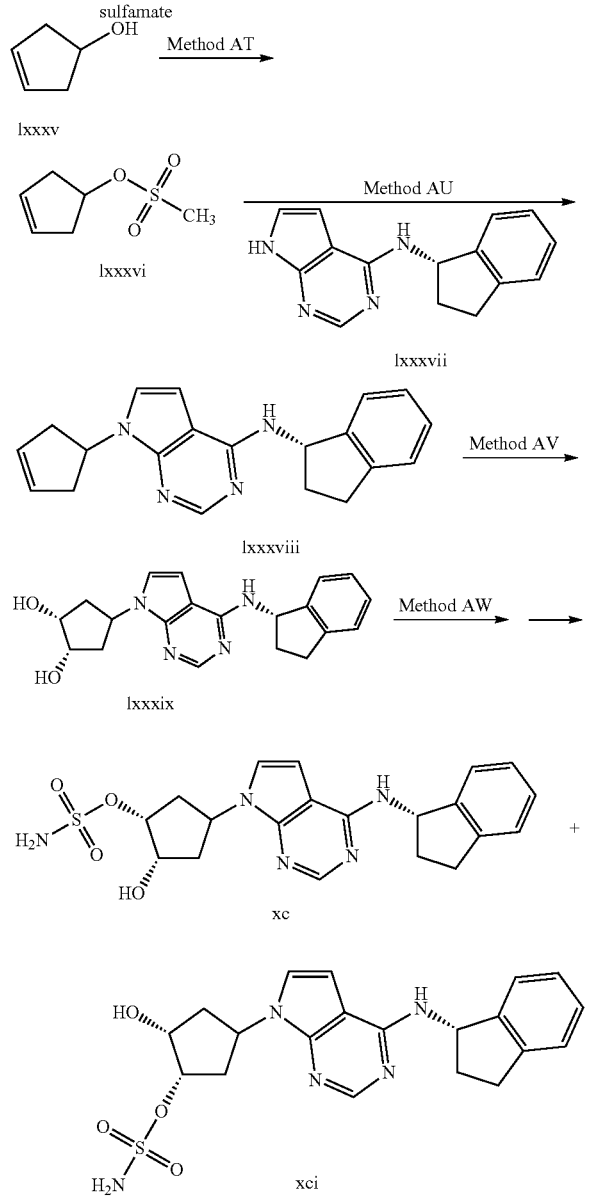

Compounds of formula (I) wherein X is O and m=0 can be prepared from 3-cyclopentene-1-ol (lxxxv). As shown in Scheme 16, alcohol lxxxv is activated by transformation to a suitable leaving group, such as mesylate lxxxvi using methanesulfonyl chloride and an appropriate base, such as pyridine and DMAP in DCM (Method AT). Treatment of mesylate lxxxvi with base lxxxvii in the presence of cesium carbonate in DMF under elevated temperature (Method AU) affords lxxxviii. Treatment of alkene lxxxviii with an appropriate chiral dihydroxylation agent, such as AD-mix-α (Sigma-Aldrich) in tert-butyl alcohol (Method AV) gives diol lxxxix, which upon sulfamation with chlorosulfonamide as described in Method J affords a diastereoisomeric mixture of sulfamates xc and xci (Method AW).

The invention further provides synthetic intermediates useful for the preparation of the compounds of formula (I). In one embodiment, the invention provides a compound of formula (IX):

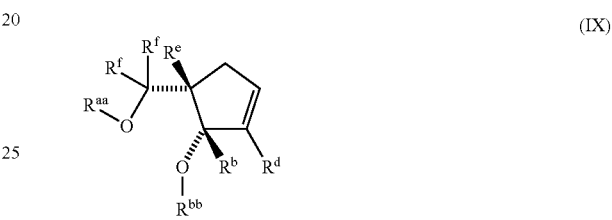

wherein:

depicted stereochemical configurations indicate absolute stereochemistry;

$R^b$ is fluoro, $C_{1-4}$ aliphatic, or $Cl_{1-4}$ fluoroaliphatic;

$R^a$ and $R^{bb}$ are each independently hydrogen or a hydroxyl protecting group, or $R^{aa}$ and $R^{bb}$ together form a cyclic diol protecting group; and the variables $R^d$, $R^e$, and $R^f$ have the values and preferred values described above for formula (I).

As used herein, the term "hydroxyl protecting group" refers to a chemical group that i) reacts with a hydroxyl functional group of a substrate to form a protected substrate; ii) is stable to reaction conditions to which the protected substrate will be subjected; and iii) is removable from a protected substrate to liberate the hydroxyl functional group under conditions that are compatible with other functionality present in the substrate. The hydroxyl groups of 1,2- and 1,3-diols may be individually protected or may be jointly protected with a cyclic diol protecting group. Examples of suitable hydroxyl protecting groups and diol protecting groups may be found in T. W. Greene and P. G. M. Wuts, "Protective Groups in Organic Synthesis", 3rd Ed., John Wiley & Sons Inc., NY (1999).

In a particular embodiment, the compound of formula (VIII) is represented by the formula:

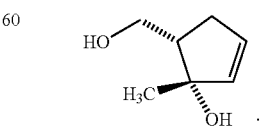

The invention also provides a compound of formula (X):

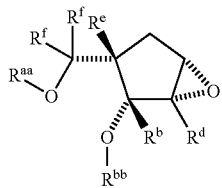
(X)

wherein:
depicted stereochemical configurations indicate absolute stereochemistry;
$R^{aa}$ is hydrogen or a hydroxyl protecting group; and
$R^{bb}$ is hydrogen or a hydroxyl protecting group; or
$R^{aa}$ and $R^{bb}$ together form a cyclic diol protecting group; and
the variables $R^b$, $R^d$, $R^e$, and $R^f$ have the values and preferred values described above for formula (I).

In one embodiment, the compound of formula (X) is characterized by formula (Xa):

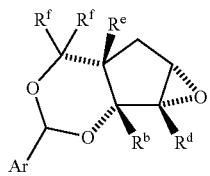
(Xa)

wherein Ar is an optionally substituted aryl group. In some embodiments, Ar is an optionally substituted phenyl group. In certain embodiments, Ar is para-methoxy-phenyl.

In certain particular embodiments, the compound of formula (Xa) is selected from the group consisting of:

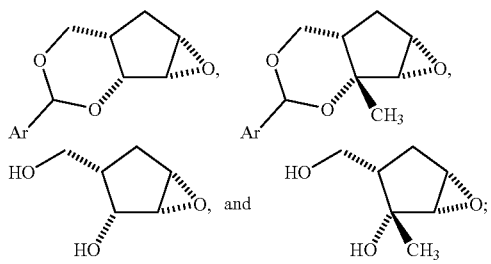

wherein Ar is as described above for formula (Xa).

The invention also provides a compound of formula (XI) or formula (XII):

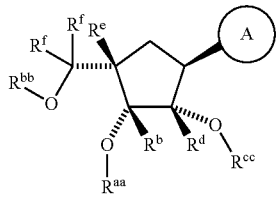
(XI)

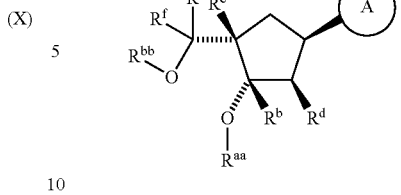
(XII)

wherein:
depicted stereochemical configurations indicate absolute stereochemistry;
$R^{aa}$ is hydrogen or a hydroxyl protecting group; and
$R^{bb}$ is hydrogen or a hydroxyl protecting group;
$R^{cc}$ is hydrogen or a hydroxyl protecting group; or
$R^{aa}$ and $R^{bb}$ together form a cyclic diol protecting group; or
$R^{aa}$ and $R^{cc}$ together form a cyclic diol protecting group; and
Ring A and the variables $R^b$, $R^d$, $R^e$, and $R^f$ have the values and preferred values described above for formula (I).

In some embodiments, the compound is characterized by formula (XIa) or (XIIa)

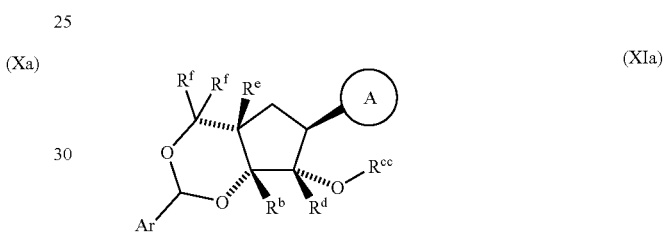
(XIa)

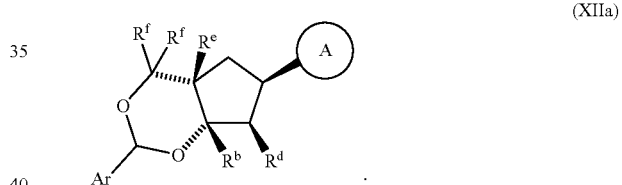
(XIIa)

In certain embodiments, the invention relates to a compound selected from the group consisting of:

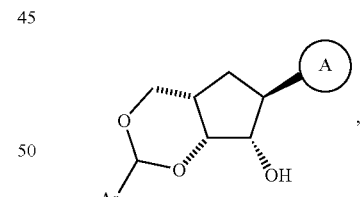

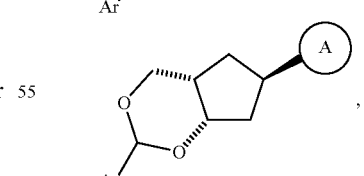

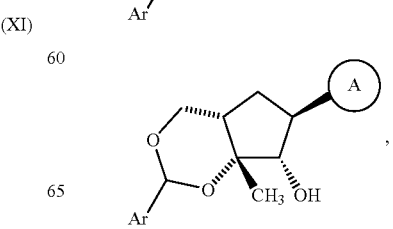

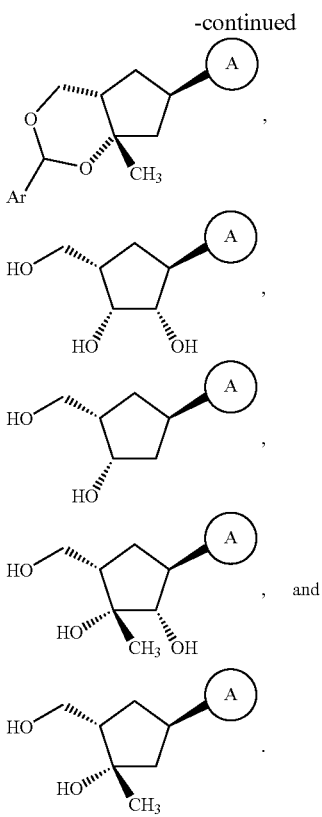

In certain other embodiments, the invention relates to a compound selected from the group consisting of:

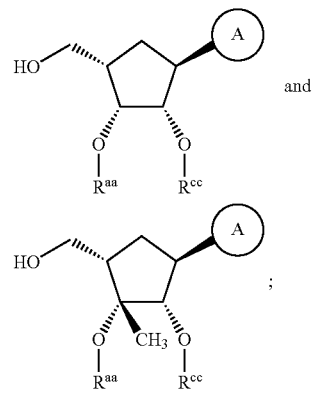

wherein $R^{aa}$ and $R^{cc}$ are each independently a hydroxyl protecting group, or $R^{aa}$ and $R^{cc}$ together form a cyclic diol protecting group.

In certain other embodiments, the invention relates to a compound selected from the group consisting of:

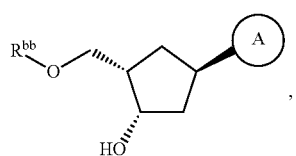

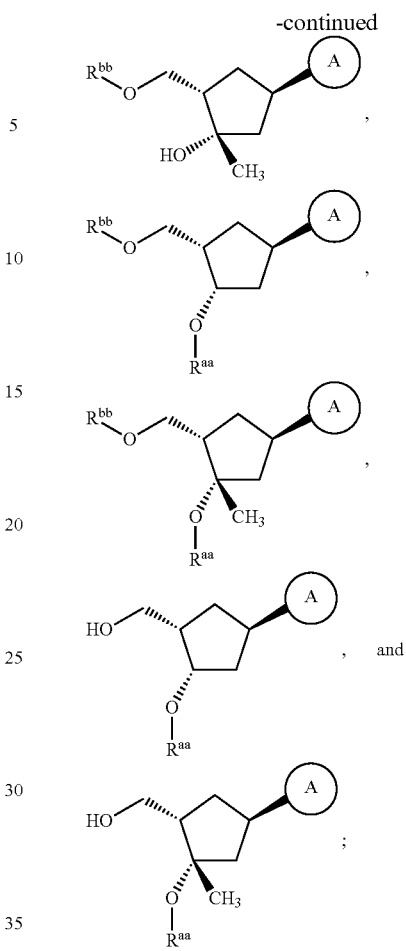

wherein $R^{aa}$ and $R^{bb}$ are each independently a hydroxyl protecting group. In some embodiments, $R^{aa}$ and $R^{bb}$ are selected so as to allow selective protection and deprotection. In certain embodiments, $R^{aa}$ is an acyl protecting group, and $R^{bb}$ is a silyl protecting group. In a particular embodiment, $R^{aa}$ is acetyl or substituted acetyl, and $R^{bb}$ is tert-butyl-dimethylsilyl or tert-butyldiphenylsilyl.

Uses of Compounds of the Invention

The compounds of this invention are useful inhibitors of E1 enzyme activity. In particular, the compounds are designed to be inhibitors of NAE, UAE, and/or SAE. Inhibitors are meant to include compounds which reduce the promoting effects of E1 enzymes in ubl conjugation to target proteins (e.g., reduction of ubiquitination, neddylation, sumoylation), reduce intracellular signaling mediated by ubl conjugation, and/or reduce proteolysis mediated by ubl conjugation (e.g., inhibition of cullin-dependent ubiquitination and proteolysis (e.g., the ubiquitin-proteasome pathway)). Thus, the compounds of this invention may be assayed for their ability to inhibit the E1 enzyme in vitro or in vivo, or in cells or animal models according to methods provided in further detail herein, or methods known in the art. The compounds may be assessed for their ability to bind or mediate E1 enzyme activity directly. Alternatively, the activity of compounds may be assessed through indirect cellular assays, or assays of downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates, sumoylated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are described below in the Experimental section and/or are known in the art.

One embodiment of this invention relates to a composition comprising a compound of this invention or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the present compounds, similar to the metabolically labile esters or carbamates, which are capable of producing the parent compounds described herein in vivo, are within the scope of this invention.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and Remington: The Science and Practice of Pharmacy, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

In some embodiments, the invention relates to an acid addition salt of a compound of formula I formed by protonation of a basic moiety in the molecule. In certain such embodiments, the invention relates to a hydrochloride salt of a compound of formula I.

In some other embodiments, the invention relates to a base addition salt of a compound of formula I formed by deprotonation of the sulfamate (X=O) moiety, the sulfamide (X=NH) moiety, or the sulfonamide (X=CH$_2$) moiety, as applicable. In some such embodiments, the invention relates to a sodium or potassium salt of a compound of formula I.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include, but are not limited to, ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as, but not limited to, an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes; e.g., to mask taste, to affect the site of dissolution or absorption, or to prolong drug action. Coatings may be applied to a tablet or to granulated particles for use in a capsule.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically; especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). Preferably, the composition is formulated for administration to a patient having or at risk of developing or experiencing a recurrence of the relevant disorder being treated. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of compound or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

One embodiment of the invention relates to a method of inhibiting or decreasing E1 enzyme activity in a sample comprising contacting the sample with a compound of this invention, or composition comprising a compound of the invention. The sample, as used herein, includes, without limitation, sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In another embodiment, the invention provides a method for treating a patient having a disorder, a symptom of a disorder, at risk of developing or experiencing a recurrence of a disorder, comprises administering to the patient a compound or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE, UAE activity).

For example, methods of the invention are useful in treatment of disorders involving cellular proliferation, including, but not limited to, disorders which require an effective cullin-dependent ubiquitination and proteolysis pathway (e.g., the ubiquitin proteasome pathway) for maintenance and/or progression of the disease state. The methods of the invention are useful in treatment of disorders mediated via proteins (e.g., NFκB activation, $p27^{Kip}$ activation, $p21^{WAF/CIP1}$ activation, p53 activation) which are regulated by E1 activity (e.g., NAE activity, UAE activity, SAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sidberlasts (RARS), (refractory anemia with excess blasts (RAEB), and RAEB in transformation (RAEB-T); and myeloproliferative syndromes.

In some embodiments, the compound or composition of the invention is used to treat a patient having or at risk of developing or experiencing a recurrence in a cancer selected from the group consisting of colorectal cancer, ovarian cancer, lung cancer, breast cancer, gastric cancer, prostate cancer, and pancreatic cancer. In certain preferred embodiments, the cancer is selected from the group consisting of lung cancer, colorectal cancer, ovarian cancer and a hematologic cancer.

Depending on the particular disorder or condition to be treated, in some embodiments, the E1 enzyme inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The E1 inhibitor of the invention may be administered with the other therapeutic agent in a single dosage form or as a separate dosage form. When administered as a separate dosage form, the other therapeutic agent may be administered prior to, at the same time as, or following administration of the E1 inhibitor of the invention.

In some embodiments, the E1 enzyme inhibitor of the invention is administered in conjunction with a therapeutic agent selected from the group consisting of cytotoxic agents, radiotherapy, and immunotherapy appropriate for treatment of proliferative disorders and cancer. Non-limiting examples of cytotoxic agents suitable for use in combination with the E1 enzyme inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs including, e.g., CC-5013 and CC-4047; protein tyrosine kinase inhibitors, including, e.g., imatinib mesylate and gefitinib; proteasome inhibitors, including, e.g., bortezomib; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

In order that this invention be more fully understood, the following preparative and testing examples are set forth. These examples are for the purpose of illustration only and are not to be construed as limiting the scope of the invention in any way.

EXAMPLES

Abbreviations

AA ammonium acetate
AcOH acetic acid
AcCN acetonitrile
AIBN 2,2'-azobisisobutyronitrile
Boc tert-butoxycarbonyl
DCM dichloromethane
DEAD diethyl azodicarboxylate
DIBAL diisobutylaluminum hydride
DIPEA N,N-diisopropylethylamine
DMAP N,N-dimethyl-4-aminopyridine
DMF dimethylformamide
EtOAc ethyl acetate
EtOH ethanol
FA formic acid
h hours
KO-t-Bu potassium tert-butoxide
LC/MS liquid chromatography mass spectrum
LiHMDS lithium bis(trimethylsilyl)amide
m-CPBA meta-chloroperbenzoic acid
MeOH methanol
$MgSO_4$ magnesium sulfate
min minutes
MS mass spectrum
MWI microwave irradiation
NIS N-iodosuccinimide
NMO N-methylmorpholine-N-oxide
rt room temperature
TBAF tetra-n-butylammonium fluoride
TBAI tetra-n-butylammonium iodide
TBDMS tert-butyldimethylsilyl
TFA trifluoroacetic acid
THF tetrahydrofuran
TPAP tetrapropylammonium perruthenate Analytical LC-MS Methods Spectra were run on a Phenominex Luna 5 μm C18 50×4.6 mm column on a Hewlett-Packard HP1100 at 2.5 mL/min for a 3 minute run using the following gradients:
Formic Acid Standard (FA Standard): Acetonitrile containing zero to 100 percent 0.1% formic acid in water.
Ammonium Acetate Standard (AA Standard): Acetonitrile containing zero to 100 percent 10 mM AA in water.

Example 1

((1S,2S,4R)-4-{4-[(1S)-2,3-Dihydro-1H-inden-1-ylamino]-7H-pyrrolo[2,3-d]-pyrimidin-7-yl}-2-hydroxycyclopentyl)methyl sulfamate (Compound I-35)

Step a: (1R,2R,3S,5S)-3-(Hydroxymethyl)-6-oxabicyclo[3.1.0]hexan-2-ol (1S,5S)-5-(Hydroxymethyl)cyclopent-2-en-1-ol (3.19 g, 27.9 mmol) was dissolved in DCM (143 mL) and the solution was cooled to 0° C. 3-Chloroperbenzoic acid (7.52 g, 33.5 mmol) was added and the mixture was stirred at rt for 4 h. TLC indicated complete conversion. Silica gel (20 g) was added, the mixture was concentrated to dryness and was purified via silica gel chromatography eluting with a gradient of 0 to 100% EtOAc in DCM to afford the title compound (2.75 g, 76%). LC/MS: $R_t$=0.37 min, $ES^+$ 131 (AA standard).

Step b: (1aS,1bR,5aS,6aS)-3-(4-Methoxyphenyl) hexahydrooxireno[4,5]cyclopenta[1,2-d]-[1,3]dioxine (1R,2R,3S,5S)-3-(Hydroxymethyl)-6-oxabicyclo[3.1.0] hexan-2-ol (3.65 g, 21.0 mol) was dissolved in DCM (121 mL) and the solution was cooled to 0° C. 1-(Dimethoxymethyl)-4-methoxybenzene (10.7 mL, 63.1 mmol) was added followed by pyridinium p-toluenesulfonate (530. mg, 2.11 mmol). The mixture was stirred at rt overnight. TLC indicated complete conversion. The reaction mixture was concentrated in vacuo and the residue was purified via silica gel chromatography eluting with a gradient of 0 to 50% EtOAc in hexanes to afford the title compound (4.10 g, 78%). LC/MS: $R_t$=1.68 min, ES+ 249 (AA standard).

Step c: N-[(1S)-2,3-Dihydro-1H-inden-1-yl]-7H-pyrrolo[2,3-d]pyrimidin-4-amine

4-Chloro-1H-pyrrolo[2,3-d]pyrimidine (2.10 g, 13.6 mmol) was dissolved in 1-butanol (60.0 mL) and N,N-diisopropylethylamine (3.57 mL, 20.5 mmol) was added followed by (S)-(+)-1-aminoindan (1.93 mL, 15.0 mmol). The mixture was heated to reflux for 60 h, cooled down to rt and the solvent was evaporated to dryness. The residue was purified via silica gel chromatography eluting with a gradient of 0 to 100% EtOAc in DCM to afford the title compound (2.72 g, 80%). LC/MS: $R_t$=1.42 min, ES+ 251 (AA standard).

Step d: (4aS,6R,7S,7aR)-6-{4-[(1S)-2,3-Dihydro-1H-inden-1-ylamino]-7H-pyrrolo[2,3-d]-pyrimidin-7-yl}-2-(4-methoxyphenyl)hexahydrocyclopenta[d][1,3]dioxin-7-ol N-[(1S)-2,3-Dihydro-1H-inden-1-yl]-7H-pyrrolo[2,3-d]pyrimidin-4-amine (3.70 g, 14.8 mmol) was dissolved in DMF (49.4 mL) under an atmosphere of nitrogen. Sodium hydride (546 mg, 13.6 mmol) was added and the suspension was stirred at 70° C. for 10 min to give a clear solution. (1aS,1bR,5aS,6aS)-3-(4-Methoxyphenyl)hexahydrooxireno[4,5]-cyclopenta[1,2-d][1,3]dioxine (2.82 g, 11.4 mmol) dissolved in DMF (35.3 mL) was added to the solution above and the reaction was stirred at 110° C. for 2 h. The reaction mixture was cooled down, quenched with saturated aqueous sodium chloride solution (30 mL), extracted with EtOAc (3×50 mL), dried with MgSO$_4$, filtered, and evaporated under high vacuum. The residue was purified via silica gel chromatography eluting with a gradient of 30 to 100% EtOAc in hexanes to afford the title compound (3.90 g, 69%). LC/MS: $R_t$=1.86 min, ES+ 500. (AA standard).

Step e: O-[(4aS,6R,7S,7aR)-6-{4-[(1S)-2,3-Dihydro-1H-inden-1-ylamino]-7H-pyrrolo-[2,3-d]pyrimidin-7-yl}-2-(4-methoxyphenyl)hexahydrocyclopenta[d][1,3]dioxin-7-yl] O-phenyl thiocarbonate (4aS,6R,7S,7aR)-6-{4-[(1S)-2,3-Dihydro-1H-inden-1-ylamino]-7H-pyrrolo-[2,3-d]pyrimidin-7-yl}-2-(4-methoxyphenyl)hexahydrocyclopenta[d][1,3]dioxin-7-ol (4.00 g, 8.02 mmol) was dissolved in DCM (169 mL) under an atmosphere of argon and 4-(dimethylamino)-pyridine (2.94 g, 24.1 mmol) was added followed by phenyl chlorothionocarbonate (2.22 mL, 16.0 mmol). The mixture was stirred at rt for 1 hour. The solvent was concentrated in vacuo and purified via silica gel chromatography eluting with a gradient of 20 to 100% EtOAc in hexanes on a column pre-treated with 1% TEA in hexanes to afford the title compound (5.00 g, 99%). LC/MS: $R_t$=2.34 min, ES+ 636 (AA standard).

Step f: N-[(1S)-2,3-Dihydro-1H-inden-1-yl]-7-[(4aS,6R,7aS)-2-(4-methoxyphenyl)-hexahydrocyclopenta[d][1,3]dioxin-6-yl]-7H-pyrrolo[2,3-d]pyrimidin-4-amine O-[(4aS,6R,7S,7aR)-6-{4-[(1S)-2,3-Dihydro-1H-inden-1-ylamino]-7H-pyrrolo-[2,3-d]pyrimidin-7-yl}-2-(4-methoxyphenyl)hexahydrocyclopenta[d][1,3]dioxin-7-yl] O-phenyl thiocarbonate (5.00 g, 7.88 mmol) was dissolved in toluene (150. mL) under an atmosphere of nitrogen and tri-n-butyltin hydride (4.24 mL, 15.8 mmol) was added followed by 2,2'-azo-bis-isobutyronitrile (259 mg, 1.58 mmol). The solution was heated to reflux for 30 min, the mixture was cooled down, the solvent was concentrated to 30 mL and the residue was purified via silica gel chromatography eluting with a gradient of 30 to 100% EtOAc in hexanes to afford the title compound (3.00 g, 79%). LC/MS: $R_t$=2.12 min, ES+ 483 (AA standard).

Step g: (1S,2S,4R)-4-{4-[(1S)-2,3-Dihydro-1H-inden-1-ylamino]-7H-pyrrolo[2,3-d]-pyrimidin-7-yl}-2-(hydroxymethyl)cyclopentanol N-[(1S)-2,3-Dihydro-1H-inden-1-yl]-7-[(4aS,6R,7aS)-2-(4-methoxyphenyl)-hexahydrocyclopenta[d][1,3]dioxin-6-yl]-7H-pyrrolo[2,3-d]pyrimidin-4-amine (3.00 g, 5.90 mmol) was dissolved in THF (11.6 mL), water (11.6 mL) and AcOH (34.9 mL, 614 mmol) were added. The mixture was stirred at rt under an atmosphere of argon for 60 h. The mixture was concentrated under reduced pressure and the residue was purified via silica gel chromatography eluting with a gradient of 0 to 10% MeOH in DCM to afford the title compound (2.10 g, 98%). LC/MS: $R_t$=1.46 min, ES+ 365 (AA standard).

Step h: (1S,2S,4R)-2-({[tert-Butyl(dimethyl)silyl]oxy}methyl)-4-{4-[(1S)-2,3-dihydro-1H-inden-1-ylamino]-7H-pyrrolo[2,3-d]pyrimidin-7-yl}cyclopentyl acetate (1S,2S,4R)-4-{4-[(1S)-2,3-Dihydro-1H-inden-1-ylamino]-7H-pyrrolo[2,3-d]-pyrimidin-7-yl}-2-(hydroxymethyl)cyclopentanol (3.00 g, 8.23 mmol), 1H-imidazole (1.68 g, 24.7 mmol) and 4-(dimethylamino)-pyridine (100 mg, 0.818 mmol) were dissolved in DMF (90.0 mL) under an atmosphere of argon and the solution was cooled to 0° C. tert-Butyldimethylsilyl chloride (1.24 g, 8.23 mmol) was added and the mixture was stirred at rt for 2 h. LC/MS indicated complete conversion. The reaction was quenched with saturated aqueous sodium chloride solution (30 mL), extracted with EtOAc (3×50 mL), dried with MgSO$_4$, filtered, and concentrated in vacuo. The remaining DMF was removed under high vacuum. Crude (1S,2S,4R)-2-({[tert-butyl(dimethyl)silyl]oxy}methyl)-4-{4-[(1S)-2,3-dihydro-1H-inden-1-ylamino]-7H-pyrrolo[2,3-d]pyrimidin-7-yl}cyclopentanol (3.94 g, 8.23 mmol) and 4-(dimethylamino)-pyridine (100. mg, 0.818 mol) were dissolved in pyridine (70.0 mL) and acetic anhydride (4.66 mL, 49.4 mmol) was added. The mixture was stirred at rt overnight. The solvent was evaporated and the remaining pyridine was removed under high vacuum. The residue was purified via silica gel chromatography eluting with a gradient of 10 to 66% EtOAc in hexanes to afford the title compound (3.66 g, 86%). LC/MS: $R_t$=2.51 min, ES+ 521 (AA standard).

Step i: (1S,2S,4R)-4-{4-[(1S)-2,3-Dihydro-1H-inden-1-ylamino]-7H-pyrrolo[2,3-d]-pyrimidin-7-yl}-2-(hydroxymethyl)cyclopentyl acetate (1S,2S,4R)-2-({[tert-Butyl(dimethyl)silyl]oxy}methyl)-4-{4-[(1S)-2,3-dihydro-1H-inden-1-ylamino]-7H-pyrrolo[2,3-d]pyrimidin-7-yl}cyclopentyl acetate (3.66 g, 7.03 mmol) was dissolved in THF (31.3 mL) and pyridine (31.3 mL, 387 mmol) in a polypropylene vial and the solution was cooled to 0° C. Pyridine hydrofluoride (8.61 mL, 95.6 mmol) was added dropwise and the mixture was stirred at rt for 1 hour. The resulting solution was added dropwise into a solution of saturated aqueous sodium bicarbonate (150 mL), extracted with EtOAc (3×50 mL), dried with MgSO₄, filtered, and concentrated in vacuo. The residue was purified via silica gel chromatography eluting with a gradient of 0 to 10% MeOH in DCM to afford the title compound (2.30 g, 80%). LC/MS: $R_t$=1.64 min, ES⁺ 407 (AA standard).

Step j: (1S,2S,4R)-2-{[(Aminosulfonyl)oxy]methyl}-4-{4-[(1S)-2,3-dihydro-1H-inden-1-ylamino]-7H-pyrrolo[2,3-d]pyrimidin-7-yl}cyclopentyl acetate A 2.00 M solution of chlorosulfonamide in AcCN was prepared as follows: FA (2.30 mL, 61.0 mmol) was added dropwise, with stirring to chlorosulfonyl isocyanate (5.20 mL, 59.7 mmol) under nitrogen at 0° C. After the addition was complete and the mixture had solidified, AcCN (22.5 mL) was added. The resulting solution was left to stand under a vented source of nitrogen overnight at rt.

(1S,2S,4R)-4-{4-[(1S)-2,3-Dihydro-1H-inden-1-ylamino]-7H-pyrrolo[2,3-d]-pyrimidin-7-yl}-2-(hydroxymethyl)cyclopentyl acetate (2.30 g, 5.38 mol) was dissolved in AcCN (108 mL) and TEA (3.75 mL, 26.9 mmol) was added. The solution was cooled to 0° C. and a 2.00 M solution of chlorosulfonamide in AcCN (5.38 mL, 10.8 mmol, as prepared above) was added. The mixture was stirred at rt for 45 min. TLC indicated 50% conversion. Additional 2.00 M chlorosulfonamide in AcCN solution (5.38 mL, 10.8 mmol) was added and the mixture was stirred at rt for 15 min. At this time, TLC indicated complete conversion. The mixture was quenched with MeOH (3.00 mL), and the solvent was removed in vacuo. The residue was purified via silica gel chromatography eluting with a gradient of 0 to 10% MeOH in EtOAc to afford the title compound (2.45 g, 94%). LC/MS: $R_t$=1.68 min, ES⁺ 486 (AA standard).

Step k: ((1S,2S,4R)-4-{4-[(1S)-2,3-Dihydro-1H-inden-1-ylamin]-7H-pyrrolo[2,3-d]-pyrimidin-7-yl}-2-hydroxycyclopentyl)methyl sulfamate (Compound I-35)

(1S,2S,4R)-2-{[(Aminosulfonyl)oxy]methyl}-4-{4-[(1S)-2,3-dihydro-1H-inden-1-ylamino]-7H-pyrrolo[2,3-d]pyrimidin-7-yl}cyclopentyl acetate (2.45 g, 4.54 mmol) was dissolved in a 7.00 M solution of ammonia in MeOH (108 mL) and the mixture was stirred at rt for 5 days. The solvent was removed in vacuo, re-dissolved in DCM and the filtered residue was purified via silica gel chromatography eluting with a gradient of 0 to 10% MeOH in DCM to afford the title compound (1.80 g, 90%). ¹H NMR (CD₃OD, 400 MHz, δ): 8.16 (s, 1H), 7.26-7.12 (m, 5H), 6.63 (d, J=3.6 Hz, 1H), 5.85 (dd, J=7.6, 7.6 Hz, 1H), 5.46-5.40 (m, 1H), 4.50-4.47 (m, 1H), 4.37 (d, J=7.6, 9.6 Hz, 1H), 4.19 (dd, J=7.4, 9.6 Hz, 1H), 3.08-3.02 (m, 1H), 2.96-2.87 (m, 1H), 2.85-2.75 (m, 1H), 2.67-2.59 (m, 1H), 2.37-2.20 (m, 3H), 2.07-1.97 (m, 2H) ppm. LC/MS: $R_t$=1.54 min, ES⁺ 444 (AA standard).

Step l: ((1S,2S,4R)-4-{4-[(1S)-2,3-Dihydro-1H-inden-1-ylamino]-7H-pyrrolo[2,3-d]pyrimidin-7-yl}-2-hydroxycyclopentyl)methyl sulfamate, Potassium salt ((1S,2S,4R)-4-{4-[(1S)-2,3-Dihydro-1H-inden-1-ylamino]-7H-pyrrolo[2,3-d]-pyrimidin-7-yl}-2-hydroxycyclopentyl)methyl sulfamate (2.64 g, 5.66 mmol) was dissolved in MeOH (43.0 mL) and a 1.002 M solution of potassium hydroxide in water (5.64 mL, 5.65 mmol) was added at rt and the mixture was stirred for 1 hour. The solvent was removed in vacuo and the solid residue was dried under high vacuum to afford the title compound (2.87 g, 100%). ¹H NMR (CD₃OD, 300 MHz, δ): 8.16 (s, 1H), 7.26-7.12 (m, 5H), 6.62 (d, J=3.9 Hz, 1H), 5.85 (dd, J=7.8, 7.8 Hz, 1H), 5.50-5.40 (m, 1H), 4.51-4.48 (m, 1H), 4.22 (dd, J=8.6, 10.0 Hz, 1H), 4.05 (dd, J=6.6, 10.0 Hz, 1H), 3.10-3.00 (m, 1H), 2.96-2.85 (m, 1H), 2.81-2.71 (m, 1H), 2.68-2.58 (m, 1H), 2.37-2.13 (m, 3H), 2.07-1.94 (m, 2H) ppm. LC/MS: $R_t$=1.54 min, ES⁺ 444 (AA standard).

Example 2

((1S,2S,4R)-4-{4-[(1R)-2,3-Dihydro-1H-inden-1-ylamino]-7H-pyrrolo[2,3-d]-pyrimidin-7-yl}-2-hydroxycyclopentyl)methyl sulfamate (Compound I-13)

Step a:
4-(Benzylsulfanyl)-7H-pyrrolo[2,3-d]pyrimidine

To a round bottomed flask with a stir bar was added 4-chloro-1H-pyrrolo-[2,3-d]pyrimidine (5.07 g, 33.0 mmol), 1.00 M of KO-t-Bu in THF (49.5 mL, 49.5 mmol), and benzenemethanethiol (5.81 mL, 49.5 mmol) in isopropyl alcohol (350 mL). The reaction mixture was heated to reflux at 85° C. under an atmosphere of nitrogen. After 48 h, the reaction mixture was cooled and solvent was removed in vacuo. To the residue was added water (300 mL) and the solution was filtered to collect the resulting white solid. The solid was washed with diethyl ether and MeOH and dried under vacuum to afford the product as a white solid (6.29 g, 79% yield). LC/MS: $R_t$=1.68 min, ES⁺ 242 (FA standard). Reference: Pathak, A. K., Pathak, V., Seitz, L. E., Suling, W. J., Reynolds, R. C. *J. Med. Chem.*, 2004, 47, 273-276.

Step b: (4aS,6R,7S,7aR)-6-[4-(Benzylsulfanyl)-7H-pyrrolo[2,3-d]pyrimidin-7-yl]-2-(4-methoxyphenyl)hexahydrocyclopenta[d][1,3]dioxin-7-ol A round-bottomed flask under an atmosphere of argon was charged with 4-(benzylsulfanyl)-7H-pyrrolo[2,3-d]pyrimidine (194 mg, 0.804 mmol), and DMF (5.00 mL) followed by a 1.00 M solution of lithium hexamethyldisilazide in THF (0.603 mL, 0.603 mmol). The reaction mixture was heated to 60° C. After 10 min, (1aS,1bR,5aS,6aS)-3-(4-methoxyphenyl)hexahydrooxireno[4,5]cyclopenta[1,2-d][1,3]dioxine (100. mg, 0.403 mmol, as prepared in Example 1a-b) in DMF (2.00 mL) was added and the reaction was heated to 110° C. After 6 h, the reaction mixture was cooled to rt and saturated aqueous sodium chloride solution (50.0 mL) was added. The aqueous layer was washed with EtOAc (2×50 mL). The combined organic layers were washed with water (2×100 mL), dried over MgSO₄, filtered and concentrated in vacuo. Purification via silica gel chromatography eluting with a gradient of 0 to 100% EtOAc in hexanes afforded the title compound as a white solid (197 mg, 93%). LC/MS: $R_t$=2.07 min, ES⁺ 490. (FA standard).

Step c: O-[(4aS,6R,7S,7aR)-6-[4-(Benzylsulfanyl)-7H-pyrrolo[2,3-d]pyrimidin-7-yl]-2-(4-methoxyphenyl)hexahydrocyclopenta[d][1,3]dioxin-7-yl] O-phenyl thiocarbonate To a solution of (4aS,6R,7S,7aR)-6-[4-(benzylsulfanyl)-7H-pyrrolo[2,3-d]-pyrimidin-7-yl]-2-(4-methoxyphenyl)hexahydrocyclopenta[d][1,3]dioxin-7-ol (990. mg, 2.02 mmol) in DCM (57.0 mL) was added 4-(dimethylamino)pyridine (748 mg, 6.07 mmol) and phenyl chlorothionocarbonate (0.565 mL, 4.04 mol) under an atmosphere of nitrogen and the yellow reaction was stirred at rt. After 12 h, the dark yellow solution was purified via silica gel chromatography eluting with 10% EtOAc in hexanes, and then 10% MeOH in DCM on a column pre-treated with 1% TEA in hexanes to afford the title compound as a yellow oil (1.77 g, 97%). LC/MS: $R_t$=2.47 min, $ES^+$ 626 (FA standard).

Step d: 4-(Benzylsulfanyl)-7-[(4aS,6R,7aS)-2-(4-methoxyphenyl)hexahydrocyclopenta[d]-[1,3]dioxin-6-yl]-7H-pyrrolo[2,3-d]pyrimidine To a solution of O-[(4aS,6R,7S,7aR)-6-[4-(benzylsulfanyl)-7H-pyrrolo[2,3-d]-pyrimidin-7-yl]-2-(4-methoxyphenyl)hexahydrocyclopenta[d][1,3]dioxin-7-yl] O-phenyl thiocarbonate (1.77 g, 1.98 mmol) in toluene (91.0 mL) was added 2,2'-azo-bis-isobutyronitrile (67.7 mg, 0.404 mmol) and tri-n-butyltin hydride (1.11 mL, 4.00 mmol) under an atmosphere of nitrogen. The yellow solution was heated to reflux at 140° C. After 2 h, the reaction mixture was cooled, silica gel was added, and the solvent was removed in vacuo. Silica gel chromatography eluting with a gradient of 0 to 100% EtOAc in hexanes afforded the title compound as a semi-solid (800 mg, 85%). LC/MS: $R_t$=2.38 min, $ES^+$ 475 (FA standard).

Step e: 4-(Benzylsulfonyl)-7-[(4aS,6R,7aS)-2-(4-methoxyphenyl)hexahydrocyclopenta[d]-[1,3]dioxin-6-yl]-7H-pyrrolo[2,3-d]pyrimidine To a round bottomed flask with a stir bar was added (benzylsulfanyl)-7-[(4aS,6R,7aS)-2-(4-methoxyphenyl)hexahydrocyclopenta[d][1,3]dioxin-6-yl]-7H-pyrrolo-[2,3-d]pyrimidine (693 mg, 1.32 mmol) and DCM (32.5 mL). Sodium bicarbonate (400 mg, 4.76 mmol) was added followed by 3-chloroperbenzoic acid (754 mg, 3.36 mol) and the reaction mixture was stirred for 12 h. The reaction mixture was then treated with saturated aqueous sodium bicarbonate solution, extracted with DCM and the combined organic layers were dried over $MgSO_4$, filtered and concentrated in vacuo. Silica gel chromatography eluting with a gradient of 0 to 100% EtOAc in hexanes afforded the product as a white solid (219 mg, 32%). LC/MS: $R_t$=1.94 min, $ES^+$ 506 (FA standard).

Step f: N-[(1R)-2,3-Dihydro-1H-inden-1-yl]-7-[(4aS,6R,7aS)-2-(4-methoxyphenyl)-hexahydrocyclopenta[d][1,3]dioxin-6-yl]-7H-pyrrolo[2,3-d]pyrimidin-4-amine In a 0.5-2 mL microwave vial, 4-(benzylsulfonyl)-7-[(4aS,6R,7aS)-2-(4-methoxyphenyl)hexahydrocyclopenta[d][1,3]dioxin-6-yl]-7H-pyrrolo[2,3-d]pyrimidine (100 mg, 0.198 mmol), (R)-(−)-1-aminoindan (0.127 mL, 0.989 mmol), and DIPEA (0.172 mL, 0.989 mol) were dissolved in ethanol (1.22 mL). The vial was sealed and heated to 110° C. overnight. The solution was then concentrated in vacuo and the resulting material was purified via silica gel chromatography eluting with a gradient of 20 to 50% EtOAc in hexanes to afford the product as an orange oil (70.0 mg, 73%). LC/MS: $R_t$=1.42 min, $ES^+$ 483 (FA standard).

Step g: (1S2S,4R)-4-{4-[(1R)-2,3-Dihydro-1H-inden-1-ylamino]-7H-pyrrolo[2,3-d]-pyrimidin-7-yl}-2-(hydroxymethyl)cyclopentanol N-[(1R)-2,3-Dihydro-1H-inden-1-yl]-7-[(4aS,6R,7aS)-2-(4-methoxyphenyl)-hexahydrocyclopenta[d][1,3]dioxin-6-yl]-7H-pyrrolo[2,3-d]pyrimidin-4-amine (70.0 mg, 0.145 mmol) was added to a solution of AcOH (0.742 mL, 13.0 mmol), THF (0.235 mL) and water (0.261 mL). The solution was stirred at rt for 4 days before being concentrated in vacuo. Silica gel chromatography eluting with a gradient of 0 to 10% MeOH in DCM afforded the title compound (27.6 mg, 52%). LC/MS: $R_t$=0.94 min, $ES^+$ 365 (FA standard).

Step h: tert-Butyl(chlorosulfonyl)carbamate

To a stirred solution of chlorosulfonyl isocyanate (3.20 mL, 36.0 mmol) in benzene (15.0 mL) in a water bath at rt was added tert-butyl alcohol (3.50 mL, 36.2 mmol) dropwise via syringe under an atmosphere of nitrogen. After 2 h, the mixture was diluted with hexanes (30.0 mL) and the resulting white precipitate was filtered and washed with hexanes (3×20 mL). The collected solid was dried in a vacuum desiccator under house vacuum for 10 min to afford the title compound as a white solid (5.08 g, 65%). The product was stored under nitrogen in a freezer. $^1$H NMR (300 MHz, $CDCl_3$, δ): 8.44 (br s, 1H), 1.57 (s, 9H) ppm. LC/MS: $R_t$=0.939 min, $ES^+$ 215 (AA standard). Reference: F. Hirayama et al., *Biorg. Med. Chem.*, 2002, 10, 1509-1523.

Step i: tert-Butyl{[((1S,2S,4R)-4-{4-[(1R)-2,3-Dihydro-1H-inden-1-ylamino]-7H-pyrrolo-[2,3-d]pyrimidin-7-yl}-2-hydroxycyclopentyl)methoxy]sulfonyl}carbamate (1S,2S,4R)-4-{4-[(1R)-2,3-Dihydro-1H-inden-1-ylamino]-7H-pyrrolo[2,3-d]-pyrimidin-7-yl}-2-(hydroxymethyl)cyclopentanol (27.6 mg, 0.117 mmol) and 2,6-di-tert-butyl-4-methylpyridine (48.5 mg, 0.236 mmol) were suspended in AcCN (1.57 mL) and cooled to 0° C. tert-Butyl (chlorosulfonyl)carbamate was added and the mixture was allowed to warm to rt overnight. The reaction was quenched via addition of MeOH (1.00 mL) and concentrated in vacuo. Silica gel chromatography eluting with a gradient of 0 to 10% MeOH in DCM afforded the title compound (15.2 mg, 37%). LC/MS: $R_t$=1.29 min, $ES^+$ 544 (FA standard).

Step j: ((1S,2S,4R)-4-{4-[(1R)-2,3-Dihydro-1H-inden-1-ylamino]-7H-pyrrolo[2,3-d]-pyrimidin-7-yl)-2}-hydroxycyclopentyl)methyl sulfamate (Compound I-13)

tert-Butyl{[((1S,2S,4R)-4-{4-[(1R)-2,3-dihydro-1H-inden-1-ylamino]-7H-pyrrolo[2,3-d]pyrimidin-7-yl}-2-hydroxycyclopentyl)methoxy]sulfonyl}carbamate (31.0 mg, 0.0570 mmol) was dissolved in DCM (0.803 mL) and trifluoroacetic acid (0.803 mL, 10.4 mmol) was added. The solution was stirred at rt for 15 min before being concentrated in vacuo. The residue was taken up in MeOH (5.00 mL), treated with solid sodium bicarbonate (300 mg) and stirred for 10 min. Filtration and silica gel chromatography eluting with a gradient of 0 to 10% MeOH in DCM afforded the title compound (7.20 mg, 58%). $^1$H NMR (400 MHz, $CD_3OD$, δ): 8.17 (s, 1H), 7.27-7.14 (m, 5H), 6.64 (d, J=3.5 Hz, 1H), 5.86 (t, J=7.5 Hz, 1H), 5.49-5.42 (m, 1H), 4.51-4.48 (m, 1H), 4.38 (dd, J=7.5, 9.8 Hz, 1H), 4.21 (dd, J=7.3, 9.8 Hz, 1H), 3.10-3.03 (m, 1H), 2.97-2.88 (m, 1H), 2.86-2.76 (m, 1H), 2.68-2.60 (m, 1H), 2.37-2.21 (m, 3H), 2.08-1.97 (m, 2H) ppm. LC/MS: $R_t$=1.16 min, $ES^+$ 444 (FA standard).

Example 3

{(1S,2R,3S,4R)-2,3-Dihydroxy-4-[4-(phenylsulfanyl)-7H-pyrrolo[2,3-d]-pyrimidin-7-yl]cyclopentyl}methyl sulfamate (Compound 1-53)

Step a: 4-(Phenylsulfanyl)-7H-pyrrolo[2,3-d]pyrimidine

To a solution of 4-chloro-1H-pyrrolo[2,3-d]pyrimidine (1.69 g, 11.0 mmol) and TEA (4.60 mL, 33.0 mmol) in 1-butanol (25.0 mL) was added benzenethiol (3.39 mL, 33.0 mmol), and the mixture was refluxed at 140° C. overnight. The reaction was then cooled to rt and concentrated in vacuo. The off-white solid was purified by silica gel chromatography eluting with a gradient of 0 to 35% EtOAc in DCM to afford the product (2.29 g, 92%). LC/MS: $R_t$=1.55 min, ES$^+$ 228 (FA standard).

Step b: (4aS,6R,7S,7aR)-2-(4-Methoxyphenyl)-6-[4-(phenylsulfanyl)-1H-pyrrolo[3,2-c]-pyridin-1-yl]hexahydrocyclopenta[d][1,3]dioxin-7-ol A mixture of 4-(phenylsulfanyl)-7H-pyrrolo[2,3-d]pyrimidine (895 mg, 3.94 mmol) and NaH (148 mg, 3.69 mmol) in dry DMF (12.0 mL) was stirred at 60° C. for 10 min. Then (1aS,1bR,5aS,6aS)-3-(4-methoxyphenyl)hexahydrooxireno[4,5]cyclopenta[1,2-d][1,3]-dioxine (611 mg, 2.46 mmol) was added and the mixture was heated to 110° C. for 5 h. The reaction mixture was then cooled to rt, quenched with saturated aqueous sodium chloride solution and the solution was extracted twice with EtOAc. The combined organics were dried over sodium sulfate, filtered and concentrated in vacuo. The crude product mixture was purified by silica gel chromatography eluting with a gradient of 5 to 30% EtOAc in DCM to afford the title compound (96.5 mg, 8.24%). LC/MS: $R_t$=1.95 min, ES$^+$ 476 (FA standard).

Step c: (1S,2R,3S,5R)-3-(Hydroxymethyl)-5-[4-(phenylsulfanyl)-7H-pyrrolo[2,3-d]-pyrimidin-7-yl]cyclopentane-1,2-diol To a solution of AcOH (1.04 mL, 18.3 mmol), THF (0.330 mL), and water (0.366 mL) was added (4aS,6R,7S,7aR)-2-(4-methoxyphenyl)-6-[4-(phenylsulfanyl)-1H-pyrrolo[3,2-c]pyridin-1-yl]hexahydrocyclopenta[d][1,3]dioxin-7-ol (96.7 mg, 0.203 mmol). The reaction solution was stirred at rt for 48 h then concentrated in vacuo. The resulting oil was purified by silica gel chromatography eluting with a gradient of 60 to 100% EtOAc in hexanes to afford the title compound (32.0 mg, 44%). LC/MS: $R_t$=1.33 min, ES$^+$ 358 (FA standard).

Step d: {(3aR,4S,6R,6aS)-2,2-Dimethyl-6-[4-(phenylsulfanyl)-7H-pyrrolo[2,3-d]pyrimidin-7-yl]tetrahydro-3aH-cyclopenta[d][1,3]dioxol-4-yl}methanol (1S,2R,3S,5R)-3-(Hydroxymethyl)-5-[4-(phenylsulfanyl)-7H-pyrrolo[2,3-d]-pyrimidin-7-yl]cyclopentane-1,2-diol (320 mg, 0.0895 mmol), 2,2-dimethoxypropane (0.0549 mL, 0.446 mmol), and p-toluenesulfonic acid monohydrate (17.0 mg, 0.0895 mmol) were dissolved in acetone (2.20 mL) and stirred at rt overnight. Then the reaction was quenched with saturated sodium bicarbonate solution and approximately half the solvent was removed in vacuo. The resulting residue was diluted with water and extracted with DCM (3×). Combined organics were dried over sodium sulfate, filtered, and concentrated in vacuo to afford the title compound as a white foam (35.5 mg, 99%), which was used without further purification. LC/MS: $R_t$=1.72 min, ES$^+$ 389 (FA standard).

Step e: {(3aR,4R,6R,6aS)-2,2-Dimethyl-6-[4-(phenylsulfanyl-7H-pyrrolo[2,3-d]pyrimidin-7-yl]tetrahydro-3aH-cyclopenta[d][1,3]dioxol-4-yl}methyl sulfamate A solution of {(3aR,4S,6R,6aS)-2,2-dimethyl-6-[4-(phenylsulfanyl)-7H-pyrrolo[2,3-d]pyrimidin-7-yl]tetrahydro-3aH-cyclopenta[d][1,3]dioxol-4-yl}methanol (35.5 mg, 0.0893 mmol) and pyridine (0.0325 mL, 0.402 mmol) in dry DCM (1.00 mL) was cooled with an ice bath. To this solution was added a 2.00 M chlorosulfonamide solution in AcCN (0.178 mL, 0.356 mmol, as prepared in Example 1j) and the reaction was allowed to warm to rt and stirred for 4 h. The mixture was diluted with DCM, washed with water, and extracted with DCM (3×). Combined organics were dried over sodium sulfate, filtered, and concentrated in vacuo. The resulting oil was purified by silica gel chromatography eluting with a gradient of 50 to 70% EtOAc in hexanes to afford the title compound as a white solid (14.4 mg, 34%). LC/MS: $R_t$=1.81 min, ES$^+$ 477 (FA standard).

Step f: {(1R,2R,3S,4R)-2,3-Dihydroxy-4-[4-(phenylsulfanyl)-7H-pyrrolo[2,3-d]pyrimidin 7-yl]cyclopentyl}methyl sulfamate (Compound I-53)

{(3aR,4R,6R,6aS)-2,2-Dimethyl-6-[4-(phenylsulfanyl)-7H-pyrrolo[2,3-d]-pyrimidin-7-yl]tetrahydro-3aH-cyclopenta[d][1,3]dioxol-4-yl}methyl sulfamate (14.4 mg, 30.2 mmol) was stirred in 1.00 mL of 90% trifluoroacetic acid in water for 3 h at rt. The solvent was then removed in vacuo and the resulting oil was purified by silica gel chromatography eluting with a gradient of 60 to 100% EtOAc in hexanes to afford the title compound (7.50 mg, 57%). $^1$H NMR (400 MHz, CD$_3$OD, δ): 8.45 (s, 1H), 7.66-7.36 (m, 2H), 7.51-7.41 (m, 4H), 5.92 (d, J=3.8 Hz, 1H), 5.13-5.06 (m, 1H), 4.58-4.55 (dd, J=3.8, 9.0 Hz, 1H), 4.42-4.37 (dd, J=8.0, 9.8 Hz, 1H), 4.18-4.14 (m, 2H), 2.92-2.82 (m, 1H), 2.24-2.08 (m, 2H) ppm. LC/MS: $R_t$=1.38 min, ES$^+$ 437 (FA standard).

Example 4

[(1S,2S,4R)-2-Hydroxy-4-(4-{[(1R)-1-phenylethyl]amino}-7H-pyrrolo[2,3-d]-pyrimidin-7-yl)cyclopentyl]methyl sulfamate (Compound I-7)

The title compound was prepared following the procedure described in Example 1a-k using R-(+)-α-methylbenzylamine in step c. $^1$H NMR (400 MHz, CD$_3$OD, δ): 8.05 (s, 1H), 7.41-7.38 (m, 2H), 7.31-7.26 (m, 2H), 7.21-7.16 (m, 2H), 6.71 (d, J=3.5 Hz, 1H), 5.46-5.38 (m, 2H), 4.50-4.46 (m, 1H), 4.38-4.34 (dd, J=7.5, 9.8 Hz, 1H), 4.21-4.17 (dd, J=7.3, 9.8 Hz, 1H), 2.84-2.74 (m, 1H), 2.35-2.15 (m, 3H), 2.06-1.98 (m, 1H), 1.59 (d, J=6.8 Hz 3H) ppm. LC/MS: $R_t$=1.16 min, ES$^+$ 432 (FA standard).

Example 5

[(1S,2S,4R)-2-Hydroxy-4-(4-{methyl[(1S)-1-phenylethyl]amino}-7H-pyrrolo-[2,3-d]pyrimidin-7-yl)cyclopentyl]methyl sulfamate (Compound I-3)

The title compound was prepared following the procedure described in Example 1a-k using (S)-(−)-N,α-dimethylbenzylamine in step c. $^1$H NMR (CD$_3$OD, 300 MHz, δ): 8.16 (s, 1H), 7.34-7.20 (m, 6H), 6.64 (d, J=3.6 Hz, 1H), 6.41-6.34 (m, 1H), 5.54-5.43 (m, 1H), 4.51-4.48 (m, 1H), 4.24 (dd, J=9.6, 9.6 Hz, 1H), 4.07 (dd, J=6.9, 9.6 Hz, 1H), 3.03 (s, 3H), 2.80-2.70 (m, 1H), 2.37-2.14 (m, 3H), 2.02-1.88 (m, 1H), 1.64 (d, J=7.2 Hz, 3H), ppm. LC/MS: R$_t$=1.64 min, ES$^+$ 446 (AA standard).

Example 6

((1S,2S,4R)-4-{4-[(4S)-3,4-Dihydro-2H-chromen-4-ylamino]-7H-pyrrolo[2,3-d]-pyrimidin-7-yl}-2-hydroxycyclopentyl)methyl sulfamate (Compound I-12)

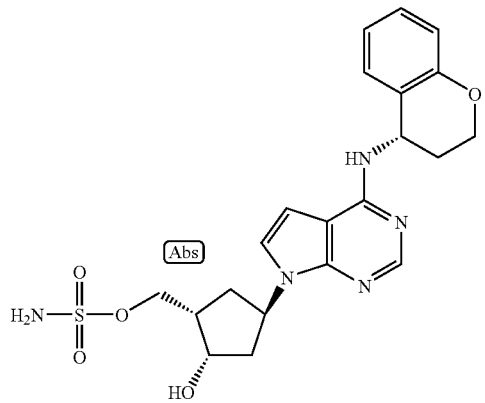

The title compound was prepared following the procedure described in Example 1a-k using (4S)-chroman-4-amine in step c. $^1$H NMR (CD$_3$OD, 400 MHz, δ): 8.28 (s, 1H), 7.43 (d, J=3.6 Hz, 1H), 7.27-7.20 (m, 2H), 6.94-6.85 (m, 3H), 5.56-5.48 (m, 1H), 5.34-5.30 (m, 1H), 4.54-4.49 (m, 1H), 4.38 (dd, J=7.4, 9.8 Hz, 1H), 4.33-4.29 (m, 2H), 4.21 (dd, J=7.6, 9.8 Hz, 1H), 2.90-2.80 (m, 1H), 2.39-2.05 (m, 6H) ppm. LC/MS: R$_t$=1.51 min, ES$^+$ 460 (AA standard).

Example 7

((1S,2S,4R)-4-{4-[(2,6-Difluorobenzyl)amino]-7H-pyrrolo[2,3-d]pyrimidin-7-yl}-2-hydroxycyclopentyl)methyl sulfamate (Compound I-15)

The title compound was prepared following the procedure described in Example 1a-k using (2,6-difluorophenyl)methanamine in step c. $^1$H NMR (CD$_3$OD, 300 MHz, δ): 8.17 (s, 1H), 7.39-7.29 (m, 1H), 7.16 (d, J=3.6 Hz, 1H), 7.00-6.94 (m, 2H), 6.60 (d, J=3.6 Hz, 1H), 5.48-5.37 (m, 1H), 4.80 (s, 2H), 4.50-4.46 (m, 1H), 4.36 (dd, J=7.6, 9.6 Hz, 1H), 4.19 (dd, J=7.2, 9.6 Hz, 1H), 2.85-2.72 (m, 1H), 2.36-2.00 (m, 4H) ppm. LC/MS: R$_t$=1.42 min, ES$^+$ 454 (AA standard).

Example 8

{(1S,2S,4R)-4-[4-(Benzylamino)-7H-pyrrolo[2,3-d]pyrimidin-7-yl]-2-hydroxycyclopentyl}methyl sulfamate (Compound I-49)

The title compound was prepared following the procedure described in Example 1a-k using benzylamine in step c. $^1$H NMR (CD$_3$OD, 400 MHz, δ): 8.12 (s, 1H), 7.36-7.20 (m, 6H), 6.62 (d, J=3.6 Hz, 1H), 5.49-5.40 (m, 1H), 4.76 (s, 2H), 4.50-4.48 (m, 1H), 4.37 (dd, J=7.6, 10.0 Hz, 1H), 4.20 (dd, J=7.6, 10.0 Hz, 1H), 2.85-2.76 (m, 1H), 2.36-2.19 (m, 3H), 2.08-2.00 (m, 1H) ppm. LC/MS: R$_t$=1.20 min, ES$^+$ 418 (FA standard).

Example 9

[(1S,2S,4R)-2-Hydroxy-4-(4-{[(1S)-1-phenylethyl]amino}-7H-pyrrolo[2,3-d]-pyrimidin-7-yl)cyclopentyl]methyl sulfamate (Compound I-4)

The title compound was prepared following the procedure described in Example 1a-k using (1S)-(−)-α-methylbenzylamine in step c. $^1$H NMR (400 MHz, CD$_3$OD, δ): 8.05 (s, 1H), 7.41-7.39 (d, J=7.6 Hz, 2H), 7.31-7.27 (m, 2H), 7.22-7.17 (m, 2H), 6.72 (d, =3.3 Hz, 1H), 5.46-5.38 (m, 2H), 4.48-4.47 (br s, 1H), 4.37 (dd, J=7.6, 9.6 Hz, 1H), 4.21-4.17 (m, 1H), 2.84-2.75 (m, 1H), 2.37-2.18 (m, 3H), 2.07-1.94 (m, 1H), 1.61-1.59 (d, J=7.0 Hz, 3H) ppm. LC/MS: R$_t$=1.50 min, ES$^+$ 432 (AA standard).

Example 10

((1S,2S,4R)-4-{4-[Benzyl(methyl)amino]-7H-pyrrolo[2,3-d]pyrimidin-7-yl}-2-hydroxycyclopentyl)methyl sulfamate (Compound I-10)

The title compound was prepared following the procedure described in Example 2a-j using N-methylbenzylamine in step f. $^1$H NMR (400 MHz, DMSO-d6, δ): 8.24 (s, 1H), 7.44-7.25 (m, 5H), 7.31-7.23 (m, 3H), 6.64 (br s, 1H), 5.49-5.37 (m, 1H), 5.04 (s, 2H), 4.37-4.30 (m, 1H), 4.23 (dd, J=7.0, 9.7 Hz, 1H), 4.04 (dd, J=8.0, 9.6 Hz, 1H), 3.35 (s, 3), 2.77-2.64 (m, 1H), 2.22-1.87 (m, 4H) ppm. LC/MS: R$_t$=1.51 min, ES$^+$ 432 (AA standard).

Example 11

((1S,2S,4R)-4-{4-[(2-Chlorobenzyl)amino]-7H-pyrrolo[2,3-d]pyrimidin-7-yl}-2-hydroxycyclopentyl)methyl sulfamate (Compound I-1)

The title compound was prepared following the procedure described in Example 2a-j using 2-chlorobenzylamine in step f. $^1$H NMR (400 MHz, DMSO-d6, δ): 8.10 (s, 1H), 8.03-7.94 (m, 1H), 7.48-7.42 (m, 1H), 7.38 (s, 1H), 7.36-7.24 (m, 4H), 6.65 (d, J=3.2 Hz, 1H), 5.36 (dt, J=8.9, 14.2 Hz, 1H), 4.89 (d, J=3.9 Hz, 1H), 4.76 (d, J=5.9 Hz, 2H), 4.36-4.30 (m, 1H), 4.24 (dd, J=7.0, 9.7 Hz, 1H), 4.05 (dd, J=8.1, 9.5 Hz, 1H), 2.77-2.66 (m, 1H), 2.24-2.02 (m, 3H), 1.99-1.89 (m, 1H) ppm. LC/MS: R$_t$=1.51 min, ES$^+$ 452 (AA standard).

Example 12

{(1S,2S,4R)-2-Hydroxy-4-[4-(methylamino)-7H-pyrrolo[2,3-d]pyrimidin-7-yl]-cyclopentyl}methyl sulfamate and ((1S,2S,4R)-4-{4-[(1S)-2,3-dihydro-1H-inden-1-yl(methyl)amino]-7H-pyrrolo[2,3-d]pyrimidin-7-yl}-2-hydroxycyclopentyl)methyl sulfamate (Compounds I-40 and I-6)

Step a:
tert-Butyl(1S)-2,3-dihydro-1H-inden-1-ylcarbamate

To a solution of (S)-(+)-1-aminoindan (1.24 g, 9.22 mmol) in THF (20.0 mL) was added TEA (1.42 mL, 10.1 mmol)

followed by di-tert-butyldicarbonate (2.07 g, 9.22 mmol) and the mixture was stirred under an atmosphere of nitrogen for 24 h. The mixture was concentrated in vacuo and purified via silica gel chromatography eluting with a gradient of 0 to 20% EtOAc in hexanes to afford the title compound as a white solid (2.02 g, 94%). LC/MS: $R_t$=1.94 min, $ES^+$ 234 (AA standard).

Step b: tert-Butyl(1S)-2,3-dihydro-1H-inden-1-yl (methyl)carbamate

To a solution of tert-butyl(1S)-2,3-dihydro-1H-inden-1-ylcarbamate (1.82 g, 7.80 mmol) in THF (50.0 mL) under an atmosphere of argon at 0° C. was added 60% sodium hydride in mineral oil (968 mg, 24.2 mmol) and the suspension was allowed to warm to rt and stir for 30 min. Iodomethane (1.52 mL, 24.2 mmol) was added and the mixture was stirred overnight. The reaction was then quenched via addition of saturated ammonium chloride solution (10.0 mL) and was concentrated in vacuo. The mixture was then partitioned between water (20 mL) and DCM (50 mL) and the aqueous layer was extracted with DCM (3×50 mL). The combined organic layers were dried over $MgSO_4$, filtered, concentrated in vacuo and purified by silica gel chromatography eluting with a gradient of 0 to 20% EtOAc in hexanes to afford the title compound as a clear, colorless oil (1.84 g, 95%). LC/MS: $R_t$=2.21 min, $ES^+$ 248 (AA standard).

Step c: (1S)-N-Methylindan-1-amine, hydrochloride salt

To a solution of tert-butyl(1S)-2,3-dihydro-1H-inden-1-yl (methyl)carbamate (1.84 g, 7.44 mmol) in MeOH (50.0 mL) under an atmosphere of nitrogen was added hydrochloric acid (6.00 mL, 72.4 mmol) and the mixture was stirred overnight. The reaction was concentrated in vacuo to afford the title compound as a white solid without further purification (1.35 g, 99%). LC/MS: $R_t$=0.85 min, $ES^+$ 148 (AA standard).

Step d: tert-Butyl{[((1S,2S,4R)-4-{4-[(1S)-2,3-dihydro-1H-inden-1-yl(methyl)amino]-7H-pyrrolo[2,3-d]pyrimidin-7-yl}-2-hydroxycyclopentyl)methoxy]sulfonyl}carbamate The title compound was prepared following the procedure described in Example 2a-i using (1S)-N-methylindan-1-amine, hydrochloride salt in step f. LC/MS: $R_t$=1.55 min, $ES^+$ 558 (AA standard).

Step e: {(1S,2S,4R)-2-Hydroxy-4-[4-(methylamino)-7H-pyrrolo[2,3-d]pyrimidin-7-yl]-cyclopentyl}methyl sulfamate and ((1S,2S4R)-4-{4-[(1S)-2,3-dihydro-1H-inden-1-yl(methyl)amino]-7H-pyrrolo[2,3-d]pyrimidin-7-yl}-2-hydroxycyclopentyl)methyl sulfamate (Compounds I-40 and I-6)

To a solution of tert-butyl {[((1S,2S,4R)-4-{4-[(1S)-2,3-dihydro-1H-inden-1-yl(methyl)amino]-7H-pyrrolo[2,3-d]pyrimidin-7-yl}-2-hydroxycyclopentyl)methoxy]sulfonyl}carbamate (97.9 mg, 0.176 mmol) in DCM (5.00 mL) under an atmosphere of nitrogen was added trifluoroacetic acid (5.00 mL, 64.9 mmol). LC/MS after 10 min indicated the presence of both products, and the mixture was concentrated in vacuo and purified via silica gel chromatography eluting with a gradient of 0 to 10% MeOH in EtOAc to afford both products as clear, colorless oils (9.70 mg, 10% and 30.6 mg, 51%, respectively). Analytical data for {(1S,2S,4R)-2-Hydroxy-4-[4-(methylamino)-7H-pyrrolo[2,3-d]pyrimidin-7-yl]-cyclopentyl}methyl sulfamate (Compound I-40): $^1$H NMR (400 MHz, $CD_3OD$, δ): 8.18 (s, 1H), 7.38 (d, J=3.6 Hz, 1H), 6.74 (d, J=3.1 Hz, 1H), 5.53-5.42 (m, 1H), 4.51-4.47 (m, 1H), 4.37 (dd, J=7.5, 9.8 Hz, 1H), 4.19 (dd, J=7.4, 9.7 Hz, 1H), 3.34 (s, 3H), 3.14 (br s, 3H), 2.90-2.75 (m, 1H), 2.37-2.18 (m, 3H), 2.12-1.96 (m, 1H) ppm. LC/MS: $R_t$=1.03 min, $ES^+$ 342 (AA standard). Analytical data for ((1S,2S,4R)-4-{4-[(1S)-2,3-dihydro-1H-inden-1-yl(methyl)amino]-7H-pyrrolo[2,3-d]pyrimidin-7-yl}-2-hydroxycyclopentyl)methyl sulfamate (Compound I-6): $^1$H NMR (400 MHz, $CD_3OD$, δ): 8.28 (s, 1H), 7.54 (d, J=3.8 Hz, 1H), 7.39-7.21 (m, 4H), 7.02 (d, J=3.8 Hz, 1H), 6.26 (dd, J=7.5, 7.5 Hz, 1H), 5.58 (ddd, J=5.2, 8.9, 17.9 Hz, 1H), 5.47 (s, 1H), 4.51 (dd, J=3.3, 3.3 Hz, 1H), 4.38 (dd, J=7.4, 9.8 Hz, 1H), 4.20 (dd, J=7.5, 9.7 Hz, 1H), 3.23-2.96 (m, 6H), 2.93-2.79 (m, 1H), 2.76-2.59 (m, 1H), 2.42-2.05 (m, 6H) ppm. LC/MS: $R_t$=1.89 min, $ES^+$ 458 (AA standard).

Example 13

{(1S,2S,4R)-4-[4-(Benzylamino)-5-fluoro-7H-pyrrolo[2,3-d]pyrimidin-7-yl]-2-hydroxycyclopentyl}methyl sulfamate (Compound I-31)

Step a: 4-Chloro-5-fluoro-7H-pyrrolo[2,3-d]pyrimidine

To a stirred solution of 4-chloro-1H-pyrrolo[2,3-d]pyrimidine (3.00 g, 19.5 mmol) in AcCN (148 mL) was added Selectfluor™ (1-chloromethyl-4-fluoro-1,4-diazoniabicyclo[2.2.2]octane bis(tetrafluoroborate)), 10.4 g, 29.4 mmol) and AcOH (29.8 mL, 524 mmol), and then the mixture was allowed to stir for 26 hrs at 70° C. under an atmosphere of nitrogen. After cooling to rt, the mixture was concentrated in vacuo and the mixture was co-evaporated with dry toluene (2×30 mL). The residue was dissolved in a solution of 50% DCM in EtOAc and filtered through a pad of silica gel which was thoroughly washed. The filtrate was concentrated in vacuo, the residue was purified by silica gel chromatography eluting with a gradient of 0 to 30% EtOAc in DCM to afford the title compound as a light brown solid (1.22 g, 36%). LC/MS: $R_t$=1.51 min, $ES^+$ 243 (AA standard).

Step b: {(1S,2S,4R)-4-[4-(Benzylamino)-5-fluoro-7H-pyrrolo[2,3-d]pyrimidin-7-yl]-2-hydroxycyclopentyl}methyl sulfamate (Compound I-31)

The title compound was prepared following the procedure described in Example 1a-k using benzylamine and 4-chloro-5-fluoro-7H-pyrrolo[2,3-d]pyrimidine in step c. $^1$H NMR (400 MHz, $CD_3OD$, δ): 8.09 (s, 1H), 7.37-7.32 (m, 2H), 7.31-7.26 (m, 2H), 7.23-7.19 (m, 1H), 7.06 (d, J=2.0 Hz, 1H), 5.50-5.42 (m, 1H), 4.76 (br s, 2H), 4.47-4.43 (m, 1H), 4.34 (dd, J=7.8, 9.8 Hz, 1H), 4.17 (dd, J=7.2, 9.8 Hz, 1H), 2.81-2.72 (m, 1), 2.29 (ddd, J=1.5, 8.0 Hz, 14.0 Hz, 1H), 2.25-2.13 (m, 2H), 1.98 (ddd, J=5.0, 9.4, 14.0 Hz, 1H). LC/MS: $R_t$=1.56 min, $ES^+$ 436 (AA standard).

Example 14

((1S,2S,4R)-4-{4-[(Cyclohexylmethyl)amino]-7H-pyrrolo[2,3-d]pyrimidin-7-yl}-2-hydroxycyclopentyl)methyl sulfamate (Compound I-29)

The title compound was prepared following the procedure described in Example 1a-k using cyclohexanemethylamine in step c. ¹H NMR (300 MHz, CD₃OD, δ): 8.08 (s, 1H), 7.17 (d, J=3.6 Hz, 1H), 6.60 (d, J=3.6 Hz, 1H), 5.47-5.35 (m, 1H), 4.50-4.46 (m, 1H), 4.36 (dd, J=7.6, 9.8 Hz, 1H), 4.19 (dd, J=7.3, 9.8 Hz, 1H), 3.35 (br s, 1H), 3.34 (br s, 2H), 3.32 (br s, 1H), 2.85-2.72 (m, 1H), 2.36-2.15 (m, 3H), 2.01 (ddd, J=4.9, 9.2, 14.3 Hz, 1H), 1.88-1.60 (m, 6H), 1.36-1.15 (m, 3H), 1.06-0.91 (m, 2H). LC/MS: $R_t$=1.60 min, ES⁺ 424 (AA standard).

Example 15

((1S,2R,3S,4R)-4-{4-[(1S)-2,3-Dihydro-1H-inden-1-ylamino]-7H-pyrrolo[2,3-d]-pyrimidin-7-yl}-2,3-dihydroxycyclopentyl)methyl sulfamate (Compound I-17)

Step a: (1R,2S,3R,5S)-3-{4-[(1S)-2,3-Dihydro-1H-inden-1-ylamino]-7H-pyrrolo[2,3-d]-pyrimidin-7-yl}-5-(hydroxymethyl)cyclopentane-1,2-diol To a solution of (4aS,6R,7R,7aR)-6-{4-[(1S)-2,3-dihydro-1H-inden-1-ylamino]-7H-pyrrolo[2,3-d]pyrimidin-7-yl}-2-(4-methoxyphenyl)-7-methylhexahydrocyclopenta[d]-[1,3]dioxin-7-ol (312 mg, 0.594 mmol, as prepared following the procedure in Example 1a-d, using (S)-(+)-1-aminoindan in step c) in THF (1.17 mL) and water (1.17 mL) was added AcOH (3.51 mL, 61.7 mmol) under an atmosphere of nitrogen. The mixture was stirred at rt overnight. The solvent was removed in vacuo and the residue was purified by silica gel chromatography eluting with a gradient of 0 to 10% MeOH in DCM to afford the title compound as a white solid (182 mg, 76%). LC/MS: $R_t$=0.85 min, ES⁺ 381 (FA standard).

Step b: ((3aR,4S,6R,6aS)-6-}4-[(1S)-2,3-Dihydro-1H-inden-1-ylamino]-7H-pyrrolo[2,3-d]-pyrimidin-7-yl}-2,2-dimethyltetrahydro-3aH-cyclopenta[d][1,3]dioxol-4-yl)methanol To a suspension of (1R,2S,3R,5S)-3-{4-[(1S)-2,3-dihydro-1H-inden-1-ylamino]-7H-pyrrolo[2,3-d]pyrimidin-7-yl}-5-(hydroxymethyl)cyclopentane-1,2-diol (63.8 mg, 0.168 mmol) and 2,2-dimethoxypropane (0.103 mL, 0.838 mmol) in acetone (2.10 mL) was added p-toluenesulfonic acid monohydrate (31.9 mg, 0.168 mmol) with rapid stirring. The resulting solution was stirred overnight. The reaction was quenched with saturated aqueous sodium bicarbonate solution (1.00 mL) and the volume was reduced in vacuo. The solution was diluted with water and extracted with EtOAc. The combined organic layers were washed with saturated aqueous sodium chloride solution, dried over sodium sulfate, filtered and concentrated in vacuo. The residue was purified by silica gel chromatography eluting with a gradient of 10 to 60% EtOAc in hexanes to afford the title compound as a white solid (49.6 mg, 70.%). LC/MS: $R_t$=1.16 min, ES⁺ 421 (FA standard).

Step c: ((1S,2R,3S,4R)-4-{4-[(1S)-2,3-Dihydro-1H-inden-1-ylamino]-7H-pyrrolo[2,3-d]-pyrimidin-7-yl}-2,3-dihydroxycyclopentyl)methyl sulfamate (Compound I-17)

To a suspension of ((3aR,4S,6R,6aS)-6-{4-[(1S)-2,3-dihydro-1H-inden-1-ylamino]-7H-pyrrolo[2,3-d]pyrimidin-7-yl}-2,2-dimethyltetrahydro-3aH-cyclopenta[d][1,3]-dioxol-4-yl)methanol (45.9 mg, 0.109 mmol) and pyridine (0.0180 mL, 0.222 mmol) in AcCN (1.10 mL) and DCM (0.500 mL) at 0° C. under an atmosphere of nitrogen was added dropwise a 2.00 M solution of chlorosulfonamide in AcCN (0.110 mL, 0.220 mmol, as prepared in 1j). The suspension was stirred for 2 h and more 2.00 M of chlorosulfonamide in AcCN solution (0.150 mL, 3.00 mmol) was added. After 5 min the reaction was quenched with MeOH (1.00 mL) and the solvent was removed in vacuo. The residue was purified by silica gel chromatography eluting with a gradient of 0 to 10% MeOH in DCM to afford the title compound as a white solid (23.1 mg, 46%). ¹H NMR (400 MHz, CD₃OD, δ): 8.36 (s, 1H), 7.62 (d, J=3.1 Hz, 1H), 7.43-7.33 (m, 4H), 7.04 (d, J=3.0 Hz, 1H), 5.67 (br s, 1H), 5.25-5.20 (m, 1H), 4.61 (dd, J=3.8, 9.3 Hz, 1H), 4.48 (dd, J=2.0, 9.9 Hz, 1H), 4.27-4.22 (m, 2H), 3.74 (s, 1H), 3.27-3.20 (m, 1H), 3.13-3.05 (m, 1H), 3.02-2.90 (m, 1H), 2.87-2.77 (m, 1H), 2.35-2.19 (m, 3H) ppm. LC/MS: $R_t$=0.94 min, ES⁺ 460. (FA standard).

Example 16

((1R,4R)-4-{4-[(1S)-2,3-Dihydro-1H-inden-1-ylamino]-7H-pyrrolo[2,3-d]-pyrimidin-7-yl}cyclopent-2-en-1-yl)methyl sulfamate and ((1S,3S)-3-(4-[(1S)-2,3-dihydro-1H-inden-1-ylamino]-7H-pyrrolo[2,3-d]pyrimidin-7-yl}-cyclopentyl)methyl sulfamate (Compounds I-20 and I-11)

Step a: (1S,2R,3S,5R)-3-({[tert-Butyl(dimethyl)silyl]oxy}methyl)-5-{4-[(1S)-2,3-dihydro-1H-inden-1-ylamino]-7H-pyrrolo[2,3-d]pyrimidin-7-yl}cyclopentane-1,2-diol A solution of (1R,2S,3R,5S)-3-{4-[(1S)-2,3-dihydro-1H-inden-1-ylamino]-7H-pyrrolo[2,3-d]pyrimidin-7-yl}-5-(hydroxymethyl)cyclopentane-1,2-diol (166 mg, 0.436 mmol, as prepared in Example 15a), tert-butyldimethylsilyl chloride (69.0 mg, 0.458 mmol), 1H-imidazole (44.6 mg, 0.654 mmol) in DMF (2.00 mL) was stirred under an atmosphere of nitrogen. After 2 h additional tert-butyldimethylsilyl chloride (6.00 mg, 0.0365 mmol) was added and the solution was stirred for 1 hour. The reaction was quenched with water and extracted with EtOAc. The combined organics were washed with water and saturated aqueous sodium chloride solution, dried over sodium sulfate, filtered, and concentrated in vacuo. The residue filtered through a plug of silica gel eluting with 60% EtOAc in hexanes to afford the title compound as an off white solid (179 mg, 83%). LC/MS: $R_t$=1.51 min, ES⁺ 495 (FA standard).

Step b: (3aR,4S,6R,6aS)-4-({[tert-Butyl(dimethyl)silyl]oxy}methyl)-6-{4-[(1S)-2,3-dihydro-1H-inden-1-ylamino]-7H-pyrrolo[2,3-d]pyrimidin-7-yl}tetrahydro-3aH-cyclopenta[d][1,3]dioxole-2-thione To a solution of (1S,2R,3S,5R)-3-({[tert-butyl(dimethyl)silyl]oxy}methyl)-5-{4-[(1S)-2,3-dihydro-1H-inden-1-ylamino]-7H-pyrrolo[2,3-d]pyrimidin-7-yl}cyclopentane-1,2-diol (179 mg, 0.362 mmol) in DMF (2.00 mL) under an atmosphere of nitrogen was added 1,1'-thiocarbonyldiimidazole (72.3 mg, 0.406 mmol) and the solution was heated to 80° C. for 3 h. The solvent was removed and the residue was purified by silica gel chromatography eluting with a gradient of 0 to 50% EtOAc in hexanes to afford the title compound (158 mg, 81%). LC/MS: $R_t$=2.24 min, ES⁺ 538 (FA standard).

Step c: 7-[(1R,4R)-4-({[tert-Butyl(dimethyl)silyl]oxy}methyl)cyclopent-2-en-1-yl]-N-[(1S)-2,3-dihydro-1H-inden-1-yl]-7H-pyrrolo[2,3-d]pyrimidin-4-amine To a solution of (3aR,4S,6R,6aS)-4-({[tert-butyl(dimethyl)silyl]oxy}methyl)-6-{4-[(1S)-2,3-dihydro-1H-inden- 1-ylamino]-7H-pyrrolo[2,3-d]pyrimidin-7-yl}tetrahydro-3aH-cyclopenta[d][1,3]dioxole-2-thione (138 mg, 0.257 mmol) in THF (0.860 mL) at 0° C. under an atmosphere of nitrogen was added 1,3-dimethyl-2-phenyl-1,3,2-diazaphospholidine (0.147 mL, 0.793 mmol) dropwise. The solution was stirred for 10 min at 0° C. and then at rt for 5 h. The solvent was removed and the residue was purified by silica gel chromatography eluting with a gradient of 0 to 20% EtOAc in hexanes to afford the title compound as a clear oil (~70% purity, 81.9 mg, 48%). LC/MS: $R_t$=2.10 min, ES$^+$ 462 (FA standard).

Step d: ((1R,4R)-4-{4-[(1S)-2,3-Dihydro-1H-inden-1-ylamino]-7H-pyrrolo[2,3-d]-pyrimidin-7-yl}cyclopent-2-en-1-yl)methanol To a solution of 7-[(1R,4R)-4-({[tert-butyl(dimethyl)silyl]oxy}-methyl)cyclopent-2-en-1-yl]-N-[(1S)-2,3-dihydro-1H-inden-1-yl]-7H-pyrrolo[2,3-d]pyrimidin-4-amine (81.9 mg, 0.178 mmol) in pyridine (0.800 mL) and THF (0.800 mL) at 0° C. under an atmosphere of nitrogen was added dropwise pyridine hydrofluoride (0.0500 mL, 0.555 mol). The solution was warmed to rt and stirred overnight. The reaction was quenched with saturated aqueous sodium bicarbonate solution and diluted with EtOAc. The layers were separated and the aqueous layer was extracted with EtOAc (3×20 mL). The combined organic layers were dried over sodium sulfate, filtered and concentrated in vacuo. The residue was purified by silica gel chromatography eluting with a gradient of 0 to 5% MeOH in DCM to afford the title compound as a white solid (~70% purity, 35.7 mg, 41%). LC/MS: $R_t$=1.03 min, ES$^+$ 347 (FA standard).

Step e: ((1R,4R)-4-{4-[(1S)-2,3-Dihydro-1H-inden-1-ylamino]-7H-pyrrolo[2,3-d]-pyrimidin-7-yl}cyclopent-2-en-1-yl)methyl sulfamate (Compound I-20)

To a solution of ((1R,4R)-4-{4-[(1S)-2,3-dihydro-1H-inden-1-ylamino]-7H-pyrrolo[2,3-d]pyrimidin-7-yl}cyclopent-2-en-1-yl)methanol (35.7 mg, 0.103 mmol) and pyridine (0.0417 mL, 0.515 mmol) in AcCN (1.00 mL) at 0° C. under an atmosphere of nitrogen was added dropwise a 2.00 M solution of chlorosulfonamide in AcCN (0.260 mL, 0.520 mmol, as prepared in 1j). The solution was stirred for 1 hour. The reaction was quenched with saturated aqueous sodium bicarbonate solution and partitioned between water and EtOAc. The layers were separated and the aqueous layer was extracted with EtOAc (2×20 mL). The combined organic layers were washed with saturated aqueous sodium chloride solution, dried overسodium sulfate, filtered and concentrated in vacuo. The residue was purified by silica gel chromatography eluting with a gradient of 0 to 5% MeOH in DCM to afford the title compound as a solid (28.9 mg, 66%). $^1$H NMR (400 MHz, CDCl$_3$, δ): 8.36 (s, 1H), 7.35 (d, J=7.2 Hz, 1H), 7.30-7.18 (m, 3H), 6.89 (d, J=3.6 Hz, 1H), 6.32 (d, J=3.5 Hz, 1H), 6.14-6.12 (m, 1H), 6.04-5.97 (m, 2H), 5.89 (br s, 1H), 4.19 (dd, J=1.2, 6.0 Hz, 2H), 3.43-3.37 (m, 1H), 3.09-3.01 (m, 1H), 2.98-2.90 (m, 1H), 2.77-2.69 (m, 1H), 2.46-2.39 (m, 1H), 2.07-1.93 (m, 3H) ppm. LC/MS: $R_t$=1.24 min, ES$^+$ 426 (FA standard).

Step f: ((1S,3S)-3-{4-[(1S)-2,3-Dihydro-1H-inden-1-ylamino]-7H-pyrrolo[2,3-d]pyrimidin-7-yl}cyclopentyl)methyl sulfamate (Compound I-11)

A suspension of ((1R,4R)-4-{4-[(1S)-2,3-dihydro-1H-inden-1-ylamino]-7H-pyrrolo[2,3-d]pyrimidin-7-yl}cyclopent-2-en-1-yl)methyl sulfamate (17.3 mg, 0.0406 mmol) and 10% palladium on carbon (8.60 mg) in EtOAc (0.500 mL) was put under an atmosphere of hydrogen. After 3 h the flask was purged with nitrogen and the suspension was filtered through Celite eluting with EtOAc to afford the title compound as a white solid (10.8 mg, 62%). $^1$H NMR (400 MHz, CDCl$_3$, δ): 8.36 (s, 1H), 7.36 (d, J=7.3 Hz, 1H), 7.29-7.15 (m, 3H), 7.00 (d, J=3.4 Hz, 1H), 6.33 (d, J=3.4 Hz, 1H), 5.91-5.87 (m, 1H), 5.41 (br s, 2H), 5.23-5.15 (m, 2H), 4.26 (dd, J=5.8, 9.8 Hz, 1H), 4.18 (dd, J=6.2, 9.8 Hz, 1H), 3.09-3.02 (m, 1H), 2.99-2.90 (m, 1H), 2.36-2.27 (m, 2H), 2.21-2.12 (m, 2H), 2.09-1.93 (m, 3H), 1.66-1.57 (m, 1H) ppm. LC/MS: $R_t$=1.24 min, ES$^+$ 428 (FA standard).

Example 17

[(1S,2S,4R)-2-Hydroxy-4-(4-{[(5-methylisoxazol-3-yl)methyl]amino}-1H-pyrrolo[2,3-d]pyridazin-1-yl)cyclopentyl]methyl sulfamate (Compound I-41)

Step a: N-[(5-Methylisoxazol-3-yl)methyl]-7H-pyrrolo[2,3-d]pyrimidin-4-amine

4-Chloro-H-pyrrolo[2,3-d]pyrimidine (1.14 g, 7.43 mmol), (5-methyl-3-isoxazolyl)methylamine (1.00 g, 8.92 mmol) and DIPEA (1.94 mL, 11.1 mmol) were added to 1-butanol (9.13 mL). The mixture was heated at 190° C. for 1600 seconds using MWI in three batches. The combined reactions were concentrated in vacuo to give a brown oil. The residue was purified by silica gel chromatography eluting with EtOAc to afford the title compound as a yellow solid (1.22 g, 72%). LC/MS: $R_t$=0.63 min, ES$^+$ 230. (FA standard).

Step b: [(1S,2S,4R)-2-Hydroxy-4-(4-{[(5-methylisoxazol-3-yl)methyl]amino}-1H-pyrrolo-[2,3-d]pyridazin-1-yl)cyclopentyl]methyl sulfamate (Compound I-41)

The title compound was prepared following the procedure described in Example 1d-k using N-[(5-methylisoxazol-3-yl)methyl]-7H-pyrrolo[2,3-d]pyrimidin-4-amine in step d. $^1$H NMR (400 MHz, CD$_3$OD, δ): 8.22 (s, 1H), 7.26 (d, J=3.6 Hz, 1H), 6.63 (d, J=3.6 Hz, 1H), 6.14 (s, 1H), 5.55-5.44 (m, 1H), 4.81 (s, 2H), 4.59 (br s, 1H), 4.42 (dd, J=7.6, 9.6 Hz, 1H), 4.25 (dd, J=7.4, 9.8 Hz, 1H), 2.91-2.79 (m, 1H), 2.41 (s, 3H), 2.40-2.22 (m, 3H), 2.15-2.04 (m, 1H) ppm. LC/MS: $R_t$=0.89 min, ES$^+$ 423 (FA standard).

Example 18

[(1S,2S,4R)-4-(4-Anilino-1H-pyrrolo[2,3-d]pyridazin-1-yl)-2-hydroxycyclopentyl]methyl sulfamate (Compound I-39)

The title compound was prepared following the procedure described in Example 17a-b using aniline in step a. $^1$H NMR (400 MHz, CD$_3$OD, δ): 8.18 (s, 1H), 7.62 (d, J=7.6 Hz, 2H), 7.31 (dd, J=7.5, 8.4 Hz, 2H), 7.23 (d, J=3.7 Hz, 1H), 7.06 (t, J=7.4 Hz, 1H), 6.22 (d, J=3.7 Hz, 1H), 5.50-5.39 (m, 1H), 4.46 (br s, 1H), 4.34 (dd, J=7.6, 7.6 Hz, 1H), 4.16 (dd, J=7.4, 7.4 Hz, 1H), 2.89-2.73 (m, 1H), 2.37-2.15 (m, 3H), 2.09-1.97 (m, 1H) ppm. LC/MS: $R_t$=1.03 min, ES$^+$ 404 (FA standard).

Example 19

[(1S,2S,4R)-2-Hydroxy-4-(4-{[2-(trifluoromethyl)benzyl]amino}-1H-pyrrolo-[2,3-d]pyridazin-1-yl)cyclopentyl]methyl sulfamate (Compound I-47)

The title compound was prepared following the procedure described in Example 17a-b using 2-(trifluoromethyl)benzylamine in step a. $^1$H NMR (400 MHz, CD$_3$OD, δ): 8.08 (s, 1H), 7.66 (d, J=7.7 Hz, 1H), 7.47 (d, J=4.0 Hz, 2H), 7.42-7.34 (m, 1H), 7.19 (d, J=3.7 Hz, 1H), 6.60 (d, J=3.2 Hz, 1H), 5.50-5.36 (m, 1H), 4.94 (s, 1H), 4.45 (br s, 1H), 4.34 (dd, J=7.5, 7.6 Hz, 1H), 4.16 (dd, J=7.4, 7.4 Hz, 1H), 3.27 (q, J=1.6, 3.3 Hz, 1H), 2.94-2.73 (m, 1H), 2.35-2.15 (m, 3H), 2.06-1.96 (m, 1H) ppm. LC/MS: $R_t$=1.25 min, ES$^+$ 486 (FA standard).

Example 20

((1S,2S,4R)-4-{4-[(Cyclopropylmethyl)amino]-7H-pyrrolo[2,3-d]pyrimidin-7-yl}-2-hydroxycyclopentyl)methyl sulfamate (Compound I-25)

Step a: (1S,2S,4R)-4-{4-[(Cyclopropylmetbyl)amino]-7H-pyrrolo[2,3-d]pyrimidin-7-yl}-2-(hydroxymethyl)cyclopentanol The title compound was prepared following the procedure described in Example 1a-g using cyclopropylmethylamine in step c. LC/MS: $R_t$=0.90 min, ES$^+$ 303 (FA standard).

Step b: 7-[(1R,3S,4S)-3-{[tert-Butyl(dimethyl)silyl]oxy}-4-({[tert-butyl(dimethyl)silyl]oxy}-methyl)cyclopentyl]-N-(cyclopropylmethyl)-7H-pyrrolo[2,3-d]pyrimidin-4-amine (1S,2S,4R)-4-{4-[(Cyclopropylmethyl)amino]-7H-pyrrolo[2,3-d]pyrimidin-7-yl}-2-(hydroxymethyl)cyclopentanol (280. mg, 0.923 mmol) was stirred in DMF (3.00 mL). tert-Butyldimethylsilyl chloride (698 mg, 4.63 mmol) was added followed by 1H-imidazole (142 mg, 2.08 mmol) and 4-(dimethylamino)-pyridine (10.0 mg, 0.0818 mmol). The reaction was stirred for 1 h then diluted with water and extracted with EtOAc (3×15 mL). The organic layer was dried over MgSO$_4$, filtered and concentrated in vacuo. The resulting oil was dried under high vacuum overnight. The residue was purified by silica gel chromatography eluting with a gradient of 0 to 15% EtOAc in hexanes to afford the title compound (203 mg, 41%). LC/MS: $R_t$=2.16 min, ES$^+$ 531 (FA standard).

Step c: ((1S,2S,4R)-2-{[tert-Butyl(dimethyl)silyl]oxy}-4-{4-[(cyclopropylmethyl)amino]-7H-pyrrolo[2,3-d]pyrimidin-7-yl}cyclopentyl)methanol 7-[(1R,3S,4S)-3-{[tert-Butyl(dimethyl)silyl]oxy}-4-({[tert-butyl(dimethyl)silyl]-oxy}methyl)cyclopentyl]-N-(cyclopropylmethyl)-7H-pyrrolo[2,3-d]pyrimidin-4-amine (100. mg, 0.188 mmol) was dissolved in THF (0.900 mL) and pyridine (0.900 mL). Pyridine hydrofluoride (7 drops) was added and the reaction was stirred for 5 h. Additional pyridine hydrofluoride (3 drops) was added and the reaction was stirred for 2 h before being quenched with saturated aqueous sodium bicarbonate solution. The aqueous layer was extracted using EtOAc (3×10 mL), and the combined organic extracts were dried over MgSO$_4$, filtered, and concentrated in vacuo. The residue was purified by silica gel chromatography eluting with a gradient of 0 to 50% EtOAc in hexanes to afford the title compound (47.0 mg, 50%). LC/MS: $R_t$=1.53 min, ES$^+$ 417 (FA standard).

Step d: ((1S,2S,4R)-2-{[tert-Butyl(dimethyl)silyl]oxy}-4-{4-[(cyclopropylmethyl)amino]-7H-pyrrolo[2,3-d]pyrimidin-7-yl}cyclopentyl)methyl sulfamate ((1S,2S,4R)-2-{[tert-Butyl(dimethyl)silyl]oxy}-4-{4-[(cyclopropylmethyl)amino]-7H-pyrrolo[2,3-d]pyrimidin-7-yl}cyclopentyl)methanol (74.0 mg, 0.178 mmol) was dissolved in AcCN (3.50 mL) and cooled to 0° C. TEA (0.0500 mL, 0.355 mmol) was added followed by a 2.00 M solution of chlorosulfonamide in AcCN (0.178 mL, 0.356 mmol, as prepared in 1j). The reaction was stirred for 2 h, quenched with MeOH and concentrated in vacuo. The material was taken on to the next step without further purification. LC/MS: $R_t$=1.51 min, ES$^+$ 496 (FA standard).

Step e: ((1S,2S,4R)-4-{4-[(Cyclopropylmethyl)amino]-7H-pyrrolo[2,3-d]pyrimidin-7-yl}-2-hydroxycyclopentyl)methyl sulfamate (Compound I-25)

((1S,2S,4R)-2-{[tert-Butyl(dimethyl)silyl]oxy}-4-{4-[(cyclopropylmethyl)amino]-7H-pyrrolo[2,3-d]pyrimidin-7-yl}cyclopentyl)methyl sulfamate (88.0 mg, 0.178 mmol) was dissolved in THF (1.00 mL) and pyridine (3.00 mL). Pyridine hydrofluoride (12 drops) was added and the reaction was stirred for 3 h. The reaction was quenched using saturated aqueous sodium bicarbonate solution. The aqueous layer was extracted with EtOAc (3×10 mL), and the combined organic extracts were dried over MgSO$_4$, filtered, and concentrated in vacuo. The residue was purified by silica gel chromatography eluting with 5% MeOH in DCM. The compound was re-purified via silica gel chromatography eluting with 10% MeOH in DCM to afford the title compound (3.00 mg, 4.4%). $^1$H NMR (400 MHz, CD$_3$OD, δ): 8.05 (s, 1H), 7.15 (d, J=3.6 Hz, 1H), 6.59 (d, J=3.6 Hz, 1H), 5.45-5.32 (m, 1H), 4.56 (br s, 1H), 4.45 (br s, 1H), 4.33 (dd, J=7.6, 7.6 Hz, 1H), 4.15 (dd, J=7.4, 7.4 Hz, 1H), 3.34 (d, J=6.9 Hz, 2H), 2.83-2.68 (m, 1H), 2.35-2.08 (m, 3H), 2.05-1.93 (m, 1H), 1.33-1.03 (m, 3H), 0.93-0.77 (m, 1H) ppm. LC/MS: $R_t$=0.85 min, ES$^+$ 382 (FA standard).

Example 21

((1S,2S,4R)-4-{4-[(4-Chlorobenzyl)oxy]-7H-pyrrolo[2,3-d]pyrimidin-7-yl}-2-hydroxycyclopentyl)methyl sulfamate (Compound I-34)

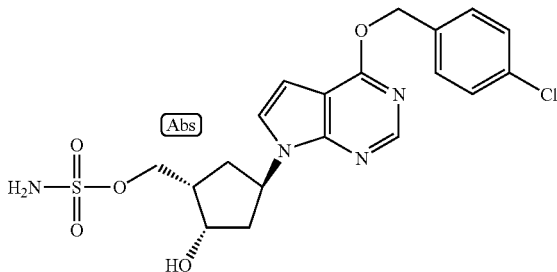

Step a: 4-[(4-Chlorobenzyl)oxy]-7H-pyrrolo[2,3-d]pyrimidine

To a 0.375 M solution of aqueous potassium hydroxide (26.2 mL, 9.83 mmol) was added (4-chlorophenyl)methanol (464 mg, 3.26 mmol) and the mixture was heated to 80° C. for 30 min. Then 4-chloro-1H-pyrrolo[2,3-d]pyrimidine (500 mg, 3.26 mmol) was added and the mixture was refluxed at 130° C. After 6 h, additional (4-chlorophenyl)methanol (100. g, 0.701 mmol) was added and the solution was heated to 115° C. overnight. The reaction was cooled to rt and diluted with water. The solution was then extracted with EtOAc (2×) and DCM (2×). The combined organic layers were dried over sodium sulfate, filtered, and concentrated in vacuo. The resulting crude oil was purified by silica gel chromatography eluting with a gradient of 5 to 30% EtOAc in DCM to afford the product as a white solid (210 mg, 25%). LC/MS: $R_t$=1.72 min, ES$^+$ 260. (FA standard).

Step b: ((1S,2S,4R)-4-{4-[(4-Chlorobenzyl)oxy]-7H-pyrrolo[2,3-d]pyrimidin-7-yl}-2-hydroxycyclopentyl)methyl sulfamate (Compound I-34)

The title compound was prepared following the procedure described in Example 1d-g and then Example 2i-j, using 4-[(4-Chlorobenzyl)oxy]-7H-pyrrolo[2,3-d]-pyrimidine in step 1d. $^1$H NMR (400 MHz, CD$_3$OD, δ): 8.35 (s, 1H), 7.51-7.34 (m, 5H), 6.56 (d, J=3.5 Hz, 1H), 5.55 (s, 2H), 5.54-5.46 (m, 1H), 4.52-4.48 (m, 1H), 4.37 (dd, J=7.8, 10.0 Hz, 1H), 4.20 (dd, J=7.3, 9.8 Hz, 1H), 2.90-2.80 (m, 1H), 2.34-2.20 (m, 3H), 2.11-2.03 (m, 1H) ppm. LC/MS: $R_t$=1.81 min, ES$^+$ 453 (FA standard).

Example 22

{(1S,2S,4R)-4-[4-(Benzylsulfanyl)-7H-pyrrolo[2,3-d]pyrimidin-7-yl]-2-hydroxycyclopentyl}methyl sulfamate (Compound I-32)

The title compound was prepared following the procedure described in Example 2a-d and g-j. $^1$H NMR (400 MHz, CD$_3$OD, δ): 8.54 (s, 1H), 7.45-7.36 (m, 3H), 7.28-7.14 (m, 3H), 6.47 (d, J=3.6 Hz, 1H), 5.51-5.43 (m, 1H), 4.58 (s, 2H), 4.49-4.45 (m, 1H), 4.33 (dd, J=7.6, 9.7 Hz, 1H), 4.16 (dd, J=7.3, 9.7 Hz, 1H), 2.87-2.78 (m, 1H), 2.62 (s, 2H), 2.32-2.15 (m, 3H), 2.08-2.01 (m, 1H) ppm. LC/MS: $R_t$=1.97 min, ES$^+$ 435 (FA standard).

Example 23

((1S,2S,4R)-4-{4-[(4-Chlorobenzyl)amino]-7H-pyrrolo[2,3-d]pyrimidin-7-yl}-2-hydroxycyclopentyl)methyl sulfamate (Compound I-45)

The title compound was prepared following the procedure described in Example 2a-j using 4-chlorobenzylamine in step f. $^1$H NMR (400 MHz, CD$_3$OD, δ): 8.10 (s, 1H), 7.34-7.28 (m, 4H), 7.21 (d, J=3.6 Hz, 1H), 6.59 (d, J=3.6 Hz, 1H), 5.47-5.39 (m, 1H), 4.73 (s, 2H), 4.50-4.48 (m, 1H), 4.25 (dd, J=8.3, 9.9 Hz, 1H), 4.09 (dd, J=6.8, 10.0 Hz, 1H), 3.35-3.33 (m, 2H), 2.81-2.71 (m, 1H), 2.35-2.29 (m, 1H), 2.26-2.15 (m, 2H), 2.02-1.96 (m, 1H) ppm. LC/MS: $R_t$=5.39 min, ES$^+$ 452 (FA standard, long purity method)

Example 24

((1S,2S,4R)-4-{4-[(3-Chlorobenzyl)amino]-7H-pyrrolo[2,3-d]pyrimidin-7-yl}-2-hydroxycyclopentyl)methyl sulfamate (Compound I-51)

The title compound was prepared following the procedure described in Example 2a-j using 3-chlorobenzylamine in step f. $^1$H NMR (400 MHz, CD$_3$OD, δ): 8.22 (s, 1H), 7.44-7.31 (m, 5H), 6.78 (d, J=3.6 Hz, 1H), 5.56-5.48 (m, 1H), 4.82 (s, 2H), 4.56-4.52 (m, 1H), 4.42 (dd, J=7.5, 9.8 Hz, 1H), 4.25 (dd, J=7.3, 9.8 Hz, 1H), 2.92-2.83 (m, 1H), 2.42-2.26 (m, 3H), 2.15-2.08 (m, 1H) ppm. LC/MS: $R_t$=1.51 min, ES$^+$ 452 (FA standard).

Example 25

((1S,2S,4R)-4-{4-[(4-Chloro-2-methylbenzyl)amino]-7H-pyrrolo[2,3-d]-pyrimidin-7-yl}-2-hydroxycyclopentyl)methyl sulfamate (Compound I-48)

The title compound was prepared following the procedure described in Example 2a-j using 4-chloro-2-methylbenzylamine in step f. $^1$H NMR (400 MHz, CD$_3$OD, δ): 8.12 (s, 1H), 7.26-7.21 (m, 3H), 7.14-7.11 (m, 1H), 6.66 (d, J=3.5 Hz, 1H), 5.49-5.41 (m, 1H), 4.69 (s, 2H), 4.50-4.47 (m, 1H), 4.36 (dd, J=7.5, 9.8 Hz, 1H), 4.19 (dd, J=7.5, 9.8 Hz, 1H), 2.86-2.76 (m, 1), 2.36 (s, 3H), 2.33-2.19 (m, 3H), 2.08-2.01 (m, 1H) ppm. LC/MS: $R_t$=1.11 min, ES$^+$ 466 (FA standard).

Example 26

((1S,2S,4R)-2-Hydroxy-4-{4-[(2-methoxybenzyl)amino]-7H-pyrrolo[2,3-d]-pyrimidin-7-yl}cyclopentyl)methyl sulfamate (Compound I-43)

The title compound was prepared following the procedure described in Example 2a-j using 2-methoxybenzylamine in step f. $^1$H NMR (400 MHz, CD$_3$OD, δ): 8.08 (s, 1H), 7.24-7.18 (m, 3H), 6.96 (d, J=7.8 Hz, 1H), 6.85 (dt, J=0.8, 7.3 Hz, 1H), 6.61 (d, J=3.5 Hz, 1H), 5.47-5.39 (m, 1H), 4.72 (s, 2H), 4.50-4.46 (m, 1H), 4.36 (dd, J=7.5, 9.8 Hz, 1H), 4.19 (dd, J=7.3, 9.8 Hz, 1H), 3.87 (s, 3H), 2.84-2.75 (m, 1H), 2.35-2.18 (m, 3H), 2.06-1.99 (m, 1H) ppm. LC/MS: $R_t$=1.16 min, ES$^+$ 448 (FA standard).

Example 27

((1S,2S,4R)-4-{4-[(3,4-Dichlorobenzyl)amino]-7H-pyrrolo[2,3-d]pyrimidin-7-yl}-2-hydroxycyclopentyl)methyl sulfamate (Compound I-24)

The title compound was prepared following the procedure described in Example 2a-j using 3,4-dichlorobenzylamine in step f. $^1$H NMR (400 MHz, CD$_3$OD, δ): 8.15 (s, 1H), 7.51 (d, J=2.0 Hz, 1H), 7.46 (d, J=8.3 Hz, 1H), 7.30-7.27 (m, 2H), 6.65 (d, J=3.5 Hz, 1H), 5.48-5.41 (m, 1H), 4.74 (s, 2H), 4.49 (t, J=4.0 Hz, 1H), 4.37 (dd, J=7.5, 9.8 Hz, 1H), 4.20 (dd, J=7.5, 9.8 Hz, 1H), 2.86-2.77 (m, 1H), 2.36-2.20 (m, 3H), 2.08-2.01 (m, 1H) ppm. LC/MS: $R_t$=1.16 min, ES$^+$ 486 (FA standard).

Example 28

((1S,2S,4R)-2-Hydroxy-4-{4-[(1S)-1,2,3,4-tetrahydronaphthalen-1-ylamino]-7H-pyrrolo[2,3-d]pyrimidin-7-yl}cyclopentyl)methyl sulfamate (Compound I-37)

The title compound was prepared following the procedure described in Example 2a-j using (S)-(+)-1,2,3,4-tetrahydro-1-naphthylamine in step f. $^1$H NMR (400 MHz, CD$_3$OD, δ): 8.16 (s, 1H), 7.26-7.07 (m, 5H), 6.63 (d, J=3.5 Hz, 1H), 5.56-5.50 (m, 1H), 5.49-5.41 (m, 1H), 4.50 (m, 1H), 4.38 (dd, J=7.5, 9.8 Hz, 1H), 4.20 (dd, J=7.3, 9.8 Hz, 1H), 2.93-2.76 (m, 3H), 2.37-2.20 (m, 3H), 2.17-1.82 (m, 5H) ppm. LC/MS: $R_t$=1.29 min, ES$^+$ 458 (FA standard).

Example 29

((1S,2R,3S,4R)-4-{4-[(4-Chlorobenzyl)amino]-7H-pyrrolo[2,3-d]pyrimidin-7-yl}-2,3-dihydroxycyclopentyl)methyl sulfamate (Compound I-22)

The title compound was prepared following the procedure described in Example 2a-d and g-j using 4-chlorobenzylamine in step f. $^1$H NMR (300 MHz, CD$_3$OD, δ): 8.11 (s, 1H), 7.34-7.21 (m, 5H), 6.60 (d, J=3.6 Hz, 1H), 5.06-4.97 (m, 1H), 4.74 (s, 2H), 4.51 (dd, J=3.6, 9.2 Hz, 1H), 4.40 (dd, J=8.0, 9.6 Hz, 1H), 4.18-4.14 (m, 2H), 2.88-2.78 (m, 1H), 2.23-2.02 (m, 2H) ppm. LC/MS: $R_t$=1.46 min, ES$^+$ 468 (AA standard).

Example 30

((1S,2S,4R)-4-{6-[(4-Chlorobenzyl)amino]-9H-purin-9-yl}-2-hydroxycyclopentyl)methyl sulfamate (Compound I-23)

The title compound was prepared following the procedure described in Example 1a-f and Example 2h-j, using 4-chlorobenzylamine and 6-chloro-9H-purine in step 1c. $^1$H NMR (300 MHz, CD$_3$OD, δ): 8.23 (s, 1H), 8.14 (s, 1H), 7.35-7.25 (m, 4H), 5.31-5.22 (m, 1H), 4.79 (s, 2H), 4.51-4.49 (br s, 1H), 4.37 (dd, J=7.5, 9.6 Hz, 1H), 4.23-4.17 (m, 1H), 2.93-2.87 (m, 1H), 2.47-2.30 (m, 2H), 2.28-2.10 (m, 2H) ppm. LC/MS: $R_t$=1.42 min, ES$^+$ 453 (AA standard).

Example 31

[(1S,2S,4R)-2-Hydroxy-4-(4-methyl-7H-pyrrolo[2,3-d]pyrimidin-7-yl)cyclopentyl]methyl sulfamate (Compound I-46)

Step a: 4-Methyl-7H-pyrrolo[2,3-d]pyrimidine

A 3.00 M solution of magnesium chloride in THF (13.0 mL, 39.0 mmol) was added dropwise to a stirred solution of 4-chloro-1H-pyrrolo[2,3-d]pyrimidine (2.50 g, 16.3 mmol) and ferric acetylacetonate (700. mg 1.98 mmol) in THF (30.0 mL) under an atmosphere of argon. The resulting reaction mixture was stirred at rt for 8 h. The mixture was poured onto a mixture of ice (100 mL) and ammonium chloride (1.00 g) and the mixture was extracted with chloroform. Volatiles were removed in vacuo, and C-18 column chromatography eluting with a gradient of 0 to 60% AcCN in water with 0.1% AA afforded the title compound (1.50 g, 69%). LC/MS: $R_t$=0.94 min, ES$^+$ 134 (AA standard).

Step b: [(1S,2S,4R)-2-Hydroxy-4-(4-methyl-7H-pyrrolo[2,3-d]pyrimidin-7-yl)cyclopentyl]-methyl sulfamate (Compound I-46)

The title compound was prepared following the procedure described in Example 1a-k using 4-methyl-7H-pyrrolo[2,3-d]pyrimidine in step c. $^1$H NMR (CD$_3$OD, 300 MHz, δ): 8.69 (s, 1H), 7.68 (d, J=3.6 Hz, 1H), 6.82 (d, J=3.6 Hz, 1H), 5.63-5.51 (m, 1H), 4.53-4.49 (m, 1H), 4.37 (dd, J=7.5, 9.9 Hz, 1H), 4.20 (dd, J=7.5, 9.9 Hz, 1H), 2.90-2.80 (m, 1H), 2.77 (s, 3H), 2.36-2.05 (m, 4H) ppm. LC/MS: $R_t$=0.50 min, ES$^+$ 327 (FA standard).

Example 32

{(1S,2S,4R)-2-Hydroxy-4-[4-(2-phenylethyl)-7H-pyrrolo[2,3-d]pyrimidin-7-yl]-cyclopentyl}methyl sulfamate (Compound I-28)

The title compound was prepared following the procedure described in Example 31a-b using chloro(2-phenylethyl)magnesium in step a. $^1$H NMR (CD$_3$OD, 300 MHz, δ): 8.62 (s, 1H), 7.48 (d, J=3.9 Hz, 1H), 7.19-7.09 (m, 5H), 6.57 (d, J=3.9 Hz, 1H), 5.55-5.46 (m, 1H), 4.49-4.46 (m, 1H), 4.35 (dd, J=7.8, 9.6 Hz, 1H), 4.18 (dd, J=7.5, 9.6 Hz, 1H), 3.28-3.24 (m, 2H), 3.10-3.04 (m, 2H), 2.88-2.80 (m, 1H), 2.31-2.01 (m, 4H) ppm. LC/MS: $R_t$=1.56 min, ES$^+$ 417 (AA standard).

Example 33

{(1S,2S,4R)-2-Hydroxy-4-[4-(2-methyl-2-phenylpropyl)-7H-pyrrolo[2,3-d]-pyrimidin-7-yl]cyclopentyl}methyl sulfamate (Compound I-50)

The title compound was prepared following the procedure described in Example 31a-b using chloro(2-methyl-2-phenylpropyl)magnesium in step a. $^1$H NMR (400 MHz, CD$_3$OD, δ): 8.62 (s, 1H), 7.37-7.34 (m, 2H), 7.25-7.21 (m, 2H), 7.16-7.12 (m, 1H), 6.15 (d, 1H), 5.56-5.47 (m, 1H), 4.49-4.48 (br s, 1H), 4.37 (dd, J=7.6, 9.6 Hz, 1H), 4.22-4.17 (m, 1H), 2.93-2.87 (m, 1H), 2.89-2.80 (m, 1H), 2.31-2.19 (m, 3H), 2.07-2.00 (m, 1H), 1.43 (s, 6H) ppm. LC/MS: $R_t$=1.59 min, ES$^+$ 445 (AA standard).

Example 34

{(1S,2S,4R)-4-[4-(Acetylamino)-7H-pyrrolo[2,3-d]pyrimidin-7-yl]-2-hydroxycyclopentyl}methyl sulfamate and [(1S,2S,4R)-4-(4-amino-7H-pyrrolo[2,3-d]pyrimidin-7-yl)-2-hydroxycyclopentyl]methyl sulfamate (Compounds I-9 and I-18)

Step a: (1S,2S,4R)-4-(4-Amino-7H-pyrrolo[2,3-d]pyrimidin-7-yl)-2-(hydroxymethyl)cyclopentanol A solution of N-(2,4-dimethoxybenzyl)-7-[(4aS,6R,7aS)-2-(4-methoxyphenyl)-hexahydrocyclopenta[d][1,3]dioxin-6-yl]-7H-pyrrolo[2,3-d]pyrimidin-4-amine (123 mg, 0.238 mmol, prepared following the procedure described in Example 1a-f using 2,4-dimethoxybenzylamine in step c) and AcOH (1.00 mL, 17.6 mmol) in water (0.500 mL) and THF (0.500 mL) were stirred at rt overnight. The reaction mixture was concentrated in vacuo and purification by silica gel chromatography eluting with a gradient of 0 to 10% MeOH in DCM afforded the title compound (43.0 mg, 73%). LC/MS: $R_t$=0.15 min, ES$^+$ 249 (FA standard).

Step b: (1S,2S,4R)-4-(4-Amino-7H-pyrrolo[2,3-d]pyrimidin-7-yl)-2-({[tert-butyl(dimethyl)silyl]oxy}methyl)cyclopentanol To a solution of (1S,2S,4R)-4-(4-amino-7H-pyrrolo[2,3-d]pyrimidin-7-yl)-2-(hydroxymethyl)cyclopentanol (43.0 mg, 0.173 mmol) and imidazole (25.0 mg, 0.367 mmol) in dry DMF (2.00 mL) at 0° C. was added tert-butyldimethylsilyl chloride (29.0 mg, 0.192 mmol). The solution was stirred at rt for 2 h and concentrated in vacuo, the residue was dissolved in water and extracted with EtOAc. The combined organic extracts were dried over MgSO$_4$, filtered and concentrated in vacuo to afford the title compound (50.8 mg, 81%), which was taken on without further purification. LC/MS: $R_t$=1.38 min, ES$^+$ 364 (FA standard).

Step c: (1S,2S,4R)-4-[4-(Acetylamino)-7H-pyrrolo [2,3-d]pyrimidin-7-yl]-2-({[tert-butyl(dimethyl)silyl]oxy}methyl)cyclopentyl acetate To a solution of (1S,2S,4R)-4-(4-amino-7H-pyrrolo[2,3-d]pyrimidin-7-yl)-2-({[tert-butyl(dimethyl)silyl]oxy}methyl)cyclopentanol (125 mg, 0.345 mmol) in pyridine (2.00 mL) at 0° C. was added acetic anhydride (0.380 mL, 4.03 mmol). The solution was stirred at rt overnight. The reaction mixture was diluted with DCM and water. The layers were separated and the aqueous layer was extracted with DCM. The combined organic layers were dried over MgSO$_4$, filtered and concentrated in vacuo. The residue was purified by silica gel chromatography eluting with a gradient of 0 to 50% EtOAc in hexanes to afford the title compound (47.8 mg, 31%). LC/MS: $R_t$=1.68 min, ES$^+$ 447 (FA standard).

Step d: (1S,2S,4R)-4-[4-(Acetylamino)-7H-pyrrolo [2,3-d]pyrimidin-7-yl]-2-(hydroxymethyl)cyclopentyl acetate To a solution of (1S,2S,4R)-4-[4-(acetylamino)-7H-pyrrolo[2,3-d]pyrimidin-7-yl]-2-(}[tert-butyl(dimethyl)silyl]oxy}methyl)cyclopentyl acetate (47.0 mg, 0.105 mmol) in a mixture of THF (2.00 mL) and pyridine (2.00 mL) was added pyridine hydrofluoride (10 drops). After 2 h, additional pyridine hydrofluoride (15 drops) was added and the solution stirred for an additional 2 h. The reaction was quenched via addition of saturated aqueous sodium bicarbonate solution and extracted with EtOAc (2×50 mL). The combined organic extracts were dried over MgSO$_4$, filtered and concentrated in vacuo. The residue was purified via silica gel chromatography eluting with a gradient of 0 to 10% MeOH in DCM to afford the title compound (29.0 mg, 83%). LC/MS: $R_t$=0.76 min, ES$^+$ 333 (FA standard).

Step e: (1S,2S,4R)-4-[4-(Acetylamino)-7H-pyrrolo [2,3-d]pyrimidin-7-yl]-2-}[(aminosulfonyl)oxy]methyl}cyclopentyl acetate A solution of (1S,2S,4R)-4-[4-(acetylamino)-7H-pyrrolo[2,3-d]pyrimidin-7-yl]-2-(hydroxymethyl)cyclopentyl acetate (63.0 mg, 0.190 mmol) and pyridine (0.0800 mL, 0.989 mmol) in AcCN (5.00 mL) at 0° C. was stirred for 15 min. A 0.641 M solution chlorosulfonamide in AcCN (0.640 mL, 0.410 mmol, as prepared in 1j) was then added slowly. After 2 h another portion of the chlorosulfonamide solution (0.72 mL, 0.462 mmol) was added and the reaction was stirred for 1 hour. The reaction was then concentrated in vacuo and the residue was purified by silica gel chromatography eluting with a gradient of 0 to 10% MeOH in DCM to afford the title compound (78.0 mg, 100%). LC/MS: $R_t$=0.81 min, ES$^+$ 412 (FA standard).

Step f: {(1S,2S,4R)-4-[4-(Acetylamino)-7H-pyrrolo [2,3-d]pyrimidin-7-yl]-2-hydroxycyclopentyl}methyl sulfamate and [(1S,2S, 4R)-4-(4-amino-7H-pyrrolo-[2,3-d]pyrimidin-7-yl)-2-hydroxycyclopentyl]methyl sulfamate (Compounds I-9 and I-18)

To neat (1S,2S,4R)-4-[4-(acetylamino)-7H-pyrrolo[2,3-d]pyrimidin-7-yl]-2-{[(aminosulfonyl)oxy]methyl} cyclopentyl acetate (78.0 mg, 0.190 mmol) was added a 7 M solution of ammonia in MeOH (5.00 mL) was stirred at rt overnight. LC/MS showed partial conversion to the intermediate monoacetylated compound, the desired product and some starting material remaining. The reaction mixture was concentrated in vacuo and the residue was purified by reverse phase chromatography to afford {(1S,2S,4R)-4-[4-(acetylamino)-7H-pyrrolo[2,3-d]pyrimidin-7-yl]-2-hydroxycyclopentyl}methyl sulfamate (0.900 mg, 1.3%) and [(1S,2S,4R)-4-(4-amino-7H-pyrrolo[2,3-d]pyrimidin-7-yl)-2-hydroxycyclopentyl] methyl sulfamate (6.50 mg, 11%). Analytical data for {(1S, 2S,4R)-4-[4-(acetylamino)-7H-pyrrolo[2,3-d]pyrimidin-7-yl]-2-hydroxycyclopentyl}methyl sulfamate (Compound I-9): $^1$H NMR (400 MHz, CD$_3$OD, δ): 8.48 (s, 1H), 7.47 (d, J=3.8 Hz, 1H), 6.82 (d, J=3.8, 1H), 5.65-5.48 (m, 1H), 4.60-4.45 (m, 1H), 4.40-4.27 (m, 1H), 4.24-4.11 (m, 1H), 2.98-2.80 (m, 1H), 2.42-2.13 (m, 6H), 2.18-1.93 (m, 1H) ppm. LC/MS: $R_t$=0.98 min, ES$^+$ 370. (FA standard). Analytical data for [(1S,2S,4R)-4-(4-amino-7H-pyrrolo[2,3-d]pyrimidin-7-yl)-2-hydroxycyclopentyl]methyl sulfamate (Compound I-18): $^1$H NMR (400 MHz, CD$_3$OD, δ): 8.09 (s, 1H), 7.30 (d, J=3.8 Hz, 1H), 6.66 (d, J=3.5 Hz, 1H), 5.51-5.41 (m, 1H), 4.51-4.48 (m, 1H), 4.39-4.33 (m, 1H), 4.21-4.16 (m, 1H), 2.85-2.79 (m, 1H), 2.33-2.18 (m, 3H), 2.09-2.00 (m, 1H) ppm. LC/MS: $R_t$=0.85 min, ES$^+$ 328 (FA standard).

Example 35

((1S,2S,4R)-4-{4-[(1,3-Benzodioxol-5-ylmethyl) amino]-7H-pyrrolo[2,3-d]-pyrimidin-7-yl}-2-hydroxycyclopentyl)methyl sulfamate Compound (I-26)

The title compound was prepared following the procedure described in Example 2a-j using 1-(1,3-benzodioxol-5-yl) methanamine in step f. $^1$H-NMR (400 MHz, CD$_3$OD, δ): 8.09 (s, 1H), 7.15 (d, J=3.6 Hz, 1H), 6.81 (s, 1H), 6.79 (d, J=9.9 Hz, 1H), 6.70 (d, J=7.8 Hz, 1H), 6.56 (d, J=3.6 Hz, 1H), 5.85 (s, 2H), 5.45-5.35 (m, 1H), 4.62 (s, 2H), 4.49-4.42 (m, 1H), 4.33 (dd, J=7.6, 7.6 Hz, 1H), 4.16 (dd, J=7.3, 7.3 Hz, 1H), 2.86-2.70 (m, 1H), 2.35-2.10 (m, 3H), 2.05-1.94 (m, 1H) ppm. LC/MS: $R_t$=1.07 min, ES$^+$ 462 (FA standard).

Example 36

((1S,2S,4R)-2-Hydroxy-4-{4-[(1-naphthylmethyl) amino]-7H-pyrrolo[2,3-d]-pyrimidin-7-yl}cyclopentyl)methyl sulfamate (Compound I-38)

The title compound was prepared following the procedure described in Example 2a-j using 1-(1-naphthyl)methanamine in step f. $^1$H NMR (400 MHz, CD$_3$OD, δ): 8.13 (s, 1H), 8.11-8.05 (m, 1H), 7.89-7.84 (m, 1H), 7.77 (d, J=8.2 Hz, 1H), 7.52-7.43 (m, 3H), 7.42-7.35 (m, 1H), 7.15 (d, J=3.6 Hz, 1H), 6.56 (d, J=3.3 Hz, 1H), 5.45-5.37 (m, 1H), 5.19 (s, 2H), 4.48-4.42 (m, 1H), 4.34 (dd, J=7.6, 7.6 Hz, 1H), 4.17 (dd, J=7.3, 7.4 Hz, 1H), 2.83-2.71 (m, 1H), 2.35-2.15 (m, 3H), 2.06-1.96 (m, 1H) ppm. LC/MS: $R_t$=1.24 min, 468 ES+(FA standard).

Example 37

[(1S,2S,4R)-2-Hydroxy-4-(4-{[4-(trifluoromethyl) benzyl]amino}-7H-pyrrolo-[2,3-d]pyrimidin-7-yl) cyclopentyl]methyl sulfamate (Compound I-8)

The title compound was prepared following the procedure described in Example 2a-j using 1-[4-(trifluoromethyl)phenyl]methanamine in step f. $^1$H NMR (CD$_3$OD, 400 MHz, δ): 8.08 (s, 1H), 7.56 (d, J=8.2 Hz, 2H), 7.48 (d, J=8.2 Hz, 2H), 7.18 (d, J=3.5 Hz, 1H), 6.58 (d, J=3.6 Hz, 1H), 5.43-5.34 (m, 1H), 4.80 (s, 2H), 4.45 (br s, 1H), 4.33 (dd, J=2.1, 7.6 Hz, 1H), 4.16 (dd, J=2.3, 7.4 Hz, 1H), 2.81-2.72 (m, 1H), 2.31-2.10 (m, 3H), 2.05-1.97 (m, 1H) ppm. LC/MS: R$_t$=1.33 min, ES$^+$ 486 (FA standard).

Example 38

[(1S,2S,4R)-4-(4-{[4-Chloro-2-(trifluoromethyl) benzyl]amino}-7H-pyrrolo-[2,3-d]pyrimidin-7-yl)-2-hydroxycyclopentyl]methyl sulfamate (Compound I-42)

The title compound was prepared following the procedure described in Example 2a-j using 1-[4-chloro-2-(trifluoromethyl)phenyl]methanamine in step f. $^1$H NMR (CD$_3$OD, 400 MHz, δ): 8.11 (s, 1H), 7.70 (s, 1H), 7.65-7.46 (m, 2H), 7.23 (d, J=3.6 Hz, 1H), 6.61 (d, J=3.4 Hz, 1H), 5.48-5.39 (m, 1H), 4.93 (s, 2H), 4.49 (br s, 1H), 4.36 (dd, J=2.1, 7.6 Hz, 1H), 4.20 (dd, J=2.3, 7.4 Hz, 1H), 2.87-2.74 (m, 1H), 2.38-2.12 (m, 3H), 2.09-1.97 (m, 1H) ppm. LC/MS: R$_t$=1.29 min, ES$^+$ 520 (FA standard).

Example 39

((1S,2S,4R)-4-{4-[(2,4-Dichlorobenzyl)amino]-7H-pyrrolo[2,3-d]pyrimidin-7-yl}-2-hydroxycyclopentyl)methyl sulfamate (Compound I-19)

The title compound was prepared following the procedure described in Example 2a-j using 1-(2,4-dichlorophenyl)methanamine in step f. $^1$H NMR (CD$_3$OD, 400 MHz, δ): 8.10 (s, 1H), 7.46 (s, 1H), 7.32 (d, J=8.3 Hz, 1H), 7.29-7.20 (m, 2H), 6.61 (d, J=3.5 Hz, 1H), 5.54-5.37 (m, 1H), 4.92-4.74 (s, 2H), 4.49 (br s, 1H), 4.37 (dd, J=2.1, 7.6 Hz, 1H), 4.19 (dd, J=2.4, 7.3 Hz, 1H), 2.88-2.72 (m, 1H), 2.40-2.17 (m, 3H), 2.11-1.98 (m, 1H) ppm. LC/MS: R$_t$=1.37 min, ES$^+$ 488 (FA standard).

Example 40

((1S,2S,4R)-4-{4-[(3,5-Dichlorobenzyl)amino]-7H-pyrrolo[2,3-d]pyrimidin-7-yl}-2-hydroxycyclopentyl)methyl sulfamate (Compound I-16)

The title compound was prepared following the procedure described in Example 2a-j using 1-(3,5-dichlorophenyl)methanamine in step f. $^1$H NMR (CD$_3$OD, 400 MHz, δ): 8.10 (s, 1H), 7.35-7.23 (m, 3H), 7.19 (d, J=3.6 Hz, 1H), 6.58 (d, J=3.6 Hz, 1H), 5.49-5.35 (m, 1), 4.69 (s, 2H), 4.45 (br s, 1H), 4.33 (dd, J=2.1, 7.6 Hz, 1H), 4.16 (dd, J=2.4, 7.3 Hz, 1H), 2.85-2.72 (m, 1H), 2.38-2.13 (m, 3H), 2.07-1.94 (m, 1H) ppm. LC/MS: R$_t$=1.38 min, ES$^+$ 488 (FA standard).

Example 41

[(1S,2S,4R)-2-Hydroxy-4-(4-{[(1R,2S)-2-methoxy-2,3-dihydro-1H-inden-1-yl]-amino}-7H-pyrrolo[2,3-d]pyrimidin-7-yl)cyclopentyl]methyl sulfamate (Compound I-52)

Step a: tert-Butyl [(1R,2S)-2-hydroxy-2,3-dihydro-1H-inden-1-yl]carbamate (1R,2S)-1-Aminoindan-2-ol (1.83 g, 12.3 mmol) was dissolved in DCM (70.0 mL) and TEA (3.42 mL, 24.5 mmol) was added. Di-tert-butyldicarbonate (2.81 g, 12.9 mmol) was added at rt and the reaction mixture was stirred for 5 h. The solution was concentrated in vacuo and purified via silica gel chromatography eluting with a gradient of 0 to 100% EtOAc in hexanes to afford the title compound (3.12 g, 100%). LC/MS: R$_t$=1.55 min, ES$^+$ 250. (AA standard).

Step b: tert-Butyl [(1R,2S)-2-methoxy-2,3-dihydro-1H-inden-1-yl]carbamate

A mixture of tert-butyl [(1R,2S)-2-hydroxy-2,3-dihydro-1H-inden-1-yl]-carbamate (680 mg, 2.73 mmol), DMF (21.1 mL), barium monoxide (5.02 g, 32.7 mmol), barium hydroxide (2.80 g, 16.4 mmol) and iodomethane (1.70 mL, 27.3 mmol) was stirred overnight. LC/MS showed no starting material. The reaction was quenched via addition of a saturated solution of sodium bicarbonate and was extracted with DCM. The organic layer was washed with water (3×), dried over sodium sulfate and concentrated in vacuo. The residue was purified via silica gel chromatography eluting with a gradient of 0 to 50% EtOAc in hexanes to afford the title compound (178 mg, 25%). LC/MS: R$_t$=1.24 min, ES$^+$ 264 (AA standard).

Step c: (1R,2S)-2-Methoxyindan-1-amine

To tert-butyl [(1R,2S)-2-methoxy-2,3-dihydro-1H-inden-1-yl]carbamate (253 mg, 0.961 mmol) was added a 4.00 M solution of hydrochloric acid in 1,4-dioxane (5.00 mL) and the mixture was stirred for 10 min, after which a white solid crashed out. The suspension was concentrated in vacuo and co-evaporated with toluene to afford a white solid, which was dissolved in water. The solution was adjusted to pH 10 via addition of sodium carbonate. The mixture was then extracted with diethyl ether (3×30 mL) and the organic extracts were concentrated in vacuo to afford the title compound (150 mg, 99%). LC/MS: R$_t$=0.85 min, ES$^+$ 164 (AA standard).

Step d: [(1S,2S,4R)-2-Hydroxy-4-(4-{[(1R,2S)-2-methoxy-2,3-dihydro-1H-inden-1-yl]-amino}-7H-pyrrolo[2,3-d]pyrimidin-7-yl)cyclopentyl]methyl sulfamate (Compound I-52)

The title compound was prepared following the procedure described in Example 2a-j using (1R,2S)-2-methoxyindan-1-amine in step f. $^1$H NMR (CD$_3$OD, 400 MHz, δ): 8.20 (s, 1H), 7.27-7.14 (m, 5H), 6.67 (d, J=3.6 Hz, 1H), 5.90 (d, J=5.2 Hz, 1H), 4.49 (t, J=3.5 Hz, 1H), 4.37 (dd, J=7.6, 9.7 Hz, 1H), 4.31-4.28 (m, 1H), 4.20 (dd, J=7.3, 9.7 Hz, 1H), 3.31-3.29 (m, 4H), 3.19-3.05 (m, 2H), 2.85-2.77 (m, 1H), 2.37-2.20 (m, 3H), 2.08-2.00 (m, 1H) ppm. LC/MS: R$_t$=1.46 min, ES$^+$ 474 (AA standard).

Example 42

[(1S,2S,4R)-4-(4-{[(1S)-3,3-Dimethyl-2,3-dihydro-1H-inden-1-yl]amino}-7H-pyrrolo[2,3-d]pyrimidin-7-yl)-2-hydroxycyclopentyl]methyl sulfamate and—
[(1S,2S,4R)-4-(4-{[(1R)-3,3-dimethyl-2,3-dihydro-1H-inden-1-yl]amino}-7H-pyrrolo[2,3-d]pyrimidin-7-yl)-2-hydroxycyclopentyl]methyl sulfamate (Compounds I-14 and I-21)

Step a: 3,3-Dimethylindan-1-one oxime

To a solution of 3,3-dimethylindan-1-one (1.16 g, 7.21 mmol) and hydroxylamine hydrochloride (1.31 g, 18.8 mmol) in MeOH (20.0 mL) was added a solution of sodium hydroxide (765 mg, 19.1 mmol) in water (10.0 mL). The mixture was heated to 80° C. for 2 h. The cooled reaction was concentrated in vacuo and partitioned between DCM and water. The organic layer was separated and concentrated in vacuo to afford the title compound as an oil (1.23 g, 97%). LC/MS: $R_t$=1.61 min, ES$^+$ 176 (AA standard).

Step b: 3,3-Dimethylindan-1-amine 3,3-Dimethylindan-1-one oxime (1.22 g, 6.96 mmol) was dissolved in MeOH (20.0 mL) and palladium (10 weight percent on carbon, 50% water wet, 148 mg) was added. The reaction was placed under an atmosphere of hydrogen and was stirred overnight. The mixture was then filtered through Celite, washed through with MeOH and the filtrates concentrated in vacuo to afford the product as a grey oil (1.12 g, 100%). LC/MS: $R_t$=1.04 min, ES$^+$ 162 (AA standard).

Step c: [(1S,2S,4R)-4-(4-{[((1S)-3,3-Dimethyl-2,3-dihydro-1H-inden-1-yl]amino}-7H-pyrrolo[2,3-d]pyrimidin-7-yl)-2-hydroxycyclopentyl]methyl sulfamate and—[(1S,2S,4R)-4-(4-{[(1R)-3,3-dimethyl-2,3-dihydro-1H-inden-1-yl]amino}-7H-pyrrolo[2,3-d]pyrimidin-7-yl)-2-hydroxycyclopentyl]methyl sulfamate (Compounds I-14 and I-21)

The title compounds were prepared following the procedure described in Example 1a-g and then Example 2i-j using 3,3-dimethylindan-1-amine in step 1c. The mixture was separated into its component diastereomers via chiral HPLC (Chiralpac-AS-RH, 20 mm ID×250 mm, 5 micron column eluting with 55% water in AcCN with 0.1% AA at 6 mL/minute): Peak A—21.4 min, [(1S,2S,4R)-4-(4-{[(1R)-3,3-dimethyl-2,3-dihydro-1H-inden-1-yl]amino}-7H-pyrrolo[2,3-d]pyrimidin-7-yl)-2-hydroxycyclopentyl]methyl sulfamate, R-enantiomer (Compound I-21). Peak B—22.6 min, [(1S,2S,4R)-4-(4-{[(1S)-3,3-dimethyl-2,3-dihydro-1H-inden-1-yl]amino}-7H-pyrrolo[2,3-d]pyrimidin-7-yl)-2-hydroxycyclopentyl]methyl sulfamate, S-enantiomer (Compound I-14). $^1$H NMR (CD$_3$OD, 300 MHz, δ): 8.16 (s, 1H), 7.28-7.10 (m, 5H), 6.63 (d, J=3.6 Hz, 1H), 5.93 (t, J=8.1 Hz, 1H), 5.51-5.38 (m, 1H), 4.48 (br s, 1H), 4.37 (dd, J=7.6, 9.7 Hz, 1H), 4.20 (dd, J=7.4, 9.6 Hz, 1H), 2.88-2.72 (m, 1H), 2.47 (dd, J=7.3, 12.4 Hz, 1H), 2.37-2.19 (m, 3H), 2.03 (ddd, J=4.5, 9.2, 13.9 Hz, 1H), 1.93 (dd, J=9.1, 12.3 Hz, 1H), 1.42 (s, 3H), 1.27 (s, 3H) ppm. LC/MS: $R_t$=1.66 min, ES$^+$ 472 (AA standard).

Example 43

[(1S,2S,4R)-4-(4-{[(1S)-3,3-Dimethyl-2,3-dihydro-1H-inden-1-yl]amino}-7H-pyrrolo[2,3-d]pyrimidin-7-yl)-2-hydroxycyclopentyl]methyl sulfamate (Compound I-14), Chiral synthesis Step a: (2R)-2-{[(1S)-3,3-Dimethyl-2,3-dihydro-1H-inden-1-yl]amino}-2-phenylethanol To a solution of 3,3-dimethylindan-1-one (925 mg, 5.77 mmol) and (R)-(−)-2-phenylglycinol (893 mg, 6.51 mmol) in toluene (10.0 mL) was added p-toluenesulfonic acid monohydrate (62.5 mg, 0.328 mmol). The reaction was heated to reflux under an atmosphere of nitrogen for 90 min. At this point, the mixture was cooled and diluted with toluene (10.0 mL). The mixture was washed with saturated aqueous sodium bicarbonate solution and water. The organic layer was concentrated in vacuo and the residue was dissolved in THF (10.0 mL) and cooled to 0° C. Acetic acid (1.13 mL, 19.9 mmol) was added, followed by sodium borohydride (251 mg, 6.64 mmol) and the reaction was allowed to warm to rt overnight. The mixture was partitioned between DCM and saturated aqueous sodium bicarbonate solution. The organic layer was concentrated and silica gel chromatography eluting with a gradient of 5 to 35% EtOAc in DCM afforded the title compound (1.49 g, 74%). LC/MS: $R_t$=1.92 min, ES$^+$ 282 (AA standard).

Step b: (1S)-3,3-Dimethylindan-1-amine

A solution of (2R)-2-{[(1S)-3,3-dimethyl-2,3-dihydro-1H-inden-1-yl]amino}-2-phenylethanol (1.44 g, 5.13 mmol) in MeOH (40.0 mL) was added to a stirred solution of lead tetraacetate (3.75 g, 8.03 mmol) in MeOH (60.0 mL) at 0° C. dropwise over 20 min. After stirring for 45 min, the reaction was quenched via addition of a 10% solution of sodium carbonate in water (76.0 mL) and the mixture was stirred for 10 min. DCM (200 mL) was then added and the layers were separated. The aqueous layer was extracted with DCM (50.0 mL). The combined organic layers were concentrated in vacuo and the residue was dissolved in ethanol (190 mL) and treated with a 10.4 M aqueous solution of hydrochloric acid (5.70 mL, 59.3 mmol). The resulting mixture was then heated to reflux for 16 h. The cooled reaction was concentrated in vacuo and partitioned between water (150 mL) and diethyl ether (50.0 mL). The aqueous layer was adjusted to pH 10 via addition of sodium carbonate and extracted with diethyl ether (3×50.0 mL). The combined organic layers were concentrated in vacuo and silica gel chromatography eluting with a gradient of 0 to 10% MeOH in DCM to afford the title compound as a pale yellow oil (420 mg, 51%). $^1$H NMR (CD$_3$OD, 300 MHz, δ): 7.34-7.14 (m, 4H), 4.45-4.37 (m, 1H), 2.38 (dd, J=7.1, 12.4 Hz, 1H), 1.73 (br s, 2H), 1.60 (dd, J=8.7, 12.4 Hz, 1H), 1.39 (s, 3H), 1.19 (s, 3H) ppm.

Step c: [(1S,2S,4R)-4-(4-{[(1S)-3,3-Dimethyl-2,3-dihydro-1H-inden-1-yl]amino}-7H-pyrrolo[2,3-d]pyrimidin-7-yl)-2-hydroxycyclopentyl]methyl sulfamate (Compound I-14)

The title compound was prepared following the procedure described in Example 1a-g and then Example 2i-j using (1S)-3,3-dimethylindan-1-amine in step 1c. Chiral HPLC showed co-elution with the compound synthesized in Example 42c, Peak B. Analytical data identical to Example 42c.

Example 44

[(1S,2S,4R)-4-(4-{[(1S)-5-Chloro-2,3-dihydro-1H-inden-1-yl]amino}-7H-pyrrolo[2,3-d]pyrimidin-7-yl)-2-hydroxycyclopentyl]methyl sulfamate, Potassium salt (Compound I-27)

The title compound was prepared following the procedure described in Example 43a-b and then Example 2f-j using 5-chloroindan-1-one in step 43a and (1S)-5-chloroindan-1-amine in step 2f. The potassium salt was formed following the procedure described in Example 11. $^1$H NMR (CD$_3$OD, 300 MHz, δ): 8.17 (s, 1H), 7.28-7.10 (m, 4H), 6.62 (d, J=3.6 Hz, 1H), 5.82 (t, J=7.7 Hz, 1H), 5.44 (qd, J=4.6, 8.3 Hz, 1H), 4.48 (br s, 1H), 4.37 (dd, J=7.6, 9.7 Hz, 1H), 4.19 (dd, J=7.4, 9.7 Hz, 1H), 4.09 (q, J=7.1 Hz, 1H), 3.05 (ddd, J=3.3, 8.6, 15.9 Hz, 1H), 2.98-2.71 (m, 2H), 2.64 (dtd, J=3.5, 7.7, 11.2 Hz, 1H), 2.38-2.14 (m, 3H), 2.05 (dd, J=4.4, 8.6 Hz, 1H) ppm. LC/MS: $R_t$=1.58 min, $ES^+$ 478 (AA standard).

Example 45

[(1S,2S,4R)-4-(4-{[(1S)-5-fluoro-2,3-dihydro-1H-inden-1-yl]amino}-7H-pyrrolo-[2,3-d]pyrimidin-7-yl)-2-hydroxycyclopentyl]methyl sulfamate (Compound I-36)

The title compound was prepared following the procedure described in Example 44 using 5-fluoroindan-1-one. $^1$H NMR (CD$_3$OD, 400 MHz, δ): 8.17 (s, 1H), 7.25-7.19 (m, 2H), 6.99-6.85 (m, 2H), 6.63 (d, J=3.6 Hz, 1H), 5.81 (t, J=7.5 Hz, 1H), 5.49-5.41 (m, 1H), 4.49 (t, J=3.6 Hz 1H), 4.37 (dd, J=7.6, 9.7 Hz, 1H), 4.20 (dd, J=7.4, 9.7 Hz, 1H), 3.12-3.02 (m, 1H), 2.95-2.87 (m, 1H), 2.84-2.75 (m, 1H), 2.69-2.61 (m, 1H), 2.36-2.19 (m, 3H), 2.10-1.97 (m, 2H) ppm. LC/MS: $R_t$=1.56 min, $ES^+$ 462 (AA standard).

Example 46

[(1S,2S,4R)-4-(4-{[(1S)-5-bromo-2,3-dihydro-1H-inden-1-yl]amino}-7H-pyrrolo[2,3-d]pyrimidin-7-yl)-2-hydroxycyclopentyl]methyl sulfamate (Compound I-33)

The title compound was prepared following the procedure described in Example 44 using 5-bromoindan-1-one. $^1$H NMR (CD$_3$OD, 400 MHz, δ): 8.17 (s, 1H), 7.42 (s, 1H), 7.29 (d, J=8.1 Hz, 1H), 7.19-7.14 (m, 2H), 6.63 (d, J=3.6 Hz, 1H), 5.82 (t, J=7.8 Hz, 1H), 5.49-5.41 (m, 1H), 4.49 (br s, 1H), 4.38 (dd, J=7.6, 9.7 Hz, 1H), 4.20 (dd, J=7.4, 9.7 Hz, 1H), 3.08-3.01 (m, 1H), 2.96-2.88 (m, 1H), 2.85-2.75 (m, 1H), 2.67-2.59 (m, 1H), 2.36-2.20 (m, 3H), 2.08-1.99 (m, 2H) ppm. LC/MS: $R_t$=1.64 min, $ES^+$ 524 (AA standard).

Example 47

((1S,2S,4R)-4-{4-[(4-Chlorobenzyl)amino]-7H-pyrrolo[2,3-d]pyrimidin-7-yl}-2-hydroxy-2-methylcyclopentyl)methyl sulfamate (Compound I-5)

Step a: (1S,5S)-5-({[tert-Butyl(diphenyl)silyl]oxy}methyl)cyclopent-2-en-1-ol

To a solution of (1S,5S)-5-(hydroxymethyl)cyclopent-2-en-1-ol (1.14 g, 9.99 mmol) in DCM (50.0 mL) was added TEA (4.18 mL, 30.0 mmol) and DMAP (60.0 mg, 0.491 mmol). The solution was cooled to 0° C., tert-butylchlorodiphenylsilane (3.90 mL, 15.0 mol) was added and the mixture was stirred at rt for 2 h. TLC indicated complete conversion, and the reaction was quenched by addition of MeOH (1.00 mL). Concentration in vacuo and silica gel chromatography eluting with a gradient of 0 to 100% EtOAc in hexanes afforded the title compound (2.88 g, 86%). LC/MS: $R_t$=2.51 min, $ES^+$ 353 (AA standard).

Step b: (5S)-5-({[tert-Butyl(diphenyl)silyl]oxy}methyl)cyclopent-2-en-1-one (1S,5S)-5-({[tert-Butyl(diphenyl)silyl]oxy}methyl)cyclopent-2-en-1-ol (460. mg, 1.30 mmol) was dissolved in DCM (15.0 mL) and pyridinium dichromate (1.47 g, 3.91 mmol) was added. The mixture was stirred at rt overnight, at which point LC/MS indicated complete conversion. The mixture was diluted with DCM (15.0 mL), filtered and concentrated in vacuo. Silica gel chromatography eluting with 0 to 50% EtOAc in hexanes afforded the title compound (400. mg, 79%). LC/MS: $R_t$=2.42 min, $ES^+$ 351 (AA standard).

Step c: (1S,5S)-5-({[tert-Butyl(diphenyl)silyl]oxy}methyl)-1-methylcyclopent-2-en-1-ol A solution of (5S)-5-({[tert-butyl(diphenyl)silyl]oxy}methyl)cyclopent-2-en-1-one (250. mg, 0.713 mmol) in diethyl ether (10.0 mL) under an atmosphere of nitrogen was cooled to −40° C. and a 1.60 M solution of methyllithium in diethyl ether (0.579 mL, 0.926 mmol) was added slowly and the mixture was stirred at −40° C. for 3 h. TLC indicated complete conversion, and the reaction was quenched via addition of saturated aqueous ammonium chloride (5.00 mL), extracted with EtOAc (3×10.0 mL), dried over MgSO$_4$, filtered, and concentrated in vacuo. Silica gel chromatography eluting with a gradient of 0 to 50% EtOAc in hexanes afforded the title compound (190 mg, 73%). Stereochemistry of the product was confirmed using ROESY analysis. LC/MS: $R_t$=2.55 min, $ES^+$ 367 (AA standard).

Step d: (1S,5S)-5-(Hydroxymethyl)-1-methylcyclopent-2-en-1-ol

To a solution of (1S,5S)-5-({[tert-butyl(diphenyl)silyl]oxy}methyl)-1-methylcyclopent-2-en-1-ol (560 mg, 1.53 mmol) in THF (29.5 mL) at 0° C. was added 1.00 M of tetra-n-butylammonium fluoride in THF (3.06 mL, 3.06 mmol). The mixture was stirred at rt for 2 h, at which point the solvent was concentrated in vacuo and the residue was purified by silica gel chromatography eluting with a gradient of 50 to 100% EtOAc in hexanes to afford the title compound (181 mg, 92%). LC/MS: $R_t$=0.76 min, $ES^+$ 129 (AA standard).

Step e: (1S,2R,3S,5S)-3-(Hydroxymethyl)-2-methyl-6-oxabicyclo[3.1.0]hexan-2-ol

To a solution of (1S,5S)-5-(hydroxymethyl)-1-methylcyclopent-2-en-1-ol (0.181 g, 0.00141 mol) in DCM (18.0 mL) was added sodium bicarbonate (237 mg, 2.82 mmol) and the mixture was cooled to 0° C. To this mixture was added 3-chloroperbenzoic acid (380. mg, 1.69 mmol) and the reaction was stirred at rt for 4 h. The solvent was removed in vacuo and silica gel chromatography eluting with a gradient of 0 to 100% EtOAc in DCM afforded the title compound (200 mg, 98%). LC/MS: $R_t$=0.52 min, $ES^+$ 145 (AA standard).

Step f: (1aS,1bR,5aS,6aS)-3-(4-Methoxyphenyl)-1b-methylhexahydrooxireno[4,5]-cyclopenta[1,2-d][1,3]dioxine To a solution of (1S,2R,3S,5S)-3-(hydroxymethyl)-2-methyl-6-oxabicyclo[3.1.0]-hexan-2-ol (200 mg, 1.39 mmol) in DCM (13.0 mL) at 0° C. was added dimethoxy(4-methoxyphenyl)methane (0.709 mL, 4.16 mmol) followed by pyridinium p-toluenesulfonate (35.0 mg, 0.139 mmol) and the mixture was stirred at rt overnight. TLC showed complete conversion. Silica gel chromatography eluting with a gradient of 0 to 50% EtOAc in hexanes afforded the title compound (215 mg, 59%). LC/MS: $R_t$=1.72 min, $ES^+$ 263 (AA standard).

Step g: ((1S,2S,4R)-4-{4-[(4-Chlorobenzyl)amino]-7H-pyrrolo[2,3-d]pyrimidin-7-yl}-2-hydroxy-2-methylcyclopentyl)methyl sulfamate (Compound I-5)

The title compound was prepared following the procedure described in Example 1d-i using (1aS,1bR,5aS,6aS)-3-(4-

Methoxyphenyl)-1b-methylhexahydrooxireno-[4,5]cyclopenta[1,2-d][1,3]dioxine and 4-chlorobenzylamine in step d. $^1$H NMR (CD$_3$OD, 400 MHz, δ): 8.20 (s, 1H), 7.46 (d, J=3.6 Hz, 1H), 7.37 (s, 4H), 6.82 (d, J=3.6 Hz, 1H), 5.48-5.40 (m, 1H), 4.78 (s, 2H), 4.41 (dd, J=6.0, 10.0 Hz, 1H), 4.14 (dd, J=8.2, 10.0 Hz, 1H), 2.69-2.64 (m, 1H), 2.39-2.16 (m, 4H), 1.47 (s, 3H) ppm. LC/MS: R$_t$=1.55 min, ES$^+$ 466 (AA standard).

Example 48

(1S,2S,4R)-4-{4-[(1S)-2,3-Dihydro-1H-inden-1-ylamino]-7H-pyrrolo[2,3-d]-pyrimidin-7-yl}-2-hydroxy-2-methylcyclopentyl)methyl sulfamate (Compound I-30)

The title compound was prepared following the procedure described in Example 47 using (S)-(+)-1-aminoindan in step g. $^1$H NMR (CD$_3$OD, 400 MHz, δ): 8.25 (s, 1H), 7.48 (d, J=3.6 Hz, 1H), 7.34-7.23 (m, 4H), 6.89 (d, J=3.6 Hz, 1H), 5.61-5.56 (m, 1H), 5.50-5.43 (m, 1H), 4.42 (dd, J=6.0, 10.0 Hz, 1H), 4.15 (dd, J=8.0, 10.0 Hz, 1H), 3.18-3.10 (m, 1H), 3.03-2.97 (m, 1H), 2.75-2.64 (m, 1H), 2.39-2.07 (m, 5H), 1.48 (s, 3H) ppm. LC/MS: R$_t$=1.57 min, ES$^+$ 458 (AA standard).

Example 49

[(1S,2S,4R)-4-(4-{[2-(difluoromethoxy)benzyl]amino}-7H-pyrrolo[2,3-d]-pyrimidin-7-yl)-2-hydroxycyclopentyl]methyl sulfamate (Compound I-2)

The title compound was prepared following the procedure described in Example 2a-j, using 2-difluoromethoxybenzylamine in step f. $^1$H NMR (CD$_3$OD, 400 MHz, δ): 8.10 (s, 1H), 7.35-7.26 (m, 2H), 7.22 (d, J=3.7 Hz, 1H), 7.17-7.13 (m, 2H), 6.87 (t, J=74.2 Hz, 1H), 6.62 (d, J=3.6 Hz, 1H), 5.45-5.20 (m, 1H), 4.80 (s, 2H), 4.49-4.47 (m, 1H), 4.36 (dd, J=7.6, 9.7 Hz, 1H), 4.19 (dd, J=7.3, 9.7 Hz, 1H), 2.86-2.75 (m, 1H), 2.35-2.19 (m, 3H), 2.07-2.00 (m, 1H) ppm. LC/MS: R$_t$=1.03 min, ES$^+$ 484 (FA standard).

Example 50

[(1S,2S,4R)-4-(5-ethynyl-4-methyl-7H-pyrrolo[2,3-d]pyrimidin-7-yl)-2-hydroxycyclopentyl]methyl sulfamate (Compound I-44)

Step a: 5-iodo-7-[(4aS,6R,7aS)-2-(4-methoxyphenyl)hexahydrocyclopenta[d][1,3]dioxin-6-yl]-4-methyl-7H-pyrrolo[2,3-d]pyrimidine To a solution of 7-[(4aS,6R,7aS)-2-(4-methoxyphenyl)hexahydrocyclopenta[d]-[1,3]dioxin-6-yl]-4-methyl-7H-pyrrolo[2,3-d]pyrimidine (363 mg, 0.995 mmol, as prepared in Example 1a-f) in DCM (15.0 mL) was added N-iodosuccinimide (256 mg, 1.14 mmol), and the mixture was stirred at rt overnight. Silica gel chromatography eluting with a gradient of 25 to 100% EtOAc in hexanes afforded the title compound (253 mg, 52%). LC/MS: R$_t$=2.03 min, ES$^+$ 492 (AA standard).

Step b: 7-[(4aS,6R,7aS)-2-(4-methoxyphenyl)hexahydrocyclopenta[d][1,3]dioxin-6-yl]-4-methyl-5-[(trimethylsilyl)ethynyl]-7H-pyrrolo[2,3-d]pyrimidine To a suspension of 5-iodo-7-[(4aS,6R,7aS)-2-(4-methoxyphenyl)-hexahydrocyclopenta[d][1,3]dioxin-6-yl]-4-methyl-7H-pyrrolo[2,3-d]pyrimidine (337 mg, 0.685 mmol), copper(I) iodide (26.0 mg, 0.137 mmol), dichlorobis(triphenylphosphine)-palladium(II) (48.0 mg, 0.0684 mmol) and DIPEA (0.240 mL, 1.38 mmol) in DMF (20.0 mL) was added ethynyltrimethylsilane (188 mg, 1.91 mmol) and the mixture was stirred at rt overnight. The reaction mixture was quenched via addition of saturated aqueous sodium bicarbonate solution and extracted with EtOAc. The combined organic layers were dried over MgSO$_4$, filtered, and concentrated in vacuo. Silica gel chromatography eluting with a gradient of 0 to 75% EtOAc in hexanes afforded the title compound (314 mg, 99%). LC/MS: R$_t$=2.38 min, ES$^+$ 462 (AA standard).

Step c: 5-ethynyl-7-[(4aS,6R,7aS)-2-(4-methoxyphenyl)hexahydrocyclopenta[d][1,3]-dioxin-6-yl]-4-methyl-7H-pyrrolo[2,3-d]pyrimidine Potassium carbonate (191 mg, 1.38 mmol) was added to a solution of 7-[(4aS,6R,7aS)-2-(4-methoxyphenyl)hexahydrocyclopenta[d][1,3]dioxin-6-yl]-4-methyl-5-[(trimethylsilyl)ethynyl]-7H-pyrrolo[2,3-d]pyrimidine (314 mg, 0.680 mmol) in MeOH (10.0 mL), and the mixture was stirred at rt overnight. The reaction mixture was diluted with EtOAc, washed with saturated aqueous sodium bicarbonate solution, dried over MgSO$_4$, filtered, and concentrated in vacuo to afford the title compound as an oil (215 mg, 81%). LC/MS: R$_t$=1.94 min, ES$^+$ 390 (AA standard).

Step d: [(1S,2S,4R)-4-(5-ethynyl-4-methyl-7H-pyrrolo[2,3-d]pyrimidin-7-yl)-2-hydroxycyclopentyl]methyl sulfamate (Compound I-44)

The title compound was prepared following the procedure described in Example 1g-j, using 5-ethynyl-7-[(4aS,6R,7aS)-2-(4-methoxyphenyl)hexahydrocyclopenta[d]-[1,3]dioxin-6-yl]-4-methyl-7H-pyrrolo[2,3-d]pyrimidine in step g. $^1$H NMR (CD$_3$OD, 400 MHz, δ): 8.63 (s, 1H), 7.87 (s, 1H), 5.47-5.58 (m, 1H), 4.51-4.47 (m, 1H), 4.36 (dd, J=7.5, 9.5 Hz, 1H), 4.19 (dd, J=7.5, 10.0 Hz, 1H), 3.65 (s, 1H), 3.48-3.46 (m, 1H), 3.13-3.11 (m, 1H), 2.90 (s, 3H), 2.33-2.20 (m, 2H), 2.00-2.12 (m, 1H) ppm. LC/MS: R$_t$=1.16 min, ES$^+$ 351 (AA standard).

Example 51

[(1S,2S,4R)-4-(4-{[(1S)-4-fluoro-2,3-dihydro-1H-inden-1-yl]amino}-7H-pyrrolo[2,3-d]pyrimidin-7-yl)-2-hydroxycyclopentyl]methyl sulfamate (Compound I-61)

The title compound was prepared following the procedure described in Example 2a-j using (R)-4-chloro-2,3-dihydro-1H-inden-1-yl amine in step f. $^1$H NMR (CD$_3$OD, 400 MHz, δ): 8.27 (s, 1H), 7.44 (d, J=3.21 Hz, 1H) 7.30-7.24 (m, 1H), 7.15 (d, J=7.5, 1H), 7.02 (t, J=8.64, 8.64 Hz, 1H), 6.86 (d, J=2.93 Hz, 1H), 5.67 (t, J=6.99, 6.99 Hz, 1H), 5.56-5.48 (m, 1H), 4.52-4.48 (m, 1H), 4.37 (dd, J=9.76, 7.49 Hz, 1H), 4.19 (dd, J=9.75, 7.44 Hz, 1H), 3.22-3.14 (m, 1H), 3.02-2.93 (m, 1H), 2.90-2.70 (m, 2H), 2.38-2.04 (m, 5H), ppm. LC/MS: R$_t$=1.10 min, ES+ 462 (FA standard).

Example 52

[(1R,2R,4S)-4-(4-{[(1S)-4,7-difluoro-2,3-dihydro-1H-inden-1-yl]amino}-7H-pyrrolo[2,3-d]pyrimidin-7-yl)-2-hydroxycyclopentyl]methyl sulfamate (Compound I-62)

The title compound was prepared following the procedure described in Example 2a-j using (S)-4,7-difluoro-2,3-dihydro-1H-inden-1-yl amine in step f. ¹H NMR (CD₃OD, 400 MHz, δ): 8.17 (s, 1H), 7.17 (d, J=3.8 Hz, 1H), 6.99 (m, 1H), 6.89 (m, 1H), 6.60 (d, J=3.5 Hz, 1H), 6.05 (t, J=5.5 Hz, 1H), 5.48-5.41 (m, 1H), 4.48 (t, J=6.8 Hz, 1H), 4.36 (dd, J=7.5, 9.8 Hz, 1H), 4.19 (dd, J=7.3, 9.8 Hz, 1H), 3.20-3.11 (m, 1H), 2.98-2.89 (m, 1H), 2.84-2.75 (m, 1H), 2.70-2.60 (m, 1H), 2.35-2.20 (m, 3H), 2.19-2.09 (m, 1H), 2.07-1.99 (m, 1H). LC/MS: R$_t$=1.07 min, ES⁺ 480 (FA standard).

Example 53

[(1S,2S,4R)-4-(4-{[(1R)-4-chloro-2,3-dihydro-1H-inden-1-yl]amino}-7H-pyrrolo[2,3-d]pyrimidin-7-yl)-2-hydroxycyclopentyl]methyl sulfamate (Compound I-63)

The title compound was prepared following the procedure described in Example 2a-j using (R)-4-chloro-2,3-dihydro-1H-inden-1-yl amine in step f. ¹H NMR (CD₃OD, 400 MHz, δ): 8.18 (s, 1H), 7.24-7.12 (m, 4H), 6.64 (d, J=3.6 Hz, 1H), 5.91 (t, J=8.1 Hz, 1H), 5.51-5.39 (m, 1H), 4.49 (t, J=7.2 Hz, 1H), 4.37 (dd, J=7.7, 9.8 Hz, 1H), 4.19 (dd, J=7.3, 9.8 Hz, 1H), 3.18-3.07 (m, 1H), 2.98-2.85 (m, 1H), 2.84-2.74 (m, 1H), 2.72-2.60 (m, 1H), 2.38-2.17 (m, 3H), 2.11-1.98 (m, 2H). LC/MS: R$_t$=1.16 min, ES⁺ 478 (FA standard).

Example 54

((1S,2S,4R)-4-(4-((S)-4-chloro-2,3-dihydro-1H-inden-1-ylamino)-7H-pyrrolo[2,3-d]pyrimidin-7-yl)-2-hydroxycyclopentyl)methyl sulfamate (Compound I-64)

The title compound was prepared following the procedure described in Example 2a-j using (S)-4-chloro-2,3-dihydro-1H-inden-1-yl amine in step f. ¹H NMR (CD₃OD, 400 MHz, δ): 8.30 (s, 1H), 7.52 (br s, 1H), 7.38-7.23 (m, 3H), 6.93 (br s, 1H), 5.69-5.50 (m, 2H), 4.54-4.47 (m, 1H), 4.37 (dd, J=7.3, 9.8 Hz, 1H), 4.19 (dd, J=7.3, 9.5 Hz, 1H), 3.25-3.15 (m, 1H), 3.07-2.96 (m, 1H), 2.92-2.82 (m, 1H), 2.82-2.71 (m, 1H), 2.40-2.06 (m, 5H). LC/MS: R$_t$=1.64 min, ES⁺ 478 (AA standard).

Example 55

[(1S,2S,4R)-4-(4-{[(1R)-4-bromo-2,3-dihydro-1H-inden-1-yl]amino}-7H-pyrrolo[2,3-d]pyrimidin-7-yl)-2-hydroxycyclopentyl]methyl sulfamate (Compound I-65)

The title compound was prepared following the procedure described in Example 44 using 4-bromoindan-1-one. ¹H-NMR (400 MHz, MeOD, δ): 8.17 (s, 1H), 7.39 (d, J=7.9 Hz, 1H), 7.22 (d, J=7.5 Hz, 1H), 7.19 (d, J=3.7 Hz, 1H), 7.08 (t, J=7.7 Hz, 1H), 6.62 (d, J=3.6 Hz, 1H), 5.96 (t, J=7.8 Hz, 1H), 5.44 (m, 1H), 4.48 (t, J=3.5 Hz, 1H), 4.37 (dd, J=7.6 Hz, 9.7 Hz, 1H), 4.19 (dd, J=7.3 Hz, 9.7 Hz, 1H), 3.09 (ddd, J=3.2 Hz, 9.1 Hz, 16.3 Hz, 1H), 2.89 (td, J=8.4 Hz, 16.6 Hz, 1H), 2.79 (m, 1H), 2.65 (dtd, J=3.3 Hz, 8.0 Hz, 12.7 Hz, 1H), 2.27 (m, 3H), 2.05 (m, 2H). LC/MS: R$_t$=1.66 min, ES⁺ 524 (AA standard).

Example 56

[(1R,2R,4S)-4-(4-{[(1S)-7-fluoro-2,3-dihydro-1H-inden-1-yl]amino}-7H-pyrrolo[2,3-d]pyrimidin-7-yl)-2-hydroxycyclopentyl]methyl sulfamate (Compound I-66)

The title compound was prepared following the procedure described in Example 44 using 7-fluoroindan-1-one. ¹H NMR (CD₃OD, 400 MHz, δ): 8.17 (s, 1H), 7.29-7.22 (m, 1H), 7.16 (d, J=3.5 Hz, 1H), 7.09 (d, J=7.5 Hz, 1H), 6.86 (t, J=9.0 Hz, 1H), 6.61 (d, J=3.8 Hz, 1H), 6.00 (t, J=7.5 Hz, 1H), 5.48-5.39 (m, 1H), 4.48 (t, J=6.8 Hz, 1H), 4.36 (dd, J=7.5, 9.8 Hz, 1H), 4.19 (dd, J=7.3, 9.8 Hz, 1H), 3.20-3.11 (m, 1H), 2.97-2.88 (m, 1H), 2.85-2.74 (m, 1H), 2.65-2.55 (m, 1H), 2.36-2.18 (m, 3H), 2.14-1.98 (m, 1H). LC/MS: R$_t$=1.16 min, ES⁺ 462 (formic acid standard).

Step a: 1-(4-chlorophenyl)-3-methylbutan-2-ol

Magnesium (5.02 g, 0.206 mol) was covered in dry ether (50 mL, 0.5 mol) under an atmosphere of nitrogen. Iodine (0.254 g, 0.001 mol) was added to the reaction, followed by approximately 1 mL of a solution of 1-chloro-4-(chloromethyl)-benzene (32.20 g, 0.200 mol) in ether (25.0 mL, 0.238 mol). An exotherm was noted and the mixture reached reflux. The slow addition of solution was continued over 90 minutes to maintain a gentle reflux. On completion of the addition, the reaction was heated for 30 minutes at 45° C. The reaction was then cooled to 0° C. Isobutyraldehyde (25.19 mL, 0.2774 mol) in Ether (20 mL, 0.2 mol) was then added slowly over 2 hours at 0° C. On completion of the addition the reaction was allowed to warm to room temperature and stir overnight. The reaction was then quenched with ice (200 g) and acidified with 2M HCl (100 mL). The organic phase was separated and the aqueous was extracted twice with more ether. The combined organic phase was evaporated and the residue was purified by silica gel chromatography, eluting with 0 to 10% methanol in dichloromethane to yield the product, 17.8 g (45%). ¹H NMR (300 MHz, CDCl₃, δ): 7.22 (m, 4H), 3.56 (m, 1H), 2.81 (dd, J=3.3 Hz, 13.7 Hz, 1H), 2.58 (dd, J=9.4 Hz, 13.7 Hz, 1H), 1.74 (dt, J=6.5 Hz, 12.9 Hz, 1H), 1.45 (s, 1H), 1.00 (s, 3H), 0.98 (s, 3H).

Step b: 6-chloro-1,1-dimethylindane

Concentrated sulfuric acid (45.0 mL) was added to water (5.00 mL) carefully and allowed to cool down to room temperature. 1-(4-chlorophenyl)-3-methylbutan-2-ol (17.8 g, 0.0896 mol) was added portionwise over 30 minutes. After the addition, the mixture was left to stir at room temperature for 2 hours. The mixture was then poured onto ice and the aqueous layer was extracted with ether. The organic phase was washed water and then dried over magnesium sulphate and concentrated to yield crude product. The residue was purified by filtration through a plug of silica, eluting with dichloromethane, to yield the product, 12.6 g (78%). ¹H-NMR (400 MHz, CDCl₃, δ): 7.10 (m, 3H), 2.85 (t, J=7.2 Hz, 1H), 1.94 (t, J=7.2 Hz, 1H), 1.25 (s, 6H).

Step c: 5-chloro-3,3-dimethylindan-1-one 6-chloro-1,1-dimethylindane (2.19 g, 0.0121 mol) was dissolved in acetone (50 mL), and 1.41 M solution of magnesium sulfate in water (9.02 mL) was added, followed by potassium permanganate (3.83 g, 0.0242 mol). The mixture was stirred at room temperature overnight. 1:1 water:isopropanol was then added to the mixture and this was stirred for 1 hour. The mixture was then evaporated to an aqueous residue and ethyl acetate was added. The mixture was filtered, washing the collected solids with EtOAc, and the filtrates were separated. The organic phase was concentrated, and the residue was purified by silica gel chromatography, eluting with 20 to 100% dichloromethane in hexanes to yield the product, 1.25 g (46%). ¹H-NMR (400 MHz, CDCl, δ) 7.62 (d, J=8.3 Hz, 1H), 7.47 (d, J=1.6 Hz, 1H), 7.34 (dd, J=1.8 Hz, 8.1 Hz, 1H), 2.60 (s, 2H), 1.42 (s, 6H).

Step d: ((1S,2S,4R)-4-(4-((S)-5-chloro-3,3-dimethyl-2,3-dihydro-1H-inden-1-ylamino)-7H-pyrrolo[2,3-d]pyrimidin-7-yl)-2-hydroxycyclopentyl)methyl sulfamate (Compound I-67)

The title compound was prepared following the procedure described in Example 44 using 5-chloro-3,3-dimethylindan-1-one. ¹H NMR (CD$_3$OD, 400 MHz, δ): 8.16 (bs, 1H); 7.22 (bs, 1H); 7.20 (d, J=3.77 Hz, 1H); 7.16-7.14 (m, 2H); 6.62 (d, J=3.51 Hz, 1H); 5.91 (t, J=7.28 Hz, 1H); 5.50-5.40 (m, 1H); 4.49 (t, J=3.01 Hz, 1H); 4.33 (dd, J=7.78, 2.00 Hz); 4.16 (dd, J=7.28 Hz, 2.51 Hz); 2.85-2.74 (m, 1H); 2.53-2.45 (m, 1H); 2.37-2.18 (m, 3H); 2.08-1.94 (m, 2); 1.43 (s, 3H); 1.28 (s, 3). LC/MS: R$_t$=1.42 min, ES$^+$ 506 (FA standard).

Example 57

((1S,2S,4R)-4-{4-[(1S)-2,3-dihydro-1H-inden-1-ylamino]-5-fluoro-7H-pyrrolo[2,3-d]pyrimidin-7-yl}-2-hydroxycyclopentyl)methyl sulfamate (Compound I-68)

The title compound was prepared following the procedure described in Example 1a-g and then Example 2i-j using (S)-1-aminoindane and 4-chloro-5-fluoro-7H-pyrrolo[2,3-d]pyrimidine in step 1c. ¹H NMR (CD$_3$OD, 400 MHz, δ): 8.18 (s, 1H), 7.30-7.14 (m, 5H), 5.82 (t, J=7.8, 7.8 Hz, 1H), 5.55-5.45 (m, 1H), 4.48-4.44 (m, 1H), 4.35 (dd, J=9.72, 7.37 Hz, 1H), 4.18 (dd, J=9.72, 7.37 Hz, 1H), 3.11-3.02 (m, 1H), 2.98-2.88 (m, 1H), 2.88-2.73 (m, 1H), 2.71-2.63 (m, 1H), 2.34-2.16 (m, 3H), 2.10-1.96 (m, 2H) ppm. LC/MS: R$_t$=1.50 min, ES$^+$ 462 (FA standard).

Example 58

[(1S,2S,4R)-4-(5-fluoro-4-}[(1R,2S)-2-methoxy-2,3-dihydro-1H-inden-1-yl]amino}-7H-pyrrolo[2,3-d]pyrimidin-7-yl)-2-hydroxycyclopentyl]methyl sulfamate (Compound I-69)

The title compound was prepared following the procedure described in Example 1a-g and then Example 2i-j using (1R,2S)-2-methoxyindan-1-amine and 4-chloro-5-fluoro-7H-pyrrolo[2,3-d]pyrimidine in step 1c. ¹H NMR (CD$_3$OD, 400 MHz, δ): 8.20 (s, 1H), 7.27-7.13 (m, 4H), 7.10 (d, J=2.3 Hz, 1H), 5.88 (d, J=5.3 Hz, 1H), 5.49 (br s, 1H), 4.47 (t, J=7.3 Hz, 1H), 4.35 (dd, J=7.5, 9.8 Hz, 1H), 4.31-4.28 (m, 1H), 4.18 (dd, J=7.5, 9.8 Hz, 1H), 3.39 (s, 3H), 3.19-3.03 (m, 2H), 2.83-2.75 (m, 1H), 2.34-2.16 (m, 3H), 2.03-1.97 (m, 1H). LC/MS: R$_t$=1.55 min, ES$^+$ 492 (formic acid standard).

Example 59

(1S,2S,4R)-2-hydroxy-4-(4-{[(1R,2S)-2-isopropoxy-2,3-dihydro-1H-inden-1-yl]-amino}-7H-pyrrolo[2,3-d]pyrimidin-7-yl)cyclopentyl]methyl sulfamate (Compound I-70)

The title compound was prepared following the procedure described in Example 41a-d, using ethyl iodide in step b. ¹H NMR (CD$_3$OD, 400 MHz, δ): 8.19 (s, 1H), 7.29-7.17 (m, 5H), 6.65 (d, J=3.6 Hz, 1H), 5.73 (d, J=5.1 Hz, 1H), 5.50-5.44 (m, 1H), 4.49-4.48 (m, 1H), 4.42-4.35 (m, 2H), 4.20 (dd, J=7.3, 9.8 Hz, 1H), 3.66-3.56 (m, 2H), 3.51-3.43 (m, 1H), 3.12 (d, J=3.8 Hz, 2H), 2.81 (m, 1H), 2.37-2.20 (m, 3H), 2.08-2.03 (m, 1H), 1.70-1.56 (m, 1H), 1.53-1.36 (m, 1H), 1.05 (t, J=7.0 Hz), 0.97-0.90 (m, 2H) ppm. LC/MS: R$_t$=1.59 min, ES$^+$ 488 (AA standard).

Example 60

(1S,2S,4R)-2-hydroxy-4-(4-{[(1R,2S)-2-isopropoxy-2,3-dihydro-1H-inden-1-yl]-amino}-7H-pyrrolo[2,3-d]pyrimidin-7-yl)cyclopentyl]methyl sulfamate (Compound I-54)

The title compound was prepared following the procedure described in Example 41a-d, using isopropyl iodide in step b. ¹H NMR (CD$_3$OD, 400 MHz, δ): 8.20 (s, 1H), 7.31-7.18 (m, 5H), 6.67 (d, J=3.6 Hz, 1H), 5.82 (d, J=5.4 Hz, 1H), 5.51-5.44 (m, 1H), 4.53-4.48 (m, 21), 4.37 (dd, J=7.6, 9.7 Hz, 1H), 4.20 (dd, J=7.3, 9.7 Hz, 1H), 3.67-3.61 (m, 1H), 3.18-3.02 (m, 2H), 2.84-2.78 (m, 1H), 2.37-2.00 (m, 4H), 1.09 (d, J=6.1 Hz, 3H), 0.93 (d, J=6.1 Hz, 3H). LC/MS: R$_t$=1.68 min, ES$^+$ 502 (AA standard).

Example 61

[(1S,2S,4R)-2-hydroxy-4-(4-{[(1R,2S)-2-hydroxy-2,3-dihydro-1H-inden-1-yl]amino}-7H-pyrrolo[2,3-d]pyrimidin-7-yl)cyclopentyl]methyl sulfamate (Compound I-71)

The title compound was prepared following the procedure described in Example 2a-j using (1R,2S)-2-hydroxyindan-1-amine in step f. ¹H NMR (CD$_3$OD, 400 MHz, δ): 8.18 (s, 1H), 7.29-7.16 (m, 5H), 6.68 (d, J=3.8 Hz, 1H), 5.77 (d, J=4.5 Hz, 1H), 5.53-5.40 (m, 1H), 4.72-4.68 (m, 1H), 4.51-4.47 (m, 1H), 4.37 (dd, J=7.5, 9.5 Hz, 1H), 4.21 (dd, J=7.5, 9.8 Hz, 1H), 3.24-3.18 (m, 1H), 3.02-2.95 (m, 1H), 2.87-2.78 (m, 1H), 2.39-2.19 (m, 3H), 2.09-2.00 (m, 1H). LC/MS: R$_t$=0.90 min, ES$^+$ 460 (formic acid standard).

Example 62

[(1S,2S,4R)-2-hydroxy-4-(4-{[(1R,2R_-2-methoxy-2,3-dihydro-1H-inden-1-yl]amino}-7H-pyrrolo[2,3-d]pyrimidin-7-yl)cyclopentyl]methyl sulfamate (Compound I-72)

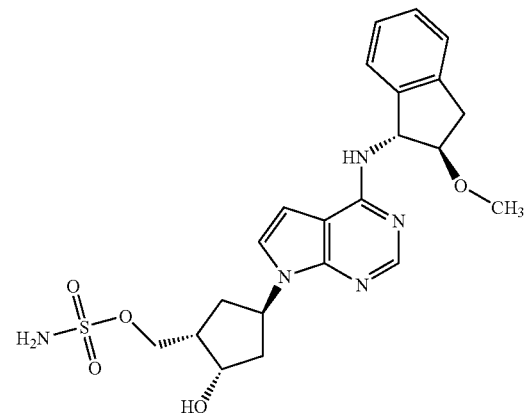

Step a: 2-[(1R,2R)-2-hydroxy-2,3-dihydro-1H-inden-1-yl]-1H-isoindole-1,3(2H)-dione A suspension of (1R,2R)-1-aminoindan-2-ol (1.40 g, 0.00938 mol), phthalic anhydride (1.39 g, 0.00938 mol), and N,N-diisopropylethylamine (1.63 mL, 0.00935 mol) in toluene (141 mL) in a 250 mL round bottom flask equipped with a Dean-Stark trap and condenser was stirred at reflux under an atmosphere of nitrogen 18 h. The reaction mixture was cooled to rt. TLC showed complete conversion of starting material to a higher $R_f$ spot. $^1$H NMR of an aliquot sample partitioned between EtOAc and water confirmed that reaction was complete. The reaction mixture was concentrated to a pale white and pale brown solid, redissolved in EtOAc (25 mL), washed with 1N HCl (2×10 mL), aqueous saturated NaHCO$_3$ (1×10 mL), and brine (1×10 mL), dried over Na$_2$SO$_4$, filtered, concentrated, and dried on high vacuum to give the product as an off-white solid (2.53 g, 97%). $^1$H NMR (CDCl$_3$, 400 MHz, δ): 7.86-7.84 (m, 2H), 7.74-7.72 (m, 2H), 7.26-7.25 (m, 2H), 7.20-7.14 (m, 1H), 7.01 (d, J=7.5 Hz, 1H), 5.67 (d, J=6.3 Hz, 1H), 5.14 (m, 1H), 3.58 (dd, J=7.5, 16.1 Hz, 1H), 2.97 (dd, J=6.8, 15.8 Hz, 1H), 2.12 (s, 1H) ppm.

Step b: 2-[(1R,2R)-2-methoxy-2,3-dihydro-1H-inden-1-yl]-1H-isoindole-1,3(2H)-dione To a solution of 2-[(1R,2R)-2-hydroxy-2,3-dihydro-1H-inden-1-yl]-1H-isoindole-1,3(2H)-dione (0.860 g, 0.00308 mol) in THF (30 mL) at 0° C. under an atmosphere of nitrogen was added a 1.0 M solution of lithium hexamethyldisilazide in THF (3.39 mL, 0.00339 mol). The reaction mixture was stirred for 20 minutes, followed by the addition of methyl iodide (0.575 mL, 0.00924 mol). The cold bath was removed, and the reaction mixture was allowed to stir and warm to rt over 18 h. The reaction was monitored by $^1$H NMR. The reaction mixture was then re-cooled to 0° C. To the reaction mixture was added 1.0 M solution of lithium hexamethyldisilazide in THF (3.39 mL, 0.00339 mol). The reaction mixture was stirred for 15 minutes, followed by addition of methyl iodide (0.575 mL, 0.00924 mol). The cold bath was removed, and the reaction mixture was allowed to stir at rt for 22 h. $^1$H NMR indicated 80:20 product/starting material. The reaction was quenched with aqueous 1N HCl solution and then concentrated in vacuo. The residue was partitioned between EtOAc and water. The organic phase was washed with saturated NaHCO$_3$ and brine, dried over Na$_2$SO$_4$, filtered, and concentrated. The oil was purified by silica gel chromatography, eluting with a gradient of hexanes to 10% EtOAc in hexanes) to obtain product (4.18 g, 46%). LC/MS: $R_t$=1.90 min, ES$^+$ 294 (AA standard).

Step c: (1R,2R)-2-methoxyindan-1-amine

To a mixture of 2-[(1R,2R)-2-methoxy-2,3-dihydro-1H-inden-1-yl]-1H-isoindole-1,3(2H)-dione (4.13 g, 0.00141 mol) in ethanol (3.38 mL) under an atmosphere of argon was added hydrazine (0.0442 mL, 0.0580 mol). The reaction mixture was allowed to stir at rt overnight. White solid byproduct crashed out of solution. TLC showed no starting material. The reaction mixture was concentrated, and the residue was suspended in DCM and filtered. The filtrate was concentrated in vacuo. $^1$H NMR showed that the reaction had not gone to completion. The yellow oil was therefore stirred at reflux for 3 h. LCMS confirmed reaction was complete. The reaction mixture was cooled to rt, concentrated in vacuo, triturated with DCM, filtered, and the filtrate was concentrated in vacuo to give product as a yellow oil (0.154 g, 64%). LC/MS: $R_t$=0.68 min, ES$^+$ 164 (AA standard).

Step d: [(1S,2S,4R)-2-hydroxy-4-(4-{[(1R,2R_-2-methoxy-2,3-dihydro-1H-inden-1-yl]amino}-7H-pyrrolo[2,3-d]pyrimidin-7-yl)cyclopentyl]methyl sulfamate (Compound I-70)

The title compound was prepared following the procedure described in Example 2a-j using (1R,2R)-2-methoxyindan-1-amine in step f. $^1$H NMR (CD$_3$OD, 400 MHz, δ): 8.18 (s, 1H), 7.22-7.19 (m, 3H), 7.15-7.14 (m, 2H), 6.63 (d, J=3.4 Hz, 1H), 5.84 (d, J=5.9 Hz, 1H), 5.49-5.51 (m, 1H), 4.50-4.48 (m, 1H), 4.37 (dd, J=7.5, 9.8 Hz, 1H), 4.25-4.18 (m, 2H), 3.47 (s, 3H), 3.37 (dd, J=7.3, 15.8 Hz, 1H), 2.87 (dd, J=6.8, 15.7 Hz, 1H), 2.83-2.77 (m, 1H), 2.33-2.20 (m, 3H), 2.07-2.00 (m, 1H), 1.94 (s, 1H) ppm. LC/MS: $R_t$=1.51 min, ES$^+$ 474 (AA standard).

Example 63

2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethanesulfonamide (Compound I-59)

Step a: 7-[(1R,3S,4S)-3-[tert-butyl(dimethyl)silyl]oxy-4-([tert-butyl(dimethyl)silyl]oxymethyl)cyclopentyl]-N-[(1S)-2,3-dihydro-1H-inden-1-yl]-7H-pyrrolo[2,3-d]pyrimidin-4-amine (1S,2S,4R)-4-{4-[(1S)-2,3-dihydro-1H-inden-1-ylamino]-7H-pyrrolo[2,3-d]pyrimidin-7-yl}-2-(hydroxymethyl)cyclopentanol (0.787 g, 0.00216 mol), 1H-imidazole (0.588 g, 0.00864 mol) and N,N-dimethylaminopyridine (0.022 g, 0.00018 mol) were dissolved in N,N-dimethylformamide (24 mL) under an atmosphere of nitrogen. After 2 hours, additional tert-butyldimethylsilyl chloride (0.500 g, 0.00332 mol) was added, and the mixture was stirred for a further 1 hour. The mixture was quenched with brine and extracted with ethyl acetate. The organic phase was evaporated and the residue was purified by silica gel chromatography, eluting with 0 to 100% ethyl acetate in dichloromethane, to yield 1.17 g (92%) of the title compound. $^1$H-NMR (300 MHz, CDCl$_3$, δ): 8.40 (s, 1H), 7.29 (m, 5H), 7.00 (d, J=3.6 Hz, 1H), 6.33 (d, J=3.3 Hz, 1H), 5.89 (dd, J=7.3 Hz, 15.3 Hz, 1H), 5.46 (ddd, J=4.3 Hz, 8.5 Hz, 18.1 Hz, 1H), 4.48 (t, J=3.1 Hz, 1H), 3.79 (dd, J=7.2 Hz, 9.9 Hz, 1H), 3.60 (dd, J=6.8 Hz, 9.9 Hz, 1H), 3.00 (m, 1H), 2.75 (dtd, J=4.0 Hz, 7.6 Hz, 11.7 Hz, 1H), 2.45 (d, J=4.0 Hz, 1H), 2.22 (d, J=4.0 Hz, 3H), 1.96 (d, J=4.0 Hz, 2H), 0.90 (s, 18H), 0.08 (s, 12H).

Step b: ((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methanol 7-[(1R,3S,4S)-3-[tert-butyl(dimethyl)silyl]oxy-4-([tert-butyl(dimethyl)silyl]-oxymethyl)cyclopentyl]-N-[(1S)-2,3-dihydro-1H-inden-1-yl]-7H-pyrrolo[2,3-d]pyrimidin-4-amine (1.66 g, 0.00280 mol) was dissolved in a mixture of tetrahydrofuran (6.6 mL), water (6.6 mL, 0.36 mol), and acetic acid (19 mL, 0.34 mol). The solution was then heated to 40° C. overnight. The mixture was then cooled and evaporated, azeotroped with toluene (2×50 mL) and the residue was purified by silica gel chromatography eluting with 0 to 100% ethyl acetate in dichloromethane to yield the product as a white solid, 1.05 g (74%). LC/MS: $R_t$=1.68 min, ES$^+$ 479 (AA standard).

Step c: (1R,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentanecarbaldehyde ((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methanol (257.0 mg, 0.0005369 mol) was dissolved in methylene chloride (10.0 mL) under argon. N-Methylmorpholine N-oxide (126 mg, 0.00107 mol), and 4 Å molecular sieves (250 mg, freshly flame dried) were then added and the mixture was stirred for 10 minutes at room temperature. Tetrapropylammonium perruthenateVII (18.9 mg, 0.0000537 mol) was then added, and the resulting dark green solution was stirred for 1 h at room temperature. The reaction mixture was filtered through a silica gel plug, eluting with DCM (20 mL), followed by 50% ethyl acetate in DCM (150 mL). The eluate was evaporated to provide the product as a clear light green oil. The residue was carried on to the next reaction without further purification.

Step d: Ethyl (E)-2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethylenesulfonate To a stirred solution of (diethoxy-phosphoryl)-methanesulfonic acid ethyl ester (285 mg, 0.00110 mol) in tetrahydrofuran (5.0 mL) was added, dropwise, 2.5 M of n-butyllithium in hexane (440 µL, 0.00110 mol) at −78° C. under atmosphere of nitrogen. The mixture was then stirred for 30 minutes. To this solution was added, dropwise, a solution of (1R,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentanecarbaldehyde (212.0 mg, 0.0004447 mol) in tetrahydrofuran (5.0 mL) at −78° C. The resulting pink solution was stirred for 1.5 h at −78° C. The reaction mixture was warmed and quenched by addition of saturated NH$_4$Cl (30 mL). The resultant mixture was extracted with DCM (3×30 mL). The combined organic layers were dried over MgSO$_4$, filtered, and concentrated in vacuo. The residue was purified by silica gel chromatography with 30 to 50% ethyl acetate in hexane to yield the product as a colorless oil, 132 mg (51%). LC/MS: $R_t$=2.55 min, ES$^+$ 583 (AA standard).

Step e: Ethyl 2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonate Ethyl-2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethylenesulfonate (132.0 mg, 0.0002265 mol) was dissolved in ethanol (8.0 mL) and sodium borohydride (42.8 mg, 0.00113 mol) was added. The reaction mixture was stirred at room temperature overnight. The mixture was quenched with NH$_4$Cl solution, and the mixture was concentrated to remove the ethanol. The aqueous residue was then extracted with dichloromethane, and the organic phase was concentrated. The residue was purified by silica gel chromatography 15% ethyl acetate in dichloromethane to yield the product, 92 mg (69%). LC/MS: $R_t$=2.51 min, ES$^+$ 585 (AA standard).

Step f: N,N,N-tributylbutan-1-aminium 2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonate Ethyl 2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonate (92 mg, 0.0001573 mol) and tetra-n-butylammonium iodide (62.0 mg, 0.000168 mol) were dissolved in acetone (2.5 mL, 0.034 mol) and the mixture was heated using microwave irradiation at 140° C. for 70 seconds. The cooled reaction mixture was concentrated to dryness to yield the crude product, 140 mg. LC/MS: $R_t$=1.75 min, ES$^+$ 557 (AA standard).

Step g: 2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonamide N,N,N-tributylbutan-1-aminium 2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonate (66.0 mg, 0.0000744 mol) was dissolved in methylene chloride (2.0 mL, 0.031 mol) and N,N-dimethylformamide (5.50 µL, 0.0000710 mol) was added. The mixture was cooled to 0° C. and thionyl chloride (50.0 µL, 0.000685 mol) was added dropwise. The reaction was allowed to stir at 0° C. for 2.5 h. The reaction mixture was diluted with toluene and concentrated to dryness. The residue was again azeotroped with toluene. The residue was eluted down a silica cartridge (~3 g) with 0 to 10% THF/DCM to yield the acid chloride intermediate, 42 mg. The acid chloride was taken up in a 0.500 M solution of ammonia in 1,4-dioxane (5.00 mL) and the resultant solution was stirred overnight at room temperature under an atmosphere of nitrogen. The mixture was then evaporated and the residue was partitioned between DCM and water. The organic phase was evaporated to yield the crude product, 35 mg (85%). LC/MS: $R_t$=1.64 min, ES$^+$ 556 (AA standard).

Step h: 2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethanesulfonamide (Compound I-59)

2-((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)ethanesulfonamide (32 mg, 0.000057 mol) was dissolved in tetrahydrofuran (1.0 mL, 0.012 mol) and a 1.00 M solution of tetra-n-butylammonium fluoride in tetrahydrofuran (0.100 mL) was added. The mixture was stirred at room temperature for 1 hour. The reaction mixture was quenched with a little water and then concentrated. Purification of the residue by silica gel chromatography, eluting with 0 to 100% of (9:1 EtOAc:EtOH) in DCM, afforded the desired product, (9 mg, 40%). $^1$H-NMR (400 MHz, MeOD, δ): 8.16 (s, 1H), 7.19 (m, 5H), 6.62 (d, J=3.6 Hz, 1H), 5.85 (t, J=7.7 Hz, 1H), 5.43 (dddd, J=4.2 Hz, 8.4 Hz, 8.4 Hz, 8.4 Hz, 1H), 4.35 (t, J=3.7 Hz, 1H), 3.13 (m, 3H), 2.91 (m, 1H), 2.63 (m, 1H), 2.49 (m, 1H), 2.35 (ddd, J=1.2 Hz, 8.1 Hz, 13.8 Hz, 1H), 2.05 (m, 6H). LC/MS: $R_t$=1.07 min, ES$^+$ 442 (AA standard).

Example 64

(E)-2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethylenesulfonamide (Compound I-73)

Step a: tert-Butyl{[(E)-2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)vinyl]sulfonyl}carbamate tert-Butyl{[(diphenylphosphoryl)methyl]sulfonyl}carbamate (602 mg, 1.45 mmol) was dissolved in THF (50.0 mL) under an atmosphere of argon, a 1.60 M solution of n-butyllithium in hexane (1.81 mL, 2.89 mmol) was added at −50° C., and the resultant mixture was stirred for 1 h. A solution of (1R,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentanecarbaldehyde (300 mg, 0.60 mmol) in THF (8.0 mL) was added to the mixture, and the resulting mixture was stirred for 30 min at room temperature. After quenching by addition of water (200 mL), the mixture was extracted with EtOAc (100 mL×3). The organic layer was dried over $MgSO_4$, filtered, and concentrated in vacuo. The residue was purified via silica gel chromatography eluting with a gradient of 10 to 60% EtOAc in hexane to afford the title compound (84.0 mg, 21%). LC/MS: $R_t$=1.90 min, $ES^+$ 654 (FA standard).

Step b: (E)-2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethylenesulfonamide tert-Butyl {[(E)-2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)vinyl]sulfonyl}carbamate (120 mg, 0.17 mmol) was dissolved in DCM (10.0 mL) under an atmosphere of argon, and EtOH (0.05 mL, 8.72 mmol) was added at room temperature. To this mixture was added $ZnBr_2$ (0.10 mg, 0.44 mmol), and the resulting mixture was stirred for 4 h. After quenching by addition of water (20 mL), the mixture was stirred for 1 h, and then was extracted with DCM (30 mL×3). The organic layer was dried over $MgSO_4$, filtered, and concentrated in vacuo. The residue was purified via silica gel chromatography, eluting with a gradient of 0 to 10% MeOH in DCM, to afford the title compound (91.8 mg, 90%). LC/MS: $R_t$=1.64 min, $ES^+$ 554 (FA standard).

Step c: (E)-2-((1S,2S,4R)-4-{4-[(1S)-2,3-dihydro-1H-inden-1-ylamino]-7H-pyrrolo[2,3-d]pyrimidin-7-yl}-2-hydroxycyclopentyl)ethylenesulfonamide (Compound I-73)

(E)-2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethylenesulfonamide (30 mg, 0.05 mmol) was dissolved in THF (2.00 mL). To this solution was added at room temperature a 1M solution of tetra-n-butylammonium fluoride in THF (0.08 mL, 0.08 mmol), and the resulting mixture was stirred for 1 h. The reaction mixture was quenched by the addition of brine (20 mL) and extracted with EtOAc (30 mL×3). The organic layer was dried over $MgSO_4$, filtered, and concentrated in vacuo. The residue was purified via silica gel chromatography, eluting with a gradient of 5 to 15% MeOH in DCM, to afford the title compound (21.3 mg, 81%). $^1$H NMR ($CD_3OD$, 400 MHz, δ): 8.17 (s, 1H), 7.27-7.11 (m, 5H), 6.88 (dd, J=7.8, 15.1 Hz, 1H), 6.63 (d, J=3.5 Hz, 1H), 6.57 (dd, J=1.0, 15.1 Hz, 1H), 5.85 (dd, J=7.7, 7.8 Hz, 1H), 5.47 (ddd, J=4.6, 8.6, 18.1 Hz, 1H), 4.44-4.42 (m, 1H), 3.30-3.21 (m, 1H), 3.05 (ddd, J=3.4, 8.8, 15.8 Hz, 1H), 2.96-2.83 (m, 1H), 2.66-2.58 (m, 1H), 2.44 (dt, J=10.0, 13.8 Hz, 1H), 2.37 (ddd, J=1.8, 8.3, 13.8 Hz, 1H), 2.29 (ddd, J=4.6, 8.3, 13.8 Hz, 1H), 2.10-1.92 (m, 2H) ppm. LC/MS: $R_t$=5.00 min, $ES^+$ 440 (FA long purity).

Example 65

N-[((1S,2S,4R)-4-{4-[(1S)-2,3-dihydro-1H-inden-1-ylamino]-7H-pyrrolo[2,3-d]-pyrimidin-7-yl}-2-hydroxycyclopentyl)methyl]sulfamide (Compound I-56)

Step a: tert-butyl(aminosulfonyl)[((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methyl]carbamate ((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methanol (700.0 mg, 0.001462 mol), N-Boc-sulfonamide (398 mg, 0.00203 mol) and triphenylphosphine (575 mg, 0.00219 mol) were dissolved in ethyl acetate (28 mL, 0.28 mol) at 50° C. under an atmosphere of nitrogen. Diethyl azodicarboxylate (350.0 µL, 0.002223 mol) was added over 2-3 min and the mixture was stirred at 50° C. for 30 minutes. The cooled mixture was evaporated and the residue purified by silica gel chromatography, eluting with 10 to 100% ethyl acetate in hexanes, to yield the product as a white solid, 636 mg (66%). LC/MS: $R_t$=2.55 min, $ES^+$ 657 (AA standard).

Step b: tert-butyl(aminosulfonyl)[((1S,2S,4R)-4-{4-[(1S)-2,3-dihydro-1H-inden-1-ylamino]-7H-pyrrolo[2,3-d]pyrimidin-7-yl-2-hydroxycyclopentyl)methyl]carbamate tert-Butyl(aminosulfonyl)[((1S,2S,4R)-2-[tert-butyl(dimethyl)silyl]oxy-4-4-[(1S)-2,3-dihydro-1H-inden-1-ylamino]-7H-pyrrolo[2,3-d]pyrimidin-7-yl)cyclopentyl)methyl]carbamate (457 mg, 0.000696 mol) was dissolved in tetrahydrofuran (10.0 mL), 1.00 M aqueous hydrochloric acid (10.0 mL), and ethanol (10.0 mL). The mixture was stirred at room temperature overnight. Sodium bicarbonate (842 mg, 0.0100 mol) was added to the mixture, followed by water (10 mL). The mixture was then concentrated to ~20 mL volume, and this aqueous residue was extracted with EtOAc (2×50 mL). The separated organics were concentrated in vacuo and the residue was purified by silica gel chromatography, eluting with 100% ethyl acetate to yield the product, 362 mg (96%). LC/MS: $R_t$=1.77 min, $ES^+$ 543 (AA standard).

Step c: N-[((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl]sulfamide (Compound I-56)

tert-Butyl(aminosulfonyl)[((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl]carbamate (345 mg, 0.000636 mol) was dissolved in 2:1 methylene chloride:trifluoroacetic acid (20 mL: 10 mL) and left to stand for 15 minutes at room temperature. The mixture was diluted with toluene (30 mL) and evaporated to dryness. The residue was then re-subjected to the same conditions and azeotroped with toluene after completion. The residue was purified by silica gel chromatography, eluting with 5 to 10% Methanol in dichloromethane, to yield the product, 135 mg (48%). $^1$H-NMR (400 MHz, MeOD) δ 8.16 (s, 1H), 7.19 (m, 5H), 6.62 (d, J=3.6 Hz, 1H), 5.85 (t, J=7.8 Hz, 1H) 5.43 (ddd, J=4.6 Hz, 8.5 Hz, 17.8 Hz, 1H), 4.46 (t, J=3.6 Hz, 1H), 3.15 (dd, J=7.1 Hz, 12.9 Hz, 1H), 3.05 (ddd, J=3.3 Hz, 8.7 Hz, 15.4 Hz, 1H), 2.91 (m, 1H), 2.63 (m, 1H), 2.33 (ddd, J=1.5 Hz, 8.0 Hz, 13.8 Hz, 1H), 2.20 (m, 2H), 2.02 (m, 2H). LC/MS: $R_t$=1.45 min, ES$^+$ 443 (AA standard).

Example 66

N-{[(1S,2S,4R)-4-(4-{[(1R,2S)-2-methoxy-2,3-dihydro-1H-inden-1-yl]amino}-7H-pyrrolo[2,3-d]pyrimidin-7-yl)-2-hydroxycyclopentyl]methyl}sulfamide (Compound I-74)

The title compound was prepared following the procedures described in Example 64a-b and Example 66a-c starting from (1S,2S,4R)-4-{4-[(1R,2S)-2-methoxy-2,3-dihydro-1H-inden-1-ylamino]-7H-pyrrolo[2,3-d]pyrimidin-7-yl}-2-(hydroxymethyl)cyclopentanol (Example 41). $^1$H-NMR (300 MHz, MeOD) δ 8.20 (s, 1H), 7.21 (m, 5H), 6.66 (d, J=3.6 Hz, 1H) 5.92 (d, J=5.3 Hz, 1H) 5.43 (m, 1H), 4.47 (t, J=3.5 Hz, 1H), 4.30 (dt, J=2.8 Hz, 5.2 Hz, 1H), 3.35 (s, 3H), 3.15 (m, 3H), 2.64 (m, 1H), 2.27 (m, 3H), 2.03 (ddd, J=4.7 Hz, 9.0 Hz, 13.6 Hz, 1H). LC/MS: $R_t$=6.88 min, ES$^+$ 473 (AA purity).

Example 67

N-[((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl]-N-methylsulfamide (Compound I-75)

Step a: N-[((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methyl]-N-methylsulfamide tert-Butyl(aminosulfonyl)[((1S,2S,4R)-2-[tert-butyl(dimethyl)silyl]oxy-4-{4-[(1S)-2,3-dihydro-1H-inden-1-ylamino]-7H-pyrrolo[2,3-d]pyrimidin-7-yl}cyclopentyl)methyl]carbamate (108 mg, 0.000164 mol) was dissolved in tetrahydrofuran (2.0 mL) under an atmosphere of nitrogen. Lithium tetrahydroaluminate (12.5 mg, 0.000329 mol) was added and the mixture heated at 50° C. for 80 minutes. The reaction was then cooled, quenched with water and acidified to ~pH 6 with 1M HCl. This mixture was then extracted with ethyl acetate, the separated organic phase was evaporated, and the residue was purified by silica gel chromatography, eluting with 10 to 100% ethyl acetate in hexanes, to yield the product, 25 mg (27%). LC/MS: $R_t$=2.34 min, ES$^+$ 571 (AA standard).

Step b: N-[((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl]-N-methylsulfamide (Compound I-75)

N-[((1S,2S,4R)-2-[tert-Butyl(dimethyl)silyl]oxy-4-{4-[(1S)-2,3-dihydro-1H-inden-1-ylamino]-7H-pyrrolo[2,3-d]pyrimidin-7-yl}cyclopentyl)methyl]-N-methylsulfamide (25.0 mg, 0.0000438 mol) was dissolved in tetrahydrofuran (2.0 mL), ethanol (2.0 mL) and 1.00 M of hydrochloric acid in water (2.0 mL). The mixture was stirred overnight at room temperature. The solution was evaporated to dryness, and the residue was dissolved in methanol and treated with a 7.00 M solution of ammonia in methanol (0.1 mL). Solvents were again evaporated, and the residue was purified by silica gel chromatography, eluting with 2 to 10% methanol in dichloromethane to yield the product, 9.8 mg (49%). $^1$H-NMR (400 MHz, MeOD) δ 8.16 (s, 1H), 7.19 (m, 5H), 6.62 (d, 1H, J=3.6 Hz), 5.84 (t, J=7.7 Hz, 1H), 5.43 (ddd, J=4.5 Hz, 8.6 Hz, 12.8 Hz, 1H), 4.43 (t, J=3.7 Hz, 1H), 3.25 (dd, J=8.1 Hz, 13.7 Hz, 1H), 3.14 (dd, J=7.2 Hz, 13.7 Hz, 1H), 3.05 (ddd, J=3.3 Hz, 8.8 Hz, 15.8 Hz, 1H), 2.91 (m, 1H), 2.74 (m, 1H, 2.63 (m, 1H), 2.34 (ddd, J=1.1 Hz, 7.8 Hz, 13.6 Hz, 1H), 2.20 (m, 2H, 1.99 (m, 2H). LC/MS: $R_t$=1.51 min, ES$^+$ 457 (AA standard).

Example 68

((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)methyl methanesulonate (Compound I-76)

Step a: ((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)methyl methanesulonate ((1S,2S,4R)-2-{[tert-Butyl(dimethyl)silyl]oxy}-4-{4-[(1S)-2,3-dihydro-1H-inden-1-ylamino]-7H-pyrrolo[2,3-d]pyrimidin-7-yl}cyclopentyl)methanol (0.345 g, 0.721 mmol) was dissolved in methylene chloride (5.00 mL, 78.0 mmol) under an atmosphere of argon. Triethylamine (0.251 mL, 1.80 mmol) was added, and the solution was cooled to 0° C. Methanesulfonyl chloride (0.0669 mL, 0.865 mmol) was added in one portion. The solution was stirred at 0° C. under an atmosphere of argon for 30 minutes. The solution was diluted with EtOAc, washed with water and brine, dried over anhydrous sodium sulfate, filtered, and concentrated in vacuo to give the title compound (0.415 g, 89%). LC/MS: $R_t$=2.45 min, ES$^+$ 557 (AA standard).

Step b: ((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)acetonitrile ((1S,2S,4R)-2-{[tert-Butyl(dimethyl)silyl]oxy}-4-{4-[(1S)-2,3-dihydro-1H-inden-1-ylamino]-7H-pyrrolo[2,3-d]pyrimidin-7-yl}cyclopentyl)methyl methanesulonate (0.415 g, 0.641 mmol) was dissolved in dimethyl sulfoxide (7.00 mL, 98.6 mmol) under an atmosphere of argon. Sodium cyanide (0.166 g, 3.28 mmol) was added, and the mixture was stirred at 60° C. for 24 h. The reaction mixture was heated for an additional 24 h at 70° C. The reaction mixture was cooled to ambient temperature, diluted with EtOAc, washed with water and brine, dried over anhydrous sodium sulfate, filtered, and concentrated in vacuo. The residue was purified via silica gel chromatography, eluting with a gradient of 0 to 40% EtOAc in methylene chloride, to afford the title compound (0.306 g, 98%). LC/MS: $R_t$=1.85 min, ES$^+$ 488. (FA standard).

Step c. ((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)acetaldehyde ((1S,2S,4R)-2-{[tert-Butyl(dimethyl)silyl]oxy}-4-{4-[(1S)-2,3-dihydro-1H-inden-1-ylamino]-7H-pyrrolo[2,3-d]

pyrimidin-7-yl}cyclopentyl)acetonitrile (0.150 g, 0.308 mmol) was dissolved in methylene chloride under an atmosphere of argon and cooled to −78° C. Diisobutylaluminum hydride (1.0M in methylene chloride, 0.340 mL, 0.340 mmol) was added to the solution and the reaction mixture was stirred for 30 minutes at −78° C. After a second addition of diisobutylaluminum hydride (1.0M in methylene chloride, 0.340 mL, 0.340 mmol), the solution was stirred for an additional 30 minutes at −78° C. A third addition of diisobutylaluminum hydride (1.0M in methylene chloride, 0.340 mL, 0.340 mmol) was made, and the solution was stirred for another 30 minutes at −78° C. The reaction was quenched with a saturated solution of sodium potassium tartrate tetrahydrate. EtOAc was added and the mixture was stirred until the layers were clear. The layers were separated. The aqueous layer was extracted with diethyl ether. The combined organic extracts were washed with brine, dried over anhydrous sodium sulfate, filtered and concentrated in vacuo to give the title compound (0.160 g, 100%). LC/MS: $R_t$=1.80 min, ES$^+$ 491 (FA standard).

Step d: 2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethanol ((1S,2S,4R)-2-{[tert-Butyl(dimethyl)silyl]oxy}-4-{4-[(1S)-2,3-dihydro-1H-inden-1-ylamino]-7H-pyrrolo[2,3-d]pyrimidin-7-yl}cyclopentyl)acetaldehyde (0.164 g, 0.314 mmol) was dissolved in methanol (5.00 mL, 123 mmol) under an atmosphere of argon and cooled to 0° C. Sodium tetrahydroborate (0.0291 g, 0.754 mmol) was added and the reaction was stirred for 10 minutes. Additional sodium tetrahydroborate (0.0143 g, 0.377 mmol) was added, and the reaction mixture was stirred for another 30 minutes. The reaction was quenched with water, extracted with EtOAc, dried over anhydrous sodium sulfate, filtered, and concentrated in vacuo. The residue was purified by silica gel chromatography, eluting with a gradient of 0 to 100% EtOAc in methylene chloride, to afford the title compound (0.0694 g, 45%). LC/MS: $R_t$=1.65 min, ES$^+$ 494 (FA standard).

Step e: 2-((1S,2S,4R)-2-{[tert-butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethyl sulfamate ((1S,2S,4R)-2-{[tert-Butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethanol (0.0694 g, 0.141 mmol) was dissolved in acetonitrile (3.00 mL, 57.4 mmol) and methylene chloride (2.00 mL, 31.2 mmol) under an atmosphere of argon. Triethylamine (0.0589 mL, 0.422 mmol) was added, and the solution was cooled to 0° C. Chlorosulfonamide (2.00M in acetonitrile, 0.141 mL) was added and the solution was immediately warmed to room temperature. After 30 minutes, additional chlorosulfonamide (2.00M in acetonitrile, 0.141 mL) and triethylamine (0.0589 mL, 0.422 mmol) were added and the reaction was stirred for 30 minutes. The reaction was quenched with methanol and a 1:1 solution of saturated sodium bicarbonate and water. The mixture was extracted with EtOAc. The combined organic extracts were washed with brine, dried over anhydrous sodium sulfate, filtered, and concentrated in vacuo. The residue was purified by silica gel chromatography, eluting with 0 to 50% EtOAc in methylene chloride, to give the title compound (0.0805 g, 55%). LC/MS: $R_t$=1.70 min, ES$^+$ 573 (FA standard).

Step f: 2-((1S,2S,4R)-4-{4-[(1S)-2,3-dihydro-1H-inden-1-ylamino]-7H-pyrrolo[2,3-d]-pyrimidin-7-yl}-2-hydroxycyclopentyl)ethyl sulfamate (Compound I-76)

2-((1S,2S,4R)-2-{[tert-Butyl(dimethyl)silyl]oxy}-4-{4-[(1S)-2,3-dihydro-1H-inden-1-ylamino]-7H-pyrrolo[2,3-d]pyrimidin-7-yl}cyclopentyl)ethyl sulfamate (0.0442 g, 0.0773 mmol) was dissolved in pyridine (0.344 mL, 4.25 mmol) and tetrahydrofuran (0.345 mL, 4.25 mmol). The solution was cooled to 0° C. Pyridine hydrofluoride (0.500 mL, 5.55 mmol) was added dropwise. The solution was warmed to room temperature. After one hour, pyridine hydrofluoride (0.500 mL, 5.55 mmol) was added. After two hours, pyridine hydrofluoride (0.500 mL, 5.55 mmol) was added. The solution was stirred for 24 h. The reaction was quenched with dropwise addition of saturated sodium bicarbonate, and the mixture was extracted with EtOAc. The combined organic extracts were dried over anhydrous sodium sulfate, filtered, and concentrated in vacuo. The residue was purified by silica gel chromatography, eluting with 0 to 5% MeOH in EtOAc, to give the title compound (0.005 g, 0.01 mmol). $^1$H NMR (CD$_3$OD, 400 MHz, δ): 8.17 (s, 1H), 7.28-7.12 (m, 5H) 6.67 (d, J=3.61 Hz 1H) 5.58 (t, J=7.44, 7.44 Hz 1H), 5.48-5.40 (m, 1H), 4.40-4.35 (m, 1H), 4.28-4.17 (m, 2H), 3.10-3.02 (m, 1H), 2.98-2.88 (m, 1H), 2.68-2.47 (m, 1H), 2.57-2.47 (m, 1H), 2.38-1.98 (m, 5H), 1.89-1.80 (m, 1H) ppm. LC/MS: $R_t$=1.25 min, ES$^+$ 458 (FA standard).

Example 70

Diastereoisomeric mixture of (1S,2R,4R)-4-{4-[(1S)-2,3-dihydro-1H-inden-1-ylamino]-7H-pyrrolo[2,3-d]pyrimidin-7-yl}-2-hydroxycyclopentyl sulfamate and (1R,2S,4S)-4-{[(1S)-2,3-dihydro-1H-inden-1-ylamino]-7H-pyrrolo[2,3d]-pyrimidin-7-yl}-2-hydroxycyclopentyl sulfamate (Compounds I-77 and I-78)

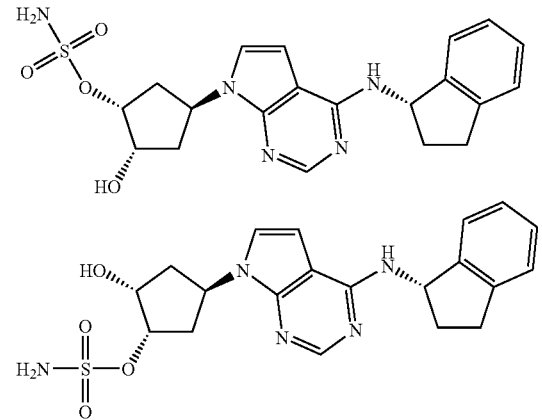

Step a: Cyclopent-3-en-1-yl methanesulfonate

3-Cyclopentene-1-ol (0.500 g, 5.94 mmol) was stirred in DCM (95 mL). Pyridine (2.40 mL), N,N-dimethylaminopyridine (0.10 g, 1.00 mmol) and methanesulfonyl chloride (0.690 mL, 8.92 mmol) were added, and the reaction mixture was stirred at 35° C. for 4 h. N,N-Dimethylaminopyridine (0.14 g, 1.2 mmol) and methanesulfonyl chloride (0.69 mL, 8.92 mmol) were added, and the reaction was stirred overnight. TLC indicated complete conversion. The reaction mixture was cooled and concentrated. The residue was purified by silica gel chromatography, eluting with DCM, to afford the title compound as a clear oil (0.660 g, 68%).

Step b: 7-Cyclopent-3-en-1-yl-N-[(1S)-2,3-dihydro-1H-inden-1-yl]-7H-pyrrolo[2,3-d]-pyrimidin-4-amine N-[(1S)-2,3-Dihydro-1H-inden-1-yl]-7H-pyrrolo[2,3-d]pyrimidin-4-amine (1.32 g, 5.29 mmol) was azeotroped with toluene and placed under high vacuum for 30 min. N,N-Dimethylformamide (17.7 mL) was added, followed by cesium carbonate (1.99 g, 6.10 mmol). The mixture was stirred at 70° C. for 10 min. Cyclopent-3-en-1-yl methanesulfonate (0.660 g, 4.07 mmol) in N,N-dimethylformamide (12.6 mL) was added dropwise. The reaction mixture was heated to 110° C. for 1 h. The reaction mixture was cooled, quenched with brine and diluted with $H_2O$. The aqueous layer was extracted with EtOAc (3×), washed with $H_2O$ and brine, dried ($Na_2SO_4$), filtered, and concentrated. The residue was purified by via silica gel chromatography, eluting with a gradient of 0 to 5% MeOH in DCM followed by 25 to 50% EtOAc in hexanes, to afford the title compound as a pale brown solid (0.684 g, 53%). LC/MS: $R_t$=1.38 min, $ES^+$ 317 (FA standard).

Step c: (1R,2S,4S)-4-{4-[(1S)-2,3-dihydro-1H-inden-1-ylamino]-7H-pyrrolo[2,3-d]pyrimidin-7-yl}cyclopentane-1,2-diol 7-Cyclopent-3-en-1-yl-N-[(1S)-2,3-dihyrdo-1H-inden-1-yl]-7H-pyrrolo[2,3-d]pyrimidin-4-amine (0.312 g, 0.986 mmol) was stirred in tert-butyl alcohol (4.9 mL) and $H_2O$ (4.9 mL). AD-mix-α (Sigma-Aldrich, 1.4 g) was added, and the suspension was stirred at rt overnight. TLC indicated complete conversion. The reaction was quenched with sodium sulfite (1.48 g, 11.7 mmol), and the mixture was stirred for 5 h. The reaction mixture was diluted with EtOAc and $H_2O$, and the aqueous layer was extracted with EtOAc (2×). The organic layer was dried ($Na_2SO_4$), filtered, and concentrated. The residue was purified via silica gel chromatography, eluting with EtOAc, to afford the title compound as a white solid (0.190 g, 55%).

Step d: Diastereoisomeric mixture of (1S,2R,4R)-4-{4-[(1S)-2,3-dihydro-1H-inden-1-ylamino]-7H-pyrrolo[2,3-d]pyrimidin-7-yl}-2-hydroxycyclopentyl sulfamate and (1R,2S,4S)-4-{4-[(1S)-2,3-dihydro-1H-inden-1-ylamino]-7H-pyrrolo[2,3-d]pyrimidin-7-yl}-2-hydroxycyclopentyl sulfamate (Compounds I-77 and I-78)

(1R,2S,4S)-4-{4-[(1S)-2,3-Dihydro-1H-inden-1-ylamino]-7H-pyrrolo[2,3-d]pyrimidin-7-yl}cyclopentane-1,2-diol (0.080 g, 0.23 mmol) was azeotroped with toluene and then was dissolved in anhydrous acetonitrile (2.3 mL). Pyridine (0.0369 mL, 0.458 mmol) was added. The reaction mixture was cooled to 0° C., and a 2N solution of chlorosulfonamide in acetonitrile (0.144 mL) was added dropwise. The reaction was stirred for 1 h, and then additional 2N chlorosulfonamide in acetonitrile (0.028 mL) was added. After 30 min, additional 2N chlorosulfonamide in acetonitrile (0.0342 mL) was added, and the reaction mixture was stirred for 2 h. The reaction was quenched with methanol, and the mixture was concentrated in vacuo. The residue was purified by preparative thin layer chromatography using DCM:AcCN:MeOH (50:45:5). The relevant band was cut, washed with acetone, filtered, and concentrated to give a mixture of diastereomers as a white solid. (11 mg, 11%). $^1$H NMR (CDCl$_3$, 400 NMR, δ): 8.36-8.27 (m, 1H); 7.38-7.09 (m, 5H); 6.90-6.80 (m, 1H); 6.36-6.20 (m, 1H); 5.95-5.76 (m, 1H); 5.51-5.22 (m, 2H); 4.83-4.68 (m, 1H); 3.87-3.72 (m, 1H); 3.12-2.83 (m, 2H); 2.75-2.53 (m, 1H); 2.50-2.14 (m, 2H); 2.08-1.79 (m, 2H) ppm. LC/MS: $R_t$=1.16 min, $ES^+$ 430 (FA standard).

The following additional compounds of formula (I) were also prepared:

[(1R,2R,4S)-2-hydroxy-4-(4-{[(1R,2R)-2-(methoxymethyl)-2,3-dihydro-1H-inden-1-yl]amino}-7H-pyrrolo[2,3-d]pyrimidin-7-yl)cyclopentyl]methylsulfamate (Compound I-79)

$^1$H NMR (CD$_3$OD, 400 MHz, δ): 8.20 (s, 1H), 7.32-7.16 (m, 5H), 6.64 (d, J=3.6 Hz, 1H), 5.97 (d, J=7.0 Hz, 1H), 5.50-5.41 (m, 1H), 4.51-4.46 (m, 1H), 4.36 (dd, J=7.5, 9.8 Hz, 1H), 4.19 (dd, J=7.3, 9.8 Hz, 1H), 3.53-3.40 (m, 1H), 3.41-3.35 (m, 1H), 3.18 (s, 3H), 3.11-2.95 (m, 3H), 2.84-2.75 (m, 1H), 2.33 (ddd, J=1.4, 7.7, 13.5 Hz, 1H), 2.29-2.19 (m, 2H), 2.04 (ddd, J=4.9, 9.5, 14.2 Hz, 1H) ppm. LC/MS: $R_t$=11.24 min, $ES^+$ 488 (FA long purity).

[(1R,2R,4S)-2-hydroxy-4-(4-{[(1S,2S)-2-(methoxymethyl)-2,3-dihydro-1H-inden-1-yl]amino}-7H-pyrrolo[2,3-d]pyrimidin-7-yl)cyclopentyl]methylsulfamate (Compound I-80)

$^1$H NMR (CD$_3$OD, 400 MHz, δ): 8.20 (s, 1H), 7.32-7.16 (m, 5H), 6.64 (d, J=3.6 Hz, 1H), 5.97 (d, J=7.0 Hz, 1H), 5.50-5.41 (m, 1H), 4.51-4.46 (m, 1H), 4.36 (dd, J=7.5, 9.8 Hz, 1H), 4.19 (dd, J=7.3, 9.8 Hz, 1H), 3.53-3.40 (m, 1H), 3.41-3.35 (m, 1H), 3.18 (s, 3H), 3.11-2.95 (m, 3H), 2.84-2.75 (m, 1H), 2.33 (ddd, J=1.4, 7.7, 13.5 Hz, 1H), 2.29-2.19 (m, 2H), 2.04 (ddd, J=4.9, 9.5, 14.2 Hz, 1H) ppm. LC/MS: $R_t$=11.24 min, $ES^+$ 488 (FA long purity).

[(1R,2R,4S)-2-hydroxy-4-(4-{[(1R,2R)-2-methyl-2,3-dihydro-1H-inden-1-yl]amino}-7H-pyrrolo[2,3-d]pyrimidin-7-yl)cyclopentyl]methylsulfamate (Compound I-81)

$^1$H NMR (CD$_3$OD, 400 MHz, δ): 8.17 (s, 1H), 7.32-7.16 (m, 5H), 6.69 (d, J=3.6 Hz, 1H), 5.86 (d, J=7.2 Hz, 1H), 5.50-5.41 (m, 1H), 4.51-4.47 (m, 1H), 4.38 (dd, J=9.7, 7.6 Hz, 1H), 4.20 (dd, J=7.4, 9.7 Hz, 1H), 3.14-3.08 (m, 1H), 2.95-2.88 (m, 1H), 2.83-2.72 (m, 2H), 2.37-2.20 (m, 3H), 2.09-2.00 (m, 1H), 0.98 (d, J=7.1 Hz, 3H) ppm. LC/MS: $R_t$=7.93 min, $ES^+$ 458 (AA long purity).

[(1R,2R,4S)-2-hydroxy-4-(4-{[(1S,2S)-2-methyl-2,3-dihydro-1H-inden-1-yl]amino}-7H-pyrrolo[2,3-d]pyrimidin-7-yl)cyclopentyl]methylsulfamate (Compound I-82)

$^1$H NMR (CD$_3$OD, 400 MHz, δ): 8.17 (s, 1H), 7.32-7.16 (m, 5H), 6.69 (d, J=3.6 Hz, 1H), 5.86 (d, J=7.2 Hz, 1H), 5.50-5.41 (m, 1H), 4.51-4.47 (m, 1H), 4.38 (dd, J=9.7, 7.6 Hz, 1H), 4.20 (dd, J=7.4, 9.7 Hz, 1H), 3.14-3.08 (m, 1H), 2.95-2.88 (m, 1H), 2.83-2.72 (m, 2H), 2.37-2.20 (m, 3H), 2.09-

2.00 (m, 1H), 0.98 (d, J=7.1 Hz, 3H) ppm. LC/MS: R$_t$=7.93 min, ES$^+$ 458 (AA long purity).

[(1R,2R,4S)-2-hydroxy-4-(4-{[(1R,2R)-2-ethyl-2,3-dihydro-1H-inden-1-yl]amino}-7H-pyrrolo[2,3-d]pyrimidin-7-yl)cyclopentyl]methylsulfamate (Compound I-83)

$^1$H NMR (CD$_3$OD, 400 MHz, δ): 8.17 (s, 1H), 7.31-7.15 (m, 5H), 6.66 (d, J=3.60 Hz, 1H), 5.94 (d, J=7.28 Hz, 1H), 5.48-5.41 (m, 1H), 4.48 (dd, J=3.98, 3.03 Hz, 1H), 4.36 (dd, J=9.74, 7.58 Hz, 1H), 4.19 (dd, J=9.73, 7.33 Hz, 1H), 3.07-3.01 (m, 1H), 2.91-2.76 (m, 2H), 2.65-2.54 (m, 1H), 2.38-2.19 (m, 3H), 2.03 (ddd, J=13.95, 9.17, 4.93 Hz, 1H), 1.59 (ddd, J=13.33, 7.40, 5.81 Hz, 1H), 1.38-1.28 (m, 1H), 0.93 (t, J=7.41 Hz, 3H) ppm. LC/MS: R$_t$=8.36 min, ES$^+$ 472 (AA long purity).

[(1R,2R,4S)-2-hydroxy-4-(4-{[(1S,2S)-2-ethyl-2,3-dihydro-1H-inden-1-yl]amino}-7H-pyrrolo[2,3-d]pyrimidin-7-yl)cyclopentyl]methylsulfamate (Compound I-84)

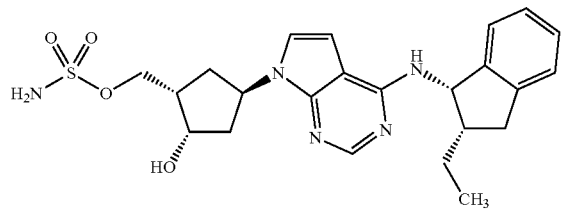

$^1$H NMR (CD$_3$OD, 400 MHz, δ): 8.17 (s, 1H), 7.31-7.15 (m, 5H), 6.66 (d, J=3.60 Hz, 1H), 5.94 (d, J=7.28 Hz, 1H), 5.48-5.41 (m, 1H), 4.48 (dd, J=3.98, 3.03 Hz, 1H), 4.36 (dd, J=9.74, 7.58 Hz, 1H), 4.19 (dd, J=9.73, 7.33 Hz, 1H), 3.07-3.01 (m, 1H), 2.91-2.76 (m, 2H), 2.65-2.54 (m, 1H), 2.38-2.19 (m, 3H), 2.03 (ddd, J=13.95, 9.17, 4.93 Hz, 1H), 1.59 (ddd, J=13.33, 7.40, 5.81 Hz, 1H), 1.38-1.28 (m, 1H), 0.93 (t, J=7.41 Hz, 3H) ppm. LC/MS: R$_t$=8.36 min, ES$^+$ 472 (AA long purity).

((1S,2S,4R)-2-hydroxy-4-(4-((1R,2S)-2-methoxy-1,2,3,4-tetrahydronaphthalen-1-ylamino)-7H-pyrrolo[2,3-d]pyrimidin-7-yl)cyclopentyl)methyl sulfamate (Compound I-85)

$^1$H NMR (CD$_3$OD, 400 MHz, δ): 8.17 (s, 1H), 7.25 (d, J=7.4, 1H), 7.20 (d, J=3.6 Hz, 1H), 7.15-7.06 (m, 3H), 6.66 (d, J=3.6 Hz, 1H), 5.81 (m, 1H), 5.50-5.40 (m, 1H), 4.49 (m, 1H), 4.37 (dd, J=3.3, 7.0 Hz, 1H), 4.20 (dd, J=7.3, 9.7 Hz, 1H), 3.85-3.82 (m, 1H), 3.42 (s, 3H), 3.06-2.96 (m, 1H), 2.84-2.73 (m, 2H), 2.38-2.18 (m, 4H), 2.08-2.18 (m, 2H) ppm. LC/MS: R$_t$=1.51 min, ES$^+$ 488 (AA standard).

((1S,2S,4R)-4-(4-((S)-2,3-dihydro-1H-inden-1-ylamino)-7H-pyrrolo[2,3-d]pyrimidin-7-yl)-2-methoxycyclopentyl)methyl sulfamate (Compound I-86)

$^1$H NMR (CD$_3$OD, 400 MHz, δ): 8.13 (s, 1H), 7.23-7.08 (m, 5H), 6.60 (d, J=3.6 Hz, 1H), 5.81 (t, J=7.69, 15.4 Hz, 1H), 5.36-5.25 (m, 1H), 4.32 (dd, J=7.5, 9.6 Hz, 1H), 4.13 (dd, J=7.3, 9.6 Hz, 1H), 4.02-4.00 (m, 1H), 3.32 (s, 3H), 3.06-2.98 (m, 1H), 2.94-2.77 (m, 2H), 2.63-2.54 (m, 1M), 2.54-2.48 (m, 1H), 2.18-2.08 (m, 2H) ppm. LC/MS: R$_t$=8.10 min, ES$^+$458 (AA standard).

Example 69

Enzyme Preparation

All protein accession numbers provided herein refer to the Entrez Protein database maintained by the National Center for Biotechnology Information (NCBI), Bethesda, Md.

Generation of E1 Enzymes

Following manufacturer instructions, baculoviruses were generated with the Bac-to-Bac Expression System (Invitrogen) for the following proteins: untagged NAEα (APPBP1; NP_003896.1), N-terminally His-tagged NAEβ (UBE1C; NP_003959.3), untagged SAEα (SAE1; NP_005491.1), N-terminally His-tagged SAEβ (UBA2; NP_005490.1), N-terminally His-tagged murine UAE (UBE1X; NP_033483). NAEα/His-NAEβ and SAEα/His-SAEβ complexes were generated by co-infection of Sf9 cells, which were harvested after 48 hours. His-mUAE was generated by single infection of Sf9 cells and harvested after 72 hours. Expressed proteins were purified by affinity chromatography (Ni—NTA agarose, Qiagen) using standard buffers.

Generation of E2 Enzymes

Ubc12 (UBE2M; NP_003960.1), Ubc9 (UBE2I; NP_003336.1), Ubc2 (UBE2A; NP_003327.2) were subcloned into pGEX (Pharmacia) and expressed as N-terminally GST tagged fusion proteins in E. coli. Expressed proteins were purified by conventional affinity chromatography using standard buffers.

Generation of Ubl Proteins

Nedd8 (NP_006147), Sumo-1 (NP_003343) and Ubiquitin (with optimized codons) were subcloned into pFLAG-2 (Sigma) and expressed as N-terminally Flag tagged fusion proteins in E. coli. Expressed proteins were purified by conventional chromatography using standard buffers.

Example 70

E1 Enzyme Assays

Nedd8-Activating Enzyme (NAE) HTRF Assay.

The NAE enzymatic reaction totaled 50 μL and contained 50 mM HEPES (pH 7.5), 0.05% BSA, 5 mM MgCl$_2$, 20 μM ATP, 250 μM GSH, 0.01 μM Ubc12-GST, 0.075 μM Nedd8-Flag and 0.28 nM recombinant human NAE enzyme. The enzymatic reaction mixture, with and without compound inhibitor, was incubated at 24° C. for 90 minutes in a 384-well plate before termination with 25 μL of Stop/Detection buffer (0.1M HEPES pH 7.5, 0.05% Tween20, 20 mM EDTA, 410 mM KF, 0.53 nM Europium-Cryptate labeled monoclonal anti-FLAG M2 antibody (CisBio International) and 8.125 μg/mL PHYCOLINK goat anti-GST allophycocyanin (XL-APC) antibody (Prozyme)). After incubation for 3 hours at 24° C., quantification of the FRET was performed on the Analyst™ HT 96.384 (Molecular Devices).

Compounds I-1 to I-54, I-56, I-59, I-61 to I-76, and I-79 to I-85 exhibited IC$_{50}$ values less than or equal to 10 μM in this assay. Compounds I-1, I-2, I-3, I-4, I-6, I-7, I-8, I-12, I-13, I-14, I-15, I-16, I-17, I-18, I-19, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-54, I-56, I-59, I-61, I-62, I-63, I-64, I-65, I-66, I-67, I-68, I-69, I-70, I-71, I-72, I-73, I-74, I-76, I-78, I-79, I-80, I-81, I-82, I-83, I-84, and I-85 exhibited $IC_{50}$ values less than or equal to 100 nM in this assay.

Sumo-Activating Enzyme (SAE) HTRF Assay.

The SAE enzymatic reaction was conducted as outlined above for NAE except that Ubc12-GST and Nedd8-Flag were replaced by 0.01 µM Ubc9-GST and 0.125 µM Sumo-Flag respectively and the concentration of ATP was 0.5 µM. Recombinant human SAE (0.11 nM) was the source of enzyme.

Ubiquitin-Activating Enzyme (UAE) HTRF Assay.

The UAE enzymatic reaction was conducted as outlined above for NAE except that Ubc12-GST and Nedd8-Flag were replaced by 0.005 µM Ubc2-GST and 0.125 µM Ubiquitin-Flag respectively and the concentration of ATP was 0.1 µM. Recombinant mouse UAE (0.3 nM) was the source of enzyme.

Example 71

Cellular Assays

Selected compounds of formula (I) were tested in cellular assays:

Anti-Proliferation Assay (WST)

Calu-6 (2400/well) or other tumor cells in 80 µL of appropriate cell culture medium (MEM for Calu6, Invitrogen) supplemented with 10% fetal bovine serum (Invitrogen) was seeded in wells of a 96-well cell culture plate and incubated for 24 hours in a tissue culture incubator. Compound inhibitors were added in 20 µL culture media to the wells and the plates was incubated for 72 hours at 37° C. 10% final concentration of WST-1 reagent (Roche) was added to each well and incubated for 3.5 hours (for Calu6) at 37° C. The optical density for each well was read at 450 nm using a spectrophotometer (Molecular Devices). Percent inhibition was calculated using the values from a DMSO control set to 100% viability.

Anti-Proliferation Assay (ATPLite)

Calu-6 (1500 cells/well) or other tumor cells were seeded in 72 µL of appropriate cell culture medium (MEM for Calu6, Invitrogen) supplemented with 10% fetal bovine serum (Invitrogen) in wells of a 384-well Poly-D-Lysine coated cell culture plate. Compound inhibitors were added in 8 µL 10% DMSO/PBS to the wells and the plates were incubated for 72 hours at 37° C. Cell culture medium was aspirated, leaving 25 µL in each well. 25 µL of ATPlite 1step™ reagent (Perkin Elmer) was added to each well. The luminescence for each well was read using the LeadSeeker Microplate Reader (Molecular Devices). Percent inhibition was calculated using the values from a DMSO control set to 100% viability.

Example 72

In Vivo Assays

Selected compounds of formula (I) were tested in in vivo assays.

In Vivo Tumor Efficacy Model

Calu6 ($5 \times 10^6$ cells), HCT116 ($2 \times 10^6$ cells) or other tumor cells in 100 µL phosphate buffered saline were aseptically injected into the subcutaneous space in the right dorsal flank of female Ncr nude mice (age 5-8 weeks, Charles River) using a 26-gauge needle. Beginning on day 7 after inoculation, tumors were measured twice weekly using a vernier caliper. Tumor volumes were calculated using standard procedures ($0.5 \times$ (length$\times$width$^2$)). When the tumors reached a volume of approximately 200 mm$^3$ mice were randomized into groups and injected intravenously in the tail vein with compound inhibitor (100 µL) at various doses and schedules. Alternatively, compound inhibitor may be delivered to mice by intraperitoneal or subcutaneous injection or oral administration. All control groups received vehicle alone. Tumor size and body weight was measured twice a week and the study terminated when the control tumors reached approximately 2000 mm$^3$.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

While a number of embodiments of this invention have been described, it is apparent that the provided basic examples may be altered to convey other embodiments, which utilize the compounds and methods of this invention. It will thus be appreciated that the scope of this invention has been represented herein by way of example and is not intended to be limited by the specific embodiments, rather is defined by the appended claims.

What is claimed is:

1. A compound of formula (VIIIa):

(VIIIa)

or a pharmaceutically acceptable salt thereof, wherein:
stereochemical configurations depicted at asterisked positions indicate relative stereochemistry;
Q is C($R^k$);
$R^a$ is —OH;
$R^b$ is hydrogen, fluoro, or $C_{1-4}$ aliphatic;
$R^c$ is hydrogen, —OH, or —OCH$_3$;
$R^d$ is hydrogen;
$R^8$ is hydrogen or $C_{1-4}$ aliphatic;
$R^k$ is hydrogen;
each $R^p$ independently is fluoro; —OR$^{5x}$; —N(R$^{4x}$)(R$^{4y}$); —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); or $C_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$);
each $R^{8p}$ independently is fluoro; —OR$^{5x}$; —N(R$^{4x}$)(R$^{4y}$); —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); or $C_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$); provided that when two $R^{8p}$ are attached to the same carbon atom, one must be selected from the group consisting of fluoro; —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); and C$_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$); or two R$^{8p}$ on the same carbon atom together form =O or =C(R$^{5x}$)$_2$;

R$^{4x}$ is hydrogen, C$_{1-4}$ alkyl, C$_{1-4}$ fluoroalkyl, or C$_{6-10}$ ar(C$_{1-4}$)alkyl, the aryl portion of which is optionally substituted;

R$^{4y}$ is hydrogen; C$_{1-4}$ alkyl; C$_{1-4}$ fluoroalkyl; C$_{6-10}$ ar(C$_{1-4}$)alkyl, the aryl portion of which is optionally substituted; optionally substituted 5- or 6-membered aryl; optionally substituted heteroaryl; or optionally substituted heterocyclyl ring; or R$^{4x}$ and R$^{4y}$, taken together with the nitrogen atom to which they are attached, form an optionally substituted 4- to 8-membered heterocyclyl ring having, in addition to the nitrogen atom, 0-2 ring heteroatoms independently selected from the group consisting of N, O, and S;

each R$^{5x}$ independently is hydrogen, C$_{1-4}$ alkyl, C$_{1-4}$ fluoroalkyl, or an optionally substituted C$_{6-10}$ aryl, or optionally substituted C$_{6-10}$ ar(C$_{1-4}$)alkyl;

wherein:

in each recitation of optionally substituted aryl, the aryl group, when substituted, contains on one or more unsaturated carbon atoms a substituent independently selected from the group consisting of
halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, if on an unsaturated carbon atom, contains on one or more unsaturated carbon atoms, a substituent independently selected from the group consisting of
halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; and in each recitation of optionally substituted heterocyclyl, the heterocyclyl group, when substituted, if on a saturated carbon atom, contains on one or more saturated carbon atoms, a substituent independently selected from the group consisting of
halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms independently selected from the group consisting of N, O, and S; and each occurrence of R* is independently hydrogen, aliphatic, aryl, heteroaryl, or heterocyclyl group;

s is 0, 1, or 2; and t is 0, 1, or 2.

2. A pharmaceutical composition comprising a compound of claim 1 or a pharmaceutically acceptable salt thereof, and a pharmaceutically acceptable carrier.

3. The pharmaceutical composition of claim 2, formulated for administration to a human patient.

4. The compound of claim 1, or a pharmaceutically acceptable salt thereof, wherein:

R$^b$ and R$^c$ are each hydrogen;

R$^8$ is hydrogen;

R$^{8p}$ is fluoro, —OR$^{5x}$, C$_{1-4}$ aliphatic optionally substituted with —OR$^{5x}$, or C$_{1-4}$ fluoroaliphatic optionally substituted with —OR$^{5x}$;

s is 0 or 1; and t is 0.

5. A pharmaceutical composition comprising a compound of claim 4 or a pharmaceutically acceptable salt thereof, and a pharmaceutically acceptable carrier.

6. [(1S,2S,4R)-2-Hydroxy-4-(4-{[(1R,2S)-2-methoxy-2,3-dihydro-1H-inden-1-yl]amino}-7H-pyrrolo[2,3-d]pyrimidin-7-yl)cyclopentyl]methyl sulfamate, or a pharmaceutically acceptable salt thereof.

7. A pharmaceutical composition comprising the compound of claim 6 or a pharmaceutically acceptable salt thereof, and a pharmaceutically acceptable carrier.

8. ((1S,2S,4R)-4-{4-[(1S)-2,3-Dihydro-1H-inden-1-ylamino]-7H-pyrrolo-[2,3-d]pyrimidin-7-yl}-2-hydroxycyclopentyl)methyl sulfamate, or a pharmaceutically acceptable salt thereof.

9. A pharmaceutical composition comprising the compound of claim 8 or a pharmaceutically acceptable salt thereof, and a pharmaceutically acceptable carrier.

* * * * *